US007601816B2

(12) United States Patent
Simmons et al.

(10) Patent No.: US 7,601,816 B2
(45) Date of Patent: Oct. 13, 2009

(54) ANTIBODIES TO CYCLOOXYGENASE VARIANTS

(75) Inventors: Daniel Simmons, Provo, UT (US); N. Vishvanath Chandrasekharan, Provo, UT (US)

(73) Assignee: Brigham Young University, Provo, UT (US)

( * ) Notice: Subject to any disclaimer, the term of this patent is extended or adjusted under 35 U.S.C. 154(b) by 0 days.

(21) Appl. No.: 11/601,208

(22) Filed: Nov. 17, 2006

(65) Prior Publication Data
US 2007/0065445 A1 Mar. 22, 2007

Related U.S. Application Data

(62) Division of application No. 10/260,937, filed on Sep. 28, 2002, now Pat. No. 7,179,627.

(60) Provisional application No. 60/411,575, filed on Sep. 16, 2002, provisional application No. 60/373,661, filed on Apr. 16, 2002, provisional application No. 60/373,225, filed on Apr. 15, 2002, provisional application No. 60/326,133, filed on Sep. 28, 2001.

(51) Int. Cl.
*C07K 16/00* (2006.01)
*C07K 16/40* (2006.01)
(52) U.S. Cl. ............... 530/387.9; 530/387.1; 530/388.1; 530/388.26; 530/389.1
(58) Field of Classification Search ....................... None
See application file for complete search history.

(56) References Cited

U.S. PATENT DOCUMENTS

| | | | | |
|---|---|---|---|---|
| 5,543,297 | A | 8/1996 | Cromlish et al. | 435/25 |
| 5,643,960 | A | 7/1997 | Breitner et al. | 514/570 |
| 6,025,395 | A | 2/2000 | Breitner et al. | 514/570 |
| 6,048,850 | A | 4/2000 | Young et al. | 514/183 |
| 6,107,087 | A | 8/2000 | O'Neill et al. | 435/325 |
| 6,187,756 | B1 | 2/2001 | Lee et al. | 514/26 |
| 6,638,744 | B2 | 10/2003 | Wisnewski et al. | 435/189 |
| 2002/0064845 | A1 | 5/2002 | Wisnewski et al. | 435/183 |

FOREIGN PATENT DOCUMENTS

| | | |
|---|---|---|
| JP | 01228479 | 9/1989 |
| JP | 10324698 | 12/1998 |
| WO | WO 01/11026 | 2/2001 |
| WO | WO 01/55320 | 8/2001 |
| WO | WO 01/90125 | 11/2001 |
| WO | WO 02/071928 | 9/2002 |

OTHER PUBLICATIONS

Attwood Science 2000; 290:471-473.*
Skolnick et al. Trends in Biotech. 2000; 18(1):34-39.*
Lederman et al. Molecular Immunology 28: 1171-1181, 1991.*
Li et al. PNAS 77: 3211-3214, 1980.*
Ballou, et al. "Nociception in Cyclooxygenase Isozyme-Deficient Mice", *Proc. Natl. Acad. Sci.*, 97(18):10272-10276 (2000).
Botting, "Mechanism of Action of Acetaminophen: Is There A Cyclooxygenase 3?", *Clin, Infect. Dis.*, 31(Suppl. 5):S202-10 (2000).
Breitner, et al., "Delayed Onset of Alzheimer's Disease With Nonsteroidal Anti-inflammatory and Histamine H2 Blocking Drugs", *Neurobiology of Aging*, 16(4):523-530 (1995).
DeWitt, et al., "PGH Synthase Isoenzyme Selectivity: The Potential for Safer Nonsteroidal Antiinflammatory Drugs", *Amer. J Med.*, 95(Suppl. 2A):40S-44S (1993).
Griffin, et al., "Brain Interleukin 1 and S-100 Immunoreactivity Are Elevated in Down Syndrome and Alzheimer Disease", *Proc. Natl. Acad. Sci.*, 88:7611-7615 (1989).
Herschmann et al., "TIS10, A Mitogen-inducible Glucocortiocoid-inhibited Gene That Encodes A Second Prostaglandin Synthase/Cyclooxygenase Enzyme", *J. Lipid Mediators*, 6:89-99 (1993).
Hla & Neilson, "Human Cyclooxygenase-2 cDNA", *Proc. Natl. Acad. Sci.*, 89:7384-7388 (1992).
Jang, et al., "Cancer Chemopreventive Activity of Resveratrol, A Natural Product Derived From Grapes", *Science*, 275:218-220 (1997).
Johnson, et al., "Complement mRNA In The Mammalian Brain: Responses to Alzheimer's Disease and Experimental Brain Lesioning", *Neurobiol. Aging*, 13:641-648 (1992).
Lipsky, P.E. & Isakson, P.C., "Outcome of Specific COX-2 Inhibition in Rheumatoid Arthritis", *Journal of Rheumatol.*, 24(Suppl. 49):9-14 (1997).
Masferrer, et al., "Selective Inhibition of Inducible Cyclooxygenase 2 in vivo is Antiinflammatory and Nonulcerogenic", *Proc. Natl. Acad. Sci.*, 91:3228-3232 (1994).
McGeer, P.L. & Rogers, J., "Anti-inflammatory Agents As A Therapeutic Approach to Alzheimer's Disease", *Neurology*, 42(2):447-449 (1992).
McGeer, P.L. & McGeer, E.G., "The Inflammatory System of Brain: Implications For Therapy of Alzheimer and Other Neurodegenerative Diseases", *Brain Res. Rev.*, 21(2):195-218 (1995).
McGeer, et al., "Anti-inflammatory Drugs and Alzheimer's Disease", *The Lancet*, 335(8696):1037 (1990).
Schnabel, J., "New Alzheimer's Therapy Suggested", *Science* 260(515):1719-1720 (1993).

(Continued)

*Primary Examiner*—Phillip Gambel
*Assistant Examiner*—Sharon Wen
(74) *Attorney, Agent, or Firm*—Howrey LLP

(57) ABSTRACT

The invention relates to the isolation of novel cyclooxygenase type 1 (COX-1) variant enzymes. More specifically, the invention relates to the identification of cyclooxygenase transcripts harboring inton 1, or fragment thereof, of cyclooxygenase 1. The invention further relates to the diagnosis of aberrant cyclooxygenase type 1 variant gene or gene product; the identification, production, and use of compounds which modulate cyclooxygenase type 1 variant gene expression or the activity of the cyclooxygenase type 1 variant gene product including but not limited to nucleic acid encoding cyclooxygenase type 1 variants and homologues, analogues, and deletions thereof, as well as antisense, ribozyme, triple helix, antibody, and polypeptide molecules as well as small inorganic molecules; and pharmaceutical formulations and routes of administration for such compounds.

10 Claims, 52 Drawing Sheets

OTHER PUBLICATIONS

Simmons, et al., "Drug Inhibition and Cellular Regulation of Prostaglandin G/H Synthase Isoenzyme 2", *J. Lipid Mediators*, 6:113-117(1993).

Vane, "Towards A Better Aspirin", *Nature*, 367(6460):215 (1994).

Xie, et al., "Expression of A Mitogen-Responsive Gene Encoding Prostaglandin Synthase in Regulated by mRNA Splicing", *Proc. Natl. Acad. Sci.*, 88:2692-2696 (1991).

Yamagata, et al., "Expression of A Mitogen-inducible Cyclooxygenase in Brain Neurons: Regulation by Synaptic Activity and Glucocorticoids", *Neuron*, 11(2):371-386 (1993).

Wang, L-H et al., "Characterization of the Promoter of Human Prostaglandin H Synthase-1 Gene", *Biochem Biophys. Res. Commun.*, 190:406-411(1993).

Treismann et al., EMBL Database Accession No. P1; T13049 (1999).

Vogiagis et al., "Cyclooxygenase-1 and An Alternatively Spliced mRNA in the Rat Stomach: Effects of Aging and Ulcers", *Am. J. Physiol. Gastrointest Liver Physiol.*, May 2000, vol. 278, No. 5, pp. G820-G827.

Funk et al., P2319, NCBI, 1991.

Takahashi Y et al., "Immunoaffinity Purification and cDNA Cloning of Human Platelet Prostaglandin Endoperoxide Synthase (Cyclooxygenase)", *Biochem. Biophys. Res. Commun.*, 182:433-438 (1992).

EBI Accession No. EM_PAT: AX082876, EMBL Database, Feb. 28, 2001, "Sequence 5 from Patent WO0111026."

EBI Accession No. EM_HUM: S78220, EMBL Database, Nov. 26, 1993, "prostaglandin endoperoxide synthase [human, platelets, mRNA, 1812 nt]."

EBI Accession No. EM_HUM: S36271, EMBL Database, Feb. 16, 1993, "prostaglandin G/H synthase [human, lung, fibroblast, mRNA, 2435 nt]."

EBI Accession No. UNIPROT: P18488, UniProt Database, Nov. 1, 1990, "Homeotic protein empty spiracles."

\* cited by examiner

```
         1       8                                                                                                       98
Human    ---MLARALL LCAVLALSHT ANPCCSHPCQ NRGVCMSVGF DQYKCDCTRT GFYGENCSTP EFLTRIKLFL KPTPNTVHYI LTHFKGFWNV VNNIPFLRNA IMSYVLTSRS
Ovine    ---MLARALL LCAAV-VCGA ANPCCSHPCQ NRGVCMSVGF DQYKCDCTRI GFYGENCTTP EFLTRIKLLL KPTPDTVHYI LTHFKGVWNI VAKISFLRNM IMRYVLTSRS
Canine   ---MLARALV LCAALAVVRA ANPCCSHPCQ NQGICMSTGF DQYKCDCTRT GFYGENCSTP EFLTRIKLYL KPTPNTVHYI LTHFKGVWNI VNNIPFLRNT IMKYVLTSRS
Bovine   ---MLARALL LCAAVALSGA ANPCCSHPCQ NRGVCMSVGF DQYQCDCTRT GFYGENCSTP EFLTRIKLLL KPTPNTVHYI LTHFKGVWNI VAKISFLRNM IMRYVLTSRS
Equine   ---MLARALL LCVALALGHA ANPCCSNPCQ NRGVCMSVGF DQYQCDCTRT GFYGENCSTP EFLTRIKLFL KPTPNTVHYI LTHFKGVWNI VNSPFLRNA VMKYVLVSRS
Rabbit   ---MLARALL LCAAVALSHA ANPCCSNPCQ NRGVCMTMGF DQYKCDCTRT GFYGENCSTP EFLTRIKLLL KPTPDTVHYI LTHFKGVWNI VNSIPFLRNS IMKYVLTSRS
Guinea   ---MLARALL LCAALALGQA ANPCCSNPCQ NRGECLSVGF DRYKCDCTRT GYYGENCTTP EFLTRIKLLL KPTPNTVHYI LTHFKGVWNI VNNIPFLRNA IMTYVLTSRS
Murine   ---MLFRAVL LCAALGLSQA ANPCCSNPCQ NRGECMSTGF DQYKCDCTRT GFYGENCTTP EFLTRIKLLL KPTPNTVHYI LTHFKGVWNI VNNIPFLRSL IMKYVLTSRS
Rat      ---MLFRAVL LCACPGLSHA ANPCCSNPCQ NRGECMSIGF DQVKCDCTRI GFYGENCSTP RFLTRIKLPL KPTPNTVHYI LTHFKGVWNI VNNIPFLRIQ SMRVVLTSRS
Mink     ---MLARAGL LCASLSPPHA ANPCCSLPCQ NQGVCMSIGF DQVMCDCSRI GFYGENCSTP EFLTRVKLLL KPTPNTVHYI LTHFKGVWNI VNKIPFLADV IMKYVLTSRS
Chicken  ---MLLPCAL LAALLAAGHA ANPCCSLPCQ NRGVCMTIGF DRVECDCTRI GYYGKNCTTP EFFTWLKLIL KPAPNTIHYI LTHFKGVWNI INNISFLRDT IMRVVLTPRS
Rainbow  MNRVICIILL LAVGLYFCEG VDPCCAQPCE NRGLCNSKGF DNYECDCTRI GYYGKNCTTP EFLTWIKISL KPAPNTIHYI LTHYKGLWNV INKITFVRNA IMSYVLTSRS
Brook    MNKVCIILL LTVGLYFCEG VDPCCAQPCE NRGLCNSKGF DNYECDCTRI GYYGKNCTTP EFLTWIKISL KPAPNTVHYI LTHYKGLWNV INKITFVRNA IMSYVLTSRS Signal peptide       EGF - like domain/dimerization domain (1)                    Membrane-binding domain 108                                                                                                             208
Human    HLIDSPPTYN ADYGYKSWEA FSNLSYYTRA LPPYPDDCPT PLGVKGKKQL PDSNEIVEKL LLRRKFIPDP QGSNLMFAFF AQHFTHQFFK TDHKRGPAFT NGLGHGVDLN
Ovine    HLIESPPTYN VHYSYKSWEA FSNLSYYTRA LPPVPDDCPT PMGVKGRKEL PDSKEVVKKV LLRRKFIPDP QGTNLMFAFF AQHFTHQFFK TDIERGPAFT KGKNHGVDLS
Canine   HLIESPPTYN VNYGYKSWEA FSNLSYYTRA LPPVPDDCPT PMGVKGKKEL PDSKEIVEKF LLRRKFIPDP QGTNMMFAFF AQHFTHQFFK TDHKRGPAFT KGLGHGVDLN
Bovine   HLIESPPTYN VHYSYKSWEA FSNLSYYTRA LPPVPDDCPT PMGVKGRKEL PDSKEVVKKV LLRRKFIPDP QGTNMMFAFF AQHFTHQFFK TDFERGPAFT KGKNHGVDLS
Equine   HLIESPPTYN AQYGYKSWES FSNLSYYTRA LPPVADGCPT PMGVKGKKEL PDSKEIVEKF LLRRKFIPDP QGTNMMFAFF AQHFTHQFFK TDPKRGPAFT KGLGHGVDLS
Rabbit   HMIDSPPTYN VHYNYKSWEA FSNLSYYTRA LPPVADDCPT PMGVKGKKEL PDSKDVVEKL LLRRKFIPDP QGTNMMFAFF AQHFTHQFFK TDLKRGPAFT KGLGHGVDLN
Guinea   HLIDSPPTYN AHYGYKSWEA FSNLSYYTRA LPPVADDCPT PMGVKGKKEL PDSNEVLEKV LLRRKFIPDP QGTNMMFAFF AQHFTHQFFK SDQKRGPAFT TGLAHGVDLS
Murine   YLIDSPPTYN VHYGYKSWEA FSNLSYYTRA LPPVRDDCPT PMGVKGNKEL PDSKEVLEKS LLRREFIPDP QGSNMMFAFF AQHFTHQFFK TDHKRGPAFT RGLGHGVDLN
Rat      HLIDSPPTYN VHYGYKSWEA FSNLSYYTRA LPPVADDCPT PMGVKGNKEL PDSKEVLEKV LLRRKFIPDP QGTNMMFAFF AQHFTHQFFK TDQKRGPAFT RGLGHGVDLN
Mink     HCIEPPPTYN VHYAYKSWEA FSNLSYYTRA LPPVADDCPT PMGVKGKKEL PDSKEIVEKF LLRRKFIPDP QGTNMMFAFF AQHFTHQFFK TDQKRGPGFT KGLGHGVDLS
Chicken  HLIDSPPTYN SDYSYKSWEA YSNLFYYTRT LPPLPKDCPT PMGVKGKKEL PDSKLIVEKF LLRRKFIPDP QGTNMMFTFF AQHFTHQFFK TDQKKGPGFT KAYGHGVDLN
Rainbow  HLVDSPPTYN ADYGYKSWEA YSNLSYYTRT LPPLPKDCPT PMGTAGRAVL PDVKLIVEKV LLRRKFIPDP QGSNLMFAFF AQHFTHQFFK SDFMKGPAFT SDLKGPAFT KALGHGVDLN
Brook    HLVDSPPTYN ADYGYKSWEA YSNLSYYTRT LPPLPKDCPT PMGTAGRAVL PDVKLVEKV LLRRKFIPDP QGSNLMFAFF AQHFTHQFFK SDLKGPAFT KALGHGVDLN Dimerization domain (2)      Glycosylation site                                                          Distal histidine
```

```
                218                                                                                                              318
Human    HIYGETLARQ RKLRLFKDGK MKYQIIDGEM YPPTVKDTQA EMIYPPQVPE HLRFAVGQEV FGLVPGLMMY ATIWLREHNR VCDVLKQEHP EWGDEQLFQT SRLILIGETI
Ovine    HVYGESLERQ HNRRLFKDGK MKYQMINGEM YPPTVKDTQV EMIYPPHIPE HLKFAVGQEV FGLVPGLMMY ATIWLREHNR VCDVLKQEHP EWGDEQLFQT SRLILIGETI
Canine   HVYGETLDRQ HKLRLFKDGK MKYQVIDGEV YPPTVKDTQV EMIYPPHVPE HLQFAVGQEV FGLVPGLMMY ATIWLREHNR VCDVLKQEHP EWDDERLFQT SRLILIGETI
Bovine   HIYGESLERQ HKLRLFKDGK MKYQMINGEM YPPTVKDTQV EMIYPPHIPE HLKFAVGQEV FGLVPGLMMY ATIWLREHNR VCDVLKQEHP EWGDEQLFQT SRLILIGETI
Equine   HIYGETLDRQ HKLRLFKDGK MKYQIINGEV YPPTVKDTQV EMIYPPHIPE HLRFAVGQEV FGLVPGLMMY ATIWLREHNR VCDVLKQEHP EWDDEQLFQT SRLILIGETI
Rabbit   HIYGETLDRQ HKLRLFKDGK MKYQVIDGEV YPPTVKDTQV EMIYPPHIPA HLQFAVGQEV FGLVPGLMMY ATIWLREHNR VCDVLKQEHP EWDDEQLFQT SRLILIGETI
Guinea   HIYGETLDRQ HKLRLFKDGK MKYQIIDGEM YPPTVKETQV EMMYPPYIPE HARFAVGQEV FGLVPGLMMY ATIWLREHNR VCDILKQEHP EWGDEQLFQT SRLILIGETI
Murine   HIYGETLDRQ HKLRLFKDGK LKYQVIGGEV YPPTVKDTQV EMIYPPHIPE NLQFAVGQEV FGLVPGLMMY ATIWLREHNR VCDILKQEHP EWDDEQLFQT SRLILIGETI
Rat      HVYGETLDRQ HKLRLFQDGK LKYQVIGGEV YPPTVKDTQV EMIYPPHVPE HLRFAVGQEV FGLVPGLMMY ATIWLREHNR VCDVLKQEHP EWDDERLFQT SRLILIGETI
Mink     HVYGETLDRQ HKLRLFKDGK MKYQVIDGEV YPPTVKDTQA EMIYPPHVPE HLQFSVGQEV FGLVPGLMMY ATIWLREHNR VCDVLKQEHP EWDDERLFQT TRLILIGETI
Chicken  HIYGETLERQ LKLRLRKDGK LKYQMDGEM YPPLVREVGA EMHYPPQVPE EHRFAVGHEH FGLVPGLMMY ATIWLREHNR VCDVLKQEOG EWDDERLFRR TRLILIGETI
Rainbow  HVYGDTLERQ HKLRLFKDGK LKYRVLNGEV YPPLVREVGA EMHYPPQVPE EHRFAVGHEM FGLVPGLMMY ATIWLREHNR VCDVLRQEHP EWDDERIFQT TRLILIGETI
Brook    HVYGDSLERQ HKLRLFKDGK LKYQVLNGEV YPPLVREVGA EMHYPPQVPE EHRFAVGHEM FGLVPGLMMY ATIWLREHNR VCDVLRQEHP EWDDERIFQT TRLILIGETI
                328                                                                                                              428
Human    KIVIEDYVQH LSGYHFKLKF DPELLFNKQF QYQNRIAAEF NTLYHWHPLL PDTFQIHDQK YNYQQFIYNN SILLEHGITQ FVESFTRQIA GRVAGGRNVP PAVQKVSQAS
Ovine    KIVIEDYVQH LSGYHFKLKF DPELLFNQQF QYQNRIAAEF NTLYHWHPLL PDVFQIDGQE YNYQQFIYNN SVLLEHGVTQ FVESFTRQIA GRVAGRRNLP AAVEKVSKAS
Canine   KIVIEDYVQH LSGYHFKLKF DPELLFNQQF QYQNRIAAEF NTLYHWHPLL-PDTLQIDDQE YNYQQFIYNN -SILLEHGLTQ FVESFSRQIA GRVAGGRNVP AAVQQVAKAS
Bovine   KIVIEDYVQH LSGYHFKLKF DPELLFNQQF QYQNRIAAEF NTLYHWHPLL PDVFQIDGQE YNYQQFIYNN SVLLEHGLTQ FVESFTRQRA GRVAGGRNLP VAVEKVSKAS
Equine   KIVIEDYVQH LSGYHFKLKF DPELLFNQQF QYQNRIAAEF NTLYHWHPLL PDTFQIDDQE YNFQQFLYNN SILLEHGLTQ FVESFSRQIA GRVAGGRNVP AAAQKIAKAS
Rabbit   KIVIEDYVQH LSGYHFKLKF DPELLFNQQF QYQNRIAAEF NTLYHWHPLL PDTFQIDDQQ YNYQQFLYNN SILLEHGLTQ FVESFTRQIA GRVAGGRNVP PAVQKVAKAS
Guinea   KIVIEDYVQH LSGYHFKLKF DPELLFNQQF QYQNRIASEF NTLYHWHPLL PDTFQIDDQV YMFQQFLYNN SILVEHGLTQ FVESFTKQIA GRVAGGRNVP LAVQRVAKAS
Murine   KIVIEDYVQH LSGYHFKLKF DPELLFNQQF QYQNRIASEF NTLYHWHPLL PDTFNIEDQE YSFKQFLYNN SILLEHGLTQ FVESFTRQIA GRVAGGRNVP IAVQAVAKAS
Rat      KIVIEDYVQH LRGYHFQLKF DPDLLFNQQF QYQNRIASEF KTLYHWHPLL PDTFNIEDQE YTFKQFLYNN SILLEHGLAH FVESFSRQIA GRVAGGRNVP IAVQAVAKAS
Mink     KIVIEDYVRH LSGYHFSLKF DPELLFNQRF QYQNRIAAEF NTLYHWHPLL PDTLQIDDQE YNFQQFVYNN SILLEHGLTQ FGESFTRQIA GRVAGGRNVP AAVQQEQRAS
Chicken  KIVIEDYVQH LSGYHFQLKF DPELLFNQRF QYQNRIAAEF NTLYHWHPLM PDTFQIHNQE YTFQQFLYNN SIMLEHGLAH MVKSFSKQSA GRVAGGKNVP AAVQKVAKAS
Rainbow  KIVIEDYVQH LSGYHFQLKF DPELLFNQRF QYQNRIAAEF NTLYHWHPLM PETFSIEDRA YTYPQFVFNN SLVTEHGINN LVESFTKQIA GRVAGGRNLP PALGVAAKA
Brook    KIVIEDYVQH LSGYHFQLKF DPELLFNQRF QYQNRIAAEF NTLYHWHPLM PDTFSIEDRA YTYPQFVFNN SLVTEHGITN LVESFTKQIA GRVAGGRNLP PALVAVAAKA
                                              ← Active site tyrosite
                                                           ← Proximal heme ligand    ← Glycosylation site
```

*FIG. 1A-2*

```
         438
Human    IDQSRQMKYQ SFNEYRKRFM LKPYESFEEL TGEKEMSAEL EALYGDIDAV ELYPALLVEK PRPDAIFGET MVEVGAPFSL KGLMGNVICS PAYWKPSTFG GEVGFQIINT
Ovine    LDQSREMKYQ SFNEYRKRFL LKPYESFEEL TGEKEMAAEL EALYGDIDAM ELYPALLVEK PAPDAIFGET MVEAGAPFSL KGLMGNPICS PEYWKPSTFG GEVGFKIINT
Canine   IDQSRQMKYQ SLNEYRKRFR LKPYTSFEEL TGEKEMAAGL EALYGDIDAM ELYPALLVEK PRPDAIFGET MVEMGAPFSL KGLMGNPICS PDYWKPSTFG GEVGFKIINT
Bovine   IDQSREMKYQ SFNEYRKRFL VKPYESFEEL TGEKEMAAEL EFYPYPALVEK PRPDAIFGET MVEAGAPFSL KGLMGNPICS PEYWKPSTFG GEVGFKIINT
Equine   IDQSREMKYQ SLNEYRKRFR LTPYKSFEEL TGEKEMAAEL EALYGDIDAM ELYPALLVEK PRPDAIFGET MVELGAPFSL KGLGNPICS PDYWKPSTFG GEVGFKIVNT
Rabbit   IDQSRQMKYQ SLNEYRKRFL LKPYESFEEL TGEKEMAAEL EALYGDIDAV ELPPALLVER PRPDAIFGES MVEMGAPFSL KGLMGNPICS PNYWKPSTFG GEVGFKIVNT
Guinea   IEHSRKMKYQ SLNEYRKRFL MKPYTSFEEL TGEKEMAAGL EALYGDIDAM ELYPALLVEK PRPDAIFGET MVEMGAPSL KGLMGNPICS PHYWKPSTFG GEVGFQIVNT
Murine   IDQSREMKYQ SLNEYRKRFS LKPYTSFEEL TGEKEMAAEL KALYSDIDVM ELYPALLVEK PRPDAIFGET MVELGAPFSL KGLMGNPICS PQYWKPSTFG GEVGFKIINT
Rat      IDQSREMKYQ SLNEYRKRFS LKPYTSFEEL TGEKEMAAEL KALYHDIDAM ELYPALLVEK PRPDAIFGET MVELGAPFSL KGLMGNPICS PQYWKPSTFG GEVGFRIINT
Mink     IDQSRQMRYQ SLNEYRKRFM VKPYASFEEL TGEKEMAGEL EELYGDIDAM ELYPGLLVEK PRPGAIFGET MVEIGAPFSL KGLMGNPICS PDYWKPSHFG GEVGFKIINT
Chicken  IDQSRQMRYQ SLNEYRKRFM LKPFKSFEEL TGEKEMAAEL ESLYGDVDAV ELYPGLLVER PRPNAVFGET MVEIGAPFSL KGLMGNTICS PEYWKPSTFG GKVGFEIINT
Rainbow  LEHSRDMRYQ SLNAYRKRFN MRVYTSFEDL TGETELAAEL ESLYGDVDAV ELYPGLLVER PRPNAVFGET MVEMGAPYSL KGLLGNPICS PEYWMPSTFG GSVGFDILNT
Brook    LEHSRDMRYQ SLNAYRKRFN MRAYTSFEDL TGETELAAEL                                                                GSVGFDIVNT Glycosylation site   Active site valine          ASA-acetylated serine
                                                                                      597
         538
Human    ASIQSLICNN VKG-CPFTSF SVPDPELIKT VTINASSSRS GLDDINPTVL LKERSTEL
Ovine    ASIQSLICSN VKG-CPFTSF SVQDAHLTKT VTINASSSHS GLDDINPTVL LKERSTEL
Canine   ASIQSLICNN VKG-CPATAF SVQDGQLTKT VTINASSSHS GLDDINPTVL LKERSTEL
Bovine   ASIQSLICSN VKG-CPFTSF SVQDTHLTKT VTINASSSHS GLDDINPTVL LKERSTEL
Equine   ASIQSLICNN VKG-CPFTAF SVQDPQLSKA VTINASASHS GLDDVNPTVL LKERSTEL
Rabbit   ASIQSLICNN VKG-CPFTSF NVPDPQLTKT VTINASASHS RLEDINPTVL LKGRSTEL
Guinea   ASIQSLICNN VKG-CPATAF NLPDPQLAKT VTINASASHS RLEDLSPTVL LKGRSTEL
Murine   ASIQSLICNN VKG-CPFTSF NVQDPQPTKT ATINASASRS RLDDINPTVL IKRRSTEL
Rat      ASIQSLICNN VKG-CPFTAF NVQDPQATKT ATINASASHS RLDDINPTVL IKRRSTEL
Mink     ASIQSLICNN VKG-CPFTAF SVQDQLTKT VTINGSSSHS GLDDINPTVL LKERSTEL
Chicken  ASLQKLICNN VKG-CPFTAF HVLNPEPTE- ATINVSTSNT AMEDINPTLL LKEQSAEL
Rainbow  ASLERLVCNN VKGSCPWVSF QVPD-FLRAF ESASVNTSEA HLSDMNPGVL FKERTSEL
Brook    ASLERLVCNN VKGSCPWVSF QVPD-FLRAF ESASVNTSEA HLRGMPGVV FKERTLEL
```

*FIG. 1A-3*

```
B                                                           24                                           *  *                                                 74
Human                        -MSR-SLLLR FL---LFLLL L---PPLPVL LADPGAPTPV NPCCYYPCQH QGICVRFGLD RYQDCTRTG YSGPNCTIPG LWTWLRNSLR
Ovine                        -MSRQSILLR FP---LLLLL L---SPSVF  SADPGAPAPV NPCCYYPCQH QGICVRFGLD RYQDCTRTG YSGPNCTIPE IWTWLRTTLR
Canine                       -MSRGSRLHR WP---LLLLL LILLPPPPVL PAEARTPAPV NPCCYYPCQH QGICVRFGLD RYQDCTRTG YSGPNCTIPE LWTWLRNSLR
Rabbit                       -MSRSPSLR  LPVLLLLLLL LLLPPPPPVL PADPGAPAPV NPCCYFPCQH QGVCVRFGLD RYQDCTRTG YSGPNCTVPD LWTWLRSSLR
Murine                       -MSRRSLSLW FP----LLLL LLLPPTPSVL LADPGVPSPV NPCCYYPCQN NYQDCTRTG  YSGPNCTIPE IWTWLRNSLR
Rat                          -MSRRSLSLQ FP---LLLL  LLLLPPPPVL LTDAGVPSPV NPCCYYPCQN QGVCVRFGLD HYQDCTRTG  YSGPNCTIPE IWTWLRSSLR
Rainbow MSAAYIIFAL LYWEDAPAEG AYAVNLTMRE CVVWWACIL LQRLPTCRGE EVEDAST-VV NPCCYYPCQN WGVCVRFGLD RYECDCRTG  FYGQNCTIPE FWTRVHQQLK
Brook                   -MRG LVVCVWACIL LQRLPTCRGE EVKDVSTNVV NPCCYYPCQN WALCVRFGLD RYECDCRTG  FYGQNCTIPE FWTRIHQQLK
                             ————————————— Signal peptide ——————————————————————  ——————————— EGF-like domain/dimerization domain (1) ——————————

Glycosylation site →
        84                                                                                     Glycosylation site      184
Human   PSPSFTHFLL THGRMFWEFV NATFIREMLM RLVLTVRSNL IPSPPTYNSA HDYISWESFS NVSYYTRILP SVPKDCPTPM GTKGKKQLPD AQLLARRFLL RRKFIPDPQG
Ovine   PSPSFIHFML THGRMLWDFV NATFIRDTLM RLVLTVRSNL IPSPPTYNIA HDYISWESFS NVSYYTRILP SVPRDCPTPM GTKGKKQLPD AEFLSRRFLL RRKFIPDPQG
Canine  PSPSFLHFLL THGRMFWEFL NATFIRDMLM RLVLTARSNL IPSPPTYNIA HDYISWESFS NVSYYTRVLP SVPQDCPTPM GTKGKKQLPD AQLLGRRFLL RRKFIPDPQG
Rabbit  PSPTFVHYLL THVRMFWEFV NATFIRDTLM RLVLTVRSNL IPSPPTYNEAFS HDYISWEAFS NVSYYTRVLP SVPKDCPTPM GTKGKKQLPD AQVLAHRFLL RRTFIPDPQG
Murine  PSPSFTHFLL THGYWLWEFV NATFIREVLM RLVLTVRSNL IPSPPTYNLA YDYISWESFS NVSYYTRILP SVPKDCPTPM GTKGKKQLPO VQLLAQQLLL RREFIPAPQG
Rat     PSPSFTHFLL THGYIWEFV  NATFIREVLM RLVLTVRSNL IPSPPTYNTA HDYISWESFS NVSYYTRILP SVPKDCPTPM GTKGKKQLPD IHLLAQRLLL RREFIPGPQG
Rainbow PSPDVWHYIL THFHWLWNLI NRTFMRDWLM RVVLTVRSNL IPSPPTFNSK YGYLSWESYS NVSYYTRILP PVPEDCPTPM GTKGKSVLPD PKLVEKFLL  RRQFRRDPRG
Brook   PSPDVWHYIL THFHWLWNLI NRTFMRDWLM RMVLTVRSNL IPSPPTFNSK YGYLSWESYS NVSYYTRILP PVPEDCPTPM GTKGKSVLPD PKLVEKFLL  RRQFRPDPKG
        ———— Membrane-binding domain ————    ————————— Dimerization domain (2) ——————— ↖ Glycosylation site
```

*FIG. 1B-1*

```
         194                                                                                    294
Human    TNLMFAFFAQ HFTHQFFKTS GKMGPGFTKA LGHGVDLGHI YGDNLERQYQ LRLFKDGKLK YQVLDGEMYP PSVEEAPVLM HYPRGIPPQS QMAVGQEVFG LLPGLMLYAT
Ovine    TNLMFAFFAQ HFTHQFFKTS GKMGPGFTKA LGHGVDLGHI YGDNLERQYQ LRLFKDGKLK YQMLNGEVYP PSVEEAPVLM HYPRGIPPQS QMAVGQEVFG LLPGLMLYAT
Canine   TNLMFAFFAQ HFTHQFFKTS GKMGPGFTKA LGHGVDLGHI YGDNLDRQYQ LRLFKDGKLK YQVLDGEMYP PSVEEAPVLM HYPRGILPQS QMAVGQEVFG LLPGLMLYAT
Rabbit   TNLMFAFFAQ HFTHQFFKTS GKMGPGFTKA LGHGVDLGHI YGDSLERQYH LRLFKDGKLK YQVLDGEVYP PSVEEAPVLM HYPRGVPPRS QMAVGQEVFG LLPGLMLYAT
Murine   TNIMFAFFAQ HFTHQFFKTS GKMGPGFTKA LGHGVDLGHI YGDNLERQYH LRLFKDGKLK YQVLDGEVYP PSVEQASVLM RYPPGVPPER QMAVGQEVFG LLPGLMLFST
Rat      TNVLFAFFAQ HFTHQFFKTS GKMGPGFTKA LGHGVDLGHI YGDSLERQYH LRLFKDGKLK YQVLDGEVYP PSVEQASVLM RYPPGVPPEK QMAVGQEVFG LLPGLMLFST
Rainbow  TNLMFAFFAQ HFTHQFFKTR NSMGLGFTRA LGHGVDAGNV YGDNLVRQLN LRLLKDGKMK YQVVKGEAVVM RYPQETPVGQ RMAIGQEVFG LLPGLTMYAT
Brook    TNLMFAFFAQ HFTHQFFKTR NSMGLGFTSA LGHGVDAGNV YGDNLVRQLN LRLLKDGKMK YQVVKGEVYP PTVAEAPVNM RYPQGTPVGQ RMAIGQEVFG LLPGLTMYAT
                                            ↙Distal histidine
         304                                                                       Glycosylation site
                                                                                          ↘ 404
Human    LWLREHNRVC DLLKAEHPTW GDEQLFQTTR LILIGETIKI VIEEYVQQLS GYFLQLKFDP ELLFGVQFQY RNRIAMEFNH LYHWHPLMPD SFKVGSQEYS YEQFLFNTSM
Ovine    LWLREHNRVC DLLKAEHPTW GDEQLFQTAR LILIGETIKI VIEEYVQQLS GYFLQLKFDP ELLFGVQFQY RNRIAMEFNQ LYHWHPLMPD SFRVGPQDYS YEQFLFNTSM
Canine   LWLREHNRVC DLLKAEHPTW GDEQLFQTAR LILIGETIKI VIEEYVQQLS GYFLQLKFDP ELLFSVQFQY RNRIAMEFQY LYHWHPLMPD SFWGSQEYS YEQFLFNTSM
Rabbit   LWLREHNRVC DLLKAEHPTW GDEQLFQTTR LILIGETIKI VIEEYVQQLS GYFLQLKFDP EMLFSVQFQY RNRIAMEFNH LYHWHPLMPD SFQVGSQEYS YEQFLFNTSM
Murine   IWLREHNRVC DLLKEEHPTW DDEQLFQTTR LILIGETIKI VIEEYVQHLS GYFLQLKFDP ELLFRAQFQY RNRIAMEFNH LYHWHPLMPN SFQVGSQEYS YEQFLFNTSM
Rat      IWLREHNRVC DLLKEEHPTW DDEQLFQTTR LILIGETIKI IIEEYVQHLS GYFLQLKFDP ELLFRAQFQY RNRIALEFNH LYHWHPLMPD SFQVGSQEYS YEQFLFNTSM
Rainbow  LWLREHNRVC DILKAEHPTW GDEQLFQTAR LIVIGETIRI VIEEYVQHLS GYLLDLKFDP VLLFKSTFQY RNRIAVEFKH LYHWHPLMPD SFHIDGDEVP YSQFIFNTSI
Brook    LWLREHNRVC DILKAEHPTW GDEQLFQTAR LIVIGETIRI VIEEYVQHLS GYLLDLKFDP VLLFKSTFQY RNRIAVEFNQ LYHWHPLMPD SFHIDGDWS YSQFIFNTSI
                                                                         Active site tyrosine↗ ↖Proximal heme ligand
```

*FIG. 1B-2*

```
                414                                                                                                    514
Human    LVDYGVEALV DAFSRQIAGR IGGGRNMDHH ILHVAVDVIR ESREMRLQPF NEYRKRFGMK PYTSFQELVG EKEMAAELEE LYGDIDALEF YPGLLLEKCH PNSIFGESMI
Ovine    LVDYGVEALV DAFSRQPAGR IGGGRNIDHH ILHVAVDVIK ESRVLRLQPF NEYRKRFGMK PYTSFQELTG EKEMAAELEE LYGDIDALEF YPGLLLEKCH PNSIFGESMI
Canine   LTHYGIEALV DAFSRQSAGR IGGGRNIDDH VLHVAVETIK ESRELRLQPF NEYRKRFGMR PYMSFQELTG ETEMAAELEE LYGDIDALEF YPGLLLEKCH PNSIFGESMI
Rabbit   LVDYGVEALV DAFSRQSAGR IGGGRNIDHH VLHVAVEVIK ESREMRLQPF NEYRKRFGLK PYASFQELTG EKEMAAELEE LYGDIDALEF YPGLLLEKCQ PNSIFGESMI
Murine   LVDYGVEALV DAFSRQRAGR IGGGRNFDYH VLHVAVDVIR ESREMRLQPF NEYRKRFGLK PYTSFQELTG EKEMAAELEE LYGDIDALEF YPGLLLEKCQ PNSIFGESMI
Rat      LVDYGVEALV DAFSRQRAGR IGGGRNFDYH VLHVAEDVIK ESREMRLQSF NEYRKRFGLK PYTSFQEFTG EKEMAAELEE LYGDIDALEF YPGLMLEKCQ PNSLFGESMI
Rainbow  VTHYGVEKLV DAFSRQCAGQ IGGGRNIHPV VTNVAEGVIE ESRTLRLQPF NEYRKRFNLK PYTSFSDFTG EEEMARELEE LYGDIDALEF YPAIMLEKTR PNAIFGESMV
Brook    VTHYGVEKLV DAFSRQYAGQ IGGGRNIHPV VTKVAEGVIE ESRTLRLQPF NEYRKRFNLK PYTSFSDFTG EEEMARELEE LYGDIDALEF YPALMLEKTR PNAIFGESMV
                                                                                                             Active site isoleucine↗

524   ↙ASA-acetylated serine                                  *       *                                594
Human    EIGAPFSLKG LLGNPICSPE YWKPSTFGGE VGFNIVKTAT LKKLVCLNTK TCPYVSFRVP DASQDDGPAV ERPSTEL
Ovine    EMGAPFSLKG LLGNPICSPE YWKASTFGGE VGFNLVKTAT LKKLVCLNTK TCPYVSFHVP_DPRQEDRPGV ERPPTEL
Canine   EIGAPFSLKG LLGNPICSPE YWKPSTFGGE MGFNMVKTAT LKKLVCLNTK TCPYVSFRVP DPHQDGGPGV ERPSTEL
Rabbit   EIGAPFSLKG LLGNPICSPE YWKPSTFGGE VGSNLIKTAT LKKLVCLNTK TCPYVSFRVP RSSGDDGPAA ERRSTEL
Murine   EMGAPFSLKG LLGNPICSPE YWKPSTFGGD VGFNLVNTAS LKKLVCLNTK TCPYVSFRVP DYPGDDGSLV VRRSTEL
Rat      EMGAPFSLKG LLGNPICSPE YWKPSTFGGD VGFNIVNTAS LKKLVCLNTK TCPYVSFRVP DYPGDDGSVF VRPSTEL
Rainbow  EMGAPFSLKG LLGNPICSPE YWKPSTFGGQ TGFDIVNSAS LERLVCLNTN WCPYYAFNVP PAGQEPP-- RKQSTEL
Brook    EMGAPFSLKG LLGNPICSPE YWKPSTFGGQ TGFDIVNSAS LERLVCLNTN WCPYYAFNVP PAGQEPPP-- RKQSTEL
```

FIG. 1B-3

```
COX-1     MSR.S.SLRF P..LLLLLLL PPPPVL.ADP GVP.PVNPCC YYPCQHQGVC VRFGLDRYQC DCTRTGYSGP NCTIPE.WTW LR.SLRPSPS F.HFLLTHGR WLWEFVN-AT
COX-2     -------M LARALLLCAA LAL.A---- ------ANPCC S.PCQNRGVC MS.GFDQYKC DCTRTGFYGE NCTTPEFLTR IKL.LKPTPN TVHYILTHFK GVWNIVN.IP
Plexaura  ------- --MKAFLHIV VLIIFSGLFW HEVESVNPCC SFPCENGAVC VDDG-DTYTC DCTRTGYYGV NCEKPSMSTW LKSFIKPSEQ TKHFMLTHFG WFWWIVNNVQ
Gersemia  ------- -MVAKFVVFL GLQLILCSV- -VCEAVNPCC SFPCESGAVC VEDG-DKYTC DCIRIGHYGV NCEKPNWSTW FKALIAPSEE TKHFILTHFK WFWWIVNNVP
          Signal peptide                       EGF-like domain/dimerization domain (1)                  Membrane-binding domain COX-1     FIRD.LMRLV LTVRSNLIPS PPTYNSAHDY ISWESFSNVS YYTRILPSVP KDCPTPMGTK GKKQLPDAQL LA.RFLLRR. FIPDPQGTNL MFAFFAQHFT HQFFKTSGKM
COX-2     FLRN.IM.YV LTSRSHLIDS PPTYNVHYGY KSWEAFSNLS YYTRALPPV. DDCPTPMGVK GKKELPDSKE VVEKVLRRK FIPDPQGTNM MFAFFAQHFT HQFFKTD.KR
Plexaura  FIRDPIMRAA YFSRTDFIPV PHVTSYHEY ATMEAHYNRT HFARTLPPVP KNCPTPFGVS GKKILPPAEE VANKFLKRRE FIADHRNTSW LFMFFAQHFT HQFFKTVHH-
Gersemia  FIRNTVMKAA YFSRTDF-VPV PHAYTSYHDY ATMEAHYNRS YFARTLPPVP KNCPTPFGVA GKKELPPAEE VANKFLKRGK FKTDHTSTSW LFMFFAQHFT HEFFKTIYH-
                              *         Dimerization domain (2)   Glycosylation site                              Distal histidine COX-1     GPGFTKALGH GVDLGHIYGD NLERQY.LRL FKDGKLKYQV LDGEVYPPSV EEAP-VLMHY PRG.PP.SQM AVGQEVFGLL PGLMLYATLW LREHNRVCDL LKAEHPTWGD
COX-2     GPAFTKGLGH GVDLNHIYGE TLDRQHKLRL FKDGKMKYQV I.GEVYPPTV KDTQ-VEMIY PPHVPEHLRF AVGQEVFGLV PGLMYATIW LREHNRVCDV LKQEHPEWDD
Plexaura  SPAFSWG-NH GVDVSHIYGQ GVERENKLRA FKDGKLKSQM INGEEYPPYL KOVDGLKMQY LENTAEEQKF ALGHPFFSML PGLFMFATLW LREHNRVCMI LRKEHPHWED
Gersemia  SPAFTWG-NH GVDVSHIYGQ DMERQNKLRS FEDGKLKSQT INGEEWPPYL KDVDNVTMQY PPNITPEDQKF ALGHPFYSML PGLFMYASIW LREHNRVCTI LRKEHPHWVD
                                                                                             Glycosylation site COX-1     EQLFQTARLI LIGETIKIVI EEYVQHLSGY FLQLKFDPEL LF.AQFQYRN RIAMEFNHLY HWHPLMPDSF .VGSQEYSYE QFLFNTSMLV DYGVEALVDA FSRQ.AGRIG
COX-2     ERLFQTSRLI LIGETIKIVI EDYVQHLSGY HFKLKFDPEL LFNQQFQYQN RIAAEFNTLY HWHPLLPDTF QIDDQEYNFQ QF.YWNSILL EHGLTQFVES FTRQIAGRVA
Plexaura  ERIYQTAKLI ITGETIKIVI EDYINHLANY NMKLRYDPQL VFSRNYDYDN RIHLEFNHLY HWHPFSPDOF NISGTTYTIN DFMYHPEIVV KHGMSSFVNA MSSGLCGKMS
Gersemia  ERLYQTGKLI ITGELIKIVI EDYVNHLANY NLKLTYNPEL VFDHGYDYDN RIHVEFNHMY HWHPFSPDEY NISGSTYSIQ DFMYHPEIVV KHGMSSFVDS MSKGLCGQMS
          Active site tyrosine                                                           Proximal heme ligand
```

*FIG. 1C-1*

```
COX-1     GGRNIDHHVL HVAVDVIKES RELRLQPFNE YRKRFGLKPY TSFQELTGEK EMAAELEELY GDIDALEFYP GLLLEKC.PN SIFGESMIEM GAPFSLKGLL GNPICSPEYW
COX-2     GGRNVP.AVQ .VAKASIDQS R.MKYQSLNE YRKRF.LKPY .SFEELTGEK EMAAELEALY GDIDAMELYP ALVEKPRPD AIFGETMVE. GAPFSLKGLM GNPICSP.YW
Plexaura  H-HNHGQYIL DVAVEVIKYQ RKLRMQSFNN YRRHFGLPAY KSFEEMTGDP KLAAELKEVY GDWNAVDFYV GFFLEKSLPT SPFGITMIAS GAPYSLRGLL SNPVSSPTYW
Gersemia  H-HNHGAYTL DVAVEVIKHQ RELRMQSFNN YRKHFGLEPY KSFEELTGDP KMSAELQEVY GDWNAVDLYV GFFLEKGLTT SPFGITMIAF GAPYSLRGLL SNPVSSPTYW
                                                                                                                   ←ASA-acetylated serine
                                                                          Active site valine/isoleucine ↙

*                     *
COX-1     KPSTFGGEVG FNIVKTASLK KLVQLNTKT- CPVVSFRVPD ..QDDGP..E -------- RPSTEL
COX-2     KPSTFGGEVG FKIINTASIQ SLICNNVKG. CPFTSF.VQD PQLT.KTVTI NAS.SHS.LD DINPTVLLKE R-STEL
Plexaura  KPSTFGGEVG FDIVKTASVD KLFCRNIAGD CPLVTFTVPD EIAREARRNL AANI------ ----KDEL
Gersemia  KPSTFGGDVG FDMVKTASLE KLFCQNIAGE CPLVTFTVPD DIARETRKVL EA-------- ----RDEL
```

FIG. 1C-2

```
COX-1     MSR.S.SLRF P..LLLLLLL PPPPVL.ADP GVP.PWNPCC YYPCQNQGVC VRFGLDRYQC DCTRTGYSGP NCTIPE.WTW LR.SLRPSPS F.HFLLTHGR WLWEFVN-AT
COX-2     MLARALLLCA ALAL..A--- ---------- ---------- -ANPCC S.PCQNRGVC MS.GFDQYKC DCTRIGFYGE NCTTPEFLTR IKL.LKPTPN TVHYILTHFK GVWNIVN.IP
Rice      ---------- ---------- ---------- -M GSGLFKPRVH PBLRDVFSKM SF-FDKIGFL FIHAFDKRNL WHKVPVPIGL LYNTRRTLL EKYNLLAVGR SSHGALFDPK EFLYRTEDGK
A.Thaliana ---------- ---------- ---------- ---MKVITSL ISSILLKFIH KDFHEIYARM SL-LDRFLLI IVHGVDKWVP WHKLPVFLGL TLEVRRHLH QQYNLLNVGQ TPTGIRFDPA NYPYRTADGK
Tobacco   ---------- ---------- ---------- --M SLWASIKNL LLSPLRGFIH KDFHDIFERM TL-LDKLFFL IVHFVDKLNL WHRLPVFLGL LYLGARRHLH QEYNLINVGK TPVGVRSNPA DHPYRTADGK
                Signal peptide                                      EGF-like domain/dimerization domain (1)                    Membrane-binding domain COX-1     FIRD.LMRLV LTVRSNLIPS PPTYNSAHDY ISWESF--SN VSYYTRILPS VPKDCPTPMG TKGSKQLPDA QLA.RFLLR R.FIPDPQGT NLMFAFFAQH FTHQFFKTSG
COX-2     FLRN.IM.YV LTSRSHLIDS PPTYNVHYGY KSWEAF--SN LSYYTRALPP V.DDCPTPMG VKGKKELPDS KEVVEKVLLR RKFIPDPQGT NMMFAFFAQH FTHQFFKTD
Rice      YNDPHNAEAG KPKHLFWGET WSRLINRNEL MSPDPFVVAT KLLARREYKD TGKQFNILAA AWIQFMVHDW MDHMEDTGQI GITAPKEVAN ECPLKSFKFH PTKELPTNSD
A.Thaliana FNDPFNEGVG S-QNSFFGRN CPPVDQKSKL RRPDPMVVAT KLLGRKKFID TGKQFNMIAA SWIQFMIHDW IDHLEDTHQI ELVAPKEVAS KCPLSSFRFL KTKEVPTGFF
Tobacco   YNDPFNEGAG S-ELSFFGRN MLPVDQHNQL KKPDPMVVAT KLLARRNVVD TGKQFNMIAA SWIQFMIHDW IDHLEDTKQI ELRAPEVAS QCPLKSFKFF KTKEIPTGFY
                        Dimerization domain (2)                                                         Distal histidine COX-1     KMGPGFTKAL GHGVDLGHIY PPTYNSAHDY L RLFKDGKLKY QVLDGEVYPP SVEEAPVLMR YPRG.PP.SQ MAVGQEVFGL LPGLMLYATL WLREHNRVCD LLKAEHPTWG
COX-2     KRGPAFTKGL GHGVDLNHIY GETLDRQHKL RLFKDGKMKY QVI.GEVYPP TVKDTQVEMI YPPHVPEHLR FAVGQEVFGL VPGLMMYATI WLREHNRVCD VLKQEHPEWG
Rice      GIKIGHYNIR TAWWDGSAVY GNNEERAEKL RTYVDGKLVI GDD-GLL--- ---------- --LHKENG VALSGDIRNS WAGVSILQAL FVKEHNAVCD AIKEEHPNLS
A.Thaliana EIKTGSQNIR TPWWDSSVIY GSNSKTLDRV RTYKDGKLKI SEETGLL--- ---------- --LHDEDG LAISGDIRNS WAGVSALQAL FIKEHNAVCD ALKDEDDLE
Tobacco   EIKTGHLNRR TPWWDGSAIY GSNAEVLKKV RTFKYGKLKL SAD-GLL--- ---------- --EIDENG KIISGDVRNT WAGLSALQAL FVQEHNSVCD VLKKEYPELE
                                                                                                       "REHN" sequence COX-1     DEQLFQTARL ILIGETIKIV IEEYVQHLS- ---------- -GYFL QLKFDP---- ------ELLF .AQFQYRNRI AMEFNQLYHW HPLMPDSF.V GS-------- ----------
COX-2     DERLFQTSRL ILIGETIKIV IEDYVQHLS- ---------- -GYHF KLKFDP---- ------ELLF NQQFQYQNRI AAEFNTLYHW HPLLPDTFQI DD-------- ----------
Rice      DEELYRYAKL VTSAVIAKVH TIDMTVELLK TKTMRAAMRA NWYGLLGKKI KDTFGHIGGP ILGGLVGLKK PNNHGVPYSL TEEFTSVYRM HSLIPSTLKL RDPTGQPDAN
A.Thaliana DEDLYRYARL VTSAVVAKIH TIDMTVQLLK TDTLLAGMRA NWYGLLGKKF KDSFGHAGSS ILGGWGMKK PQNHGVPYSL TEDFTSVYRM HSLLPDQLHI LDIDDVPGTN
Tobacco   DEDLYRHARL VTSAVIAKVH TIDMTVELLK TDTLLAGMRA NWYGLLGKKF KDTFGHVGGS ILGGFVGMKK PENYGVPYSL TEEFTSVYRM HQLLPDNLQL RNIDATPGPN
                                                                           Active site tyrosine     Proximal heme ligand
```

*FIG. 2-1*

```
COX-1       -----QEYS YEQFL--FNT SMLVDYGVEA LVDAFSRQ.A GRIG------ ---------- GGRNIDHHVL HVAVDVIKES REMRLQPFNE YRKRFGLKPY TSFQELTGEK
COX-2       -----QEYN FQQF.--YNN SILLEHGLIQ FVESFTRQIA GRVA------ ---------- GGRNVP.AVQ .VAKASIDQS R.MKYQSLNE YRKRF.LKPY .SFEELTGEK
Rice        NSPPCLEDID IGEMIGLKGE EQLSKIGFEK QALSMGYQAC GALELWNYPS FFRNLIPQNL DGTNRSDRI- DLAALEIYRD RERSVPRYNE FRRRLFLIPI KSWEDLTSDK
A.Thaliana  KSLPLIQEIS MRDLIGRKGE ETMSHIGFTK LMVSMGHQAS GALELMNYPM WLRDIVPHDP NGQARPDHV- DLAALEIYRD RERSVPRYNE FRRSMFMIPI TKWEDLTEDE
Tobacco     KSLPLTNEIP MEDLIGSKGE ENLARIGFTK QMWSMGHQAC GALELWNYPM WMRDLIPQDV DGTDRPDHV- DLAALEIYRD RERSVARYNE FRRGMLQIPI SKWEDLTDDE COX-1       EMAAELEELY G-DIDALEFY PGLLLEKC.P NSIFGESMIE MGAPFSLKGL LGNPICSPEY WKPSTFGGEV GFNIVNTASL KKLVCLNTKT -CPYVSFRVP D..QDDGP..
COX-2       EMAAELEALY G-DIDAMELY PALLVEKPRP .GAPFSLKGL MGNPICSP.Y WKPSTFGGEV GFKIINTASI QSLICNNVKG .CPFTSF.VQ DPQLT.TVTI
Rice        DAIETIRAIY GDDVEKLDLL VGLMAEKKIK GFAISETAFN IFILMASRRL EADRFFTSNF -NEETYKKG MQWVKTEGL RDVINRHYPE ITAKWMKSSS AFSVWDADY-
A.Thaliana  EAIEVLDDVY DGDVEELDLL VGLMAEKKIK GFAISETAFY IFLIMATRRL EADRFFTSDF -NETIYKKG LEWVNTESL KDVIDRHYPD MTDKWMNSES AFSVWDSPPL
Tobacco     EVINTLREVY GDDVEELDLM VGMAAEKKIK GFAISETAFF IFLIMASRRL EADRFFTSNY -NEETYKKG LEWVNTESL KDVLDRHYPE MTEKWMNSSS AFSVWDSSPE COX-1       ERP------- ---------- ---------- -STEL
COX-2       NAS.SHS.LD DINPTVLLKE RSTEL
Rice        ---------- ---------- ---------- -----
A.Thaliana  TKNPIPLYLR IPS------- ---------- -----
Tobacco     PHNPIPLYFR VPPQ------ ---------- -----
```

FIG. 2-2

Dog

Chicken

```
                 1         10        20        30        40        50        60        70        80        90       100       110       120       130
                 |---------+---------+---------+---------+---------+---------+---------+---------+---------+---------+---------+---------+---------|
Canine
(Genebank)                                 MSREFDPEAPRNPLRLPGEPRMPGPALTSRSAGGSRLHRWPLLLLLLLLLLPPPPVLPAEARTPAPVNPCCYYPCQHQGICVRFGLDRYQCDCTRTGYSGPNCTIPELWTWLRHSLRPSPSFLHFLLTHGR
PCOX-1                                     MSREFDPEAPRNPLRLPGEPRMPGPALTSRSAGGSRLHRWPLLLLLLLLLLPPPPVLPAEARTPAPVNPCCYYPCQHQGICVRFGLDRYQCDCTRTGYSGPNCTIPELWTWLRHSLRPSPSFLHFLLTHGR
PCOX-1d657
Consensus                                  msrefdpeaprnplrlpgeprmpgpaltsrsaggsrlhrwpllllllllllppppvlpaeartpapvnpccyypcqhqgicvrfgldryqcdctrtgysgpnctipelwtwlrhslrpspsflhflllthgr 131       140       150       160       170       180       190       200       210       220       230       240       250       260
                 |---------+---------+---------+---------+---------+---------+---------+---------+---------+---------+---------+---------+---------|
Canine
(Genebank)      WFWEFINATFIRDMLMRLVLTARSNLIPSPPTYNIAHDYISWESFSNVSYYTRVLPSVPQDCPTPMGTKGKKQLPDAQLLGRRFLLRRKFIPDPQGTNLMFAFFAQHTHQFFKTSGKMGPGFTKALGHG
PCOX-1          WFWEFINATFIRDMLMRLVLTARSNLIPSPPTYNIAHDYISWESFSNVSYYTRVLPSVPQDCPTPMGTKGKKQLPDAQLLGRRFLLRRKFIPDPQGTNLMFAFFAQHTHQFFKTSGKMGPGFTKALGHG
PCOX-1d657      WFWEFINATFIRDMLMRLVLT
Consensus       wfwefinatfirdmlmrlvltarsnlipspptyniahdyiswesfsnvsyytrvlpsvpqdcptpmgtkgkkqlpdaqllgrrfllrrkfipdpqgtnlmfaffaqhthqffktsgkmgpgftkalghg 261       270       280       290       300       310       320       330       340       350       360       370       380       390
                 |---------+---------+---------+---------+---------+---------+---------+---------+---------+---------+---------+---------+---------|
Canine
(Genebank)      VDLGHIYGDNLDRQYQLRLFKDGKLKYQVLDGEMYPPSVEEAPVLMHYPRGILPGLMLYATLWLREHNRVCDLKAEHPTWGDEQLFQTARLILIGETIKIVIEEYVQQLSGYFL
PCOX-1          VDLGHIYGDNLDRQYQLRLFKDGKLKYQVLDGEMYPPSVEEAPVLMHYPRGILPGLMLYATLWLREHNRVCDLKAEHPTWGDEQLFQTARLILIGETIKIVIEEYVQQLSGYFL
PCOX-1d657                                                                                              GETIKIVIEEYVQQLSGYFL
Consensus       vdlghiygdnldrqyqlrlfkdgklkyqvldgemyppsveeapvlmhyprgilpglmlyatlwlrehnrvcdlkaehptwgdeqlfqtarlilligetikivieeyvqqlsgyfl 391       400       410       420       430       440       450       460       470       480       490       500       510       520
                 |---------+---------+---------+---------+---------+---------+---------+---------+---------+---------+---------+---------+---------|
Canine
(Genebank)      QLKFDPELLFSAQFQYRNRIAMEFNQLYHWHPLMPDSFWGSQEYSYEQFLFNISMLTHYGIEALVDAFSRQSAGRIGGGRNIDHHVLHVAVETIKESRELRLQPFNEYRKRFGMRPYMSFQELTGEKEM
PCOX-1          QLKFDPELLFSAQFQYRNRIAMEFNQLYHWHPLMPDSFWGSQEYSYEQFLFNISMLTHYGIEALVDAFSRQSAGRIGGGRNIDHHVLHVAVETIKESRELRLQPFNEYRKRFGMRPYMSFQELTGEKEM
PCOX-1d657      QLKFDPELLFSAQFQYRNRIAMEFNQLYHWHPLMPDSFWGSQEYSYEQFLFNISMLTHYGIEALVDAFSRQSAGRIGGGRNIDHHVLHVAVETIKESRELRLQPFNEYRKRFGMRPYMSFQELTGEKEM
Consensus       qlkfdpellfsaqfqyrnriamefnqlyhwhplmpdsfwgsqeysyeqflfnismlthygiealvdafsrqsagriggrniddhvlhvavetikesrelrlqpfneyrkrfgmrpymsfqeltgekem 521       530       540       550       560       570       580       590       600       610       620       630  634
                 |---------+---------+---------+---------+---------+---------+---------+---------+---------+---------+---------+----|
Canine
(Genebank)      AAELEELYGDIDALEFYPGLLLEKCHPNSIFGESMIEIGAPFSLKGLLGNPICSPEYWKPSTFGGEMGFNMWKTATLKKLVCLNLNTKTCPYVSFRVPDPHQDGGPGVERPSTELZ
PCOX-1          AAELEELYGDIDALEFYPGLLLEKCHPNSIFGESMIEIGAPFSLKGLLGNPICSPEYWKPSTFGGEMGFNMWKTATLKKLVCLNLNTKTCPYVSFRVPDPHQDGGPGVERPSTELZ
PCOX-1d657      AAELEELYGDIDALEFYPGLLLEKCHPNSIFGESMIEIGAPFSLKGLLGNPICSPEYWKPSTFGGEMGFNMWKTATLKKLVCLNLNTKTCPYVSFRVPDPHQDGGPGVERPSTELZ
Consensus       aaeleelygdidalefypglllekchpnsifgesmieigapfslkgllgnpicspeywkpstfggemgfnmwktatlkklvclnlntktcpyvsfrvpdphqdggpgverpstelz
```

*FIG. 6B*

```
              1         10        20        30        40        50        60        70        80        90       101
              |---------+---------+---------+---------+---------+---------+---------+---------+---------+---------++
Canine    GTGAGTTCGACCCTGAGGC------CCCAGG--AACCCTCTTGGCTCTCCCGGGGGAGCCTGAATGCAGGCCCAGCCTCACCTCTGCTCCGCAG
Human     GTGAGTGCGACCCCGGTGC------CCGGTGGGGAATTTCTTGGCCTCTTGGTGGCTCTTGGTGGCTCTTGAGCCTTGAATGCAGCTCAGCCCCTCATCTCTCTCCTCTGCAG
Murine    GTGAGTCCGACCCCAGTGGTGCCCCACGCGTCCCGGAATTCGGTGGCCTGCAGGCGGAGCCTAGGCTCAACTCTCTCTTCTCTGCAGGAA
Consensus GTGAGT.CGACCCcggtGc........Ccgtgg.gaA.tttctTgGCCTcC.GG.GGAGCCTtGAAtGCcAGgccca.CcCTacCTctCt.C.g.a.

1         10        20        30 34
              |---------+---------+---------+----|
Canine    REFDPEAP--RNPLRLPGEPRMPGPALTSRSA
Human     RECDPGA---RWGIFLASWWSLECQLSPSSLSSA
Murine    RESDPSGAPTRPGIRWPAGGALNARLNSLFLLQE
Consensus RE.DP.a...R.girlp....$..l..l..s.l...
```

FIG. 7

| SEQ ID NO:1 | 1   | ATGAGCCGTG | AGTTCGACCC | TGAGGCCCCC | AGGAACCCTC | TTCGCCTCCC | GGGGGAGCCT | 60   |
|-------------|-----|------------|------------|------------|------------|------------|------------|------|
|             | 61  | CGAATGCCAG | GCCCAGCCCT | CACCTCTCGC | TCCGCAGGGG | GGAGTCGCCT | GCACCGGTGG | 120  |
|             | 121 | CCGCTGCTCC | TGCTGCTGCT | GCTGCTGCTC | CGGCCGCCCC | CGGTCCTGCC | CGCGGGAAGCC | 180  |
|             | 181 | CGGACCCCGG | CGCCTGTGAA | CCCGTGTTGT | TACTACCCAT | GTCAGCACCA | AGGGATCTGT | 240  |
|             | 241 | GTCCGCTTCG | GCCTTGACCG | CTACCAGTGT | GACTGCACCC | GCACGGGCTA | TTCTGCCCCC | 300  |
|             | 301 | AACTGCACCA | TCCCCGAGCT | GTGGACCTGG | CTCCGGAATT | CACTGCGCCC | CAGTCCCTCT | 360  |
|             | 361 | TTCCTCCACT | TCCTGCTGAC | GCATGGGCGC | TGGTTTTGGG | AATTCATCAA | TGCCACCTTC | 420  |
|             | 421 | ATCCGTGACA | TGCTCATGCG | TCTGGTACTC | ACAGCGCGTT | CCAACCTTAT | CCCCAGTCCT | 480  |
|             | 481 | CCCACCTACA | ACATAGCGCA | TGACTACATC | AGCTGGGAGT | CCTTCTCCAA | TGTGAGCTAT | 540  |
|             | 541 | TACACTCGTG | TTCTGCCCTC | TGTGCCCCAA | GATTGCCCCA | CGCCCATGGG | GACCAAAGGG | 600  |
|             | 601 | AAGAAGCAGT | TGCCAGACGC | CCAACTCCTG | GGCCGTGCGT | TCCTGCTCAG | GAGGAAGTTC | 660  |
|             | 661 | ATACCTGACC | CCCAAGGCAC | CAACCTCATG | TTCGCCTTCT | TGCACAACA  | CTTCACCCAT | 720  |
|             | 721 | CAGTTCTTCA | AAACTTCTGG | CAAGATGGGT | CCTGGCTTCA | CCAAGGCCTT | GGGCCATGGG | 780  |
|             | 781 | GTAGATCTTG | GCCACATTTA | TGGGGACAAT | CTGGACCGTC | AGTATCAGCT | GCGGCTCTTT | 840  |
|             | 841 | AAGGATGGGA | AACTCAAGTA | TCAGGTTCTG | GATGGAGAGA | TGTACCCGCC | ATCTGTGGAG | 900  |
|             | 901 | GAGGGCCTG  | TGTTGATGCA | CTACCCACGG | CCCAGAGTCA | CCCAGAGTGC | GATGGCCGTG | 960  |
|             | 961 | GGCCAGGAGG | TGTTTGGGCT | GCTTCCTGGG | GCTTCCTGCT | CTCATGCTCT | ATGCCACGCT | 1020 |

FIG. 9A-1

```
1021 GAGCACAATC GTGTGTGTGA CCTGCTGAAG GCTGAGCACC CCACTTGGGG TGATGAGCAA 1080
1081 CTCTTCCAGA CGGCCCGACT CATCCTCATT CTCTTCCAGA GGGGAGACCA TCAAGATTGT GATTGAGGAG 1140
1141 TATGTGCAGC AGCTGAGTGG CTACTTCTTG CAGCTGAAGT TGACCCGGA GCTGCTGTTT 1200
1201 AGCGCCCAGT TCCAGTACCG CAACCGCATC GCCATGGAGT TCAACCAGCT GTACCACTGG 1260
1261 CACCCGCTCA TGCCAGACTC CTTCTGGGTG GGTTCCCAGG AGTACAGCTA TGAGCAGTTC 1320
1321 CTGTTCAACA CCTCCATGCT GACGCACTAC GGGATCGAGG CCCTGGTGGA TGCCTTCTCT 1380
1381 CGCCAGAGCG CGGGCCGGAT AGAAACATAG ACCACCATGT CCTGCACGTG 1440
1441 GCTGTGGAAA CCATCAAGGA TGCGGCTGC AGCCCCTTCAA TGAGTACCGC 1500
1501 AAGAGGTTTG GCATGAGGCC CTACATGTCC TTCCAGGAAC TCACAGGGGA GAAGGAGATG 1560
1561 GCAGCCGAGT TGGAGGAGCT AAACTCCATC CTAGGGAAT TGGAATTCTA CCCGGGGCT 1620
1621 CTTCTCTCCC AGTGCCATCC CCTAGGGCCT TTTGGAGAGA GTATGATAGA AATTGGGCT 1680
1681 CCCTTCTCCC TTAAGGGGCT GGGCTTCAAT CCCATCTGTT CTCCAGAGTA CTGGAAGCCA 1740
1741 AGCACATTCG GTGGTGAGAT GGGCTTCAAT ATGGTCAAGA CAGCCACACT GAAGAAGCTG 1800
1801 GTCTGCCTTA ACACCAAGAC TTGTCCCTAT GTTCCTTTCC CAGCCACACT GAAGAAGCTG 1800
1861 GATGGGGGGC CTGGTGTGCA GCGGCCGTCC ACAGAGCTCT GA 1902
```

FIG. 9A-2

```
SEQ ID NO:2   1  MSREFDPEAP  RNPLRLPGEP  RMPGPALTSR  SAGGSRLHRW  PLLLLLLLL   PPPPVLPAEA  60
             61  RTPAPVNPCC  YYPCQHQGIC  VRFGLDRYQC  DCTRTGYSGP  NCTIPELWTW  LRNSLRPSPS  120
            121  FLHFLLTHGR  WFWEFINATF  IRDMLMRLVL  TARSNLIPSP  PTYNIAHDYI  SWESFSNVSY  180
            181  YTRVLPSVPQ  DCPTPMGTKG  KKQLPDAQLL  GRRFLLRRKF  IPDPQGTNLM  FAFFAQHFTH  240
            241  QFFKTSGKMG  PGFTKALGHG  VDLGHIYGDN  LDRQYQLRLF  KDGKLKYQVL  DGEMYPPSVE  300
            301  EAPVLMHYPR  GILPQSQMAV  GQEVFGLLPG  LMLYATLWLR  EHNRVCDLLK  AEHPTWGDEQ  360
            361  LFQTARLILI  GETIKIVIEE  YVQQLSGYFL  QLKFDPELLF  SAQFQYRNRI  AMEFNQLYHW  420
            421  HPLMPDSFWV  GSQEYSYEQF  LFNTSMLTHY  GIEALVDAFS  RQSAGRIGGG  RNIDHHVLHV  480
            481  AVETIKESRE  LRLQPFNEYR  KRFGMRPYMS  FQELTGEKEM  AAELEELYGD  IDALEFYPGL  540
            541  LLEKCHPNSI  FGESMIEIGA  PFSLKGLLGN  PICSPEYWKP  STFGGEMGFN  MVKTATLKKL  600
            601  VCLNTKTCPY  VSFRVPDPHQ  DGGPGVQRPS  TELZ                                   634
```

```
SEQ ID NO:3    1 CGGCGAGCGC AGCAGCCGCC CAGAGCTATG AGCCGTGAGT TCGACCCTGA GGCCCCAGG    60
              61 AACCCTCTTC GCCTCCCGGG GGAGCCTCGA ATGCCAGGCC CAGCCCTCAC CTCTCGCTCC   120
             121 GCAGGGGGA GTCGCCTGCA CGGTGGCCG CTGCTCCTGC TGCTGCTGCT GCTGCTCCCG   180
             181 CCGCCCCCGG TCCTGCCCGC GGAAGCCCGG ACCCCGGCGC CTGTGAACCC GTGTTGTTAC   240
             241 TACCCATGTC AGCACCAAGG GATCTGTGTC CGCTTCGGCC TTGACCGCTA CCAGTGTGAC   300
             301 TGCACCCGCA CGGGCTATTC TGGCCCCAAC TGCACCATCC CCGAGCTGTG GACCTGGCTC   360
             361 CGGAATTCAC TGCGCCCCAG TCCCTCTTTC CTCCACTTCC TGCTGACGCA TGGGCGCTGG   420
             421 TTTGGGAAT TCATCAATGC CACCTTCATC CGTGACATGC TCATGCGTCT GGTACTCACA   480
             481 GCGGTTCCA ACCTTATCCC CAGTCCTCCC ACCTACAACA TAGCGCATGA CTACATCAGC   540
             541 TGGGAGTCCT TCTCCAATGT GAGCTATTAC ACTCGTGTTC TGCCCCTCTG T GCCCCAAGAT   600
             601 TGCCCCACGC CCATGGGGAC CAAAGGGAAG AAGCAGTTGC CAGAGCCCA ACTCCTGGGC   660
             661 CGTCGCTTCC TGCTCAGGAG GAAGTTCATA CCTGACCCCC AAGGCACCAA CCTCATGTTC   720
             721 GCCTTCTTTG CACAACACTT CACCCATCAG TTCTTCAAAA CTTCTGGCAA GATGGGTCCT   780
             781 GGCTTCACCA AGGCCTTGGG CCATGGGGTA GATCTTGGCC ACATTTATGG GGACAATCTG   840
             841 GACGTCAGT ATCAGCTGCG GCTCTTTAAG GATGGGAAAC TCAAGTATCA GGTTCTGGAT   900
             901 GGAGAGATGT ACCCGCCATC TGTGGAGGAG GCGCCTGTGT TGATGCACTA CCCACGGGGC   960
             961 ATTCTGCCCC AGAGTCAGAT GGCCGTGGGC CAGGAGGTGT TGGGCTGCT TCCTGGGCTC  1020
            1021 ATGCTCTATG CCACGCTCTG GCTGCGTGAG CACAATCGTG TGTGTGACCT GCTGAAGGCT  1080
            1081 GAGCACCCCA CTTGGGGTGA TGAGCAACTC TTCCAGACGG CCGACTCAT CCTCATTGGG  1140
            1141 GAGACCATCA AGATTGTGAT TGAGGAGTAT GTGCAGCAGC TGAGTGGCTA CTTCTTGCAG  1200
            1201 CTGAAGTTCG ACCCGGAGCT GCTGTTTAGC GCCCAGTTCC AGTACCGCAA CCGCATCGCC  1260
            1261 ATGGAGTTCA ACCAGCTGTA ACCACTGGCAC CGCTCATGC AGTACCCTT CAGACTCGCC CTGGGTGGGT  1320
            1321 TCCCAGGAGT ACAGCTATGA GCAGTTCCTG TTCAACACCT CCATGCTGAC GCACTACGGG  1380
```

```
1381 ATCGAGGCCC TGGTGGATGC CTTCTCTCGC CAGAGCGCCG GCCGGATTGG TGGAGGTAGA 1440
1441 AACATAGACC ACCATGTCCT GCACGTGGCT GTGGAAACCA TCAAGGAATC CCGCGAGTTG 1500
1501 CGGCTGCAGC CCTTCAATGA GTACCGCAAG AGGTTTGGCA TGAGGCCCTA CATGTCCTTC 1560
1561 CAGGAACTCA CAGGGGAGAA GGAGATGGCA GCCGAGTTGG AGGAGCTGTA TGGAGACATT 1620
1621 GATGCCTTGG AATTCTACCC GGGGCTTCTT CTGGAGAAGT GCCATCCAAA CTCCATCTTT 1680
1681 GGAGAGAGTA TGATAGAAAT TGGGGCTCCC TTCTCCCTTA AGGGCCTCCT AGGGAATCCC 1740
1741 ATCTGTCTC CAGAGTACTG GAAGCCAAGC ACATTCGGTG GTGAGATGGG CTTCAATATG 1800
1801 GTCAAGACAG CCACACTGAA GAAGCTGGTC TGCCTTAACA CCAAGACTTG TCCCTATGTT 1860
1861 TCCTTCCGTG TGCCTGACCC CCACCAGGAT GGCGGGCCTG GTGTGCAGCG GCCGTCCACA 1920
1921 GAGCTCTGAG GGGGCAGAGC AGCAGCATTC TGGAGGGTGG ACTTGTCATC CCAGAATGCT 1980
1981 GAGGCTGGGG TTAATAATCC CAAATGTTGG GTCTTTGGTT TGCCTCAAGA ATATCAAGGT 2040
2041 CAACATTTAG AACTTTGTGT CTCTCACCCA TTATCTGGAA TATCATGGTC TTGTTTGTTA 2100
2101 TTCTAGAATG CTGAATTCCT GGTTGACCAT CTAGAATGGA TGGAGTGATG CTTCTTTGGC 2160
2161 AAGCCAGAAC ACTGGTTCCT GGCCGACACG CTAGAATGTC AGACTTCTGG TTGACTTAAG 2220
2221 ACGTAGGCAT TCTCTAATGT GAAGCTCCTG ACAGAATCAT CTAGAAAGAT AGGGATTCT 2280
2281 TATTTTGCAT TCTAGAATTC TGGGCAGCCC TCCAGCATGT CTAGAATGT GAGATTTTT CACTGGCAGT 2340
2341 TCAGAATGTT GTGCTCTTGA TTGCTGATCC AAAATAGTGG CTGGTATGCC AGATCAGTCT 2400
2401 TGCTCTGAAT GCCTAGAATG GTAATTTGAT TCATTTTCCT GTTCAGTGAG ATACCCCAA 2460
2461 AGCAGGAGAA TCTACAGCCT AACCAGAGTG CATTGCCTGC CTCTGTGCCT GCCCCGAGGA 2520
2521 CTTAGGGGGC AGAGTGTTCT TCCTGGGACG CTGACTCAGA CCCTGGTCCA AGGAGCTAGA 2580
2581 ACAGGTGGGC TTTTTCCAGG TCATTGGTTG GAGGCCACCA GAGCTCTGTT GCCATCTTTG 2640
2641 TCTTGACTCA TGACAGCTGT TTCTCATGAA ACTAATAAAA TTCTTTTTCC AAAAAAAAAA 2700
2701 AAAAAA                                                          2706
```

*FIG. 9C-2*

```
SEQ ID NO:4    1 ATGAGCCGTG AGTTCGACCC TGAGGCCCCC AGGAACCCTC TTCGCCTCCC GGGGGAGCCT   60
              61 CGAATGCCAG GCCCAGCCCT CACCTCTCGC TCCGCAGGGG GGAGTCGCCT GCACCGGTGG  120
             121 CCGCTGCTCC TGCTGCTGCT GCTGCTGCTC CGGCCGCCCC CGGTCCTGCC CGCGGAAGCC  180
             181 CGGACCCCGG CGCCTGTGAA CCCGTGTTGT TACTACCCAT GTCAGCACCA AGGATCTGT   240
             241 GTCCGCTTCG GCCTTGACCG CTACCAGTGT GACTGCACCC GCACGGGCTA TTCTGGCCCC  300
             301 AACTGCACCA TCCCCGAGCT GTGGACCTGG CTCCGGAATT CACTGCGCCC CAGTCCCTCT  360
             361 TTCCTCCACT TCCTGCTGAC GCATGGGCGC TGGTTTTGGG AATTCATCAA TGCCACCTTC  420
             421 ATCCGTGACA TGCTCATGCG TCTGGTACTC ACAGGGGAGA CCATCAAGAT TGTGATTGAG  480
             481 GAGTATGTGC AGCAGCTGAG TGGCTACTTC TTGCAGCTGA AGTTCGACCC GGAGCTGCTG  540
             541 TTTAGGCCCC AGTTCCAGTA CCGCAACCGC ATCGCCATGG AGTTCAACCA GCTGTACCAC  600
             601 TGGCACCCGC TCATGCCAGA CTCCTTCTGG AGGAGTACAG CTATGAGCAG  660
             661 TTCCTGTTCA ACACCTCCAT GCTGACGCAC GTGGGTTCCC AGGCCCTGGT GGATGCCTTC  720
             721 TCTCGCCAGA GCGCCGGCCG GATTGGTGGA TACGGGATCG AGGCCCTGGT TGTCCTGCAC  780
             781 GTGGCTGTGG AAACCATCAA GGAATCCCGC GAGTTGCGGC TAGACCACAG CAATGAGTAC  840
             841 CGCAAGAGGT TGGCATGAG GCCCTACATG TCCTTCCAGG TGCAGCCCTT GGAGAAGGAG  900
             901 ATGGCAGCCG AGTTGGAGGA GCTGTATGGA TCCAAACTCC GACATTGATG CTACCCGGGG  960
             961 CTTCTTCTGG AGAAGTGCCA CCTCCTAGGG ATCTTTGGAG AGAGTATGAT AGAAATTGGG 1020
            1021 GCTCCCTTCT CCCTTAAGGG TGGTGGTGA GTTCTCCAGA GTACTGGAAG GTACTGGAAG 1080
            1081 CCAAGCACAT TCGGTGGTGA TGGGCTTC AATATGGTCA AGACAGCCAC ACTGAAGAAG 1140
            1141 CTGGTCTGCC TTAACACCAA GACTTGTCCC TATGTTTCCT TCCGTGTGCC TGACCCCCAC 1200
            1201 CAGGATGGGCG GCAGCGGCCG GCAGCGGCCG TCCACAGAGC TCTGA           1245
```

FIG. 9D

SEQ ID NO:5

| | | | | |
|---|---|---|---|---|
| 1 | MSREFDPEAP | RNPLRLPGEP | RMPGPALTSR | SAGGSRLHRW | PLLLLLLLL | PPPPVLPAEA | 60 |
| 61 | RTPAPVNPCC | YYPCQHQGIC | VRFGLDRYQC | DCTRTGYSGP | NCTIPELWTW | LRNSLRPSPS | 120 |
| 121 | FLHFLLTHGR | WFWEFINATF | IRDMLMRLVL | TGETIKIVIE | EYVQQLSGYF | LQLKFDPELL | 180 |
| 181 | FSAQFQYRNR | IAMEFNQLYH | WHPLMPDSFW | VGSQEYSYEQ | FLFNTSMLTH | YGIEALVDAF | 240 |
| 241 | SRQSAGRIGG | GRNIDHHVLH | VAVETIKESR | ELRLQPFNEY | RKRFGMRPYM | SFQELTGEKE | 300 |
| 301 | MAAELEELYG | DIDALEFYPG | LLEKCHPNS | IFGESMIEIG | APFSLKGLLG | NPICSPEYWK | 360 |
| 361 | PSTFGGEMGF | NMVKTATLKK | LVCLNTKTCP | YVSFRVPDPH | QDGGPGVQRP | STELZ | 415 |

FIG. 9E

```
SEQ ID NO:6   1 CGGGAGCTC CTGGCACCGG CGCCCGGGA GCCCGCAGTC TGCACCCGA GGGCAGCAGC    60
             61 CGCCCAGAGC TATGAGCCGT GAGTTCGACC CTGAGGCCCC CAGGAACCCT CTTCGCCTCC   120
            121 CGGGGAGCC TCGAATGCCA GGCCCAGCCC TCACCTCTCG CTCCGCAGGG GGGAGTCGCC   180
            181 TGCACCGGTG GCCGCTGCTC CTGCTGCTGC TGCTGCTGCT CCCGCGCCC CCGGTCCTGC   240
            241 CCGGGAAGC CCGGACCCCG GCGCCTGTGA ACCCGTGTTG TTACTACCA TGTCAGCACC   300
            301 AAGGGATCTG TGTCCGCTTC GGCCTTGACC GCTACCAGTG GCTACCAGTG CGCACGGGCT   360
            361 ATTCTGGCCC CAACTGCACC ATCCCCGAGC TGTGGACCTG GCTCCGGAAT TCACTGCGCC   420
            421 CCAGTCCCTC TTTCCTCCAC TCCTGCTGA CGCATGGGCG CTGGTTTTGG GAATTCATCA   480
            481 ATGCCACCTT CATCCGTGAC ATGCTCATGC GTCTGGTACT CACAGGGGAG ACCATCAAGA   540
            541 TTGTGATTGA GGAGTATGTG CAGCAGCTGA GTGGCTACTT CTTGCAGCTG AAGTTCGACC   600
            601 CGGAGCTGCT GTTTAGCGCC CAGTTCCAGT ACCGCAACCG CATCGCCATG GAGTTCAACC   660
            661 AGCTGTACCA CTGGCACCCG GTTCCTGTTC ACTCCTTCTG TGCTGACGCA GGTGGGTTCC   720
            721 GCTATGAGCA GTTCCTGTCC CTCTCGCCAG AGCGCCGGCC TGCTGACGCA CTACGGGATC   780
            781 TGGATGCCTT CTCTCGCCAG AGCGCCGGCC GGATTGGTGG AGGTAGAAAAC ATAGACCACC   840
            841 ATGTCCTGCA CGTGGCTGTG GAAAACCATCA AGGAATCCCG AGGTAGAAAC CGAGTTGCGG   900
            901 TCAATGAGTA CCGCAAGAGG TTTGGCATGA GGCCCTACAT GTCCTTCCAG GAACTCACAG   960
            961 GGGAGAAGGA GATGGCAGCC GAGTTGGAGG AGCTGTATGG AGACATTGAT GCCTTGGAAT  1020
```

*FIG. 9F-1*

```
1021 TCTACCCGGG GCTTCTTCTG GAGAAGTGCC ATCCAAACTC CATCTTTGGA GAGAGTATGA 1080
1081 TAGAAATTGG GGCTCCCTTC TCCCTTAAGG GCCTCCTAGG GAATCCCATC TGTTCTCCAG 1140
1141 AGTACTGGAA GCCAAGCACA TTCGGTGGTG AGATGGGCTT CAATATGGTC AAGACAGCCA 1200
1201 CACTGAAGAA GCTGGTCTGC CTTAACACCA AGACTTGTCC CTATGTTTCC TTCCGTGTGC 1260
1261 CTGACCCCCA CCAGGATGGC GGGCCTGGTG TGCAGCGGCC GTCCACAGAG CTCTGAGGGG 1320
1321 GCAGAGCAGC AGCATTCTGG AGGGTGGACT TGTCATCCCA GAATGCTGAG GCTGGGGTTA 1380
1381 ATAATCCCAA ATGTTGGGTC TTTGGTTTGC CTCAAGGTCA TCAAGGTCAA CATTTAGAAC 1440
1441 TTTGTGTCTC TCACCATTA TCTGGAATAT CATGGTCTTG TTTGTTATTC TAGAATGCTG 1500
1501 AATTCCTGGT TGACCATCTA GAATGGATGG AGTGATGCTT CTTGGCAAG CCAGAACACT 1560
1561 GGTTCCTGGC CGACAACCTA GAATGTCAGA CTTCTGGTTG ACTTAAGACG TAGGCATTCT 1620
1621 CTAATGTGAA GCTCCTGACA GAAAGATAGG GGATTCTTAT TTTGCATTCT 1680
1681 AGAATTCTGG GCAGCCCTCC TTTTTTTCAC TGGCAGTTCA GAATGTTGTG 1740
1741 CTCTTGATTG CTGATCCAAA AGCATGTGCT GTATGCCAGA TCAGTCTTGC TCTGAATGCC 1800
1801 TAGAATGGTA ATTTGATTCA ATAGTGGCTG CAGTGAGATA CCCCCAAAGC AGGAGAATCT 1860
1861 ACAGCCTAAC CAGAGTGCAT TTTTCCTGTT TGCCTGCCTC TGTGCCTGCC C           1901
```

```
         1041       1050       1060       1070       1080       1090       1100       1110       1120       1130       1140       1150       1160       1170
            +----------+----------+----------+----------+----------+----------+----------+----------+----------+----------+----------+----------+----------+
hcox-3(cc)   AGGCTGAGCACCCCACCTGGGCGATGAGCAGCTTTTCCAGACGACCCGCCTCATCCTCATAGGGGAGACCATCAAGATTGTCATCGAGGAGTAGTGCAGCAGCTGAGTGCTGGCTATTTCCTGCAGCTGAA
hcox-3(af)   AGGCTGAGCACCCCACCTGGGCGATGAGCAGCTTTTCCAGACGACCCGCCTCATCCTCATAGGGGAGACCATCAAGATTGTCATCGAGGAGTAGTGCAGCAGCTGAGTGCTGGCTATTTCCTGCAGCTGAA
hcox-3(del10) AGGCTGAGCACCCCACCTGGGGCGATGAGCAGCTTTTCCAGACGACCCGCCTCATCCTCATAGGGGAGACCATCAAGATTGTCATCGAGGAGTAGTGCAGCAGCTGAGTGCTGGCTATTTCCTGCAGCTGAA
hcox-3(cs)   AGGCTGAGCACCCCACCTGGGGGGGGATGAGCAGCTTTTCCAGACGACCCGCCTCATCCTCATAGGGGAGACCATCAAGATTGTCATCGAGGAGTAGTGCAGCAGCTGAGTGCTGGCTATTTCCTGCAGCTGAA 1171       1180       1190       1200       1210       1220       1230       1240       1250       1260       1270       1280       1290       1300
            +----------+----------+----------+----------+----------+----------+----------+----------+----------+----------+----------+----------+----------+
hcox-3(cc)   ATTTGACCCAGAGCTGCTGTTCGGTGTGTCCTGTTCCAGTTCCCAATACCGCAACGCATTGCCATGGCCACTGGCACCCCCTCTACCACTCTCAAGGTGGGCTCCCAGGAGTACAGC
hcox-3(af)   ATTTGACCCAGAGCTGCTGTTCGGTGTGTCCTGTTCCAGTTCCCAATACCGCAACGCATTGCCATGGCCACTGGCACCCCCTCTACCACTCTCAAGGTGGGCTCCCAGGAGTACAGC
hcox-3(del10) ATTTGACCCAGAGCTGCTGTTCGGTGTGTCCTGTTCCAGTTCCCAATACCGCAACGCATTGCCATGGCCACTGGCACCCCCTCTACCACTCTCAAGGTGGGCTCCCAGGAGTACAGC
hcox-3(cs)   ATTTGACCCAGAGCTGCTGTTCGGTGTGTCC?GTTCCAGTTCCCAATACTGCAACGCATTGCCATGGCCACTGGCACCCCCTCTACCACTCTCAAGGTGGGCTCCCAGGAGTACAGC 1301       1310       1320       1330       1340       1350       1360       1370       1380       1390       1400       1410       1420       1430
            +----------+----------+----------+----------+----------+----------+----------+----------+----------+----------+----------+----------+----------+
hcox-3(cc)   TACGAGCAGTTCTTGTTCAACACCTCCATGTTGGTGGACTATGGGGTTGAGGCCCTTGAGGCTTCTTCTCGCCAGATTGGCCCGGATCGGTGGGGGCAGGAACATCGGCTGCATG
hcox-3(af)   TACGAGCAGTTCTTGTTCAACACCTCCATGTTGGTGGACTATGGGGTTGAGGCCCTTGAGGCTTCTTCTCGCCAGATTGGCCCGGATCGGTGGGGGCAGGAACATCGGCTGCATG
hcox-3(del10) TACGAGCAGTTCTTGTTCAACACCTCCATGTTAGTGGACTATGGGGTTGAGGCCCTTGAGGCTTCTTCTCGCCAGATTGGCCCGGATCGGTGGGGGCAGGAACATCGGCTGCATG
hcox-3(cs)   TACGAGCAGTTCTTGTTCAACACCTCCATGTTgGTGGACTATGTTGAGGCCCTTGAGGCTTCTTCTCGCCAGATTACTGGCCGGatcggtggggggcaggaacatggccaccatcctgcatg 1431       1440       1450       1460       1470       1480       1490       1500       1510       1520       1530       1540       1550       1560
            +----------+----------+----------+----------+----------+----------+----------+----------+----------+----------+----------+----------+----------+
hcox-3(cc)   TGGCTGTGGATGTCATCAGGGAGTCTCGGGAGATGCGGCTGCAGCCCTTCAATGAGTAGTACCGCAAGAGGTTTGGCATGAAACCCTACACCTCCTTCCAGGAGTCGTAGGAGACTCGTAGGAGGAAGGAGAGAGTGGCAGCAGA
hcox-3(af)   TGGCTGTGGATGTCATCAGGGAGTCTCGGGAGATGCGGCTGCAGCCCTTCAATGAGTAGTACCGCAAGAGTTTGGCATGAAACCCTACACCTCCTTCCAGGAGTCGTAGGAGGAAGGAGAGAGTGGCAGCAGA
hcox-3(del10) ------------------------------------------------------------------------------------------------------------------GAGAGAAGGAGAGAAGGAGAGAGTGGCAGCAGA
hcox-3(cs)   tggctgtggatgtcatcagggagtctcgggagatgcggctgcagcccttcaatgagtagtaccgcaagagtttggcatgaaacctacacctccttccaggagctcgtaggagctcgtaggagaaggagagagtggcagcaga
```

*FIG. 16C*

```
                    1561        1570        1580        1590        1600        1610        1620        1630        1640        1650        1660        1670        1680        1690
                      |           |           |           |           |           |           |           |           |           |           |           |           |           |
hcox-3(cc)     GTTGGAGGAATCGTATGAGAGACATTGATGCGTTGGAGTTCTACCCTGGACTGCTTCTTGAAAAGTGCCATCCAAACTCTATCTTTGGGGAGAGAGTGATAGAGATGGGGCTCCCTTTTCCCTCAAGGGT
hcox-3(af)     GTTGGAGGAATCGTATGAGAGACATTGATGCGTTGGAGTTCTACCCTGGACTGCTTCTTGAAAAGTGCCATCCAAACTCTATCTTTGGGGAGAGAGTGATAGAGATGGGGCTCCCTTTTCCCTCAAGGGT
hcox-3(del10)  GTTGGAGGAATTGTATGAGAGACATTGATGCGTTGGAGTTCTACCCTGGACTGCTTCTTGAAAAGTGCCATCCAAACTCTATCTTTGGGGAGAGAGTATGATAGAGATGGGGCTCCCTCCCTTTTCCCTCAAGGGT
hcox-3(cs)     GTTGGAGGAATTGTATGAGAGACATTGATGCGTTGGAGTTCTACCCTGGACTGCTTCTTGAAAAGTGCCATCCAAACTCTATCTTTGGGGAGAGAGTATGATAGAGATGGGGCTCCCTCCCTTTTCCCTCAAGGGT 1691        1700        1710        1720        1730        1740        1750        1760        1770        1780        1790        1800        1810        1820
                      |           |           |           |           |           |           |           |           |           |           |           |           |           |
hcox-3(cc)     CTCCTAGGGAATCCCATCTGTTCTCCGGAGTACTGGAAGCCGAGCACATTGGCGGCGAGCCGAGCACACTTGGCAGCACATTTAACATTGTCAAGACGGGCGAGTGGGCTTTAACATTGTCAAGAAGCTGGTCTGCCTCAACACCAAGACCTGTCCCT
hcox-3(af)     CTCCTAGGGAATCCCATCTGTTCTCCGGAGTACTGGAAGCCGAGCACATTGGCGGCGAGCCGAGCACACTTGGCAGCACATTTAACATTGTCAAGACGGGCGAGTGGGCTTTAACATTGTCAAGAAGCTGGTCTGCCTCAACACCAAGACCTGTCCCT
hcox-3(del10)  CTCCTAGGGAATCCCATCTGTTCTCCGGAGTACTGGAAGCCGAGCACATTGGCGGCGAGCCGAGCACACTTGGCAGCACATTTAACATTGTCAAGACGGGCGAGTGGGCTTTAACATTGTCAAGAAGCTGGTCTGCCTCAACACCAAGACCTGTCCCT
hcox-3(cs)     CTCCTAGGGAATCCCATCTGTTCTCCGGAGTACTGGAAGCCGAGCACATTGGCGGCGAGCCGAGCACACTTGGCAGCACATTTAACATTGTCAAGACGGGCGAGTGGGCTTTAACATTGTCAAGAAGCTGGTCTGCCTCAACACCAAGACCTGTCCCT 1821        1830        1840        1850        1860        1870        1880      18901894
                      |           |           |           |           |           |           |           |
hcox-3(cc)     ACGTTCCTTCCGTGTGCCGGATGCCAGTCAGGATGATGGGCCTGCTGTGGAGCCGACCATCCACAGAGCTCTGA
hcox-3(af)     ACGTTCCTTCCGTGTGCCGGATGCCAGTCAGGATGATGGGCCTGCTGTGGAGCCGACCATCCACAGAGCTCTGA
hcox-3(del10)  ACGTTCCTTCCGTGTGCCGGATGCCAGTCAGGATGATGGGCCTGCTGTGGAGCCGACCATCCACAGAGCTCTGA
hcox-3(cs)     ACGTTCCTTCCGTGTGCCGGATGCCAGTCAGGATGATGGGCCTGCTGTGGAGCCGACCATCCACAGAGCTCTGA
```

*FIG. 16D* hCOX-3(cc)

SEQ ID NO:10
```
   1 atgagccgtg agtgcgaccc cggtgcccgg tgggaattt tcttgcctc ctggtggagc   60
  61 cttgaatgcc aggctcagcc cctcatctct ctcctctgca gggagtctct tgctccggtt  120
 121 cttgctgttc ctgctcctgc tcccgcccgct cccgtcctg ctcgcggacc caggggcgcc  180
 181 cacgccagtg aatccctgtt gttactatcc atgccagcac caggcatct gtgtccgctt  240
 241 cggccttgac cgctaccagt gtgactgcac cgcacgggc tattccggcc ccaactgcac  300
 301 catccctgc ctgtggacct ggctccggaa ttcactgcgg cccagccct ctttcaccca  360
 361 cttcctgctc actcacggc gctggttctg ggagtttgtc aatgccacct tcatccgaga  420
 421 gatgctcatg cgcctggtac tcacagtgcg ctccaactt atccccagtc cccaccta  480
 481 caactcagca catgactaca tcagctggga ctcttttctcc aacgtgagct attacactcg  540
 541 tattctgcc tctgtgccta aagattgccc cacaccatg cttcctgctc ggaaccaaag  600
 601 gttgccagat gcccagctcc tggcccgcg tggcctgctc agaggaagt tcatacctga  660
 661 ccccaaggc accaacctca tgtttgcctt cttgcacaa cacttcaccc accagttctt  720
 721 caaactttc gccagatgg gtcctggctt gtcctggctt taggccatg ctgcggctct  780
 781 cggccacatt tatggagaca atctggagcg tcagtatcaa ccctcggtag aagaggcgcc  840
 841 gaaactcaag taccaggtgc tggatggaga aatgtacccg cccacctgg ggcgatgagc  900
 901 tgtgtttgatg cactaccccc gaggcatccc gccccagagc gtatgccacg cagatggctg  960
 961 ggtgtttggg ctgcttcctg ggctcatgct ggctgctgct gtatgccacg cccacctgg ggcgctgctgc 1020
1021 ccgtgtgtgt gacctgctga agctgctgct ctctggctc tcctggctg gcgatgagc agcttttcca 1080
1081 gacgacccgc ctcatcctca tagggagac catcaagatt gtcatcgagg agttacgtgca 1140
1141 gcagctgagt ggctatttcc tgcagctcca atttgaccca gagctgctgt tcggtgtcca 1200
```

FIG. 17A

```
1201  gttccaatac cgcaaccgca ttgccatgga gttcaaccat ctctaccact ggcacccct  1260
1261  catgcctgac tccttcaagg tgggctccca ggagtacagc tacgagcagt tcttgttcaa  1320
1321  cacctccatg ttggtggact atggggttga ggccctggtg gatgccttct ctcgccagat  1380
1381  tgctggccgg atcggtgggg gcaggaacat ggaccaccac atcctgcatg tggctgtgga  1440
1441  tgtcatcagg gagtctcggg agatgcggct gcagcccttc aatgagtacc gcaagaggtt  1500
1501  tggcatgaaa ccctacacct cctgtagga gctcgtagga gagaaggaga tggcagcaga  1560
1561  gttggaggaa ttgtatggag acattgatgc gttgagttc tacccctgga tgcttcttga  1620
1621  aaagtgccat ccaaactcta tctttgggga gagtatgata gagattgggg ctccctttc  1680
1681  cctcaagggt ctcctaggga atcccatctg ttctccggag tactggaagc cgagcacatt  1740
1741  tgcgggcgag gtgggcttta gacttgtcaa acgtgccaca ctgaagaagc tggtctgcct  1800
1801  caacaccaag acctgtcct acgtttcctt ccgtgtgccg gatgccagtc aggatgatgg  1860
1861  gcctgctgtg gagcgacat ccacagagct ctga                               1894
```

*FIG. 17B* hCOX-3(af)

SEQ ID NO:11
```
   1 ATGAGCCGTG AGTGCGACCC CGGTGCCCGG TGGGAATTT TCTTGGCCTC CTGGTGGAGC   60
  61 CTGAATGCC AGGCTCAGCC CCTCATCTCT CTCCTCTGCA GGGAGTCTCT TGCTCCGGTT  120
 121 CTGCTGTTC CTGCTCCTGC TCCCGTCCTG CCCCGTCCTG CTCGGGGACC CAGGGGCGCC  180
 181 CACGCCAGTG AATCCCTGTT GTTACTATCC ATGCCAGCAC CAGGGCATCT GTGTCCGCTT  240
 241 CGGCCTTGAC CGCTACCAGT GTGACTGCAC CCGCACGGGC TATTCCGGCC CCAACTGCAC  300
 301 CATCCCTGGC CTGTGGACCT GGCTCCGGAA TTCACTGCGG CCCAGCCCT CTTTCACCCA  360
 361 CTTCCTGCTC ACTCACGGGC GCTGGTTCTG GGAGTTTGTC AATGCCACCT TCATCCGAGA  420
 421 GATGCTCATG CGCCTGGTAC TCACAGTGCG CTCCAACCTT ATCCCCAGTC CCCCACCTA  480
 481 CAACTCAGCA CATGACTACA TCAGCTGGGA GTCTTTCTCC AACGTGAGCT ATTACACTCG  540
 541 TATTCTGCCC TCTGTGCCTA AAGATTGCCC CACACCCATG GGAACCAAAG GGAAGAAGCA  600
 601 GTTGCCAGAT GCCCAGCTCC TGGCCCGCCG CTTCCTGCTC AGGAGGAAGT TCATACCTGA  660
 661 CCCCCAAGGC ACCAACCTCA TGTTTGCCTT CTTTGCACAA CACTTCACCC ACCAGTTCTT  720
 721 CAAAACTTCT GGCAAGATGG GTCCTGGCTT CACCAAGGCC TTGGGCCATG CTGCGGCTCT  780
 781 CGGCCACATT TATGGAGACA ATCTGGAGCG TCAGTATCAA CCCTCGGTAG AAGGATGG    840
 841 GAAACTCAAG TACCAGGTGC TGGATGGAGA AATGTGCCCG CAGATGGCTG TGGCCAGGA   900
 901 TGTGTTGATG CACTACCCC GAGGCATCCC GCCCCAGAGC CTCTGGCTAC GTGAGCACAA   960
 961 GGTGTTTGGG CTGCTTCCTG GGCTCCACG GTATGCCACG CCCCACCTGG AGCTTTCCA  1020
1021 CCGTGTGTGT GACCTGCTGA AGGCTGAGCA CCCCACCCTG CATGATGAGC GTCATCGAGG  1080
1081 GACGACCCGC CTCATCCTCA TAGGGAGAC CATCAAGATT GTCATCGAGG AGTACGTGCA  1140
1141 GCAGCTGAGT GGCTATTTCC TGCAGCTGAA ATTGACCCA ATTGACCCA GAGCTGCTGT  1200
```

FIG. 18A

```
1201 GTTCCAATAC CGCAACCGCA TTGCCATGGA GTTCAACCAT CTCTACCACT GGCACCCCT 1260
1261 CATGCCTGAC TCCTTCAAGG TGGGCTCCCA GGAGTACAGC TACGAGCAGT TCTTGTTCAA 1320
1321 CACCTCCATG TTGGTGGACT ATGGGGTTGA GGCCCTGGTG GACCCTGGTG GATGCCTTCT CTCGCCAGAT 1380
1381 TGCTGGCCGG ATCGGTGGGG GCAGGAACAT GGACCACCAC ATCCTGCATG TGGCTGTGGA 1440
1441 TGTCATCAGG GAGTCTCGGG AGATGCGGCT GCAGCCCTTC AATGAGTACC GCAAGAGGTT 1500
1501 TGGCATGAAA CCCTACACCT CCTTCCAGGA GCTCGTAGGA GAGAAGGAGA TGGCAGCAGA 1560
1561 GTTGGGAGAA TTGTATGGAG ACATTGATGC GTTGGAGTTC TACCCTGGAC TGCTTCTTGA 1620
1621 AAAGTGCCAT CCAAACTCTA TCTTTGGGGA GAGTATGATA GAGATTGGGG CTCCCTTTC 1680
1681 CCTCAAGGGT CTCCTAGGGA ATCCCATCTG TTCTCCGGAG TACTGGAAGC CGAGCACATT 1740
1741 TGGCGGGGAG GTGGGCTTTA ACATTGTCAA GACGGCCACA CTGAAGAAGC TGGTCTGCCT 1800
1801 CAACACCAAG ACCTGTCCCT ACGTTCCCTT GACGGCCACA CTGAAGAAGC CGTGTGCCG GATGCCAGTC 1860
1861 GCCTGCTGTG GAGCGACCAT CCACAGAGCT CTGA 1894
```

*FIG. 18B* hCOX-3(del10)

SEQ ID NO:12
```
   1  ATGAGCCGTG  AGTGCGACCC  CGGTGCCCGG  TGGGAATTT   TCTTGGCCTC  CTGGTGGAGC    60
  61  CTTGAATGCC  AGGCTCAGCC  CCTCATCTCT  CTCCTCTGCA  GGGAGTCTCT  TGCTCCGGTT   120
 121  CTTGCTGTTC  CTGCTCCTGC  TCCGCCGCT   CCCGTTCCTG  CTCGCGGACC  CAGGGGCGCC   180
 181  CACGCCAGTG  AATCCCTGTT  GTTACTATCC  ATGCCAGCAC  CAGGGCATCT  GTGTCCGCTT   240
 241  CGGCCTTGAC  CGTACCAGT   GTGACTGCAC  CGCACGGGC   TATTCCGGCC  CCAACTGCAC   300
 301  CATCCTGGC   CTGTGGACCT  GGCTCCGGAA  TTCGCTGCGG  CCCAGCCCT   CTTTCACCCA   360
 361  CTTCCTGCTC  ACTCACGGGC  GCTGGTTCTG  GGAGTTTGTC  AATGCCACCT  TCATCCGAGA   420
 421  GATGCTCATG  CGCCTGGTAC  TCCAAGTGCG  CTCCAACCTT  ATCCCCAGTC  CCCCACCTA   480
 481  CAACTCAGCA  CATGACTACA  TCAGCTGGGA  GTCTTTCTCC  AACGTGAGCT  ATTACACTCG   540
 541  TATTCTGCCC  TCTGTGCCTA  AAGATTGCCC  CACACCCATG  GGAACCAAAG  GGAAGAAGCA   600
 601  GTTGCCAGAT  GCCCAGCTCC  TGGCCCGCG   CTTCCTGCTC  AGGAGGAAGT  TCATACCTGA   660
 661  CCCCCAAGGC  ACCAACCTCA  TGTTTGCCTT  CTTTGCACAA  CACTTCACCC  ACCAGTTCTT   720
 721  CAAAACTTCT  GGCAAGATGG  GTCCTGGCTT  CACCAAGGCC  TTGGGCCATG  GGGTAGACCT   780
 781  CGGCCACATT  TATGGAGACA  ATCTGGAGCG  TCAGTATCAA  CTGCGGCTCT  TTAAGGATGG   840
 841  GAAACTCAAG  TACCAGGTGC  TGGATGGAGA  AATGTACCCG  CCCTCGGTAG  AGGAGGCGCC   900
 901  TGTGTTGATG  CACTACCCCC  GAGGCATCCC  GCCCCAGAGC  CAGATGGCTG  TGGGCCAGGA   960
 961  GGTGTTTGGG  CTGCTTCCTG  GGCTCATGCT  GTATGCCACG  CTCTGGCTAC  GTGAGCACAA  1020
1021  CCGTGTGTGT  GACCTGCTGA  AGGCTGAGCA  CCCCACCTGG  GGGGATGAGC  AGCTTTTCCA  1080
1081  GACGACCCGC  CTCATCCTCA  TAGGGGAGAC  CATCAAGATT  GTCATCGAGG  AGTACGTGCA  1140
1141  GCAGCTGAGT  GGCTATTTCC  TGCAGCTGAA  ATTTGACCCA  GAGCTGCTGT  TCGGTGTCCT  1200
```

FIG. 19A

```
1201 GTTCCAATAC TGCAACCGCA TTGCCATGGA GTTCAACCAT CTCTACCACT GGCACCCCCT 1260
1261 CATGCCTGAC TCCTTCAAGG TGGGCTCCCA GGAGTACAGC TACGAGCAGT TCTTGTTCAA 1320
1321 CACCTCCATG TTAGTGGACT ATGGGGTTGA GGCCCTGGTG GATGCCTTCT CTCGCCAGAT 1380
1381 TACTGGCCGG GAGAGAAGGA GATGGCAGCA GAGTTGGAGG AATTGTATGG AGACATTGAT 1440
1441 GCGTTGGAGT TCTACCCTGG ACTGCTTCTT GAAAAGTGCC ATCCAAACTC TATCTTTGGG 1500
1501 GAGAGTATGA TAGAGATTGG GGCTCCCCTT TCCCTCAAGG GTCTCCTAGG GAATCCCATC 1560
1561 TGTTCTCCGG AGTACTGGAA GCCGAGCACG TTTGGGGGCG AGGTGGGCTT TAACATTGTC 1620
1621 AAGACGGCCA CACTGAAGAA GCTGGTCTGC CTCAACACCA AGACCTGTCC CTACGTTTCC 1680
1681 TTCCGTGTGC TCAGGATGAT GCTGGTGCTG GGGCCTGCTG TGGAGCGACC ATCCACAGAG 1740
1741 CTCTGA                                                         1746
```

*FIG. 19B* hCOX-3(con-p)

```
  1 ATGAGCCGTG AGTGCGACCC CGGTGCCCGG TGGGGAATTT SEQ ID NO:13
     M  S  R  E  C  D  P     G  A  R     W  G  I  F SEQ ID NO:14
        A  V     S  A  T  P  V  P  G     G  E  F    SEQ ID NO:15
        E  P        V  R  P  R  C  P  V     G  N  F SEQ ID NO:16
 41 TCTTGGCCTC CTGGTGGAGC CTTGAATGCC AGGCTCAGCC
     L  A  S  W  W  S  L  E  C  Q     A  Q  P
     S  W  P  P  G  G  A  L  N  A     R  L  S  P
     L  G  L  L  V  E  P     M  P  G  S  A
 81 CCTCATCTCT CTCCTCTGCA GGGAGTCTCT TGCTCCGGTT
     L  I  S  L  L  C  R  E  S  L     A  P  V
     S  S  L  S  S  A     G  S  L  L     L  R  F
     P  H  L     S  P  L  Q  G  V  S     C  S  G  S
121 CTTGCTGTTC CTGCTCCTGC TCCCGCCGCT CCCCGTCCTG
     L  A  V  P  A  P  A  P  A  A  P  R  P  A
     L  L  F  L  L  L  L  P  P  L  P  V  L
     C  C  S  C  S  C  S  R  R  S  P  S  C
161 CTCGCGGACC CAGGGGCGCC CACGCCAGTG AATCCCTGTT
     R  G  P  R  G  A     H  A  S  E     S  L  L
     L  A  D  P  G  A  P  T  P  V     N  P  C  C
     S  R  T  Q  G  R  P  R  Q     I  P  V
201 GTTACTATCC ATGCCAGCAC CAGGGCATCT GTGTCCGCTT
     L  L  S  M  P  A  P     G  H  L     C  P  L
     Y  Y  P     C  Q  H  Q  G  I  C     V  R  F
     V  T  I  H  A  S  T  R  A  S     V  S  A  S
241 CGGCCTTGAC CGCTACCAGT GTGACTGCAC CCGCACGGGC
     R  P     P  L  P  V     L  H     P  H  G  L
     G  L  D  R  Y  Q  C     D  C  T     R  T  G
     A  L  T  A  T  S  V  T  A  P     A  R  A
281 TATTCCGGCC CCAACTGCAC CATCCCTGGC CTGTGGACCT
     F  R  P  Q  L  H     H  P  W  P  V  D  L
     Y  S  G  P  N  C  T  I  P  G  L  W  T  W
     I  P  A  P  T  A  P     S  L  A     C  G  P
321 GGCTCCGGAA TTCACTGCGG CCCAGCCCCT CTTTCACCCA
     A  P  E     F  T  A  A  Q  P  L     F  H  P
     L  R  N     S  L  R     P  S  P  S     F  T  H
     G  S  G  I  H  C  G  P  A  P     L  S  P  T
```

FIG. 20A hCOX-3(con-p)

```
361 CTTCCTGCTC ACTCACGGGC GCTGGTTCTG GGAGTTTGTC
     L  P  A  H  S  R  A  L  V  L  G  V  C  Q
      F  L  L  T  H  G  R  W  F  W  E  F  V
       S  C  S  L  T  G  A  G  S  G  S  L  S
401 AATGCCACCT TCATCCGAGA GATGCTCATG CGCCTGGTAC
     C  H  L  H  P  R  D  A  H  A  P  G  T
      N  A  T  F  I  R  E  M  L  M  R  L  V  L
       M  P  P  S  S  E  R  C  S  C  A  W  Y
441 TCACAGTGCG CTCCAACCTT ATCCCCAGTC CCCCCACCTA
     H  S  A  L  Q  P  Y  P  Q  S  P  H  L
      T  V  R  S  N  L  I  P  S  P  P  T  Y
       S  Q  C  A  P  T  L  S  P  V  P  P  P  T
481 CAACTCAGCA CATGACTACA TCAGCTGGGA GTCTTTCTCC
     Q  L  S  T  L  H  Q  L  G  V  F  L  Q
      N  S  A  H  D  Y  I  S  W  E  S  F  S
       T  Q  H  M  T  T  S  A  G  S  L  S  P
521 AACGTGAGCT ATTACACTCG TATTCTGCCC TCTGTGCCTA
     R  E  L  L  H  S  Y  S  A  L  C  A
      N  V  S  Y  Y  T  R  I  L  P  S  V  P  K
       T  A  I  T  L  V  F  C  P  L  C  L
561 AAGATTGCCC CACACCCATG GGAACCAAAG GGAAGAAGCA
     R  L  P  H  T  H  G  N  Q  R  E  E  A
      D  C  P  T  P  M  G  T  K  G  K  K  Q
       K  I  A  P  H  P  W  E  P  K  G  R  S  S
601 GTTGCCAGAT GCCCAGCTCC TGGCCCGCCG CTTCCTGCTC
     V  A  R  C  P  A  P  G  P  P  L  P  A  Q
      L  P  D  A  Q  L  L  A  R  R  F  L  L
       C  Q  M  P  S  S  W  P  A  A  S  C  S
641 AGGAGGAAGT TCATACCTGA CCCCCAAGGC ACCAACCTCA
     E  E  V  H  T  P  P  R  H  Q  P  H
      R  R  K  F  I  P  D  P  Q  G  T  N  L  M
       G  G  S  S  Y  L  T  P  K  A  P  T  S
681 TGTTTGCCTT CTTTGCACAA CACTTCACCC ACCAGTTCTT
     V  C  L  L  C  T  T  L  H  P  P  V  L
      F  A  F  F  A  Q  H  F  T  H  Q  F  F
       C  L  P  S  L  H  N  T  S  P  T  S  S  S
```

FIG. 20B hCOX-3(con-p)

```
721   CAAAACTTCT  GGCAAGATGG  GTCCTGGCTT  CACCAAGGCC
       Q  N  F  W   Q  D  G    S  W  L     H  Q  G  L
        K  T  S    G  K  M  G   P  G  F    T  K  A
         K  L  L    A  R  W    V  L  A  S   P  R  P
761   TTGGGCCATG  GGGTAGACCT  CGGCCACATT  TATGGAGACA
       G  P  W     G  R  P     R  P  H  L   W  R  Q
        L  G  H  G  V  D  L    G  H  I     Y  G  D  N
         W  A  M   G     T  S   A  T  F    M  E  T
801   ATCTGGAGCG  TCAGTATCAA  CTGCGGCTCT  TTAAGGATGG
       S  G  A    S  V  S  T   A  A  L        G  W
        L  E  R    Q  Y  Q     L  R  L  F   K  D  G
         I  W  S  V  S  I  N    C  G  S     L  R  M  G
841   GAAACTCAAG  TACCAGGTGC  TGGATGGAGA  AATGTACCCG
       E  T  Q  V  P  G  A     G  W  R     N  V  P  A
        K  L  K    Y  Q  V  L   D  G  E    M  Y  P
         N  S  S   T  R  C     W  M  E  K   C  T  R
881   CCCTCGGTAG  AAGAGGCGCC  TGTGTTGATG  CACTACCCCC
       L  G  R    R  G  A     C  V  D  A   L  P  P
        P  S  V  E  E  A  P    V  L  M     H  Y  P  R
         P  R      K  R  R  L   C     C     T  T  P
921   GAGGCATCCC  GCCCCAGAGC  CAGATGGCTG  TGGGCCAGGA
       R  H  P    A  P  E  P   D  G  C     G  P  G
        G  I  P    P  Q  S     Q  M  A  V   G  Q  E
         E  A  S  R  P  R  A    R  W  L    W  A  R  R
961   GGTGTTTGGG  CTGCTTCCTG  GGCTCATGCT  GTATGCCACG
       G  V  W  A  A  S  W     A  H  A    V  C  H  A
        V  F  G    L  L  P  G   L  M  L    Y  A  T
         C  L  G   C  F  L     G  S  C  C   M  P  R
1001  CTCTGGCTAC  GTGAGCACAA  CCGTGTGTGT  GACCTGCTGA
       L  A  T       A  Q      P  C  V     P  A  E
        L  W  L  R  E  H  N    R  V  C     D  L  L  K
         S  G  Y   V  S  T  T   V  C  V    T  C
1041  AGGCTGAGCA  CCCCACCTGG  GGCGATGAGC  AGCTTTTCCA
       G  A        P  H  L  G  R           A  A  F  P
        A  E  H    P  T  W     G  D  E  Q   L  F  Q
         R  L  S  T  P  P  G    A  M  S     S  F  S  R
```

*FIG. 20C* hCOX-3(con-p)

```
1081    GACGACCCGC CTCATCCTCA TAGGGGAGAC CATCAAGATT
         D  D  P  P   H  P  H    R  G  D    H  Q  D  C
          T  T  R   L  I  L  I   G  E  T   I  K  I
           R  P  A   S  S  S      G  R  P   S  R  L
1121    GTCATCGAGG AGTACGTGCA GCAGCTGAGT GGCTATTTCC
         H  R  G    V  R  A    A  A  E  W   L  F  P
          V  I  E  E   Y  V  Q   Q  L  S    G  Y  F  L
           S  S  R   S  T  C  S   S     V   A  I  S
1161    TGCAGCTGAA ATTTGACCCA GAGCTGCTGT TCGGTGTCCA
         A  A  E    I     P  R   A  A  V    R  C  P
          Q  L  K   F  D  P      E  L  L  F  G  V  Q
           C  S     N  L  T  Q   S  C  C    S  V  S  S
1201    GTTCCAATAC CGCAACCGCA TTGCCATGGA GTTCAACCAT
         V  P  I  P   Q  P  H    C  H  G    V  Q  P  S
          F  Q  Y    R  N  R  I   A  M  E   F  N  H
           S  N  T   A  T  A     L  P  W   S  T  I
1241    CTCTACCACT GGCACCCCCT CATGCCTGAC TCCTTCAAGG
          L  P  L    A  P  P    H  A     L    L  Q  G
          L  Y  H  W   H  P  L   M  P  D    S  F  K  V
           S  T  T   G  T  P  S   C  L  T    P  S  R
1281    TGGGCTCCCA GGAGTACAGC TACGAGCAGT TCTTGTTCAA
         G  L  P    G  V  Q  L   R  A  V    L  V  Q
          G  S  Q   E  Y  S    Y  E  Q  F   L  F  N
           W  A  P  R   S  T  A   T  S  S    S  C  S  T
1321    CACCTCCATG TTGGTGGACT ATGGGGTTGA GGCCCTGGTG
         H  L  H  V   G  G  L   W  G       G  P  G  G
          T  S  M    L  V  D  Y   G  V  E   A  L  V
           P  P  C   W  W  T    M  G  L  R   P  W  W
1361    GATGCCTTCT CTCGCCAGAT TGCTGGCCGG ATCGGTGGGG
          C  L  L    S  P  D    C  W  P  D   R  W  G
          D  A  F  S   R  Q  I   A  G  R    I  G  G  G
           M  P  S   L  A  R  L   L  A  G    S  V  G
1401    GCAGGAACAT GGACCACCAC ATCCTGCATG TGGCTGTGGA
         Q  E  H    G  P  P  H   P  A  C    G  C  G
          R  N  M   D  H  H     I  L  H  V   A  V  D
           A  G  T  W   T  T  T   S  C  M   W  L  W  M
```

FIG. 20D hCOX-3(con-p)

```
1441 TGTCATCAGG GAGTCTCGGG AGATGCGGCT GCAGCCCTTC
      C  H  Q  G  V  S  G  D  A  A  A  A  L  Q
       V  I  R  E  S  R  E  M  R  L  Q  P  F
        S  S  G  S  L  G  R  C  G  C  S  P  S
1481 AATGAGTACC GCAAGAGGTT TGGCATGAAA CCCTACACCT
      V  P  Q  E  V  W  H  E  T  L  H  L
       N  E  Y  R  K  R  F  G  M  K  P  Y  T  S
        M  S  T  A  R  G  L  A  N  P  T  P
1521 CCTTCCAGGA GCTCGTAGGA GAGAAGGAGA TGGCAGCAGA
      L  P  G  A  R  R  R  E  G  D  G  S  R
       F  Q  E  L  V  G  E  K  E  M  A  A  E
        P  S  R  S  S  E  R  R  R  W  Q  Q  S
1561 GTTGGAGGAA TTGTATGGAG ACATTGATGC GTTGGAGTTC
      V  G  G  I  V  W  R  H  C  V  G  V  L
       L  E  E  L  Y  G  D  I  D  A  L  E  F
        W  R  N  C  M  E  T  L  M  R  W  S  S
1601 TACCCTGGAC TGCTTCTTGA AAAGTGCCAT CCAAACTCTA
      P  W  T  A  S  K  V  P  S  K  L  Y
       Y  P  G  L  L  L  E  K  C  H  P  N  S  I
        T  L  D  C  F  L  K  S  A  I  Q  T  L
1641 TCTTTGGGGA GAGTATGATA GAGATTGGGG CTCCCTTTTC
      L  W  G  E  Y  D  R  D  W  G  S  L  F
       F  G  E  S  M  I  E  I  G  A  P  F  S
        S  L  G  R  V  R  L  G  L  P  F  P
1681 CCTCAAGGGT CTCCTAGGGA ATCCCATCTG TTCTCCGGAG
      P  Q  G  S  P  R  E  S  H  L  F  S  G  V
       L  K  G  L  L  G  N  P  I  C  S  P  E
        S  R  V  S  G  I  P  S  V  L  R  S
1721 TACTGGAAGC CGAGCACATT TGGCGGCGAG GTGGGCTTTA
      L  E  A  E  H  I  W  R  R  G  G  L
       Y  W  K  P  S  T  F  G  G  E  V  G  F  N
        T  G  S  R  A  H  L  A  A  R  W  A  L
1761 ACATTGTCAA GACGGCCACA CTGAAGAAGC TGGTCTGCCT
      H  C  Q  D  G  H  T  E  E  A  G  L  P
       I  V  K  T  A  T  L  K  K  L  V  C  L
        T  L  S  R  R  P  H  R  S  W  S  A  S
```

*FIG. 20E* hCOX-3(con-p)

```
1801  CAACACCAAG ACCTGTCCCT ACGTTTCCTT CCGTGTGCCG
       Q  H  Q  D   L  S  L    R  F  L    P  C  A  G
        N  T  K    T  C  P  Y   V  S  F    R  V  P
         T  P  R    P  V  P    T  F  P  S   V  C  R
1841  GATGCCAGTC AGGATGATGG GCCTGCTGTG GAGCGACCAT
       C  Q  S    G          W    A  C  C  G   A  T  I
        D  A  S  Q   D  D  G    P  A  V    E  R  P  S
         M  P  V    R  M  M  G    L  L  W    S  D  H
1881  CCACAGAGCT CTGA
       H  R  A  L
        T  E  L
         P  Q  S  S   D
```

FIG. 20F

SEQUENCE LISTING

<160> NUMBER OF SEQ ID NOS: 89

<210> SEQ ID NO 1
<211> LENGTH: 1902
<212> TYPE: DNA
<213> ORGANISM: Canis familiaris

<400> SEQUENCE: 1

```
atgagccgtg agttcgaccc tgaggccccc aggaaccctc ttcgcctccc gggggagcct      60
cgaatgccag gcccagccct cacctctcgc tccgcagggg ggagtcgcct gcaccggtgg     120
ccgctgctcc tgctgctgct gctgctgctc ccgccgcccc cggtcctgcc cgcggaagcc     180 cggacccegg cgcctgtgaa cccgtgttgt tactacccat gtcagcacca agggatctgt     240
gtccgcttcg gccttgaccg ctaccagtgt gactgcaccc gcacgggcta ttctggcccc     300
aactgcacca tccccgagct gtggacctgg ctccggaatt cactgcgccc cagtccctct     360
ttcctccact tcctgctgac gcatgggcgc tggttttggg aattcatcaa tgccaccttc     420
atccgtgaca tgctcatgcg tctggtactc acagcgcgtt ccaaccttat ccccagtcct     480
cccacctaca acatagcgca tgactacatc agctgggagt ccttctccaa tgtgagctat     540
tacactcgtg ttctgccctc tgtgcccaa gattgcccca cgcccatggg gaccaaaggg     600
aagaagcagt tgccagacgc ccaactcctg ggccgtcgct tcctgctcag gaggaagttc     660
atacctgacc cccaaggcac caacctcatg ttcgccttct ttgcacaaca cttcacccat     720
cagttcttca aaacttctgg caagatgggt cctggcttca ccaaggcctt gggccatggg     780
gtagatcttg gccacattta tgggacaat ctggaccgtc agtatcagct gcggctcttt     840
aaggatggga aactcaagta tcaggttctg gatggagaga tgtacccgcc atctgtggag     900
gaggcgcctg tgttgatgca ctacccacgg ggcattctgc cccagagtca gatggccgtg     960
ggccaggagg tgtttgggct gcttcctggg ctcatgctct atgccacgct ctggctgcgt    1020
gagcacaatc gtgtgtgtga cctgctgaag gctgagcacc ccacttgggg tgatgagcaa    1080
ctcttccaga cggcccgact catcctcatt ggggagacca tcaagattgt gattgaggag    1140
tatgtgcagc agctgagtgg ctacttcttg cagctgaagt tcgacccgga gctgctgttt    1200
agcgcccagt tccagtaccg caaccgcatc gccatggagt tcaaccagct gtaccactgg    1260
cacccgctca tgccagactc cttctgggtg gttcccagg agtacagcta tgagcagttc    1320
ctgttcaaca cctccatgct gacgcactac gggatcgagg cctggtgga tgccttctct    1380
```

```
cgccagagcg ccggccggat tggtggaggt agaaacatag accaccatgt cctgcacgtg    1440
gctgtggaaa ccatcaagga atcccgcgag ttgcggctgc agcccttcaa tgagtaccgc    1500
aagaggtttg gcatgaggcc ctacatgtcc ttccaggaac tcacagggga aaggagatg     1560
```

```
aagaggtttg gcatgaggcc ctacatgtcc ttccaggaac tcacagggga aaggagatg     1560 gcagccgagt tggaggagct gtatggagac attgatgcct ggaattcta cccggggctt    1620 cttctggaga agtgccatcc aaactccatc tttggagaga gtatgataga aattggggct    1680 ccccttctccc ttaagggcct cctagggaat cccatctgtt ctccagagta ctggaagcca    1740
agcacattcg gtggtgagat gggcttcaat atggtcaaga cagccacact gaagaagctg    1800
gtctgcctta acaccaagac ttgtccctat gtttccttcc gtgtgcctga ccccaccag     1860 gatggcgggc tggtgtgca gcggccgtcc acagagctct ga                        1902
```

<210> SEQ ID NO 2
<211> LENGTH: 633
<212> TYPE: PRT
<213> ORGANISM: Canis familiaris

<400> SEQUENCE: 2

```
Met Ser Arg Glu Phe Asp Pro Glu Ala Pro Arg Asn Pro Leu Arg Leu
  1               5                  10                  15

Pro Gly Glu Pro Arg Met Pro Gly Pro Ala Leu Thr Ser Arg Ser Ala
             20                  25                  30

Gly Gly Ser Arg Leu His Arg Trp Pro Leu Leu Leu Leu Leu Leu Leu
         35                  40                  45

Leu Leu Pro Pro Pro Val Leu Pro Ala Glu Ala Arg Thr Pro Ala
     50                  55                  60

Pro Val Asn Pro Cys Cys Tyr Tyr Pro Cys Gln His Gln Gly Ile Cys
 65                  70                  75                  80

Val Arg Phe Gly Leu Asp Arg Tyr Gln Cys Asp Cys Thr Arg Thr Gly
                 85                  90                  95

Tyr Ser Gly Pro Asn Cys Thr Ile Pro Glu Leu Trp Thr Trp Leu Arg
            100                 105                 110

Asn Ser Leu Arg Pro Ser Pro Ser Phe Leu His Phe Leu Leu Thr His
        115                 120                 125

Gly Arg Trp Phe Trp Glu Phe Ile Asn Ala Thr Phe Ile Arg Asp Met
    130                 135                 140

Leu Met Arg Leu Val Leu Thr Ala Arg Ser Asn Leu Ile Pro Ser Pro
145                 150                 155                 160

Pro Thr Tyr Asn Ile Ala His Asp Tyr Ile Ser Trp Glu Ser Phe Ser
                165                 170                 175

Asn Val Ser Tyr Tyr Thr Arg Val Leu Pro Ser Val Pro Gln Asp Cys
            180                 185                 190

Pro Thr Pro Met Gly Thr Lys Gly Lys Lys Gln Leu Pro Asp Ala Gln
        195                 200                 205

Leu Leu Gly Arg Arg Phe Leu Leu Arg Lys Phe Ile Pro Asp Pro
    210                 215                 220

Gln Gly Thr Asn Leu Met Phe Ala Phe Ala Gln His Phe Thr His
225                 230                 235                 240

Gln Phe Phe Lys Thr Ser Gly Lys Met Gly Pro Gly Phe Thr Lys Ala
                245                 250                 255

Leu Gly His Gly Val Asp Leu Gly His Ile Tyr Gly Asp Asn Leu Asp
            260                 265                 270

Arg Gln Tyr Gln Leu Arg Leu Phe Lys Asp Gly Lys Leu Lys Tyr Gln
        275                 280                 285
```

-continued

Val Leu Asp Gly Glu Met Tyr Pro Pro Ser Val Glu Glu Ala Pro Val
    290                 295                 300

Leu Met His Tyr Pro Arg Gly Ile Leu Pro Gln Ser Gln Met Ala Val
305                 310                 315                 320

Gly Gln Glu Val Phe Gly Leu Leu Pro Gly Leu Met Leu Tyr Ala Thr
                325                 330                 335

Leu Trp Leu Arg Glu His Asn Arg Val Cys Asp Leu Leu Lys Ala Glu
            340                 345                 350

His Pro Thr Trp Gly Asp Glu Gln Leu Phe Gln Thr Ala Arg Leu Ile
        355                 360                 365

Leu Ile Gly Glu Thr Ile Lys Ile Val Ile Glu Glu Tyr Val Gln Gln
    370                 375                 380

Leu Ser Gly Tyr Phe Leu Gln Leu Lys Phe Asp Pro Glu Leu Leu Phe
385                 390                 395                 400

Ser Ala Gln Phe Gln Tyr Arg Asn Arg Ile Ala Met Glu Phe Asn Gln
                405                 410                 415

Leu Tyr His Trp His Pro Leu Met Pro Asp Ser Phe Trp Val Gly Ser
            420                 425                 430

Gln Glu Tyr Ser Tyr Glu Gln Phe Leu Phe Asn Thr Ser Met Leu Thr
        435                 440                 445

His Tyr Gly Ile Glu Ala Leu Val Asp Ala Phe Ser Arg Gln Ser Ala
    450                 455                 460

Gly Arg Ile Gly Gly Gly Arg Asn Ile Asp His His Val Leu His Val
465                 470                 475                 480

Ala Val Glu Thr Ile Lys Glu Ser Arg Glu Leu Arg Leu Gln Pro Phe
                485                 490                 495

Asn Glu Tyr Arg Lys Arg Phe Gly Met Arg Pro Tyr Met Ser Phe Gln
            500                 505                 510

Glu Leu Thr Gly Glu Lys Glu Met Ala Ala Glu Leu Glu Glu Leu Tyr
        515                 520                 525

Gly Asp Ile Asp Ala Leu Glu Phe Tyr Pro Gly Leu Leu Leu Glu Lys
    530                 535                 540

Cys His Pro Asn Ser Ile Phe Gly Glu Ser Met Ile Glu Ile Gly Ala
545                 550                 555                 560

Pro Phe Ser Leu Lys Gly Leu Leu Gly Asn Pro Ile Cys Ser Pro Glu
                565                 570                 575

Tyr Trp Lys Pro Ser Thr Phe Gly Gly Glu Met Gly Phe Asn Met Val
            580                 585                 590

Lys Thr Ala Thr Leu Lys Lys Leu Val Cys Leu Asn Thr Lys Thr Cys
        595                 600                 605

Pro Tyr Val Ser Phe Arg Val Pro Asp Pro His Gln Asp Gly Gly Pro
    610                 615                 620

Gly Val Gln Arg Pro Ser Thr Glu Leu
625                 630

<210> SEQ ID NO 3
<211> LENGTH: 2706
<212> TYPE: DNA
<213> ORGANISM: Canis familiaris

<400> SEQUENCE: 3
cggcgagcgc agcagccgcc cagagctatg agccgtgagt tcgaccctga ggcccccagg      60
aaccctcttc gcctcccggg ggagcctcga atgccaggcc agccctcac ctctcgctcc     120

```
gcagggggga gtcgcctgca ccggtggccg ctgctcctgc tgctgctgct gctgctcccg    180 ccgccccgg tcctgcccgc ggaagccgg accccggcgc ctgtgaaccc gtgttgttac      240
tacccatgtc agcaccaagg gatctgtgtc cgcttcggcc ttgaccgcta ccagtgtgac    300
tgcacccgca cgggctattc tggccccaac tgcaccatcc ccgagctgtg gacctggctc    360
cggaattcac tgcgcccag tccctctttc ctccacttcc tgctgacgca tgggcgctgg     420
ttttgggaat tcatcaatgc caccttcatc cgtgacatgc tcatgcgtct ggtactcaca    480
gcgcgttcca accttatccc cagtcctccc acctacaaca tagcgcatga ctacatcagc    540
tgggagtcct tctccaatgt gagctattac actcgtgttc tgccctctgt gccccaagat    600
tgccccacgc ccatggggac caaagggaag aagcagttgc cagacgccca actcctgggc    660
cgtcgcttcc tgctcaggag gaagttcata cctgaccccc aaggcaccaa cctcatgttc    720
gccttctttg cacaacactt cacccatcag ttcttcaaaa cttctggcaa gatgggtcct    780
ggcttcacca aggccttggg ccatggggta gatcttggcc acatttatgg ggacaatctg    840
gaccgtcagt atcagctgcg gctctttaag gatgggaaac tcaagtatca ggttctggat    900
ggagagatgt accgccatc tgtggaggag gcgcctgtgt tgatgcacta cccacggggc     960
attctgcccc agagtcagat ggccgtgggc caggaggtgt ttgggctgct tcctgggctc    1020
atgctctatg ccacgctctg gctgcgtgag cacaatcgtg tgtgtgacct gctgaaggct    1080
gagcacccca cttggggtga tgagcaactc ttccagacgg cccgactcat cctcattggg    1140
gagaccatca agattgtgat tgaggagtat gtgcagcagc tgagtggcta cttcttgcag    1200
ctgaagttcg acccggagct gctgtttagc gcccagttcc agtaccgcaa ccgcatcgcc    1260
atggagttca ccagctgta ccactggcac ccgctcatgc cagactcctt ctgggtgggt     1320
tcccaggagt acagctatga gcagttcctg ttcaacacct ccatgctgac gcactacggg    1380
atcgaggccc tggtggatgc cttctctcgc cagagcgccg gccggattgg tggaggtaga    1440
aacatagacc accatgtcct gcacgtggct gtggaaacca tcaaggaatc ccgcgagttg    1500
cggctgcagc ccttcaatga gtaccgcaag aggtttggca tgaggcccta catgtccttc    1560
caggaactca caggggagaa ggagatggca gccgagttgg aggagctgta tggagacatt    1620
gatgccttgg aattctaccc ggggcttctt ctggagaagt gccatccaaa ctccatcttt    1680
ggagagagta tgatagaaat tggggctccc ttctccctta agggcctcct agggaatccc    1740
atctgttctc cagagtactg gaagccaagc acattcggtg gtgagatggg cttcaatatg    1800
gtcaagacag ccacactgaa gaagctggtc tgccttaaca ccaagacttg tcccctatgtt   1860 tccttccgtg tgcctgaccc ccaccaggat ggcgggcctg gtgtgcagcg gccgtccaca    1920
gagctctgag ggggcagagc agcagcattc tggagggtga acttgtcatc ccagaatgct    1980
gaggctgggg ttaataatcc caaatgttgg gtctttggtt tgcctcaaga atatcaaggt    2040
caacatttag aactttgtgt ctctcaccca ttatctggaa tatcatggtc ttgtttgtta    2100
ttctagaatg ctgaattcct ggttgaccat ctagaatgga tggagtgatg cttctttggc    2160
aagccagaac actggttcct ggccgacaac ctagaatgtc agacttctgg ttgacttaag    2220
acgtaggcat tctctaatgt gaagctcctg acagaatcat ctagaaagat aggggattct    2280
tattttgcat tctagaattc tgggcagccc tccagcatgt tgattttttt cactggcagt    2340
tcagaatgtt gtgctcttga ttgctgatcc aaaaatagtgg ctggtatgcc agatcagtct   2400
tgctctgaat gcctagaatg gtaatttgat tcatttttcct gttcagtgag ataccccaa    2460 agcaggagaa tctacagcct aaccagagtg cattgcctgc ctctgtgcct gccccgagga   2520
```

-continued

```
cttaggggc agagtgttct tcctgggacg ctgactcaga ccctggtcca aggagctaga    2580
acaggtgggc tttttccagg tcattggttg gaggccacca gagctctgtt gccatctttg    2640
tcttgactca tgacagctgt ttctcatgaa actaataaaa ttcttttcc aaaaaaaaaa    2700 aaaaaa                                                              2706
```

<210> SEQ ID NO 4
<211> LENGTH: 1245
<212> TYPE: DNA
<213> ORGANISM: Canis familiaris

<400> SEQUENCE: 4

```
atgagccgtg agttcgaccc tgaggccccc aggaaccctc ttcgcctccc gggggagcct     60
cgaatgccag gcccagccct cacctctcgc tccgcagggg ggagtcgcct gcaccggtgg    120
ccgctgctcc tgctgctgct gctgctgctc ccgccgcccc cggtcctgcc cgcggaagcc    180
cggaccccgg cgcctgtgaa cccgtgttgt tactacccat gtcagcacca agggatctgt    240
gtccgcttcg gccttgaccg ctaccagtgt gactgcaccc gcacgggcta ttctggcccc    300
aactgcacca tccccgagct gtggacctgg ctccggaatt cactgcgccc cagtccctct    360
ttcctccact tcctgctgac gcatgggcgc tggttttggg aattcatcaa tgccaccttc    420
atccgtgaca tgctcatgcg tctggtactc acagggagaa ccatcaagat tgtgattgag    480
gagtatgtgc agcagctgag tggctacttc ttgcagctga gttcgacccc ggagctgctg    540
tttagcgccc agttccagta ccgcaaccgc atcgccatgg agttcaacca gctgtaccac    600
tggcacccgc tcatgccaga ctccttctgg gtgggttccc aggagtacag ctatgagcag    660
ttcctgttca cacctccat gctgacgcac tacgggatcg aggccctggt ggatgccttc    720
tctcgccaga gcgccggccg gattggtgga ggtagaaaca tagaccacca tgtcctgcac    780
gtggctgtgg aaaccatcaa ggaatcccgc gagttgcggc tgcagcccct caatgagtac    840
cgcaagaggt ttggcatgag gccctacatg tccttccagg aactcacagg ggagaaggag    900
atggcagccg agttggagga gctgtatgga cacttgatgc cttggaatt ctacccgggg    960 cttcttctgg agaagtgcca tccaaactcc atctttggag agagtatgat agaaattggg   1020
gctcccttct cccttaaggg cctcctaggg aatcccatct gttctccaga gtactggaag   1080
ccaagcacat tcggtggtga gatgggcttc aatatggtca agacagccac actgaagaag   1140
ctggtctgcc ttaacaccaa gacttgtccc tatgtttcct tccgtgtgcc tgaccccac   1200 caggatggcg ggcctggtgt gcagcggccg tccacagagc tctga                    1245
```

<210> SEQ ID NO 5
<211> LENGTH: 414
<212> TYPE: PRT
<213> ORGANISM: Canis familiaris

<400> SEQUENCE: 5

```
Met Ser Arg Glu Phe Asp Pro Glu Ala Pro Arg Asn Pro Leu Arg Leu
 1               5                  10                  15

Pro Gly Glu Pro Arg Met Pro Gly Pro Ala Leu Thr Ser Arg Ser Ala
            20                  25                  30

Gly Gly Ser Arg Leu His Arg Trp Pro Leu Leu Leu Leu Leu Leu Leu
        35                  40                  45

Leu Leu Pro Pro Pro Pro Val Leu Pro Ala Glu Ala Arg Thr Pro Ala
    50                  55                  60
```

```
Pro Val Asn Pro Cys Cys Tyr Tyr Pro Cys Gln His Gln Gly Ile Cys
 65                  70                  75                  80

Val Arg Phe Gly Leu Asp Arg Tyr Gln Cys Asp Cys Thr Arg Thr Gly
                 85                  90                  95

Tyr Ser Gly Pro Asn Cys Thr Ile Pro Glu Leu Trp Thr Trp Leu Arg
            100                 105                 110

Asn Ser Leu Arg Pro Ser Pro Ser Phe Leu His Phe Leu Leu Thr His
        115                 120                 125

Gly Arg Trp Phe Trp Glu Phe Ile Asn Ala Thr Phe Ile Arg Asp Met
    130                 135                 140

Leu Met Arg Leu Val Leu Thr Gly Glu Thr Ile Lys Ile Val Ile Glu
145                 150                 155                 160

Glu Tyr Val Gln Gln Leu Ser Gly Tyr Phe Gln Leu Lys Phe Asp
                165                 170                 175

Pro Glu Leu Leu Phe Ser Ala Gln Phe Gln Tyr Arg Asn Arg Ile Ala
                180                 185                 190

Met Glu Phe Asn Gln Leu Tyr His Trp His Pro Leu Met Pro Asp Ser
            195                 200                 205

Phe Trp Val Gly Ser Gln Glu Tyr Ser Tyr Glu Gln Phe Leu Phe Asn
210                 215                 220

Thr Ser Met Leu Thr His Tyr Gly Ile Glu Ala Leu Val Asp Ala Phe
225                 230                 235                 240

Ser Arg Gln Ser Ala Gly Arg Ile Gly Gly Gly Arg Asn Ile Asp His
                245                 250                 255

His Val Leu His Val Ala Val Glu Thr Ile Lys Glu Ser Arg Glu Leu
            260                 265                 270

Arg Leu Gln Pro Phe Asn Glu Tyr Arg Lys Arg Phe Gly Met Arg Pro
        275                 280                 285

Tyr Met Ser Phe Gln Glu Leu Thr Gly Glu Lys Glu Met Ala Ala Glu
    290                 295                 300

Leu Glu Glu Leu Tyr Gly Asp Ile Asp Ala Leu Glu Phe Tyr Pro Gly
305                 310                 315                 320

Leu Leu Leu Glu Lys Cys His Pro Asn Ser Ile Phe Gly Glu Ser Met
                325                 330                 335

Ile Glu Ile Gly Ala Pro Phe Ser Leu Lys Gly Leu Leu Gly Asn Pro
            340                 345                 350

Ile Cys Ser Pro Glu Tyr Trp Lys Pro Ser Thr Phe Gly Gly Glu Met
        355                 360                 365

Gly Phe Asn Met Val Lys Thr Ala Thr Leu Lys Lys Leu Val Cys Leu
    370                 375                 380

Asn Thr Lys Thr Cys Pro Tyr Val Ser Phe Arg Val Pro Asp Pro His
385                 390                 395                 400

Gln Asp Gly Gly Pro Gly Val Gln Arg Pro Ser Thr Glu Leu
                405                 410

<210> SEQ ID NO 6
<211> LENGTH: 1901
<212> TYPE: DNA
<213> ORGANISM: Canis familiaris

<400> SEQUENCE: 6
cggggagctc ctggcaccgg cgccccggga gcccgcagtc tgcaccccga gcgcagcagc    60
cgcccagagc tatgagccgt gagttcgacc tgaggccccc aggaacccct cttcgcctcc   120
cgggggagcc tcgaatgcca ggcccagccc tcacctctcg ctccgcaggg gggagtcgcc   180
```

```
tgcaccggtg ccgctgctc ctgctgctgc tgctgctgct cccgccgccc ccggtcctgc     240
ccgcggaagc ccggaccccg gcgcctgtga acccgtgttg ttactaccca tgtcagcacc     300
aagggatctg tgtccgcttc ggccttgacc gctaccagtg tgactgcacc cgcacgggct     360
attctggccc caactgcacc atccccgagc tgtggacctg gctccggaat tcactgcgcc     420
ccagtccctc tttcctccac ttcctgctga cgcatgggcg ctggttttgg gaattcatca     480
atgccacctt catccgtgac atgctcatgc gtctggtact cacaggggag accatcaaga     540
ttgtgattga ggagtatgtg cagcagctga gtggctactt cttgcagctg aagttcgacc     600
cggagctgct gtttagcgcc cagttccagt accgcaaccg catcgccatg gagttcaacc     660
agctgtacca ctggcacccg ctcatgccag actccttctg ggtgggttcc caggagtaca     720
gctatgagca gttcctgttc aacacctcca tgctgacgca ctacgggatc gaggccctgg     780
tggatgcctt ctctcgccag agcgccggcc ggattggtgg aggtagaaac atagaccacc     840
atgtcctgca cgtggctgtg gaaaccatca aggaatcccg cgagttgcgg ctgcagccct     900
tcaatgagta ccgcaagagg tttggcatga ggccctacat gtccttccag gaactcacag     960
gggagaagga gatggcagcc gagttggagg agctgtatgg agacattgat gccttggaat    1020
tctacccggg gcttcttctg gagaagtgcc atccaaactc catctttgga gagagtatga    1080
tagaaattgg ggctcccttc tcccttaagg gcctcctagg gaatcccatc tgttctccag    1140
agtactggaa gccaagcaca ttcgtggtg agatgggctt caatatgtc aagacagcca     1200 cactgaagaa gctggtctgc cttaacacca agacttgtcc ctatgtttcc ttccgtgtgc    1260
ctgaccccca ccaggatggc gggcctggtg tgcagcggcc gtccacagag ctctgagggg    1320
gcagagcagc agcattctgg agggtggact tgtcatccca gaatgctgag gctggggtta    1380
ataatcccaa atgttgggtc tttggttgc ctcaagaata tcaaggtcaa catttagaac    1440
tttgtgtctc tcacccatta tctggaatat catggtcttg tttgttattc tagaatgctg    1500
aattcctggt tgaccatcta gaatggatgg agtgatgctt ctttggcaag ccagaacact    1560
ggttcctggc cgacaaccta gaatgtcaga cttctggttg acttaagacg taggcattct    1620
ctaatgtgaa gctcctgaca gaatcatcta gaaagatagg ggattcttat tttgcattct    1680
agaattctgg gcagccctcc agcatgttga ttttttttcac tggcagttca gaatgttgtg    1740
ctcttgattg ctgatccaaa atagtggctg gtatgccaga tcagtcttgc tctgaatgcc    1800
tagaatggta atttgattca ttttcctgtt cagtgagata cccccaaagc aggagaatct    1860
acagcctaac cagagtgcat tgcctgcctc tgtgcctgcc c                       1901
```

<210> SEQ ID NO 7
<211> LENGTH: 25
<212> TYPE: DNA
<213> ORGANISM: Artificial Sequence
<220> FEATURE:
<223> OTHER INFORMATION: primer

<400> SEQUENCE: 7
cggatccgcc gcccagagct atgag                                           25

<210> SEQ ID NO 8
<211> LENGTH: 30
<212> TYPE: DNA
<213> ORGANISM: Artificial Sequence
<220> FEATURE:
<223> OTHER INFORMATION: primer

```
<400> SEQUENCE: 8
cgccatcctg gtgggggtca ggcacacgga                                          30

<210> SEQ ID NO 9
<211> LENGTH: 32
<212> TYPE: DNA
<213> ORGANISM: Artificial Sequence
<220> FEATURE:
<223> OTHER INFORMATION: primer

<400> SEQUENCE: 9
cggatcctgg aataggccac cggatggaag ga                                       32

<210> SEQ ID NO 10
<211> LENGTH: 1894
<212> TYPE: DNA
<213> ORGANISM: Homo sapiens

<400> SEQUENCE: 10
atgagccgtg agtgcgaccc cggtgcccgg tggggaattt tcttggcctc ctggtggagc         60
cttgaatgcc aggctcagcc cctcatctct ctcctctgca gggagtctct tgctccggtt        120
cttgctgttc ctgctcctgc tcccgccgct ccccgtcctg ctcgcggacc caggggcgcc        180
cacgccagtg aatccctgtt gttactatcc atgccagcac cagggcatct gtgtccgctt        240
cggccttgac cgctaccagt gtgactgcac ccgcacgggc tattccggcc caactgcac         300 catccctggc ctgtggacct ggctccggaa ttcactgcgg cccagcccct cttcacccca        360
cttcctgctc actcacgggc gctggttctg ggagtttgtc aatgccacct tcatccgaga        420
gatgctcatg cgcctggtac tcacagtgcg ctccaacctt atccccagtc cccccaccta        480
caactcagca catgactaca tcagctggga gtctttctcc aacgtgagct attacactcg        540
tattctgccc tctgtgccta agattgccc cacacccatg ggaaccaaag ggaagaagcg        600
gttgccagat gcccagctcc tggcccgccg cttcctgctc aggaggaagt tcatacctga        660
cccccaaggc accaacctca tgtttgcctt ctttgcacaa cacttcaccc accagttctt        720
caaaacttct ggcaagatgg gtcctggctt caccaaggcc ttgggccatg ggtagacct        780 cggccacatt tatggagaca atctggagcg tcagtatcaa ctgcggctct ttaaggatgg        840
gaaactcaag taccaggtgc tggatggaga aatgtacccg ccctcggtag aagaggcgcc        900
tgtgttgatg cactaccccc gaggcatccc gccccagagc cagatggctg tgggccagga        960
ggtgtttggg ctgcttcctg gctcatgct gtatgccacg ctctggctac gtgagcacaa       1020
ccgtgtgtgt gacctgctga aggctgagca ccccacctgg ggcgatgagc agcttttcca       1080
gacgacccgc ctcatcctca tagggagac catcaagatt gtcatcgagg agtacgtgca       1140
gcagctgagt ggctatttcc tgcagctgaa atttgaccca gagctgctgt tcggtgtcca       1200
gttccaaata cgcaaccgca ttgccatgga gttcaaccat ctctaccact ggcaccccct       1260
catgcctgac tccttcaagg tgggctccca ggagtacagc tacgagcagt tcttgttcaa       1320
cacctccatg ttggtggact atggggttga ggccctggtg gatgccttct ctcgccagat       1380
tgctggccgg atcggtgggg gcaggaacat ggaccaccac atcctgcatg tggctgtgga       1440
tgtcatcagg gagtctcggg agatgcggct gcagccttc aatgagtacc gcaagaggtt       1500
tggcatgaaa ccctacacct ccttccagga gctcgtagga gagaaggaga tggcagcaga       1560
gttggaggaa tcgtatggag acattgatgc gttgagttc tacctgacc tgcttcttga       1620 aaagtgccat ccaaactcta tctttgggga gagtatgata gagattggg ctccctttc       1680
```

| cctcaagggt ctcctaggga atcccatctg ttctccggag tactggaagc cgagcacatt | 1740 |
| tggcggcgag gtgggcttta acattgtcaa gacggccaca ctgaagaagc tggtctgcct | 1800 |
| caacaccaag acctgtccct acgtttcctt ccgtgtgccg gatgccagtc aggatgatgg | 1860 |
| gcctgctgtg gagcgaccat ccacagagct ctga | 1894 |

<210> SEQ ID NO 11
<211> LENGTH: 1894
<212> TYPE: DNA
<213> ORGANISM: Homo sapiens

<400> SEQUENCE: 11

| atgagccgtg agtgcgaccc cggtgcccgg tggggaattt tcttggcctc ctggtggagc | 60 |
| cttgaatgcc aggctcagcc cctcatctct ctcctctgca gggagtctct tgctccggtt | 120 |
| cttgctgttc ctgctcctgc tcccgccgct ccccgtcctg ctcgcggacc caggggcgcc | 180 |
| cacgccagtg aatccctgtt gttactatcc atgccagcac cagggcatct gtgtccgctt | 240 |
| cggccttgac cgctaccagt gtgactgcac ccgcacgggc tattccgcc caactgcac | 300 |
| catccctggc ctgtggacct ggctccggaa ttcactgcgg cccagcccct ctttcaccca | 360 |
| cttcctgctc actcacgggc gctggttctg ggagtttgtc aatgccacct catccgaga | 420 |
| gatgctcatg cgcctggtac tcacagtgcg ctccaacctt atccccagtc cccccaccta | 480 |
| caactcagca catgactaca tcagctggga gtctttctcc aacgtgagct attacactcg | 540 |
| tattctgccc tctgtgccta aagattgccc cacacccatg ggaaccaaag ggaagaagca | 600 |
| gttgccagat gcccagctcc tggcccgccg cttcctgctc aggaggaagt tcatacctga | 660 |
| cccccaaggc accaacctca tgtttgcctt ctttgcacaa cacttcaccc accagttctt | 720 |
| caaaacttct ggcaagatgg gtcctggctt caccaaggcc ttgggccatg gggtagacct | 780 |
| cggccacatt tatggagaca atctggagcg tcagtatcaa ctgcggctct ttaaggatgg | 840 |
| gaaactcaag taccaggtgc tggatggaga aatgtgcccg ccctcggtag aagaggcgcc | 900 |
| tgtgttgatg cactacccc gaggcatccc gccccagagc cagatggctg tgggccagga | 960 |
| ggtgtttggg ctgcttcctg ggctcatgct gtatgccacg ctctggctac gtgagcacaa | 1020 |
| ccgtgtgtgt gacctgctga aggctgagca ccccacctgg ggcgatgagc agcttttcca | 1080 |
| gacgacccgc ctcatcctca tagggaagac catcaagatt gtcatcgagg agtacgtgca | 1140 |
| gcagctgagt ggctatttcc tgcagctgaa atttgaccca gagctgctgt tcggtgtcca | 1200 |
| gttccaatac cgcaaccgca ttgccatgga gttcaaccat ctctaccact ggcaccccct | 1260 |
| catgcctgac tccttcaagg tgggctccca ggagtacagc tacgagcagt tcttgttcaa | 1320 |
| cacctccatg ttggtggact atgggggttga ggccctggtg gatgccttct ctcgccagat | 1380 |
| tgctggccgg atcggtgggg gcaggaacat ggaccaccac atcctgcatg tggctgtgga | 1440 |
| tgtcatcagg gagtctcggg agatgcggct gcagcccttc aatgagtacc gcaagaggtt | 1500 |
| tggcatgaaa ccctacacct ccttccagga gctcgtagga gagaaggaga tggcagcaga | 1560 |
| gttggaggaa ttgtatggag acattgatgc gttggagttc taccctggac tgcttcttga | 1620 |
| aaagtgccat ccaaactcta tctttgggga gagtatgata gagattgggg ctcccttttc | 1680 |
| cctcaagggt ctcctaggga atcccatctg ttctccggag tactggaagc cgagcacatt | 1740 |
| tggcggcgag gtgggcttta acattgtcaa gacggccaca ctgaagaagc tggtctgcct | 1800 |
| caacaccaag acctgtccct acgttccctt ccgtgtgccg gatgccagtc aggatgatgg | 1860 |

| gcctgctgtg gagcgaccat ccacagagct ctga | 1894 |

<210> SEQ ID NO 12
<211> LENGTH: 1746
<212> TYPE: DNA
<213> ORGANISM: Homo sapiens

<400> SEQUENCE: 12

| atgagccgtg agtgcgaccc cggtgcccgg tggggaattt tcttggcctc ctggtggagc | 60 |
| cttgaatgcc aggctcagcc cctcatctct ctcctctgca gggagtctct tgctccggtt | 120 |
| cttgctgttc ctgctcctgc tcccgccgct ccccgtcctg ctcgcggacc aggggcgcc | 180 |
| cacgccagtg aatccctgtt gttactatcc atgccagcac cagggcatct gtgtccgctt | 240 |
| cggccttgac cgctaccagt gtgactgcac ccgcacgggc tattccggcc caactgcac | 300 |
| catccctggc ctgtggacct ggctccggaa ttcgctgcgg cccagcccct ctttcaccca | 360 |
| cttcctgctc actcacgggc gctggttctg ggagtttgtc aatgccacct tcatccgaga | 420 |
| gatgctcatg cgcctggtac tcacagtgcg ctccaacctt atcccagtc ccccaccta | 480 |
| caactcagca catgactaca tcagctggga gtctttctcc aacgtgagct attacactcg | 540 |
| tattctgccc tctgtgccta aagattgccc cacacccatg gaaccaaag ggaagaagca | 600 |
| gttgccagat gccagctcc tggcccgcgc cttcctgctc aggaggaagt tcatacctga | 660 |
| cccccaaggc accaacctca tgtttgcctt ctttgcacaa cacttcaccc accagttctt | 720 |
| caaaacttct ggcaagatgg gtcctggctt caccaaggcc ttgggccatg ggtagacct | 780 |
| cggccacatt tatggagaca atctggagcg tcagtatcaa ctgcggctct ttaaggatgg | 840 |
| gaaactcaag taccaggtgc tggatggaga aatgtacccg ccctcggtag aggaggcgcc | 900 |
| tgtgttgatg cactaccccc gaggcatccc gccccagagc cagatggctg tgggccagga | 960 |
| ggtgtttggg ctgcttcctg ggctcatgct gtatgccacg ctctggctac gtgagcacaa | 1020 |
| ccgtgtgtgt gacctgctga aggctgagca ccccacctgg ggggatgagc agcttttcca | 1080 |
| gacgacccgc ctcatcctca tagggagac catcaagatt gtcatcgagg agtacgtgca | 1140 |
| gcagctgagt ggctatttcc tgcagctgaa atttgaccca gagctgctgt tcggtgtcct | 1200 |
| gttccaatac tgcaaccgca ttgccatgga gttcaaccat ctctaccact ggcacccct | 1260 |
| catgcctgac tccttcaagg tgggctccca ggagtacagc tacgagcagt tcttgttcaa | 1320 |
| cacctccatg ttagtggact atggggttga ggccctggtg gatgccttct ctcgccagat | 1380 |
| tactggccgg gagagaagga gatggcagca gagttggagg aattgtatgg agacattgat | 1440 |
| gcgttggagt tctaccctgg actgcttctt gaaaagtgcc atccaaactc tatctttggg | 1500 |
| gagagtatga tagagattgg ggctccctt tccctcaagg gtctcctagg gaatcccatc | 1560 |
| tgttctccgg agtactggaa gccgagcaca tttggcggcg aggtgggctt taacattgtc | 1620 |
| aagacggcca cactgaagaa gctggtctgc ctcaacacca agacctgtcc ctacgttcc | 1680 |
| ttccgtgtgc cggatgccag tcaggatgat gggcctgctg tggagcgacc atccacagag | 1740 |
| ctctga | 1746 |

<210> SEQ ID NO 13
<211> LENGTH: 1894
<212> TYPE: DNA
<213> ORGANISM: Homo sapiens

<400> SEQUENCE: 13

| atgagccgtg agtgcgaccc cggtgcccgg tggggaattt tcttggcctc ctggtggagc | 60 |

```
cttgaatgcc aggctcagcc cctcatctct ctcctctgca gggagtctct tgctccggtt      120
cttgctgttc ctgctcctgc tcccgccgct ccccgtcctg ctcgcggacc aggggcgcc       180 cacgccagtg aatccctgtt gttactatcc atgccagcac cagggcatct gtgtccgctt      240
cggccttgac cgctaccagt gtgactgcac ccgcacgggc tattccggcc ccaactgcac      300
catccctggc ctgtggacct ggctccggaa ttcactgcgg cccagcccct ctttcaccca      360
cttcctgctc actcacgggc gctggttctg ggagtttgtc aatgccacct tcatccgaga      420
gatgctcatg cgcctggtac tcacagtgcg ctccaacctt atccccagtc cccccaccta      480
caactcagca catgactaca tcagctggga gtctttctcc aacgtgagct attacactcg      540
tattctgccc tctgtgccta agattgccc acacccatg ggaaccaaag ggaagaagca       600
gttgccagat gcccagctcc tggcccgccg cttcctgctc aggaggaagt tcatacctga      660
cccccaaggc accaacctca tgtttgcctt ctttgcacaa cacttcaccc accagttctt      720
caaaacttct ggcaagatgg gtcctggctt caccaaggcc ttgggccatg gggtagacct      780
cggccacatt tatggagaca atctggagcg tcagtatcaa ctgcggctct ttaaggatgg      840
gaaactcaag taccaggtgc tggatggaga aatgtacccg ccctcggtag aagaggcgcc      900
tgtgttgatg cactaccccc gaggcatccc gccccagagc cagatggctg tgggccagga      960
ggtgtttggg ctgcttcctg gctcatgct gtatgccacg ctctggctac gtgagcacaa       1020
ccgtgtgtgt gacctgctga aggctgagca ccccacctgg ggcgatgagc agcttttcca      1080
gacgacccgc ctcatcctca tagggagac catcaagatt gtcatcgagg agtacgtgca       1140
gcagctgagt ggctatttcc tgcagctgaa atttgaccca gagctgctgt cggtgtccca      1200
gttccaatac cgcaaccgca ttgccatgga gttcaaccat ctctaccact ggcacccct       1260 catgcctgac tccttcaagg tgggctccca ggagtacagc tacgagcagt tcttgttcaa     1320
cacctccatg ttggtggact atggggttga ggccctggtg gatgccttct ctcgccagat     1380
tgctggccgg atcggtgggg caggaacat ggaccaccac atcctgcatg tggctgtgga     1440
tgtcatcagg gagtctcggg agatgcggct gcagcccttc aatgagtacc gcaagaggtt     1500
tggcatgaaa ccctacacct ccttccagga gctcgtagga gagaaggaga tggcagcaga     1560
gttggaggaa ttgtatggag acattgatgc gttggagttc tacccttggac tgcttcttga    1620 aaagtgccat ccaaactcta tctttgggga gagtatgata gagattgggg ctccctttcc     1680
cctcaagggt ctcctaggga atcccatctg ttctccggag tactggaagc cgagcacatt     1740
tggcggcgag gtgggcttta acattgtcaa gacggccaca ctgaagaagc tggtctgcct     1800
caacaccaag acctgtccct acgtttcctt ccgtgtgccg gatgccagtc aggatgatgg     1860
gcctgctgtg gagcgaccat ccacagagct ctga                                  1894
```

<210> SEQ ID NO 14
<211> LENGTH: 613
<212> TYPE: PRT
<213> ORGANISM: Homo sapiens

<400> SEQUENCE: 14

Met Ser Arg Glu Cys Asp Pro Gly Ala Arg Trp Gly Ile Phe Leu Ala
1               5                   10                  15

Ser Trp Trp Ser Leu Glu Cys Gln Ala Gln Pro Leu Ile Ser Leu Leu
            20                  25                  30

Cys Arg Glu Ser Leu Ala Pro Val Leu Ala Val Pro Ala Pro Ala Pro
        35                  40                  45

-continued

```
Ala Ala Pro Arg Pro Ala Arg Gly Pro Arg Gly Ala His Ala Ser Glu
    50                  55                  60
Ser Leu Leu Leu Leu Ser Met Pro Ala Pro Gly His Leu Cys Pro Leu
65                  70                  75                  80
Arg Pro Pro Leu Pro Val Leu His Pro His Gly Leu Phe Arg Pro Gln
                85                  90                  95
Leu His His Pro Trp Pro Val Asp Leu Ala Pro Glu Phe Thr Ala Ala
            100                 105                 110
Gln Pro Leu Phe His Pro Leu Ala His Ser Arg Ala Leu Val Leu
        115                 120                 125
Gly Val Cys Gln Cys His Leu His Pro Arg Asp Ala His Ala Pro Gly
    130                 135                 140
Thr His Ser Ala Leu Gln Pro Tyr Pro Gln Ser Pro His Leu Gln Leu
145                 150                 155                 160
Ser Thr Leu His Gln Leu Gly Val Phe Leu Gln Arg Glu Leu Leu His
                165                 170                 175
Ser Tyr Ser Ala Leu Cys Ala Arg Leu Pro His Thr His Gly Asn Gln
            180                 185                 190
Arg Glu Glu Ala Val Ala Arg Cys Pro Ala Pro Gly Pro Pro Leu Pro
        195                 200                 205
Ala Gln Glu Glu Val His Thr Pro Pro Arg His Gln Pro His Val Cys
    210                 215                 220
Leu Leu Cys Thr Thr Leu His Pro Pro Val Leu Gln Asn Phe Trp Gln
225                 230                 235                 240
Asp Gly Ser Trp Leu His Gln Gly Leu Gly Pro Trp Gly Arg Pro Arg
                245                 250                 255
Pro His Leu Trp Arg Gln Ser Gly Ala Ser Val Ser Thr Ala Ala Leu
            260                 265                 270
Gly Trp Glu Thr Gln Val Pro Gly Ala Gly Trp Arg Asn Val Pro Ala
        275                 280                 285
Leu Gly Arg Arg Gly Ala Cys Val Asp Ala Leu Pro Pro Arg His Pro
    290                 295                 300
Ala Pro Glu Pro Asp Gly Cys Gly Pro Gly Gly Val Trp Ala Ala Ser
305                 310                 315                 320
Trp Ala His Ala Val Cys His Ala Leu Ala Thr Ala Gln Pro Cys Val
                325                 330                 335
Pro Ala Glu Gly Ala Pro His Leu Gly Arg Ala Ala Phe Pro Asp Asp
            340                 345                 350
Pro Pro His Pro His Arg Gly Asp His Gln Asp Cys His Arg Gly Val
        355                 360                 365
Arg Ala Ala Ala Glu Trp Leu Phe Pro Ala Ala Glu Ile Pro Arg Ala
    370                 375                 380
Ala Val Arg Cys Pro Val Pro Ile Pro Gln Pro His Cys His Gly Val
385                 390                 395                 400
Gln Pro Ser Leu Pro Leu Ala Pro Pro His Ala Leu Leu Gln Gly Gly
                405                 410                 415
Leu Pro Gly Val Gln Leu Arg Ala Val Leu Val Gln His Leu His Val
            420                 425                 430
Gly Gly Leu Trp Gly Gly Pro Gly Gly Cys Leu Leu Ser Pro Asp Cys
        435                 440                 445
Trp Pro Asp Arg Trp Gly Gln Glu His Gly Pro Pro His Pro Ala Cys
    450                 455                 460
```

-continued

```
Gly Cys Gly Cys His Gln Gly Val Ser Gly Asp Ala Ala Ala Leu
465                 470                 475                 480

Gln Val Pro Gln Glu Val Trp His Glu Thr Leu His Leu Leu Pro Gly
                485                 490                 495

Ala Arg Arg Arg Glu Gly Asp Gly Ser Arg Val Gly Gly Ile Val Trp
            500                 505                 510

Arg His Cys Val Gly Val Leu Pro Trp Thr Ala Ser Lys Val Pro Ser
        515                 520                 525

Lys Leu Tyr Leu Trp Gly Glu Tyr Asp Arg Asp Trp Gly Ser Leu Phe
    530                 535                 540

Pro Gln Gly Ser Pro Arg Glu Ser His Leu Phe Ser Gly Val Leu Glu
545                 550                 555                 560

Ala Glu His Ile Trp Arg Arg Gly Gly Leu His Cys Gln Asp Gly His
                565                 570                 575

Thr Glu Glu Ala Gly Leu Pro Gln His Gln Asp Leu Ser Leu Arg Phe
            580                 585                 590

Leu Pro Cys Ala Gly Cys Gln Ser Gly Trp Ala Cys Cys Gly Ala Thr
        595                 600                 605

Ile His Arg Ala Leu
    610

<210> SEQ ID NO 15
<211> LENGTH: 629
<212> TYPE: PRT
<213> ORGANISM: Homo sapiens

<400> SEQUENCE: 15

Ala Val Ser Ala Thr Pro Val Pro Gly Gly Glu Phe Ser Trp Pro Pro
1               5                   10                  15

Gly Gly Ala Leu Asn Ala Arg Leu Ser Pro Ser Ser Leu Ser Ser Ala
            20                  25                  30

Gly Ser Leu Leu Leu Arg Phe Leu Phe Leu Leu Leu Leu Pro Pro
        35                  40                  45

Leu Pro Val Leu Leu Ala Asp Pro Gly Ala Pro Thr Pro Val Asn Pro
    50                  55                  60

Cys Cys Tyr Tyr Pro Cys Gln His Gln Gly Ile Cys Val Arg Phe Gly
65                  70                  75                  80

Leu Asp Arg Tyr Gln Cys Asp Cys Thr Arg Thr Gly Tyr Ser Gly Pro
                85                  90                  95

Asn Cys Thr Ile Pro Gly Leu Trp Thr Trp Leu Arg Asn Ser Leu Arg
            100                 105                 110

Pro Ser Pro Ser Phe Thr His Phe Leu Leu Thr His Gly Arg Trp Phe
        115                 120                 125

Trp Glu Phe Val Asn Ala Thr Phe Ile Arg Glu Met Leu Met Arg Leu
    130                 135                 140

Val Leu Thr Val Arg Ser Asn Leu Ile Pro Ser Pro Pro Thr Tyr Asn
145                 150                 155                 160

Ser Ala His Asp Tyr Ile Ser Trp Glu Ser Phe Ser Asn Val Ser Tyr
                165                 170                 175

Tyr Thr Arg Ile Leu Pro Ser Val Pro Lys Asp Cys Pro Thr Pro Met
            180                 185                 190

Gly Thr Lys Gly Lys Lys Gln Leu Pro Asp Ala Gln Leu Leu Ala Arg
        195                 200                 205

Arg Phe Leu Leu Arg Arg Lys Phe Ile Pro Asp Pro Gln Gly Thr Asn
    210                 215                 220
```

-continued

```
Leu Met Phe Ala Phe Phe Ala Gln His Phe Thr His Gln Phe Phe Lys
225                 230                 235                 240

Thr Ser Gly Lys Met Gly Pro Gly Phe Thr Lys Ala Leu Gly His Gly
            245                 250                 255

Val Asp Leu Gly His Ile Tyr Gly Asp Asn Leu Glu Arg Gln Tyr Gln
        260                 265                 270

Leu Arg Leu Phe Lys Asp Gly Lys Leu Lys Tyr Gln Val Leu Asp Gly
            275                 280                 285

Glu Met Tyr Pro Pro Ser Val Glu Glu Ala Pro Val Leu Met His Tyr
    290                 295                 300

Pro Arg Gly Ile Pro Pro Gln Ser Gln Met Ala Val Gly Gln Glu Val
305                 310                 315                 320

Phe Gly Leu Leu Pro Gly Leu Met Leu Tyr Ala Thr Leu Trp Leu Arg
                325                 330                 335

Glu His Asn Arg Val Cys Asp Leu Leu Lys Ala Glu His Pro Thr Trp
            340                 345                 350

Gly Asp Glu Gln Leu Phe Gln Thr Thr Arg Leu Ile Leu Ile Gly Glu
        355                 360                 365

Thr Ile Lys Ile Val Ile Glu Glu Tyr Val Gln Gln Leu Ser Gly Tyr
    370                 375                 380

Phe Leu Gln Leu Lys Phe Asp Pro Glu Leu Leu Phe Gly Val Gln Phe
385                 390                 395                 400

Gln Tyr Arg Asn Arg Ile Ala Met Glu Phe Asn His Leu Tyr His Trp
                405                 410                 415

His Pro Leu Met Pro Asp Ser Phe Lys Val Gly Ser Gln Glu Tyr Ser
            420                 425                 430

Tyr Glu Gln Phe Leu Phe Asn Thr Ser Met Leu Val Asp Tyr Gly Val
        435                 440                 445

Glu Ala Leu Val Asp Ala Phe Ser Arg Gln Ile Ala Gly Arg Ile Gly
    450                 455                 460

Gly Gly Arg Asn Met Asp His His Ile Leu His Val Ala Val Asp Val
465                 470                 475                 480

Ile Arg Glu Ser Arg Glu Met Arg Leu Gln Pro Phe Asn Glu Tyr Arg
                485                 490                 495

Lys Arg Phe Gly Met Lys Pro Tyr Thr Ser Phe Gln Glu Leu Val Gly
            500                 505                 510

Glu Lys Glu Met Ala Ala Glu Leu Glu Glu Leu Tyr Gly Asp Ile Asp
        515                 520                 525

Ala Leu Glu Phe Tyr Pro Gly Leu Leu Leu Glu Lys Cys His Pro Asn
    530                 535                 540

Ser Ile Phe Gly Glu Ser Met Ile Glu Ile Gly Ala Pro Phe Ser Leu
545                 550                 555                 560

Lys Gly Leu Leu Gly Asn Pro Ile Cys Ser Pro Glu Tyr Trp Lys Pro
                565                 570                 575

Ser Thr Phe Gly Gly Glu Val Gly Phe Asn Ile Val Lys Thr Ala Thr
            580                 585                 590

Leu Lys Lys Leu Val Cys Leu Asn Thr Lys Thr Cys Pro Tyr Val Ser
        595                 600                 605

Phe Arg Val Pro Asp Ala Ser Gln Asp Asp Gly Pro Ala Val Glu Arg
    610                 615                 620

Pro Ser Thr Glu Leu
625
```

<210> SEQ ID NO 16
<211> LENGTH: 613
<212> TYPE: PRT
<213> ORGANISM: Homo sapiens

<400> SEQUENCE: 16

```
Glu Pro Val Arg Pro Arg Cys Pro Val Gly Asn Phe Leu Gly Leu Leu
 1               5                  10                  15
Val Glu Pro Met Pro Gly Ser Ala Pro His Leu Ser Pro Leu Gln Gly
             20                  25                  30
Val Ser Cys Ser Gly Ser Cys Cys Ser Cys Ser Cys Ser Arg Arg Ser
         35                  40                  45
Pro Ser Cys Ser Arg Thr Gln Gly Arg Pro Arg Gln Ile Pro Val Val
     50                  55                  60
Thr Ile His Ala Ser Thr Arg Ala Ser Val Ser Ala Ser Ala Leu Thr
 65                  70                  75                  80
Ala Thr Ser Val Thr Ala Pro Ala Arg Ala Ile Pro Ala Pro Thr Ala
                 85                  90                  95
Pro Ser Leu Ala Cys Gly Pro Gly Ser Gly Ile His Cys Gly Pro Ala
            100                 105                 110
Pro Leu Ser Pro Thr Ser Cys Ser Leu Thr Gly Ala Gly Ser Gly Ser
        115                 120                 125
Leu Ser Met Pro Pro Ser Ser Glu Arg Cys Ser Cys Ala Trp Tyr Ser
130                 135                 140
Gln Cys Ala Pro Thr Leu Ser Pro Val Pro Pro Thr Thr Gln His
145                 150                 155                 160
Met Thr Thr Ser Ala Gly Ser Leu Ser Pro Thr Ala Ile Thr Leu Val
                165                 170                 175
Phe Cys Pro Leu Cys Leu Lys Ile Ala Pro His Pro Trp Glu Pro Lys
            180                 185                 190
Gly Arg Ser Ser Cys Gln Met Pro Ser Ser Trp Pro Ala Ala Ser Cys
        195                 200                 205
Ser Gly Gly Ser Ser Tyr Leu Thr Pro Lys Ala Pro Thr Ser Cys Leu
    210                 215                 220
Pro Ser Leu His Asn Thr Ser Pro Thr Ser Ser Lys Leu Leu Ala
225                 230                 235                 240
Arg Trp Val Leu Ala Ser Pro Arg Pro Trp Ala Met Gly Thr Ser Ala
                245                 250                 255
Thr Phe Met Glu Thr Ile Trp Ser Val Ser Ile Asn Cys Gly Ser Leu
            260                 265                 270
Arg Met Gly Asn Ser Ser Thr Arg Cys Trp Met Glu Lys Cys Thr Arg
        275                 280                 285
Pro Arg Lys Arg Arg Leu Cys Cys Thr Thr Pro Glu Ala Ser Arg Pro
    290                 295                 300
Arg Ala Arg Trp Leu Trp Ala Arg Arg Cys Leu Gly Cys Phe Leu Gly
305                 310                 315                 320
Ser Cys Cys Met Pro Arg Ser Gly Tyr Val Ser Thr Thr Val Cys Val
                325                 330                 335
Thr Cys Arg Leu Ser Thr Pro Pro Gly Ala Met Ser Ser Phe Ser Arg
            340                 345                 350
Arg Pro Ala Ser Ser Ser Gly Arg Pro Ser Arg Leu Ser Ser Arg Ser
        355                 360                 365
Thr Cys Ser Ser Val Ala Ile Ser Cys Ser Asn Leu Thr Gln Ser Cys
    370                 375                 380
```

```
Cys Ser Val Ser Ser Asn Thr Ala Thr Ala Leu Pro Trp Ser Ser
385                 390                 395                 400

Thr Ile Ser Thr Thr Gly Thr Pro Ser Cys Leu Thr Pro Ser Arg Trp
            405                 410                 415

Ala Pro Arg Ser Thr Ala Thr Ser Ser Ser Cys Ser Thr Pro Pro Cys
            420                 425                 430

Trp Trp Thr Met Gly Leu Arg Pro Trp Trp Met Pro Ser Leu Ala Arg
            435                 440                 445

Leu Leu Ala Gly Ser Val Gly Ala Gly Thr Trp Thr Thr Thr Ser Cys
450                 455                 460

Met Trp Leu Trp Met Ser Ser Gly Ser Leu Gly Arg Cys Gly Cys Ser
465                 470                 475                 480

Pro Ser Met Ser Thr Ala Arg Gly Leu Ala Asn Pro Thr Pro Pro Ser
                485                 490                 495

Arg Ser Ser Glu Arg Arg Arg Trp Gln Gln Ser Trp Arg Asn Cys Met
            500                 505                 510

Glu Thr Leu Met Arg Trp Ser Ser Thr Leu Asp Cys Phe Leu Lys Ser
            515                 520                 525

Ala Ile Gln Thr Leu Ser Leu Gly Arg Val Arg Leu Gly Leu Pro Phe
530                 535                 540

Pro Ser Arg Val Ser Gly Ile Pro Ser Val Leu Arg Ser Thr Gly Ser
545                 550                 555                 560

Arg Ala His Leu Ala Ala Arg Trp Ala Leu Thr Leu Ser Arg Arg Pro
                565                 570                 575

His Arg Ser Trp Ser Ala Ser Thr Pro Arg Pro Val Pro Thr Phe Pro
            580                 585                 590

Ser Val Cys Arg Met Pro Val Arg Met Met Gly Leu Leu Trp Ser Asp
            595                 600                 605

His Pro Gln Ser Ser
        610

<210> SEQ ID NO 17
<211> LENGTH: 26
<212> TYPE: DNA
<213> ORGANISM: Artificial Sequence
<220> FEATURE:
<223> OTHER INFORMATION: primer

<400> SEQUENCE: 17
cggatcctgc gtcccgcacc ccagca                                    26

<210> SEQ ID NO 18
<211> LENGTH: 23
<212> TYPE: DNA
<213> ORGANISM: Artificial Sequence
<220> FEATURE:
<223> OTHER INFORMATION: primer

<400> SEQUENCE: 18
cggatccgcg ccatgagccg tga                                       23

<210> SEQ ID NO 19
<211> LENGTH: 30
<212> TYPE: DNA
<213> ORGANISM: Artificial Sequence
<220> FEATURE:
<223> OTHER INFORMATION: primer

<400> SEQUENCE: 19
```
cggatcctca gagctctgtg gatggtcgct                                30

<210> SEQ ID NO 20
<211> LENGTH: 13
<212> TYPE: PRT
<213> ORGANISM: Homo sapiens

<400> SEQUENCE: 20

Met Ser Arg Glu Cys Asp Pro Gly Ala Arg Trp Gly Cys
1               5                   10

<210> SEQ ID NO 21
<211> LENGTH: 13
<212> TYPE: PRT
<213> ORGANISM: Mus musculus

<400> SEQUENCE: 21

Met Ser Arg Glu Phe Asp Pro Glu Ala Pro Arg Asn Cys
1               5                   10

<210> SEQ ID NO 22
<211> LENGTH: 604
<212> TYPE: PRT
<213> ORGANISM: Homo sapiens

<400> SEQUENCE: 22

Met Leu Ala Arg Ala Leu Leu Leu Cys Ala Val Leu Ala Leu Ser His
1               5                   10                  15

Thr Ala Asn Pro Cys Cys Ser His Pro Cys Gln Asn Arg Gly Val Cys
                20                  25                  30

Met Ser Val Gly Phe Asp Gln Tyr Lys Cys Asp Cys Thr Arg Thr Gly
            35                  40                  45

Phe Tyr Gly Glu Asn Cys Ser Thr Pro Glu Phe Leu Thr Arg Ile Lys
        50                  55                  60

Leu Phe Leu Lys Pro Thr Pro Asn Thr Val His Tyr Ile Leu Thr His
65                  70                  75                  80

Phe Lys Gly Phe Trp Asn Val Val Asn Asn Ile Pro Phe Leu Arg Asn
                85                  90                  95

Ala Ile Met Ser Tyr Val Leu Thr Ser Arg Ser His Leu Ile Asp Ser
            100                 105                 110

Pro Pro Thr Tyr Asn Ala Asp Tyr Gly Tyr Lys Ser Trp Glu Ala Phe
        115                 120                 125

Ser Asn Leu Ser Tyr Tyr Thr Arg Ala Leu Pro Pro Val Pro Asp Asp
    130                 135                 140

Cys Pro Thr Pro Leu Gly Val Lys Gly Lys Lys Gln Leu Pro Asp Ser
145                 150                 155                 160

Asn Glu Ile Val Glu Lys Leu Leu Leu Arg Arg Lys Phe Ile Pro Asp
                165                 170                 175

Pro Gln Gly Ser Asn Met Met Phe Ala Phe Phe Ala Gln His Phe Thr
            180                 185                 190

His Gln Phe Phe Lys Thr Asp His Lys Arg Gly Pro Ala Phe Thr Asn
        195                 200                 205

Gly Leu Gly His Gly Val Asp Leu Asn His Ile Tyr Gly Glu Thr Leu
    210                 215                 220

Ala Arg Gln Arg Lys Leu Arg Leu Phe Lys Asp Gly Lys Met Lys Tyr
225                 230                 235                 240

Gln Ile Ile Asp Gly Glu Met Tyr Pro Pro Thr Val Lys Asp Thr Gln

```
                245                 250                 255
Ala Glu Met Ile Tyr Pro Pro Gln Val Pro Glu His Leu Arg Phe Ala
                260                 265                 270

Val Gly Gln Glu Val Phe Gly Leu Val Pro Gly Leu Met Met Tyr Ala
            275                 280                 285

Thr Ile Trp Leu Arg Glu His Asn Arg Val Cys Asp Val Leu Lys Gln
        290                 295                 300

Glu His Pro Glu Trp Gly Asp Glu Gln Leu Phe Gln Thr Ser Arg Leu
305                 310                 315                 320

Ile Leu Ile Gly Glu Thr Ile Lys Ile Val Glu Asp Tyr Val Gln
                325                 330                 335

His Leu Ser Gly Tyr His Phe Lys Leu Lys Phe Asp Pro Glu Leu Leu
            340                 345                 350

Phe Asn Lys Gln Phe Gln Tyr Gln Asn Arg Ile Ala Ala Glu Phe Asn
        355                 360                 365

Thr Leu Tyr His Trp His Pro Leu Leu Pro Asp Thr Phe Gln Ile His
        370                 375                 380

Asp Gln Lys Tyr Asn Tyr Gln Gln Phe Ile Tyr Asn Asn Ser Ile Leu
385                 390                 395                 400

Leu Glu His Gly Ile Thr Gln Phe Val Glu Ser Phe Thr Arg Gln Ile
                405                 410                 415

Ala Gly Arg Val Ala Gly Gly Arg Asn Val Pro Ala Val Gln Lys
            420                 425                 430

Val Ser Gln Ala Ser Ile Asp Gln Ser Arg Gln Met Lys Tyr Gln Ser
        435                 440                 445

Phe Asn Glu Tyr Arg Lys Arg Phe Met Leu Lys Pro Tyr Glu Ser Phe
    450                 455                 460

Glu Leu Thr Gly Glu Lys Glu Met Ser Ala Glu Leu Glu Ala Leu
465                 470                 475                 480

Tyr Gly Asp Ile Asp Ala Val Glu Leu Tyr Pro Ala Leu Leu Val Glu
                485                 490                 495

Lys Pro Arg Pro Asp Ala Ile Phe Gly Glu Thr Met Val Glu Val Gly
            500                 505                 510

Ala Pro Phe Ser Leu Lys Gly Leu Met Gly Asn Val Ile Cys Ser Pro
        515                 520                 525

Ala Tyr Trp Lys Pro Ser Thr Phe Gly Gly Glu Val Gly Phe Gln Ile
        530                 535                 540

Ile Asn Thr Ala Ser Ile Gln Ser Leu Ile Cys Asn Asn Val Lys Gly
545                 550                 555                 560

Cys Pro Phe Thr Ser Phe Ser Val Pro Asp Pro Glu Leu Ile Lys Thr
                565                 570                 575

Val Thr Ile Asn Ala Ser Ser Ser Arg Ser Gly Leu Asp Asp Ile Asn
            580                 585                 590

Pro Thr Val Leu Leu Lys Glu Arg Ser Thr Glu Leu
        595                 600

<210> SEQ ID NO 23
<211> LENGTH: 603
<212> TYPE: PRT
<213> ORGANISM: Ovis aries

<400> SEQUENCE: 23

Met Leu Ala Arg Ala Leu Leu Leu Cys Ala Ala Val Val Cys Gly Ala
 1               5                  10                  15
```

-continued

```
Ala Asn Pro Cys Cys Ser His Pro Cys Gln Asn Arg Gly Val Cys Met
             20                  25                  30

Ser Val Gly Phe Asp Gln Tyr Lys Cys Asp Cys Thr Arg Thr Gly Phe
         35                  40                  45

Tyr Gly Glu Asn Cys Thr Thr Pro Glu Phe Leu Thr Arg Ile Lys Leu
 50                  55                  60

Leu Leu Lys Pro Thr Pro Asp Thr Val His Tyr Ile Leu Thr His Phe
 65                  70                  75                  80

Lys Gly Val Trp Asn Ile Val Asn Lys Ile Ser Phe Leu Arg Asn Met
                 85                  90                  95

Ile Met Arg Tyr Val Leu Thr Ser Arg Ser His Leu Ile Glu Ser Pro
             100                 105                 110

Pro Thr Tyr Asn Val His Tyr Ser Tyr Lys Ser Trp Glu Ala Phe Ser
             115                 120                 125

Asn Leu Ser Tyr Tyr Thr Arg Ala Leu Pro Pro Val Pro Asp Asp Cys
 130                 135                 140

Pro Thr Pro Met Gly Val Lys Gly Arg Lys Glu Leu Pro Asp Ser Lys
145                 150                 155                 160

Glu Val Val Lys Lys Val Leu Leu Arg Arg Lys Phe Ile Pro Asp Pro
                 165                 170                 175

Gln Gly Thr Asn Leu Met Phe Ala Phe Phe Ala Gln His Phe Thr His
             180                 185                 190

Gln Phe Phe Lys Thr Asp Ile Glu Arg Gly Pro Ala Phe Thr Lys Gly
             195                 200                 205

Lys Asn His Gly Val Asp Leu Ser His Val Tyr Gly Glu Ser Leu Glu
 210                 215                 220

Arg Gln His Asn Arg Leu Phe Lys Asp Gly Lys Met Lys Tyr Gln
225                 230                 235                 240

Met Ile Asn Gly Glu Met Tyr Pro Pro Thr Val Lys Asp Thr Gln Val
                 245                 250                 255

Glu Met Ile Tyr Pro Pro His Ile Pro Glu His Leu Lys Phe Ala Val
             260                 265                 270

Gly Gln Glu Val Phe Gly Leu Val Pro Gly Leu Met Met Tyr Ala Thr
             275                 280                 285

Ile Trp Leu Arg Glu His Asn Arg Val Cys Asp Val Leu Lys Gln Glu
 290                 295                 300

His Pro Glu Trp Gly Asp Glu Gln Leu Phe Gln Thr Ser Arg Leu Ile
305                 310                 315                 320

Leu Ile Gly Glu Thr Ile Lys Ile Val Ile Glu Asp Tyr Val Gln His
                 325                 330                 335

Leu Ser Gly Tyr His Phe Lys Leu Lys Phe Asp Pro Glu Leu Leu Phe
             340                 345                 350

Asn Gln Gln Phe Gln Tyr Gln Asn Arg Ile Ala Ala Glu Phe Asn Thr
             355                 360                 365

Leu Tyr His Trp His Pro Leu Leu Pro Asp Val Phe Gln Ile Asp Gly
 370                 375                 380

Gln Glu Tyr Asn Tyr Gln Gln Phe Ile Tyr Asn Asn Ser Val Leu Leu
385                 390                 395                 400

Glu His Gly Val Thr Gln Phe Val Glu Ser Phe Thr Arg Gln Ile Ala
                 405                 410                 415

Gly Arg Val Ala Gly Arg Arg Asn Leu Pro Ala Ala Val Glu Lys Val
             420                 425                 430

Ser Lys Ala Ser Leu Asp Gln Ser Arg Glu Met Lys Tyr Gln Ser Phe
```

```
                    435                 440                 445
Asn Glu Tyr Arg Lys Arg Phe Leu Leu Lys Pro Tyr Glu Ser Phe Glu
    450                 455                 460

Glu Leu Thr Gly Glu Lys Glu Met Ala Ala Glu Leu Glu Ala Leu Tyr
465                 470                 475                 480

Gly Asp Ile Asp Ala Met Glu Leu Tyr Pro Ala Leu Leu Val Glu Lys
            485                 490                 495

Pro Ala Pro Asp Ala Ile Phe Gly Glu Thr Met Val Glu Ala Gly Ala
                500                 505                 510

Pro Phe Ser Leu Lys Gly Leu Met Gly Asn Pro Ile Cys Ser Pro Glu
            515                 520                 525

Tyr Trp Lys Pro Ser Thr Phe Gly Gly Glu Val Gly Phe Lys Ile Ile
        530                 535                 540

Asn Thr Ala Ser Ile Gln Ser Leu Ile Cys Ser Asn Val Lys Gly Cys
545                 550                 555                 560

Pro Phe Thr Ser Phe Ser Val Gln Asp Ala His Leu Thr Lys Thr Val
            565                 570                 575

Thr Ile Asn Ala Ser Ser Ser His Ser Gly Leu Asp Asp Ile Asn Pro
        580                 585                 590

Thr Val Leu Leu Lys Glu Arg Ser Thr Glu Leu
            595                 600

<210> SEQ ID NO 24
<211> LENGTH: 603
<212> TYPE: PRT
<213> ORGANISM: Canis familiaris

<400> SEQUENCE: 24

Met Leu Ala Arg Ala Leu Leu Leu Cys Ala Ala Val Val Cys Gly Ala
1               5                   10                  15

Ala Asn Pro Cys Cys Ser His Pro Cys Gln Asn Arg Gly Val Cys Met
            20                  25                  30

Ser Val Gly Phe Asp Gln Tyr Lys Cys Asp Cys Thr Arg Thr Gly Phe
        35                  40                  45

Tyr Gly Glu Asn Cys Thr Thr Pro Glu Phe Leu Thr Arg Ile Lys Leu
    50                  55                  60

Leu Leu Lys Pro Thr Pro Asp Thr Val His Tyr Ile Leu Thr His Phe
65                  70                  75                  80

Lys Gly Val Trp Asn Ile Val Asn Lys Ile Ser Phe Leu Arg Asn Met
                85                  90                  95

Ile Met Arg Tyr Val Leu Thr Ser Arg Ser His Leu Ile Glu Ser Pro
            100                 105                 110

Pro Thr Tyr Asn Val His Tyr Ser Tyr Lys Ser Trp Glu Ala Phe Ser
        115                 120                 125

Asn Leu Ser Tyr Tyr Thr Arg Ala Leu Pro Pro Val Pro Asp Asp Cys
    130                 135                 140

Pro Thr Pro Met Gly Val Lys Gly Arg Lys Glu Leu Pro Asp Ser Lys
145                 150                 155                 160

Glu Val Val Lys Lys Val Leu Leu Arg Arg Lys Phe Ile Pro Asp Pro
                165                 170                 175

Gln Gly Thr Asn Leu Met Phe Ala Phe Phe Ala Gln His Phe Thr His
            180                 185                 190

Gln Phe Phe Lys Thr Asp Ile Glu Arg Gly Pro Ala Phe Thr Lys Gly
        195                 200                 205
```

```
Lys Asn His Gly Val Asp Leu Ser His Val Tyr Gly Glu Ser Leu Glu
            210                 215                 220

Arg Gln His Asn Arg Arg Leu Phe Lys Asp Gly Lys Met Lys Tyr Gln
225                 230                 235                 240

Met Ile Asn Gly Glu Met Tyr Pro Pro Thr Val Lys Asp Thr Gln Val
            245                 250                 255

Glu Met Ile Tyr Pro Pro His Ile Pro Glu His Leu Lys Phe Ala Val
            260                 265                 270

Gly Gln Glu Val Phe Gly Leu Val Pro Gly Leu Met Met Tyr Ala Thr
            275                 280                 285

Ile Trp Leu Arg Glu His Asn Arg Val Cys Asp Val Leu Lys Gln Glu
            290                 295                 300

His Pro Glu Trp Gly Asp Glu Gln Leu Phe Gln Thr Ser Arg Leu Ile
305                 310                 315                 320

Leu Ile Gly Glu Thr Ile Lys Ile Val Ile Glu Asp Tyr Val Gln His
                    325                 330                 335

Leu Ser Gly Tyr His Phe Lys Leu Lys Phe Asp Pro Glu Leu Leu Phe
                    340                 345                 350

Asn Gln Gln Phe Gln Tyr Gln Asn Arg Ile Ala Ala Glu Phe Asn Thr
                    355                 360                 365

Leu Tyr His Trp His Pro Leu Leu Pro Asp Val Phe Gln Ile Asp Gly
370                 375                 380

Gln Glu Tyr Asn Tyr Gln Gln Phe Ile Tyr Asn Asn Ser Val Leu Leu
385                 390                 395                 400

Glu His Gly Val Thr Gln Phe Val Glu Ser Phe Thr Arg Gln Ile Ala
                    405                 410                 415

Gly Arg Val Ala Gly Arg Arg Asn Leu Pro Ala Ala Val Glu Lys Val
                    420                 425                 430

Ser Lys Ala Ser Leu Asp Gln Ser Arg Glu Met Lys Tyr Gln Ser Phe
            435                 440                 445

Asn Glu Tyr Arg Lys Arg Phe Leu Leu Lys Pro Tyr Glu Ser Phe Glu
450                 455                 460

Glu Leu Thr Gly Glu Lys Glu Met Ala Ala Glu Leu Glu Ala Leu Tyr
465                 470                 475                 480

Gly Asp Ile Asp Ala Met Glu Leu Tyr Pro Ala Leu Leu Val Glu Lys
                    485                 490                 495

Pro Ala Pro Asp Ala Ile Phe Gly Glu Thr Met Val Glu Ala Gly Ala
                    500                 505                 510

Pro Phe Ser Leu Lys Gly Leu Met Gly Asn Pro Ile Cys Ser Pro Glu
            515                 520                 525

Tyr Trp Lys Pro Ser Thr Phe Gly Gly Glu Val Gly Phe Lys Ile Ile
530                 535                 540

Asn Thr Ala Ser Ile Gln Ser Leu Ile Cys Ser Asn Val Lys Gly Cys
545                 550                 555                 560

Pro Phe Thr Ser Phe Ser Val Gln Asp Ala His Leu Thr Lys Thr Val
                    565                 570                 575

Thr Ile Asn Ala Ser Ser Ser His Ser Gly Leu Asp Asp Ile Asn Pro
            580                 585                 590

Thr Val Leu Leu Lys Glu Arg Ser Thr Glu Leu
            595                 600

<210> SEQ ID NO 25
<211> LENGTH: 604
<212> TYPE: PRT
```

<213> ORGANISM: Bos taurus

<400> SEQUENCE: 25

```
Met Leu Ala Arg Ala Leu Leu Cys Ala Val Ala Leu Ser Gly
 1               5                  10                  15
Ala Ala Asn Pro Cys Cys Ser His Pro Cys Gln Asn Arg Gly Val Cys
                 20                  25                  30
Met Ser Val Gly Phe Asp Gln Tyr Lys Cys Asp Cys Thr Arg Thr Gly
             35                  40                  45
Phe Tyr Gly Glu Asn Cys Thr Thr Pro Glu Phe Leu Thr Arg Ile Lys
 50                  55                  60
Leu Leu Leu Lys Pro Thr Pro Asn Thr Val His Tyr Ile Leu Thr His
 65                  70                  75                  80
Phe Lys Gly Val Trp Asn Ile Val Asn Lys Ile Ser Phe Leu Arg Asn
                 85                  90                  95
Met Ile Met Arg Tyr Val Leu Thr Ser Arg Ser His Leu Ile Glu Ser
                100                 105                 110
Pro Pro Thr Tyr Asn Val His Tyr Ser Tyr Lys Ser Trp Glu Ala Phe
            115                 120                 125
Ser Asn Leu Ser Tyr Tyr Thr Arg Ala Leu Pro Pro Val Pro Asp Asp
130                 135                 140
Cys Pro Thr Pro Met Gly Val Lys Gly Arg Lys Glu Leu Pro Asp Ser
145                 150                 155                 160
Lys Glu Val Val Lys Lys Val Leu Leu Arg Arg Lys Phe Ile Pro Asp
                165                 170                 175
Pro Gln Gly Thr Asn Leu Met Phe Ala Phe Phe Ala Gln His Phe Thr
            180                 185                 190
His Gln Phe Phe Lys Thr Asp Phe Glu Arg Gly Pro Ala Phe Thr Lys
        195                 200                 205
Gly Lys Asn His Gly Val Asp Leu Ser His Ile Tyr Gly Glu Ser Leu
210                 215                 220
Glu Arg Gln His Lys Leu Arg Leu Phe Lys Asp Gly Lys Met Lys Tyr
225                 230                 235                 240
Gln Met Ile Asn Gly Glu Met Tyr Pro Pro Thr Val Lys Asp Thr Gln
                245                 250                 255
Val Glu Met Ile Tyr Pro Pro His Val Pro Glu His Leu Lys Phe Ala
            260                 265                 270
Val Gly Gln Glu Val Phe Gly Leu Val Pro Gly Leu Met Met Tyr Ala
        275                 280                 285
Thr Ile Trp Leu Arg Glu His Asn Arg Val Cys Asp Val Leu Lys Gln
290                 295                 300
Glu His Pro Glu Trp Gly Asp Glu Gln Leu Phe Gln Thr Ser Arg Leu
305                 310                 315                 320
Ile Leu Ile Gly Glu Thr Ile Lys Ile Val Ile Glu Asp Tyr Val Gln
                325                 330                 335
His Leu Ser Gly Tyr His Phe Lys Leu Lys Phe Asp Pro Glu Leu Leu
            340                 345                 350
Phe Asn Gln Gln Phe Gln Tyr Gln Asn Arg Ile Ala Ala Glu Phe Asn
        355                 360                 365
Thr Leu Tyr His Trp His Pro Leu Leu Pro Asp Val Phe Gln Ile Asp
    370                 375                 380
Gly Gln Glu Tyr Asn Tyr Gln Gln Phe Ile Tyr Asn Asn Ser Val Leu
385                 390                 395                 400
```

```
Leu Glu His Gly Leu Thr Gln Phe Val Glu Ser Phe Thr Arg Gln Arg
                405                 410                 415

Ala Gly Arg Val Ala Gly Arg Asn Leu Pro Val Ala Val Glu Lys
            420                 425                 430

Val Ser Lys Ala Ser Ile Asp Gln Ser Arg Glu Met Lys Tyr Gln Ser
        435                 440                 445

Phe Asn Glu Tyr Arg Lys Arg Phe Leu Val Lys Pro Tyr Glu Ser Phe
    450                 455                 460

Glu Glu Leu Thr Gly Glu Lys Glu Met Ala Glu Leu Glu Ala Leu
465                 470                 475                 480

Tyr Gly Asp Ile Asp Ala Met Glu Phe Tyr Pro Ala Leu Leu Val Glu
                485                 490                 495

Lys Pro Arg Pro Asp Ala Ile Phe Gly Glu Thr Met Val Glu Ala Gly
            500                 505                 510

Ala Pro Phe Ser Leu Lys Gly Leu Met Gly Asn Pro Ile Cys Ser Pro
        515                 520                 525

Glu Tyr Trp Lys Pro Ser Thr Phe Gly Gly Glu Val Gly Phe Lys Ile
    530                 535                 540

Ile Asn Thr Ala Ser Ile Gln Ser Leu Ile Cys Ser Asn Val Lys Gly
545                 550                 555                 560

Cys Pro Phe Thr Ser Phe Ser Val Gln Asp Thr His Leu Thr Lys Thr
                565                 570                 575

Val Thr Ile Asn Ala Ser Ser Ser His Ser Gly Leu Asp Asp Ile Asn
            580                 585                 590

Pro Thr Val Leu Leu Lys Glu Arg Ser Thr Glu Leu
        595                 600

<210> SEQ ID NO 26
<211> LENGTH: 604
<212> TYPE: PRT
<213> ORGANISM: Equus caballus

<400> SEQUENCE: 26

Met Leu Ala Arg Ala Leu Leu Leu Cys Val Ala Leu Ala Leu Gly His
 1               5                  10                  15

Ala Ala Asn Pro Cys Cys Ser Asn Pro Cys Gln Asn Arg Gly Val Cys
            20                  25                  30

Met Ser Val Gly Phe Asp Gln Tyr Gln Cys Asp Cys Thr Arg Thr Gly
        35                  40                  45

Phe Tyr Gly Glu Asn Cys Ser Thr Pro Glu Phe Leu Thr Arg Ile Lys
    50                  55                  60

Leu Phe Leu Lys Pro Thr Pro Asn Thr Val His Tyr Ile Leu Thr His
65                  70                  75                  80

Phe Lys Gly Val Trp Asn Ile Val Asn Ser Phe Pro Phe Leu Arg Asn
                85                  90                  95

Ala Val Met Lys Tyr Val Leu Val Ser Arg Ser His Leu Ile Glu Ser
            100                 105                 110

Pro Pro Thr Tyr Asn Ala Gln Tyr Gly Tyr Lys Ser Trp Glu Ser Phe
        115                 120                 125

Ser Asn Leu Ser Tyr Tyr Thr Arg Ala Leu Pro Pro Val Ala Asp Gly
    130                 135                 140

Cys Pro Thr Pro Met Gly Val Lys Gly Lys Lys Glu Leu Pro Asp Ser
145                 150                 155                 160

Lys Glu Ile Val Glu Lys Phe Leu Leu Arg Arg Lys Phe Ile Pro Asp
                165                 170                 175
```

```
Pro Gln Gly Thr Asn Met Met Phe Ala Phe Ala Gln His Phe Thr
            180                 185                 190

His Gln Phe Phe Lys Thr Asp Pro Lys Arg Gly Pro Ala Phe Thr Lys
            195                 200                 205

Gly Leu Gly His Gly Val Asp Leu Ser His Ile Tyr Gly Glu Thr Leu
            210                 215                 220

Asp Arg Gln His Lys Leu Arg Leu Phe Lys Asp Gly Lys Met Lys Tyr
225                 230                 235                 240

Gln Ile Ile Asn Gly Glu Val Tyr Pro Pro Thr Val Lys Asp Thr Gln
                245                 250                 255

Val Glu Met Ile Tyr Pro Pro His Ile Pro Glu His Leu Arg Phe Ala
            260                 265                 270

Val Gly Gln Glu Val Phe Gly Leu Val Pro Gly Leu Met Met Tyr Ala
            275                 280                 285

Thr Ile Trp Leu Arg Glu His Asn Arg Val Cys Asp Val Leu Lys Gln
            290                 295                 300

Glu His Pro Glu Trp Asp Asp Glu Arg Leu Phe Gln Thr Ser Arg Leu
305                 310                 315                 320

Ile Leu Ile Gly Glu Thr Ile Lys Ile Val Ile Glu Asp Tyr Val Gln
                325                 330                 335

His Leu Ser Gly Tyr His Phe Lys Leu Lys Phe Asp Pro Glu Leu Leu
            340                 345                 350

Phe Asn Gln Gln Phe Gln Tyr Gln Asn Arg Ile Ala Ala Glu Phe Asn
            355                 360                 365

Thr Leu Tyr His Trp His Pro Leu Leu Pro Asp Thr Phe Gln Ile Asp
            370                 375                 380

Asp Gln Glu Tyr Asn Phe Gln Gln Phe Leu Tyr Asn Asn Ser Ile Leu
385                 390                 395                 400

Leu Glu His Gly Leu Thr Gln Phe Val Glu Ser Phe Ser Arg Gln Ile
                405                 410                 415

Ala Gly Arg Val Ala Gly Gly Arg Asn Val Pro Ala Ala Gln Lys
            420                 425                 430

Ile Ala Lys Ala Ser Ile Asp Gln Ser Arg Glu Met Lys Tyr Gln Ser
            435                 440                 445

Leu Asn Glu Tyr Arg Lys Arg Phe Arg Leu Thr Pro Tyr Lys Ser Phe
            450                 455                 460

Glu Glu Leu Thr Gly Glu Lys Glu Met Ala Ala Glu Leu Glu Ala Leu
465                 470                 475                 480

Tyr Gly Asp Ile Asp Ala Met Glu Leu Tyr Pro Ala Leu Leu Val Glu
                485                 490                 495

Lys Pro Arg Pro Asp Ala Ile Phe Gly Glu Thr Met Val Glu Leu Gly
            500                 505                 510

Ala Pro Phe Ser Leu Lys Gly Leu Leu Gly Asn Pro Ile Cys Ser Pro
            515                 520                 525

Asp Tyr Trp Lys Pro Ser Thr Phe Gly Gly Glu Val Gly Phe Lys Ile
            530                 535                 540

Ile Asn Thr Ala Ser Ile Gln Ser Leu Ile Cys Asn Asn Val Lys Gly
545                 550                 555                 560

Cys Pro Phe Thr Ala Phe Ser Val Gln Asp Pro Gln Leu Ser Lys Ala
                565                 570                 575

Val Thr Ile Asn Ala Ser Ala Ser His Ser Gly Leu Asp Asp Val Asn
            580                 585                 590
```

```
Pro Thr Val Leu Leu Lys Glu Arg Ser Thr Glu Leu
        595                 600
```

<210> SEQ ID NO 27
<211> LENGTH: 604
<212> TYPE: PRT
<213> ORGANISM: Oryctolagus cuniculus

<400> SEQUENCE: 27

```
Met Leu Ala Arg Ala Leu Leu Cys Ala Val Ala Leu Ser His
 1               5                  10                  15

Ala Ala Asn Pro Cys Cys Ser Asn Pro Cys Gln Asn Arg Gly Val Cys
            20                  25                  30

Met Thr Met Gly Phe Asp Gln Tyr Lys Cys Asp Cys Thr Arg Thr Gly
        35                  40                  45

Phe Tyr Gly Glu Asn Cys Ser Thr Pro Glu Phe Leu Thr Arg Ile Lys
    50                  55                  60

Leu Leu Leu Lys Pro Thr Pro Asp Thr Val His Tyr Ile Leu Thr His
65                  70                  75                  80

Phe Lys Gly Val Trp Asn Ile Val Asn Ser Ile Pro Phe Leu Arg Asn
                85                  90                  95

Ser Ile Met Lys Tyr Val Leu Thr Ser Arg Ser His Met Ile Asp Ser
            100                 105                 110

Pro Pro Thr Tyr Asn Val His Tyr Asn Tyr Lys Ser Trp Glu Ala Phe
        115                 120                 125

Ser Asn Leu Ser Tyr Tyr Thr Arg Ala Leu Pro Pro Val Ala Asp Asp
    130                 135                 140

Cys Pro Thr Pro Met Gly Val Lys Gly Lys Lys Glu Leu Pro Asp Ser
145                 150                 155                 160

Lys Asp Val Val Glu Lys Leu Leu Arg Arg Lys Phe Ile Pro Asp
                165                 170                 175

Pro Gln Gly Thr Asn Met Met Phe Ala Phe Phe Ala Gln His Phe Thr
            180                 185                 190

His Gln Phe Phe Lys Thr Asp Leu Lys Arg Gly Pro Ala Phe Thr Lys
        195                 200                 205

Gly Leu Gly His Gly Val Asp Leu Asn His Ile Tyr Gly Glu Thr Leu
    210                 215                 220

Asp Arg Gln His Lys Leu Arg Leu Phe Lys Asp Gly Lys Met Lys Tyr
225                 230                 235                 240

Gln Val Ile Asp Gly Glu Val Tyr Pro Pro Thr Val Lys Asp Thr Gln
                245                 250                 255

Val Glu Met Ile Tyr Pro Pro His Ile Pro Ala His Leu Gln Phe Ala
            260                 265                 270

Val Gly Gln Glu Val Phe Gly Leu Val Pro Gly Leu Met Met Tyr Ala
        275                 280                 285

Thr Ile Trp Leu Arg Glu His Asn Arg Val Cys Asp Val Leu Lys Gln
    290                 295                 300

Glu His Pro Glu Trp Asp Asp Glu Gln Leu Phe Gln Thr Ser Arg Leu
305                 310                 315                 320

Ile Leu Ile Gly Glu Thr Ile Lys Ile Val Ile Glu Asp Tyr Val Gln
                325                 330                 335

His Leu Ser Gly Tyr His Phe Lys Leu Lys Phe Asp Pro Glu Leu Leu
            340                 345                 350

Phe Asn Gln Gln Phe Gln Tyr Gln Asn Arg Ile Ala Ala Glu Phe Asn
        355                 360                 365
```

```
Thr Leu Tyr His Trp His Pro Leu Pro Asp Thr Phe Gln Ile Asp
    370                 375                 380

Asp Gln Gln Tyr Asn Tyr Gln Gln Phe Leu Tyr Asn Asn Ser Ile Leu
385                 390                 395                 400

Leu Glu His Gly Leu Thr Gln Phe Val Glu Ser Phe Thr Arg Gln Ile
                405                 410                 415

Ala Gly Arg Val Ala Gly Arg Asn Val Pro Pro Ala Val Gln Lys
    420                 425                 430

Val Ala Lys Ala Ser Ile Asp Gln Ser Arg Gln Met Lys Tyr Gln Ser
    435                 440                 445

Leu Asn Glu Tyr Arg Lys Arg Phe Leu Leu Lys Pro Tyr Glu Ser Phe
    450                 455                 460

Glu Glu Leu Thr Gly Glu Lys Glu Met Ala Ala Glu Leu Glu Ala Leu
465                 470                 475                 480

Tyr Gly Asp Ile Asp Ala Val Glu Leu Tyr Pro Ala Leu Leu Val Glu
                485                 490                 495

Arg Pro Arg Pro Asp Ala Ile Phe Gly Glu Ser Met Val Glu Met Gly
            500                 505                 510

Ala Pro Phe Ser Leu Lys Gly Leu Met Gly Asn Pro Ile Cys Ser Pro
        515                 520                 525

Asn Tyr Trp Lys Pro Ser Thr Phe Gly Gly Glu Val Gly Phe Lys Ile
    530                 535                 540

Val Asn Thr Ala Ser Ile Gln Ser Leu Ile Cys Asn Asn Val Lys Gly
545                 550                 555                 560

Cys Pro Phe Thr Ser Phe Asn Val Pro Asp Pro Gln Leu Thr Lys Thr
                565                 570                 575

Val Thr Ile Asn Ala Ser Ala Ser His Ser Arg Leu Glu Asp Ile Asn
            580                 585                 590

Pro Thr Val Leu Leu Lys Gly Arg Ser Thr Glu Leu
        595                 600

<210> SEQ ID NO 28
<211> LENGTH: 604
<212> TYPE: PRT
<213> ORGANISM: Cavia porcellus

<400> SEQUENCE: 28

Met Leu Ala Arg Ala Leu Leu Leu Cys Ala Leu Ala Leu Gly Gln
1               5                   10                  15

Ala Ala Asn Pro Cys Cys Ser Asn Pro Cys Gln Asn Arg Gly Glu Cys
            20                  25                  30

Leu Ser Val Gly Phe Asp Arg Tyr Lys Cys Asp Cys Thr Arg Thr Gly
        35                  40                  45

Tyr Tyr Gly Glu Asn Cys Thr Thr Pro Glu Phe Leu Thr Arg Ile Lys
    50                  55                  60

Leu Leu Leu Lys Pro Thr Pro Asn Thr Val His Tyr Ile Leu Thr His
65                  70                  75                  80

Phe Lys Gly Val Trp Asn Ile Val Asn Asn Ile Pro Phe Leu Arg Asn
                85                  90                  95

Ala Ile Met Ile Tyr Val Leu Thr Ser Arg Ser His Leu Ile Asp Ser
            100                 105                 110

Pro Pro Thr Tyr Asn Ala His Tyr Gly Tyr Lys Ser Trp Glu Ala Phe
        115                 120                 125

Ser Asn Leu Ser Tyr Tyr Thr Arg Ala Leu Pro Pro Val Ala Asp Asp
```

-continued

```
            130                 135                 140
Cys Pro Thr Pro Met Gly Val Lys Gly Lys Glu Leu Pro Asp Ser
145                 150                 155                 160

Asn Glu Val Leu Glu Lys Val Leu Leu Arg Arg Lys Phe Ile Pro Asp
                165                 170                 175

Pro Gln Gly Thr Asn Met Met Phe Ala Phe Ala Gln His Phe Thr
                180                 185                 190

His Gln Phe Phe Lys Ser Asp Gln Lys Arg Gly Pro Ala Phe Thr Thr
                195                 200                 205

Gly Leu Ala His Gly Val Asp Leu Ser His Ile Tyr Gly Glu Thr Leu
    210                 215                 220

Asp Arg Gln His Lys Leu Arg Leu Phe Lys Asp Gly Lys Met Lys Tyr
225                 230                 235                 240

Gln Ile Ile Asp Gly Glu Met Tyr Pro Pro Thr Val Lys Glu Thr Gln
                245                 250                 255

Val Glu Met Met Tyr Pro Pro Tyr Ile Pro Glu His Ala Arg Phe Ala
                260                 265                 270

Val Gly Gln Glu Val Phe Gly Leu Val Pro Gly Leu Met Met Tyr Ala
                275                 280                 285

Thr Ile Trp Leu Arg Glu His Asn Arg Val Cys Asp Val Leu Lys Gln
    290                 295                 300

Glu His Pro Glu Trp Asp Asp Glu Arg Leu Phe Gln Thr Ser Arg Leu
305                 310                 315                 320

Ile Leu Ile Gly Glu Thr Ile Lys Ile Val Ile Glu Asp Tyr Val Gln
                325                 330                 335

His Leu Ser Gly Tyr His Phe Lys Leu Lys Phe Asp Pro Glu Leu Leu
                340                 345                 350

Phe Asn Gln Gln Phe Gln Tyr Gln Asn Arg Ile Ala Ser Glu Phe Asn
                355                 360                 365

Thr Leu Tyr His Trp His Pro Leu Leu Pro Asp Thr Phe Gln Ile Asp
    370                 375                 380

Asp Gln Val Tyr Asn Phe Gln Gln Phe Leu Tyr Asn Asn Ser Ile Leu
385                 390                 395                 400

Val Glu His Gly Leu Thr Gln Phe Val Glu Ser Phe Thr Lys Gln Ile
                405                 410                 415

Ala Gly Arg Val Ala Gly Gly Arg Asn Val Pro Leu Ala Val Gln Arg
                420                 425                 430

Val Ala Lys Ala Ser Ile Glu His Ser Arg Lys Met Lys Tyr Gln Ser
                435                 440                 445

Leu Asn Glu Tyr Arg Lys Arg Phe Leu Met Lys Pro Tyr Thr Ser Phe
    450                 455                 460

Glu Glu Leu Thr Gly Glu Lys Glu Met Ala Ala Gly Leu Glu Ala Leu
465                 470                 475                 480

Tyr Gly Asp Ile Asp Ala Met Glu Leu Tyr Pro Ala Leu Leu Val Glu
                485                 490                 495

Lys Pro Arg Pro Asp Ala Ile Phe Gly Glu Thr Met Val Glu Met Gly
                500                 505                 510

Ala Pro Phe Ser Leu Lys Gly Leu Met Gly Asn Pro Ile Cys Ser Pro
                515                 520                 525

His Tyr Trp Lys Pro Ser Thr Phe Gly Gly Glu Val Gly Phe Gln Ile
    530                 535                 540

Val Asn Thr Ala Ser Ile Gln Ser Leu Ile Cys Asn Asn Val Lys Gly
545                 550                 555                 560
```

```
Cys Pro Val Thr Ala Phe Asn Leu Pro Asp Pro Gln Leu Ala Lys Thr
                565                 570                 575

Val Thr Ile Asn Ala Ser Ala Ser His Ser Arg Leu Glu Asp Leu Ser
            580                 585                 590

Pro Thr Val Leu Leu Lys Gly Arg Ser Thr Glu Leu
        595                 600
```

<210> SEQ ID NO 29
<211> LENGTH: 604
<212> TYPE: PRT
<213> ORGANISM: Mus musculus

<400> SEQUENCE: 29

```
Met Leu Phe Arg Ala Val Leu Leu Cys Ala Ala Leu Gly Leu Ser Gln
  1               5                  10                  15

Ala Ala Asn Pro Cys Cys Ser Asn Pro Cys Gln Asn Arg Gly Glu Cys
             20                  25                  30

Met Ser Thr Gly Phe Asp Gln Tyr Lys Cys Asp Cys Thr Arg Thr Gly
         35                  40                  45

Phe Tyr Gly Glu Asn Cys Thr Thr Pro Glu Phe Leu Thr Arg Ile Lys
 50                  55                  60

Leu Leu Leu Lys Pro Thr Pro Asn Thr Val His Tyr Ile Leu Thr His
 65                  70                  75                  80

Phe Lys Gly Val Trp Asn Ile Val Asn Asn Ile Pro Phe Leu Arg Ser
                 85                  90                  95

Leu Ile Met Lys Tyr Val Leu Thr Ser Arg Ser Tyr Leu Ile Asp Ser
            100                 105                 110

Pro Pro Thr Tyr Asn Val His Tyr Gly Tyr Lys Ser Trp Glu Ala Phe
        115                 120                 125

Ser Asn Leu Ser Tyr Tyr Thr Arg Ala Leu Pro Pro Val Ala Asp Asp
130                 135                 140

Cys Pro Thr Pro Met Gly Val Lys Gly Asn Lys Glu Leu Pro Asp Ser
145                 150                 155                 160

Lys Glu Val Leu Glu Lys Val Leu Leu Arg Arg Glu Phe Ile Pro Asp
                165                 170                 175

Pro Gln Gly Ser Asn Met Met Phe Ala Phe Phe Ala Gln His Phe Thr
            180                 185                 190

His Gln Phe Phe Lys Thr Asp His Lys Arg Gly Pro Gly Phe Thr Arg
        195                 200                 205

Gly Leu Gly His Gly Val Asp Leu Asn His Ile Tyr Gly Glu Thr Leu
    210                 215                 220

Asp Arg Gln His Lys Leu Arg Leu Phe Lys Asp Gly Lys Leu Lys Tyr
225                 230                 235                 240

Gln Val Ile Gly Gly Glu Val Tyr Pro Pro Thr Val Lys Asp Thr Gln
                245                 250                 255

Val Glu Met Ile Tyr Pro Pro His Ile Pro Glu Asn Leu Gln Phe Ala
            260                 265                 270

Val Gly Gln Glu Val Phe Gly Leu Val Pro Gly Leu Met Met Tyr Ala
        275                 280                 285

Thr Ile Trp Leu Arg Glu His Asn Arg Val Cys Asp Ile Leu Lys Gln
    290                 295                 300

Glu His Pro Glu Trp Gly Asp Glu Gln Leu Phe Gln Thr Ser Arg Leu
305                 310                 315                 320

Ile Leu Ile Gly Glu Thr Ile Lys Ile Val Ile Glu Asp Tyr Val Gln
```

```
                    325                 330                 335
His Leu Ser Gly Tyr His Phe Lys Leu Lys Phe Asp Pro Glu Leu Leu
                340                 345                 350

Phe Asn Gln Gln Phe Gln Tyr Gln Asn Arg Ile Ala Ser Glu Phe Asn
            355                 360                 365

Thr Leu Tyr His Trp His Pro Leu Leu Pro Asp Thr Phe Asn Ile Glu
        370                 375                 380

Asp Gln Glu Tyr Ser Phe Lys Gln Phe Leu Tyr Asn Asn Ser Ile Leu
385                 390                 395                 400

Leu Glu His Gly Leu Thr Gln Phe Val Glu Ser Phe Thr Arg Gln Ile
                405                 410                 415

Ala Gly Arg Val Ala Gly Arg Asn Val Pro Ile Ala Val Gln Ala
            420                 425                 430

Val Ala Lys Ala Ser Ile Asp Gln Ser Arg Glu Met Lys Tyr Gln Ser
        435                 440                 445

Leu Asn Glu Tyr Arg Lys Arg Phe Ser Leu Lys Pro Tyr Thr Ser Phe
    450                 455                 460

Glu Glu Leu Thr Gly Glu Lys Glu Met Ala Ala Glu Leu Lys Ala Leu
465                 470                 475                 480

Tyr Ser Asp Ile Asp Val Met Glu Leu Tyr Pro Ala Leu Leu Val Glu
                485                 490                 495

Lys Pro Arg Pro Asp Ala Ile Phe Gly Glu Thr Met Val Glu Leu Gly
            500                 505                 510

Ala Pro Phe Ser Leu Lys Gly Leu Met Gly Asn Pro Ile Cys Ser Pro
        515                 520                 525

Gln Tyr Trp Lys Pro Ser Thr Phe Gly Gly Glu Val Gly Phe Lys Ile
    530                 535                 540

Ile Asn Thr Ala Ser Ile Gln Ser Leu Ile Cys Asn Asn Val Lys Gly
545                 550                 555                 560

Cys Pro Phe Thr Ser Phe Asn Val Gln Asp Pro Gln Pro Thr Lys Thr
                565                 570                 575

Ala Thr Ile Asn Ala Ser Ala Ser His Ser Arg Leu Asp Asp Ile Asn
            580                 585                 590

Pro Thr Val Leu Ile Lys Arg Arg Ser Thr Glu Leu
        595                 600

<210> SEQ ID NO 30
<211> LENGTH: 604
<212> TYPE: PRT
<213> ORGANISM: Rattus norvegicus

<400> SEQUENCE: 30

Met Leu Phe Arg Ala Val Leu Leu Cys Ala Ala Leu Ala Leu Ser His
1               5                   10                  15

Ala Ala Asn Pro Cys Cys Ser Asn Pro Cys Gln Asn Arg Gly Glu Cys
            20                  25                  30

Met Ser Ile Gly Phe Asp Gln Tyr Lys Cys Asp Cys Thr Arg Thr Gly
        35                  40                  45

Phe Tyr Gly Glu Asn Cys Thr Thr Pro Glu Phe Leu Thr Arg Ile Lys
    50                  55                  60

Leu Leu Leu Lys Pro Thr Pro Asn Thr Val His Tyr Ile Leu Thr His
65                  70                  75                  80

Phe Lys Gly Val Trp Asn Ile Val Asn Asn Ile Pro Phe Leu Arg Asn
                85                  90                  95
```

-continued

```
Ser Ile Met Arg Tyr Val Leu Thr Ser Arg Ser His Leu Ile Asp Ser
            100                 105                 110

Pro Pro Thr Tyr Asn Val His Tyr Gly Tyr Lys Ser Trp Glu Ala Phe
            115                 120                 125

Ser Asn Leu Ser Tyr Tyr Thr Arg Ala Leu Pro Pro Val Ala Asp Asp
            130                 135                 140

Cys Pro Thr Pro Met Gly Val Lys Gly Asn Lys Glu Leu Pro Asp Ser
145                 150                 155                 160

Lys Glu Val Leu Glu Lys Val Leu Leu Arg Arg Glu Phe Ile Pro Asp
            165                 170                 175

Pro Gln Gly Thr Asn Met Met Phe Ala Phe Ala Gln His Phe Thr
            180                 185                 190

His Gln Phe Phe Lys Thr Asp Gln Lys Arg Gly Pro Gly Phe Thr Arg
            195                 200                 205

Gly Leu Gly His Gly Val Asp Leu Asn His Val Tyr Gly Glu Thr Leu
            210                 215                 220

Asp Arg Gln His Lys Leu Arg Leu Phe Gln Asp Gly Lys Leu Lys Tyr
225                 230                 235                 240

Gln Val Ile Gly Gly Glu Val Tyr Pro Pro Thr Val Lys Asp Thr Gln
            245                 250                 255

Val Asp Met Ile Tyr Pro Pro His Val Pro Glu His Leu Arg Phe Ala
            260                 265                 270

Val Gly Gln Glu Val Phe Gly Leu Val Pro Gly Leu Met Met Tyr Ala
            275                 280                 285

Thr Ile Trp Leu Arg Glu His Asn Arg Val Cys Asp Ile Leu Lys Gln
            290                 295                 300

Glu His Pro Glu Trp Asp Asp Glu Arg Leu Phe Gln Thr Ser Arg Leu
305                 310                 315                 320

Ile Leu Ile Gly Glu Thr Ile Lys Ile Val Ile Glu Asp Tyr Val Gln
            325                 330                 335

His Leu Ser Gly Tyr His Phe Lys Leu Lys Phe Asp Pro Glu Leu Leu
            340                 345                 350

Phe Asn Gln Gln Phe Gln Tyr Gln Asn Arg Ile Ala Ser Glu Phe Asn
            355                 360                 365

Thr Leu Tyr His Trp His Pro Leu Leu Pro Asp Thr Phe Asn Ile Glu
            370                 375                 380

Asp Gln Glu Tyr Thr Phe Lys Gln Phe Leu Tyr Asn Asn Ser Ile Leu
385                 390                 395                 400

Leu Glu His Gly Leu Ala His Phe Val Glu Ser Phe Thr Arg Gln Ile
            405                 410                 415

Ala Gly Arg Val Ala Gly Gly Arg Asn Val Pro Ile Ala Val Gln Ala
            420                 425                 430

Val Ala Lys Ala Ser Ile Asp Gln Ser Arg Glu Met Lys Tyr Gln Ser
            435                 440                 445

Leu Asn Glu Tyr Arg Lys Arg Phe Ser Leu Lys Pro Tyr Thr Ser Phe
            450                 455                 460

Glu Glu Leu Thr Gly Glu Lys Glu Met Ala Ala Glu Leu Lys Ala Leu
465                 470                 475                 480

Tyr His Asp Ile Asp Ala Met Glu Leu Tyr Pro Ala Leu Leu Val Glu
            485                 490                 495

Lys Pro Arg Pro Asp Ala Ile Phe Gly Glu Thr Met Val Glu Leu Gly
            500                 505                 510

Ala Pro Phe Ser Leu Lys Gly Leu Met Gly Asn Pro Ile Cys Ser Pro
```

```
                515                 520                 525
Gln Tyr Trp Lys Pro Ser Thr Phe Gly Gly Glu Val Gly Phe Arg Ile
        530                 535                 540

Ile Asn Thr Ala Ser Ile Gln Ser Leu Ile Cys Asn Asn Val Lys Gly
545                 550                 555                 560

Cys Pro Phe Ala Ser Phe Asn Val Gln Asp Pro Gln Pro Thr Lys Thr
                565                 570                 575

Ala Thr Ile Asn Ala Ser Ala Ser His Ser Arg Leu Asp Asp Ile Asn
                580                 585                 590

Pro Thr Val Leu Ile Lys Arg Arg Ser Thr Glu Leu
        595                 600

<210> SEQ ID NO 31
<211> LENGTH: 603
<212> TYPE: PRT
<213> ORGANISM: Gallus gallus

<400> SEQUENCE: 31

Met Leu Leu Pro Cys Ala Leu Ala Ala Leu Leu Ala Ala Gly His
 1               5                  10                  15

Ala Ala Asn Pro Cys Cys Ser Leu Pro Cys Gln Asn Arg Gly Val Cys
                 20                  25                  30

Met Thr Thr Gly Phe Asp Arg Tyr Glu Cys Asp Cys Thr Arg Thr Gly
                 35                  40                  45

Tyr Tyr Gly Glu Asn Cys Thr Thr Pro Glu Phe Phe Thr Trp Leu Lys
         50                  55                  60

Leu Ile Leu Lys Pro Thr Pro Asn Thr Val His Tyr Ile Leu Thr His
65                  70                  75                  80

Phe Lys Gly Val Trp Asn Ile Ile Asn Asn Ile Ser Phe Leu Arg Asp
                     85                  90                  95

Thr Ile Met Arg Tyr Val Leu Thr Ser Arg Ser His Leu Ile Asp Ser
                100                 105                 110

Pro Pro Thr Tyr Asn Ser Asp Tyr Ser Tyr Lys Ser Trp Glu Ala Tyr
            115                 120                 125

Ser Asn Leu Ser Tyr Tyr Thr Arg Ser Leu Pro Pro Val Gly His Asp
        130                 135                 140

Cys Pro Thr Pro Met Gly Val Lys Gly Lys Lys Glu Leu Pro Asp Ser
145                 150                 155                 160

Lys Leu Ile Val Glu Lys Phe Leu Leu Arg Arg Lys Phe Ile Pro Asp
                    165                 170                 175

Pro Gln Gly Thr Asn Val Met Phe Thr Phe Phe Ala Gln His Phe Thr
                180                 185                 190

His Gln Phe Phe Lys Thr Asp His Lys Lys Gly Pro Gly Phe Thr Lys
            195                 200                 205

Ala Tyr Gly His Gly Val Asp Leu Asn His Ile Tyr Gly Glu Thr Leu
        210                 215                 220

Glu Arg Gln Leu Lys Leu Arg Leu Arg Lys Asp Gly Lys Leu Lys Tyr
225                 230                 235                 240

Gln Met Ile Asp Gly Glu Met Tyr Pro Pro Thr Val Lys Asp Thr Gln
                    245                 250                 255

Ala Glu Met Ile Tyr Pro Pro His Val Pro Glu His Leu Gln Phe Ser
                260                 265                 270

Val Gly Gln Glu Val Phe Gly Leu Val Pro Gly Leu Met Met Tyr Ala
            275                 280                 285
```

```
Thr Ile Trp Leu Arg Glu His Asn Arg Val Cys Asp Val Leu Lys Gln
        290                 295                 300

Glu His Pro Glu Trp Asp Asp Glu Gln Leu Phe Gln Thr Thr Arg Leu
305                 310                 315                 320

Ile Leu Ile Gly Glu Thr Ile Lys Ile Val Ile Glu Asp Tyr Val Gln
                325                 330                 335

His Leu Ser Gly Tyr His Phe Lys Leu Lys Phe Asp Pro Glu Leu Leu
            340                 345                 350

Phe Asn Gln Arg Phe Gln Tyr Gln Asn Arg Ile Ala Ala Glu Phe Asn
        355                 360                 365

Thr Leu Tyr His Trp His Pro Leu Leu Pro Asp Thr Phe Gln Ile His
370                 375                 380

Asn Gln Glu Tyr Thr Phe Gln Gln Phe Leu Tyr Asn Asn Ser Ile Met
385                 390                 395                 400

Leu Glu His Gly Leu Ser His Met Val Lys Ser Phe Ser Lys Gln Ser
                405                 410                 415

Ala Gly Arg Val Ala Gly Gly Lys Asn Val Pro Ala Ala Val Gln Lys
            420                 425                 430

Val Ala Lys Ala Ser Ile Asp Gln Ser Arg Gln Met Arg Tyr Gln Ser
        435                 440                 445

Leu Asn Glu Tyr Arg Lys Arg Phe Met Leu Lys Pro Phe Lys Ser Phe
450                 455                 460

Glu Glu Leu Thr Gly Glu Lys Glu Met Ala Ala Glu Leu Glu Glu Leu
465                 470                 475                 480

Tyr Gly Asp Ile Asp Ala Met Glu Leu Tyr Pro Gly Leu Leu Val Glu
                485                 490                 495

Lys Pro Arg Pro Gly Ala Ile Phe Gly Glu Thr Met Val Glu Ile Gly
            500                 505                 510

Ala Pro Phe Ser Leu Lys Gly Leu Met Gly Asn Thr Ile Cys Ser Pro
        515                 520                 525

Glu Tyr Trp Lys Pro Ser Thr Phe Gly Gly Lys Val Gly Phe Glu Ile
530                 535                 540

Ile Asn Thr Ala Ser Leu Gln Lys Leu Ile Cys Asn Asn Val Lys Gly
545                 550                 555                 560

Cys Pro Phe Thr Ala Phe His Val Leu Asn Pro Glu Pro Thr Glu Ala
                565                 570                 575

Thr Ile Asn Val Ser Thr Ser Asn Thr Ala Met Glu Asp Ile Asn Pro
            580                 585                 590

Thr Leu Leu Leu Lys Glu Gln Ser Ala Glu Leu
        595                 600

<210> SEQ ID NO 32
<211> LENGTH: 607
<212> TYPE: PRT
<213> ORGANISM: Oncorhynchus mykiss

<400> SEQUENCE: 32

Met Asn Arg Val Ile Cys Ile Ile Leu Leu Leu Ala Val Gly Leu Tyr
1               5                   10                  15

Phe Cys Glu Gly Val Asp Pro Cys Cys Ala Gln Pro Cys Glu Asn Arg
                20                  25                  30

Gly Leu Cys Asn Ser Lys Gly Phe Asp Asn Tyr Glu Cys Asp Cys Thr
            35                  40                  45

Arg Thr Gly Tyr Tyr Gly Lys Asn Cys Thr Thr Pro Glu Phe Leu Thr
        50                  55                  60
```

```
Trp Ile Lys Ile Ser Leu Lys Pro Ala Pro Asn Thr Ile His Tyr Ile
 65                  70                  75                  80

Leu Thr His Tyr Lys Gly Leu Trp Asn Val Ile Asn Lys Ile Thr Phe
                 85                  90                  95

Val Arg Asn Ala Ile Met Ser Tyr Val Leu Thr Pro Arg Ser His Leu
            100                 105                 110

Val Asp Ser Pro Pro Thr Tyr Asn Ala Asp Tyr Gly Tyr Lys Ser Trp
        115                 120                 125

Glu Ala Tyr Ser Asn Leu Phe Tyr Thr Arg Thr Leu Pro Pro Leu
    130                 135                 140

Pro Lys Asp Cys Pro Thr Pro Met Gly Thr Ala Gly Arg Ala Val Leu
145                 150                 155                 160

Pro Asp Val Lys Leu Val Val Glu Lys Val Leu Leu Arg Lys Arg Phe
                165                 170                 175

Ile Pro Asp Pro Gln Gly Ser Asn Leu Met Phe Ala Phe Phe Ala Gln
            180                 185                 190

His Phe Thr His Gln Phe Phe Lys Ser Asp Phe Met Lys Gly Pro Ala
            195                 200                 205

Phe Thr Lys Ala Leu Gly His Gly Val Asp Leu Asn His Val Tyr Gly
210                 215                 220

Asp Thr Leu Glu Arg Gln His Lys Leu Arg Leu Phe Lys Asp Gly Lys
225                 230                 235                 240

Leu Lys Tyr Arg Val Leu Asn Gly Glu Val Tyr Pro Pro Leu Val Arg
                245                 250                 255

Glu Val Gly Ala Glu Met His Tyr Pro Pro Gln Val Pro Glu Glu His
            260                 265                 270

Arg Phe Ala Val Gly His Glu His Phe Gly Leu Val Pro Gly Leu Met
        275                 280                 285

Met Tyr Ala Thr Ile Trp Leu Arg Glu His Asn Arg Val Cys Asp Val
290                 295                 300

Leu Arg Gln Glu His Pro Glu Trp Asp Asp Glu Arg Ile Phe Gln Thr
305                 310                 315                 320

Thr Arg Leu Ile Leu Ile Gly Glu Thr Ile Lys Ile Val Ile Glu Asp
                325                 330                 335

Tyr Val Gln His Leu Ser Gly Tyr His Phe Gln Leu Lys Phe Asp Pro
            340                 345                 350

Glu Leu Leu Phe Asn Gln Arg Phe Gln Tyr Gln Asn Arg Ile Ala Ala
        355                 360                 365

Glu Phe Asn Thr Leu Tyr His Trp His Pro Leu Met Pro Glu Thr Phe
370                 375                 380

Ser Ile Glu Asp Arg Ala Tyr Thr Tyr Pro Gln Phe Val Phe Asn Asn
385                 390                 395                 400

Ser Leu Val Thr Glu His Gly Ile Asn Asn Leu Val Glu Ser Phe Thr
                405                 410                 415

Lys Gln Ile Ala Gly Arg Val Ala Gly Gly Arg Asn Leu Pro Pro Ala
            420                 425                 430

Leu Val Gly Val Ala Ala Lys Ala Leu Glu His Ser Arg Asp Met Arg
        435                 440                 445

Tyr Gln Ser Leu Asn Ala Tyr Arg Lys Arg Phe Asn Met Arg Val Tyr
450                 455                 460

Thr Ser Phe Glu Asp Leu Thr Gly Glu Thr Glu Leu Ala Ala Glu Leu
465                 470                 475                 480
```

```
Glu Ser Leu Tyr Gly Asp Val Asp Ala Val Glu Leu Tyr Pro Gly Leu
                485                 490                 495

Leu Val Glu Arg Pro Arg Pro Asn Ala Val Phe Gly Glu Thr Met Val
                500                 505                 510

Glu Met Gly Ala Pro Tyr Ser Leu Lys Gly Leu Leu Gly Asn Pro Ile
                515                 520                 525

Cys Ser Pro Glu Tyr Trp Met Pro Ser Thr Phe Gly Gly Ser Val Gly
                530                 535                 540

Phe Asp Ile Leu Asn Thr Ala Ser Leu Glu Arg Leu Val Cys Asn Asn
545                 550                 555                 560

Val Lys Gly Ser Cys Pro Met Val Ser Phe Gln Val Pro Asp Phe Leu
                565                 570                 575

Arg Ala Phe Glu Ser Ala Ser Val Asn Thr Ser Glu Ala His Leu Ser
                580                 585                 590

Asp Met Asn Pro Gly Val Leu Phe Lys Glu Arg Thr Ser Glu Leu
                595                 600                 605

<210> SEQ ID NO 33
<211> LENGTH: 607
<212> TYPE: PRT
<213> ORGANISM: Salvelinus fontinalis

<400> SEQUENCE: 33

Met Asn Lys Val Val Cys Ile Ile Leu Leu Leu Thr Val Gly Leu Tyr
1               5                   10                  15

Phe Cys Glu Gly Val Asp Pro Cys Cys Ala Gln Pro Cys Glu Asn Arg
                20                  25                  30

Gly Leu Cys Asn Ser Lys Gly Phe Asp Asn Tyr Glu Cys Asp Cys Thr
                35                  40                  45

Arg Thr Gly Tyr Tyr Gly Lys Asn Cys Thr Thr Pro Glu Phe Leu Thr
                50                  55                  60

Trp Ile Lys Ile Ser Leu Lys Pro Ala Pro Asn Thr Val His Tyr Ile
65                  70                  75                  80

Leu Thr His Tyr Lys Gly Leu Trp Asn Val Ile Asn Lys Ile Thr Phe
                85                  90                  95

Val Arg Asn Ala Ile Met Ser Tyr Val Leu Thr Ser Arg Ser His Leu
                100                 105                 110

Val Asp Ser Pro Pro Thr Tyr Asn Ala Asp Tyr Gly Tyr Lys Ser Trp
                115                 120                 125

Glu Ala Tyr Ser Asn Leu Ser Tyr Tyr Thr Arg Thr Leu Pro Pro Leu
                130                 135                 140

Pro Lys Asp Cys Pro Thr Pro Met Gly Thr Ala Gly Arg Ala Val Leu
145                 150                 155                 160

Pro Asp Val Lys Leu Val Val Glu Lys Val Leu Leu Arg Lys Arg Phe
                165                 170                 175

Ile Pro Asp Pro Gln Gly Ser Asn Leu Met Phe Ala Phe Phe Ala Gln
                180                 185                 190

His Phe Thr His Gln Phe Phe Lys Ser Asp Leu Lys Lys Gly Pro Ala
                195                 200                 205

Phe Thr Lys Ala Leu Gly His Gly Val Asp Leu Asn His Val Tyr Gly
                210                 215                 220

Asp Ser Leu Glu Arg Gln His Lys Leu Arg Leu Phe Lys Asp Gly Lys
225                 230                 235                 240

Leu Lys Tyr Gln Val Leu Asn Gly Glu Val Tyr Pro Pro Leu Val Arg
                245                 250                 255
```

```
Glu Val Gly Ala Glu Met His Tyr Pro Pro Gln Val Pro Glu Glu His
            260                 265                 270

Arg Phe Ala Val Gly His Glu His Phe Gly Leu Val Pro Gly Leu Met
            275                 280                 285

Met Tyr Ala Thr Ile Trp Leu Arg Glu His Asn Arg Val Cys Asp Val
            290                 295                 300

Leu Arg Gln Glu His Pro Glu Trp Asp Asp Glu Arg Ile Phe Gln Thr
305                 310                 315                 320

Thr Arg Leu Ile Leu Ile Gly Glu Thr Ile Lys Ile Val Ile Glu Asp
            325                 330                 335

Tyr Val Gln His Leu Ser Gly Tyr His Phe Gln Leu Lys Phe Asp Pro
            340                 345                 350

Glu Leu Leu Phe Asn Gln Arg Phe Gln Tyr Gln Asn Arg Ile Ala Ala
            355                 360                 365

Glu Phe Asn Thr Leu Tyr His Trp His Pro Leu Met Pro Asp Thr Phe
            370                 375                 380

Ser Ile Glu Asp Arg Ala Tyr Thr Tyr Pro Gln Phe Val Phe Asn Asn
385                 390                 395                 400

Ser Leu Val Thr Glu His Gly Ile Thr Asn Leu Val Glu Ser Phe Thr
            405                 410                 415

Lys Gln Ile Ala Gly Arg Val Ala Gly Arg Asn Leu Pro Pro Ala
            420                 425                 430

Leu Val Ala Val Ala Ala Lys Ala Leu Glu His Ser Arg Asp Met Arg
            435                 440                 445

Tyr Gln Ser Leu Asn Ala Tyr Arg Lys Arg Phe Asn Met Arg Ala Tyr
            450                 455                 460

Thr Ser Phe Glu Asp Leu Thr Gly Glu Thr Glu Leu Ala Ala Glu Leu
465                 470                 475                 480

Glu Ser Leu Tyr Gly Asp Val Asp Ala Val Glu Leu Tyr Pro Gly Leu
            485                 490                 495

Leu Val Glu Arg Pro Arg Pro Asn Ala Val Phe Gly Glu Thr Met Val
            500                 505                 510

Glu Met Gly Ala Pro Tyr Ser Leu Lys Gly Leu Leu Gly Asn Pro Ile
            515                 520                 525

Cys Ser Pro Glu Tyr Trp Met Pro Ser Thr Phe Gly Gly Ser Val Gly
            530                 535                 540

Phe Asp Ile Val Asn Thr Ala Ser Leu Glu Arg Leu Val Cys Ser Asn
545                 550                 555                 560

Val Lys Gly Ser Cys Pro Met Val Ser Phe Gln Val Pro Asp Phe Leu
            565                 570                 575

Arg Ala Phe Glu Ser Ala Ser Val Asn Thr Ser Glu Ala His Leu Arg
            580                 585                 590

Gly Met Asn Pro Gly Val Val Phe Lys Glu Arg Thr Leu Glu Leu
            595                 600                 605

<210> SEQ ID NO 34
<211> LENGTH: 580
<212> TYPE: PRT
<213> ORGANISM: Artificial Sequence
<220> FEATURE:
<223> OTHER INFORMATION: consensus sequence

<400> SEQUENCE: 34

Met Ser Arg Ser Ser Leu Arg Phe Pro Leu Leu Leu Leu Leu Leu Leu
1               5                   10                  15
```

-continued

Pro Pro Pro Pro Val Leu Ala Asp Pro Gly Val Pro Val Asn Pro
            20                  25                  30

Cys Cys Tyr Tyr Pro Cys Gln His Gln Gly Val Cys Val Arg Phe Gly
            35                  40                  45

Leu Asp Arg Tyr Gln Cys Asp Cys Thr Arg Thr Gly Tyr Ser Gly Pro
        50                  55                  60

Asn Cys Thr Ile Pro Glu Trp Thr Trp Leu Arg Ser Leu Arg Pro Ser
65                  70                  75                  80

Pro Ser Phe His Phe Leu Leu Thr His Gly Arg Trp Leu Trp Glu Phe
                85                  90                  95

Val Asn Ala Thr Phe Ile Arg Asp Leu Met Arg Leu Val Leu Thr Val
            100                 105                 110

Arg Ser Asn Leu Ile Pro Ser Pro Thr Tyr Asn Ser Ala His Asp
            115                 120                 125

Tyr Ile Ser Trp Glu Ser Phe Ser Asn Val Ser Tyr Tyr Thr Arg Ile
            130                 135                 140

Leu Pro Ser Val Pro Lys Asp Cys Pro Thr Pro Met Gly Thr Lys Gly
145                 150                 155                 160

Lys Lys Gln Leu Pro Asp Ala Gln Leu Leu Ala Arg Phe Leu Leu Arg
                165                 170                 175

Arg Phe Ile Pro Asp Pro Gln Gly Thr Asn Leu Met Phe Ala Phe Phe
            180                 185                 190

Ala Gln His Phe Thr His Gln Phe Phe Lys Thr Ser Gly Lys Met Gly
            195                 200                 205

Pro Gly Phe Thr Lys Ala Leu Gly His Gly Val Asp Leu Gly His Ile
            210                 215                 220

Tyr Gly Asp Asn Leu Glu Arg Gln Tyr Leu Arg Leu Phe Lys Asp Gly
225                 230                 235                 240

Lys Leu Lys Tyr Gln Val Leu Asp Gly Glu Val Tyr Pro Pro Ser Val
                245                 250                 255

Glu Glu Ala Pro Val Leu Met His Tyr Pro Arg Gly Pro Pro Ser Gln
            260                 265                 270

Met Ala Val Gly Gln Glu Val Phe Gly Leu Leu Pro Gly Leu Met Leu
            275                 280                 285

Tyr Ala Thr Leu Trp Leu Arg Glu His Asn Arg Val Cys Asp Leu Leu
            290                 295                 300

Lys Ala Glu His Pro Thr Trp Gly Asp Glu Gln Leu Phe Gln Thr Ala
305                 310                 315                 320

Arg Leu Ile Leu Ile Gly Glu Thr Ile Lys Ile Val Ile Glu Glu Tyr
                325                 330                 335

Val Gln His Leu Ser Gly Tyr Phe Leu Gln Leu Lys Phe Asp Pro Glu
            340                 345                 350

Leu Leu Phe Ala Gln Phe Gln Tyr Arg Asn Arg Ile Ala Met Glu Phe
            355                 360                 365

Asn His Leu Tyr His Trp His Pro Leu Met Pro Asp Ser Phe Val Gly
            370                 375                 380

Ser Gln Glu Tyr Ser Tyr Glu Gln Phe Leu Phe Asn Thr Ser Met Leu
385                 390                 395                 400

Val Asp Tyr Gly Val Glu Ala Leu Val Asp Ala Phe Ser Arg Gln Ala
                405                 410                 415

Gly Arg Ile Gly Gly Gly Arg Asn Ile Asp His His Val Leu His Val
            420                 425                 430

```
Ala Val Asp Val Ile Lys Glu Ser Arg Glu Leu Arg Leu Gln Pro Phe
            435                 440                 445

Asn Glu Tyr Arg Lys Arg Phe Gly Leu Lys Pro Tyr Thr Ser Phe Gln
            450                 455                 460

Glu Leu Thr Gly Glu Lys Glu Met Ala Ala Glu Leu Glu Glu Leu Tyr
465                 470                 475                 480

Gly Asp Ile Asp Ala Leu Glu Phe Tyr Pro Gly Leu Leu Glu Lys
                485                 490                 495

Cys Pro Asn Ser Ile Phe Gly Glu Ser Met Ile Glu Met Gly Ala Pro
            500                 505                 510

Phe Ser Leu Lys Gly Leu Leu Gly Asn Pro Ile Cys Ser Pro Glu Tyr
            515                 520                 525

Trp Lys Pro Ser Phe Thr Gly Gly Glu Val Gly Phe Asn Ile Val Lys
            530                 535                 540

Thr Ala Ser Leu Lys Lys Leu Val Cys Leu Asn Thr Lys Thr Cys Pro
545                 550                 555                 560

Tyr Val Ser Phe Arg Val Pro Asp Gln Asp Gly Pro Glu Arg Pro
                565                 570                 575

Ser Thr Glu Leu
            580

<210> SEQ ID NO 35
<211> LENGTH: 582
<212> TYPE: PRT
<213> ORGANISM: Artificial Sequence
<220> FEATURE:
<223> OTHER INFORMATION: consensus sequence

<400> SEQUENCE: 35

Met Leu Ala Arg Ala Leu Leu Leu Cys Ala Ala Leu Ala Leu Ala Ala
1               5                   10                  15

Asn Pro Cys Cys Ser Pro Cys Gln Asn Arg Gly Val Cys Met Ser Gly
            20                  25                  30

Phe Asp Gln Tyr Lys Cys Asp Cys Thr Arg Thr Gly Phe Tyr Gly Glu
            35                  40                  45

Asn Cys Thr Thr Pro Glu Phe Leu Thr Arg Ile Lys Leu Leu Lys Pro
50                  55                  60

Thr Pro Asn Thr Val His Tyr Ile Leu Thr His Phe Lys Gly Val Trp
65                  70                  75                  80

Asn Ile Val Asn Ile Pro Phe Leu Arg Asn Ile Met Tyr Val Leu Thr
                85                  90                  95

Ser Arg Ser His Leu Ile Asp Ser Pro Pro Thr Tyr Asn Val His Tyr
            100                 105                 110

Gly Tyr Lys Ser Trp Glu Ala Phe Ser Asn Leu Ser Tyr Tyr Thr Arg
            115                 120                 125

Ala Leu Pro Pro Val Asp Asp Cys Pro Thr Pro Met Gly Val Lys Gly
            130                 135                 140

Lys Lys Glu Leu Pro Asp Ser Lys Glu Val Val Glu Lys Val Leu Leu
145                 150                 155                 160

Arg Arg Lys Phe Ile Pro Asp Pro Gln Gly Thr Asn Met Met Phe Ala
                165                 170                 175

Phe Phe Ala Gln His Phe Thr His Gln Phe Phe Lys Thr Asp Lys Arg
            180                 185                 190

Gly Pro Ala Phe Thr Lys Gly Leu Gly His Gly Val Asp Leu Asn His
            195                 200                 205
```

```
Ile Tyr Gly Glu Thr Leu Asp Arg Gln His Lys Leu Arg Leu Phe Lys
210                 215                 220

Asp Gly Lys Met Lys Tyr Gln Val Ile Gly Glu Val Tyr Pro Pro Thr
225                 230                 235                 240

Val Lys Asp Thr Gln Val Glu Met Ile Tyr Pro Pro His Val Pro Glu
            245                 250                 255

His Leu Arg Phe Ala Val Gly Gln Glu Val Phe Gly Leu Val Pro Gly
            260                 265                 270

Leu Met Met Tyr Ala Thr Ile Trp Leu Arg Glu His Asn Arg Val Cys
            275                 280                 285

Asp Val Leu Lys Gln Glu His Pro Glu Trp Asp Asp Glu Arg Leu Phe
290                 295                 300

Gln Thr Ser Arg Leu Ile Leu Ile Gly Glu Thr Ile Lys Ile Val Ile
305                 310                 315                 320

Glu Asp Tyr Val Gln His Leu Ser Gly Tyr His Phe Lys Leu Lys Phe
            325                 330                 335

Asp Pro Glu Leu Leu Phe Asn Gln Gln Phe Gln Tyr Gln Asn Arg Ile
            340                 345                 350

Ala Ala Glu Phe Asn Thr Leu Tyr His Trp His Pro Leu Leu Pro Asp
            355                 360                 365

Thr Phe Gln Ile Asp Asp Gln Glu Tyr Asn Phe Gln Gln Phe Tyr Asn
370                 375                 380

Asn Ser Ile Leu Leu Glu His Gly Leu Thr Gln Phe Val Glu Ser Phe
385                 390                 395                 400

Thr Arg Gln Ile Ala Gly Arg Val Ala Gly Arg Asn Val Pro Ala
            405                 410                 415

Val Gln Val Ala Lys Ala Ser Ile Asp Gln Ser Arg Met Lys Tyr Gln
            420                 425                 430

Ser Leu Asn Glu Tyr Arg Lys Arg Phe Leu Lys Pro Tyr Ser Phe Glu
            435                 440                 445

Glu Leu Thr Gly Glu Lys Glu Met Ala Ala Glu Leu Glu Ala Leu Tyr
450                 455                 460

Gly Asp Ile Asp Ala Met Glu Leu Tyr Pro Ala Leu Leu Val Glu Lys
465                 470                 475                 480

Pro Arg Pro Asp Ala Ile Phe Gly Glu Thr Met Val Glu Gly Ala Pro
            485                 490                 495

Phe Ser Leu Lys Gly Leu Met Gly Asn Pro Ile Cys Ser Pro Tyr Trp
            500                 505                 510

Lys Pro Ser Thr Phe Gly Gly Glu Val Gly Phe Lys Ile Ile Asn Thr
            515                 520                 525

Ala Ser Ile Gln Ser Leu Ile Cys Asn Asn Val Lys Gly Cys Pro Phe
530                 535                 540

Thr Ser Phe Val Gln Asp Pro Gln Leu Thr Lys Thr Val Thr Ile Asn
545                 550                 555                 560

Ala Ser Ser His Ser Leu Asp Asp Ile Asn Pro Thr Val Leu Leu Lys
            565                 570                 575

Glu Arg Ser Thr Glu Leu
            580

<210> SEQ ID NO 36
<211> LENGTH: 589
<212> TYPE: PRT
<213> ORGANISM: Gersemia fruticosa

<400> SEQUENCE: 36
```

-continued

```
Met Val Ala Lys Phe Val Phe Leu Gly Leu Gln Leu Ile Leu Cys
 1               5                  10                  15

Ser Val Val Cys Glu Ala Val Asn Pro Cys Cys Ser Phe Pro Cys Glu
                20                  25                  30

Ser Gly Ala Val Cys Val Glu Asp Gly Asp Lys Tyr Thr Cys Asp Cys
            35                  40                  45

Thr Arg Thr Gly His Tyr Gly Val Asn Cys Glu Lys Pro Asn Trp Ser
    50                  55                  60

Thr Trp Phe Lys Ala Leu Ile Ala Pro Ser Glu Glu Thr Lys His Phe
65                  70                  75                  80

Ile Leu Thr His Phe Lys Trp Phe Trp Ile Val Asn Asn Val Pro
                85                  90                  95

Phe Ile Arg Asn Thr Val Met Lys Ala Ala Tyr Phe Ser Arg Thr Asp
                100                 105                 110

Phe Val Pro Val Pro His Ala Tyr Thr Ser Tyr His Asp Tyr Ala Thr
            115                 120                 125

Met Glu Ala His Tyr Asn Arg Ser Tyr Phe Ala Arg Thr Leu Pro Pro
    130                 135                 140

Val Pro Lys Asn Cys Pro Thr Pro Phe Gly Val Ala Gly Lys Lys Glu
145                 150                 155                 160

Leu Pro Pro Ala Glu Glu Val Ala Asn Lys Phe Leu Lys Arg Gly Lys
                165                 170                 175

Phe Lys Thr Asp His Thr Ser Thr Ser Trp Leu Phe Met Phe Phe Ala
                180                 185                 190

Gln His Phe Thr His Glu Phe Phe Lys Thr Ile Tyr His Ser Pro Ala
    195                 200                 205

Phe Thr Trp Gly Asn His Gly Val Asp Val Ser His Ile Tyr Gly Gln
    210                 215                 220

Asp Met Glu Arg Gln Asn Lys Leu Arg Ser Phe Glu Asp Gly Lys Leu
225                 230                 235                 240

Lys Ser Gln Thr Ile Asn Gly Glu Glu Trp Pro Pro Tyr Leu Lys Asp
                245                 250                 255

Val Asp Asn Val Thr Met Gln Tyr Pro Pro Asn Thr Pro Glu Asp Gln
                260                 265                 270

Lys Phe Ala Leu Gly His Pro Phe Tyr Ser Met Leu Pro Gly Leu Phe
    275                 280                 285

Met Tyr Ala Ser Ile Trp Leu Arg Glu His Asn Arg Val Cys Thr Ile
    290                 295                 300

Leu Arg Lys Glu His Pro His Trp Val Asp Glu Arg Leu Tyr Gln Thr
305                 310                 315                 320

Gly Lys Leu Ile Ile Thr Gly Glu Leu Ile Lys Ile Val Ile Glu Asp
                325                 330                 335

Tyr Val Asn His Leu Ala Asn Tyr Asn Leu Lys Leu Thr Tyr Asn Pro
                340                 345                 350

Glu Leu Val Phe Asp His Gly Tyr Asp Tyr Asp Asn Arg Ile His Val
    355                 360                 365

Glu Phe Asn His Met Tyr His Trp His Pro Phe Ser Pro Asp Glu Tyr
    370                 375                 380

Asn Ile Ser Gly Ser Thr Tyr Ser Ile Gln Asp Phe Met Tyr His Pro
385                 390                 395                 400

Glu Ile Val Val Lys His Gly Met Ser Ser Phe Val Asp Ser Met Ser
                405                 410                 415
```

-continued

Lys Gly Leu Cys Gly Gln Met Ser His His Asn His Gly Ala Tyr Thr
            420                 425                 430

Leu Asp Val Ala Val Glu Val Ile Lys His Gln Arg Glu Leu Arg Met
            435                 440                 445

Gln Ser Phe Asn Asn Tyr Arg Lys His Phe Ala Leu Glu Pro Tyr Lys
450                 455                 460

Ser Phe Glu Glu Leu Thr Gly Asp Pro Lys Met Ser Ala Glu Leu Gln
465                 470                 475                 480

Glu Val Tyr Gly Asp Val Asn Ala Val Asp Leu Tyr Val Gly Phe Phe
                485                 490                 495

Leu Glu Lys Gly Leu Thr Thr Ser Pro Phe Gly Ile Thr Met Ile Ala
            500                 505                 510

Phe Gly Ala Pro Tyr Ser Leu Arg Gly Leu Leu Ser Asn Pro Val Ser
            515                 520                 525

Ser Pro Thr Tyr Trp Lys Pro Ser Thr Phe Gly Gly Asp Val Gly Phe
530                 535                 540

Asp Met Val Lys Thr Ala Ser Leu Glu Lys Leu Phe Cys Gln Asn Ile
545                 550                 555                 560

Ala Gly Glu Cys Pro Leu Val Thr Phe Thr Val Pro Asp Asp Ile Ala
                565                 570                 575

Arg Glu Thr Arg Lys Val Leu Glu Ala Arg Asp Glu Leu
            580                 585

<210> SEQ ID NO 37
<211> LENGTH: 592
<212> TYPE: PRT
<213> ORGANISM: Plexaura homomalla

<400> SEQUENCE: 37

Met Lys Ala Phe Leu His Ile Val Val Leu Ile Ile Phe Ser Gly Leu
1               5                   10                  15

Phe Trp His Glu Val Glu Ser Val Asn Pro Cys Cys Ser Phe Pro Cys
            20                  25                  30

Glu Asn Gly Ala Val Cys Val Asp Asp Gly Asp Thr Tyr Thr Cys Asp
        35                  40                  45

Cys Thr Arg Thr Gly Tyr Tyr Gly Val Asn Cys Glu Lys Pro Ser Trp
    50                  55                  60

Ser Thr Trp Leu Lys Ser Phe Ile Lys Pro Ser Gln Thr Lys His
65                  70                  75                  80

Phe Met Leu Thr His Phe Gly Trp Phe Trp Ile Val Asn Asn Val
            85                  90                  95

Gln Phe Ile Arg Asp Pro Ile Met Arg Ala Ala Tyr Phe Ser Arg Thr
        100                 105                 110

Asp Phe Ile Pro Val Pro His Val Tyr Thr Ser Tyr His Glu Tyr Ala
    115                 120                 125

Thr Met Glu Ala His Tyr Asn Arg Thr His Phe Ala Arg Thr Leu Pro
130                 135                 140

Pro Val Pro Lys Asn Cys Pro Thr Pro Phe Gly Val Ser Gly Lys Lys
145                 150                 155                 160

Ile Leu Pro Pro Ala Glu Glu Val Ala Asn Lys Phe Leu Lys Arg Arg
            165                 170                 175

Glu Phe Ile Ala Asp His Arg Asn Thr Ser Trp Leu Phe Met Phe Phe
        180                 185                 190

Ala Gln His Phe Thr His Gln Phe Phe Lys Thr Val His His Ser Pro
    195                 200                 205

```
Ala Phe Ser Trp Gly Asn His Gly Val Asp Val Ser His Ile Tyr Gly
    210                 215                 220

Gln Gly Val Glu Arg Glu Asn Lys Leu Arg Ala Phe Lys Asp Gly Lys
225                 230                 235                 240

Leu Lys Ser Gln Met Ile Asn Gly Glu Glu Tyr Pro Pro Tyr Leu Lys
                245                 250                 255

Asp Val Asp Gly Leu Lys Met Gln Tyr Leu Glu Asn Thr Ala Glu Glu
            260                 265                 270

Gln Lys Phe Ala Leu Gly His Pro Phe Phe Ser Met Leu Pro Gly Leu
        275                 280                 285

Phe Met Phe Ala Thr Leu Trp Leu Arg Glu His Asn Arg Val Cys Met
    290                 295                 300

Ile Leu Arg Lys Glu His Pro His Trp Glu Asp Glu Arg Ile Tyr Gln
305                 310                 315                 320

Thr Ala Lys Leu Ile Ile Thr Gly Glu Thr Ile Lys Ile Val Ile Glu
                325                 330                 335

Asp Tyr Ile Asn His Leu Ala Asn Tyr Asn Met Lys Leu Arg Tyr Asp
            340                 345                 350

Pro Gln Leu Val Phe Ser Arg Asn Tyr Asp Tyr Asp Asn Arg Ile His
        355                 360                 365

Leu Glu Phe Asn His Leu Tyr His Trp His Pro Phe Ser Pro Asp Gln
    370                 375                 380

Phe Asn Ile Ser Gly Thr Thr Tyr Thr Ile Asn Asp Phe Met Tyr His
385                 390                 395                 400

Pro Glu Ile Val Val Lys His Gly Met Ser Ser Phe Val Asn Ala Met
                405                 410                 415

Ser Ser Gly Leu Cys Gly Lys Met Ser His His Asn His Gly Gln Tyr
            420                 425                 430

Thr Leu Asp Val Ala Val Glu Val Ile Lys Tyr Gln Arg Lys Leu Arg
        435                 440                 445

Met Gln Ser Phe Asn Asn Tyr Arg Arg His Phe Gly Leu Pro Ala Tyr
    450                 455                 460

Lys Ser Phe Glu Glu Met Thr Gly Asp Pro Lys Leu Ala Ala Glu Leu
465                 470                 475                 480

Lys Glu Val Tyr Gly Asp Val Asn Ala Val Asp Phe Tyr Val Gly Phe
                485                 490                 495

Phe Leu Glu Lys Ser Leu Pro Thr Ser Pro Phe Gly Ile Thr Met Ile
            500                 505                 510

Ala Ser Gly Ala Pro Tyr Ser Leu Arg Gly Leu Leu Ser Asn Pro Val
        515                 520                 525

Ser Ser Pro Thr Tyr Trp Lys Pro Ser Thr Phe Gly Gly Glu Val Gly
    530                 535                 540

Phe Asp Ile Val Lys Thr Ala Ser Val Asp Lys Leu Phe Cys Arg Asn
545                 550                 555                 560

Ile Ala Gly Asp Cys Pro Leu Val Thr Phe Thr Val Pro Asp Glu Ile
                565                 570                 575

Ala Arg Glu Ala Arg Arg Asn Leu Ala Ala Asn Ile Lys Asp Glu Leu
            580                 585                 590

<210> SEQ ID NO 38
<211> LENGTH: 619
<212> TYPE: PRT
<213> ORGANISM: Oryza sativa
```

<400> SEQUENCE: 38

```
Met Gly Ser Gly Leu Phe Lys Pro Arg Val His Pro Asp Leu Arg Asp
 1               5                  10                  15

Val Phe Ser Lys Met Ser Phe Asp Lys Ile Gly Phe Leu Phe Ile
             20                  25                  30

His Ala Phe Asp Lys Arg Asn Leu Trp His Lys Val Pro Val Pro Ile
             35                  40                  45

Gly Leu Leu Tyr Leu Asn Thr Arg Arg Thr Leu Leu Glu Lys Tyr Asn
             50                  55                  60

Leu Leu Ala Val Gly Arg Ser Ser His Gly Ala Leu Phe Asp Pro Lys
65                  70                  75                  80

Glu Phe Leu Tyr Arg Thr Glu Asp Gly Lys Tyr Asn Asp Pro His Asn
             85                  90                  95

Ala Glu Ala Gly Lys Pro Lys His Leu Phe Trp Gly Glu Thr Trp Ser
             100                 105                 110

Arg Leu Ile Asn Arg Asn Glu Leu Met Ser Pro Asp Pro Phe Val Val
             115                 120                 125

Ala Thr Lys Leu Leu Ala Arg Arg Glu Tyr Lys Asp Thr Gly Lys Gln
             130                 135                 140

Phe Asn Ile Leu Ala Ala Ala Trp Ile Gln Phe Met Val His Asp Trp
145                 150                 155                 160

Met Asp His Met Glu Asp Thr Gly Gln Ile Gly Ile Thr Ala Pro Lys
             165                 170                 175

Glu Val Ala Asn Glu Cys Pro Leu Lys Ser Phe Lys Phe His Pro Tyr
             180                 185                 190

Lys Glu Leu Pro Thr Asn Ser Asp Gly Ile Lys Ile Gly His Tyr Asn
             195                 200                 205

Ile Arg Thr Ala Trp Trp Asp Gly Ser Ala Val Tyr Gly Asn Asn Glu
             210                 215                 220

Glu Arg Ala Glu Lys Leu Arg Thr Tyr Val Asp Gly Lys Leu Val Ile
225                 230                 235                 240

Gly Asp Asp Gly Leu Leu Leu His Lys Glu Asn Gly Val Ala Leu Ser
             245                 250                 255

Gly Asp Ile Arg Asn Ser Trp Ala Gly Val Ser Ile Leu Gln Ala Leu
             260                 265                 270

Phe Val Lys Glu His Asn Ala Val Cys Asp Ala Ile Lys Glu Glu His
             275                 280                 285

Pro Asn Leu Ser Asp Glu Leu Tyr Arg Tyr Ala Lys Leu Val Thr
             290                 295                 300

Ser Ala Val Ile Ala Lys Val His Thr Ile Asp Trp Thr Val Glu Leu
305                 310                 315                 320

Leu Lys Thr Lys Thr Met Arg Ala Ala Met Arg Ala Asn Trp Tyr Gly
             325                 330                 335

Leu Leu Gly Lys Lys Ile Lys Asp Thr Phe Gly His Ile Gly Gly Pro
             340                 345                 350

Ile Leu Gly Gly Leu Val Gly Leu Lys Lys Pro Asn Asn His Gly Val
             355                 360                 365

Pro Tyr Ser Leu Thr Glu Glu Phe Thr Ser Val Tyr Arg Met His Ser
             370                 375                 380

Leu Ile Pro Ser Thr Leu Lys Leu Arg Asp Pro Thr Gly Gln Pro Asp
385                 390                 395                 400

Ala Asn Asn Ser Pro Pro Cys Leu Glu Asp Ile Asp Ile Gly Glu Met
             405                 410                 415
```

```
Ile Gly Leu Lys Gly Glu Glu Gln Leu Ser Lys Ile Gly Phe Glu Lys
            420                 425                 430

Gln Ala Leu Ser Met Gly Tyr Gln Ala Cys Gly Ala Leu Glu Leu Trp
            435                 440                 445

Asn Tyr Pro Ser Phe Phe Arg Asn Leu Ile Pro Gln Asn Leu Asp Gly
            450                 455                 460

Thr Asn Arg Ser Asp Arg Ile Asp Leu Ala Ala Leu Glu Val Tyr Arg
465                 470                 475                 480

Asp Arg Glu Arg Ser Val Pro Arg Tyr Asn Glu Phe Arg Arg Arg Leu
                485                 490                 495

Phe Leu Ile Pro Ile Lys Ser Trp Glu Asp Leu Thr Ser Asp Lys Asp
            500                 505                 510

Ala Ile Glu Thr Ile Arg Ala Ile Tyr Gly Asp Asp Val Glu Lys Leu
            515                 520                 525

Asp Leu Leu Val Gly Leu Met Ala Glu Lys Lys Ile Lys Gly Phe Ala
            530                 535                 540

Ile Ser Glu Thr Ala Phe Asn Ile Phe Ile Leu Met Ala Ser Arg Arg
545                 550                 555                 560

Leu Glu Ala Asp Arg Phe Phe Thr Ser Asn Phe Asn Glu Glu Thr Tyr
                565                 570                 575

Thr Lys Lys Gly Met Gln Trp Val Lys Thr Thr Glu Gly Leu Arg Asp
            580                 585                 590

Val Ile Asn Arg His Tyr Pro Glu Ile Thr Ala Lys Trp Met Lys Ser
            595                 600                 605

Ser Ser Ala Phe Ser Val Trp Asp Ala Asp Tyr
            610                 615

<210> SEQ ID NO 39
<211> LENGTH: 639
<212> TYPE: PRT
<213> ORGANISM: Arabidopsis thaliana

<400> SEQUENCE: 39

Met Lys Val Ile Thr Ser Leu Ile Ser Ser Ile Leu Leu Lys Phe Ile
1               5                   10                  15

His Lys Asp Phe His Glu Ile Tyr Ala Arg Met Ser Leu Leu Asp Arg
            20                  25                  30

Phe Leu Leu Leu Ile Val His Gly Val Asp Lys Met Val Pro Trp His
            35                  40                  45

Lys Leu Pro Val Phe Leu Gly Leu Thr Tyr Leu Glu Val Arg Arg His
        50                  55                  60

Leu His Gln Gln Tyr Asn Leu Leu Asn Val Gly Gln Thr Pro Thr Gly
65                  70                  75                  80

Ile Arg Phe Asp Pro Ala Asn Tyr Pro Tyr Arg Thr Ala Asp Gly Lys
                85                  90                  95

Phe Asn Asp Pro Phe Asn Glu Gly Val Gly Ser Gln Asn Ser Phe Phe
            100                 105                 110

Gly Arg Asn Cys Pro Pro Val Asp Gln Lys Ser Lys Leu Arg Arg Pro
            115                 120                 125

Asp Pro Met Val Val Ala Thr Lys Leu Leu Gly Arg Lys Lys Phe Ile
            130                 135                 140

Asp Thr Gly Lys Gln Phe Asn Met Ile Ala Ala Ser Trp Ile Gln Phe
145                 150                 155                 160

Met Ile His Asp Trp Ile Asp His Leu Glu Asp Thr His Gln Ile Glu
```

-continued

```
                165                 170                 175
Leu Val Ala Pro Lys Glu Val Ala Ser Lys Cys Pro Leu Ser Ser Phe
            180                 185                 190
Arg Phe Leu Lys Thr Lys Glu Val Pro Thr Gly Phe Phe Glu Ile Lys
        195                 200                 205
Thr Gly Ser Gln Asn Ile Arg Thr Pro Trp Trp Asp Ser Ser Val Ile
    210                 215                 220
Tyr Gly Ser Asn Ser Lys Thr Leu Asp Arg Val Arg Thr Tyr Lys Asp
225                 230                 235                 240
Gly Lys Leu Lys Ile Ser Glu Glu Thr Gly Leu Leu Leu His Asp Glu
                245                 250                 255
Asp Gly Leu Ala Ile Ser Gly Asp Ile Arg Asn Ser Trp Ala Gly Val
            260                 265                 270
Ser Ala Leu Gln Ala Leu Phe Ile Lys Glu His Asn Ala Val Cys Asp
        275                 280                 285
Ala Leu Lys Asp Glu Asp Asp Leu Glu Asp Glu Asp Leu Tyr Arg
    290                 295                 300
Tyr Ala Arg Leu Val Thr Ser Ala Val Ala Lys Ile His Thr Ile
305                 310                 315                 320
Asp Trp Thr Val Gln Leu Leu Lys Thr Asp Thr Leu Leu Ala Gly Met
                325                 330                 335
Arg Ala Asn Trp Tyr Gly Leu Leu Gly Lys Phe Lys Asp Ser Phe
            340                 345                 350
Gly His Ala Gly Ser Ser Ile Leu Gly Gly Val Val Gly Met Lys Lys
        355                 360                 365
Pro Gln Asn His Gly Val Pro Tyr Ser Leu Thr Glu Asp Phe Thr Ser
    370                 375                 380
Val Tyr Arg Met His Ser Leu Leu Pro Asp Gln Leu His Ile Leu Asp
385                 390                 395                 400
Ile Asp Asp Val Pro Gly Thr Asn Lys Ser Leu Pro Leu Ile Gln Glu
                405                 410                 415
Ile Ser Met Arg Asp Leu Ile Gly Arg Lys Gly Glu Glu Thr Met Ser
            420                 425                 430
His Ile Gly Phe Thr Lys Leu Met Val Ser Met Gly His Gln Ala Ser
        435                 440                 445
Gly Ala Leu Glu Leu Met Asn Tyr Pro Met Trp Leu Arg Asp Ile Val
    450                 455                 460
Pro His Asp Pro Asn Gly Gln Ala Arg Pro Asp His Val Asp Leu Ala
465                 470                 475                 480
Ala Leu Glu Ile Tyr Arg Asp Arg Glu Arg Ser Val Pro Arg Tyr Asn
                485                 490                 495
Glu Phe Arg Arg Ser Met Phe Met Ile Pro Ile Thr Lys Trp Glu Asp
            500                 505                 510
Leu Thr Glu Asp Glu Glu Ala Ile Glu Val Leu Asp Asp Val Tyr Asp
        515                 520                 525
Gly Asp Val Glu Glu Leu Asp Leu Leu Val Gly Leu Met Ala Glu Lys
    530                 535                 540
Lys Ile Lys Gly Phe Ala Ile Ser Glu Thr Ala Phe Tyr Ile Phe Leu
545                 550                 555                 560
Ile Met Ala Thr Arg Arg Leu Glu Ala Asp Arg Phe Thr Ser Asp
                565                 570                 575
Phe Asn Glu Thr Ile Tyr Thr Lys Lys Gly Leu Glu Trp Val Asn Thr
            580                 585                 590
```

-continued

```
Thr Glu Ser Leu Lys Asp Val Ile Asp Arg His Tyr Pro Asp Met Thr
            595                 600                 605

Asp Lys Trp Met Asn Ser Glu Ser Ala Phe Ser Val Trp Asp Ser Pro
    610                 615                 620

Pro Leu Thr Lys Asn Pro Ile Pro Leu Tyr Leu Arg Ile Pro Ser
625                 630                 635

<210> SEQ ID NO 40
<211> LENGTH: 643
<212> TYPE: PRT
<213> ORGANISM: Nicotiana tabacum

<400> SEQUENCE: 40

Met Ser Leu Val Met Ala Ser Leu Lys Asn Leu Leu Leu Ser Pro Leu
1               5                   10                  15

Arg Gly Phe Ile His Lys Asp Leu His Asp Ile Phe Glu Arg Met Thr
            20                  25                  30

Leu Leu Ser Lys Leu Leu Phe Leu Ile Val His Leu Val Asp Lys Leu
        35                  40                  45

Asn Leu Trp His Arg Leu Pro Val Phe Leu Gly Leu Leu Tyr Leu Gly
    50                  55                  60

Ala Arg Arg His Leu His Gln Glu Tyr Asn Leu Ile Asn Val Gly Lys
65                  70                  75                  80

Thr Pro Ile Gly Val Arg Ser Asn Pro Ala Asp His Pro Tyr Arg Thr
            85                  90                  95

Ala Asp Gly Lys Tyr Asn Asp Pro Phe Asn Glu Gly Ala Gly Ser Glu
            100                 105                 110

Leu Ser Phe Phe Gly Arg Asn Met Leu Pro Val Asp Gln His Asn Gln
        115                 120                 125

Leu Lys Lys Pro Asp Pro Met Val Val Ala Thr Lys Leu Leu Ala Arg
    130                 135                 140

Arg Asn Phe Val Asp Thr Gly Lys Gln Phe Asn Met Ile Ala Ala Ser
145                 150                 155                 160

Trp Ile Gln Phe Met Ile His Asp Trp Ile Asp His Leu Glu Asp Thr
                165                 170                 175

Lys Gln Ile Glu Leu Lys Ala Ala Glu Glu Val Ala Ser Gln Cys Pro
            180                 185                 190

Leu Lys Ser Phe Arg Phe Phe Lys Thr Lys Glu Ile Pro Thr Gly Phe
        195                 200                 205

Tyr Glu Ile Lys Thr Gly His Leu Asn Thr Arg Thr Pro Trp Trp Asp
    210                 215                 220

Gly Ser Ala Ile Tyr Gly Ser Asn Ala Glu Val Leu Lys Lys Val Arg
225                 230                 235                 240

Thr Phe Lys Asp Gly Lys Leu Lys Leu Ser Ala Asp Gly Leu Leu Glu
                245                 250                 255

Ile Asp Lys Asn Gly Lys Ile Ile Ser Gly Asp Val Arg Asn Thr Trp
            260                 265                 270

Ala Gly Leu Ser Ala Leu Gln Ala Leu Phe Val Gln Glu His Asn Ser
        275                 280                 285

Val Cys Asp Ala Leu Lys Lys Glu Tyr Pro Glu Leu Glu Glu Glu Asp
    290                 295                 300

Leu Tyr Arg His Ala Arg Leu Val Thr Ser Ala Val Ile Ala Lys Val
305                 310                 315                 320

His Thr Ile Asp Trp Thr Val Glu Leu Leu Lys Thr Asp Thr Leu Leu
```

```
            325                 330                 335
Ala Gly Met Arg Ala Asn Trp Tyr Gly Leu Leu Gly Lys Lys Phe Lys
        340                 345                 350

Asp Thr Phe Gly His Val Gly Gly Ser Ile Leu Gly Gly Phe Val Gly
    355                 360                 365

Met Lys Lys Pro Glu Asn Tyr Gly Val Pro Tyr Ser Leu Thr Glu Glu
370                 375                 380

Phe Thr Ser Val Tyr Arg Met His Gln Leu Leu Pro Asp Lys Leu Gln
385                 390                 395                 400

Leu Arg Asn Ile Asp Ala Thr Pro Gly Pro Asn Lys Ser Leu Pro Leu
                405                 410                 415

Thr Asn Glu Ile Pro Leu Glu Asp Leu Ile Gly Gly Lys Gly Glu Lys
            420                 425                 430

Asn Leu Ser Lys Ile Gly Phe Thr Lys Gln Met Val Ser Met Gly His
        435                 440                 445

Gln Ala Cys Gly Ala Leu Glu Leu Trp Asn Tyr Pro Val Trp Met Arg
    450                 455                 460

Asp Leu Ile Pro Gln Asp Val Asp Gly Thr Asp Arg Pro Asp His Ile
465                 470                 475                 480

Asp Leu Ala Ala Leu Glu Ile Tyr Arg Asp Arg Glu Arg Ser Val Ala
                485                 490                 495

Arg Tyr Asn Glu Phe Arg Arg Gly Met Leu Gln Ile Pro Ile Ser Lys
            500                 505                 510

Trp Glu Asp Leu Thr Asp Glu Glu Val Ile Asn Thr Leu Gly Glu
        515                 520                 525

Val Tyr Gly Asp Asp Val Glu Glu Leu Asp Leu Met Val Gly Met Ala
    530                 535                 540

Ala Glu Lys Lys Ile Lys Gly Phe Ala Ile Ser Glu Thr Ala Phe Phe
545                 550                 555                 560

Ile Phe Leu Val Met Ala Ser Arg Arg Leu Glu Ala Asp Arg Phe Phe
                565                 570                 575

Thr Ser Asn Tyr Asn Glu Glu Thr Tyr Thr Lys Lys Gly Leu Glu Trp
            580                 585                 590

Val Asn Thr Thr Glu Ser Leu Lys Asp Val Leu Asp Arg His Tyr Pro
        595                 600                 605

Glu Ile Thr Glu Lys Trp Met Asn Ser Ser Ala Phe Ser Val Trp
    610                 615                 620

Asp Ser Thr Pro Gln Pro His Asn Pro Ile Pro Leu Tyr Phe Arg Val
625                 630                 635                 640

Pro Pro Gln

<210> SEQ ID NO 41
<211> LENGTH: 93
<212> TYPE: DNA
<213> ORGANISM: Homo sapiens

<400> SEQUENCE: 41
gtgagtgcga ccccggtgcc cggtggggaa ttttcttggc ctcctggtgg agccttgaat      60
gccagctcag cccctcatct ctctcctctg cag                                  93

<210> SEQ ID NO 42
<211> LENGTH: 101
<212> TYPE: DNA
<213> ORGANISM: Mus musculus
```

```
<400> SEQUENCE: 42
gtgagtccga ccccagtggt gcccccacgc gtcccggaat tcggtggcct gcaggcggag    60
ccttgaacgc taggctcaac tctctcttcc ttctgcagga a                        01

<210> SEQ ID NO 43
<211> LENGTH: 90
<212> TYPE: DNA
<213> ORGANISM: Canis familiaris

<400> SEQUENCE: 43
gtgagttcga ccctgaggcc cccaggaacc ctcttcgcct cccggggggag cctcgaatgc   60 caggcccagc cctcacctct cgctccgcag                                    90

<210> SEQ ID NO 44
<211> LENGTH: 26
<212> TYPE: DNA
<213> ORGANISM: Artificial Sequence
<220> FEATURE:
<223> OTHER INFORMATION: exemplary motif
<220> FEATURE:
<221> NAME/KEY: misc_feature
<222> LOCATION: (1)...(26)
<223> OTHER INFORMATION: n = A,T,C or G

<400> SEQUENCE: 44
gcctcnggng gagcctygaa ygcyag                                        26

<210> SEQ ID NO 45
<211> LENGTH: 9
<212> TYPE: PRT
<213> ORGANISM: Artificial Sequence
<220> FEATURE:
<223> OTHER INFORMATION: exemplary motif
<220> FEATURE:
<221> NAME/KEY: VARIANT
<222> LOCATION: (1)...(9)
<223> OTHER INFORMATION: Xaa = Any Amino Acid

<400> SEQUENCE: 45

Met Ser Arg Glu Xaa Asp Pro Xaa Ala
 1               5

<210> SEQ ID NO 46
<211> LENGTH: 604
<212> TYPE: PRT
<213> ORGANISM: Mustela vison

<400> SEQUENCE: 46

Met Leu Ala Arg Ala Gly Leu Leu Cys Ala Ser Leu Ser Pro Pro His
 1               5                  10                  15

Ala Ala Asn Pro Cys Cys Ser Asn Pro Cys Gln Asn Gln Gly Val Cys
            20                  25                  30

Met Ser Ile Gly Phe Asp Gln Tyr Met Cys Asp Cys Ser Arg Thr Gly
        35                  40                  45

Phe Tyr Gly Glu Asn Cys Ser Thr Pro Glu Phe Leu Thr Arg Val Lys
    50                  55                  60

Leu Leu Leu Lys Pro Thr Pro Asn Thr Val His Tyr Ile Leu Thr His
65                  70                  75                  80

Phe Lys Gly Val Trp Asn Ile Val Asn Lys Ile Pro Phe Leu Ala Asp
                85                  90                  95

Val Ile Met Lys Tyr Val Arg Thr Ser Arg Ser His Cys Ile Glu Pro
            100                 105                 110
```

```
Pro Pro Thr Tyr Asn Val His Tyr Ala Tyr Lys Ser Trp Glu Ala Phe
        115                 120                 125

Ser Asn Leu Ser Tyr Tyr Thr Arg Ala Leu Pro Pro Val Ala Asp Asp
130                 135                 140

Cys Pro Thr Pro Met Gly Val Lys Gly Lys Lys Glu Leu Pro Asp Ser
145                 150                 155                 160

Lys Glu Ile Val Glu Lys Phe Leu Leu Arg Arg Lys Phe Ile Pro Asp
                165                 170                 175

Pro Gln Gly Thr Asn Met Met Phe Ala Phe Ala Gln His Phe Thr
            180                 185                 190

His Gln Phe Phe Lys Thr Asp His Lys Arg Gly Pro Gly Phe Thr Lys
        195                 200                 205

Gly Leu Gly His Gly Val Asp Leu Ser His Val Tyr Gly Glu Thr Leu
        210                 215                 220

Asp Arg Gln His Lys Leu Arg Leu Phe Lys Asp Gly Lys Met Lys Tyr
225                 230                 235                 240

Gln Val Ile Asp Gly Glu Val Tyr Pro Pro Thr Val Lys Asp Thr Gln
                245                 250                 255

Val Glu Met Ile Tyr Pro Pro His Val Pro Glu His Leu Arg Phe Ala
            260                 265                 270

Val Gly Gln Glu Val Phe Gly Leu Val Pro Gly Leu Met Met Tyr Ala
        275                 280                 285

Thr Ile Trp Leu Arg Glu His Asn Arg Val Cys Asp Val Leu Lys Gln
        290                 295                 300

Glu Gln Gly Glu Trp Asp Asp Glu Arg Leu Phe Arg Arg Ser Arg Leu
305                 310                 315                 320

Ile Leu Ile Gly Glu Thr Ile Lys Ile Val Ile Glu Asp Tyr Val Arg
                325                 330                 335

His Leu Ser Gly Tyr His Phe Ser Leu Lys Phe Asp Pro Glu Leu Leu
            340                 345                 350

Phe Asn Gln Gln Phe Gln Tyr Gln Asn Arg Ile Ala Ala Glu Phe Asn
        355                 360                 365

Thr Leu Tyr His Trp His Pro Leu Leu Pro Asp Thr Leu Gln Ile Asp
        370                 375                 380

Asp Gln Glu Tyr Asn Phe Gln Gln Phe Val Tyr Asn Asn Ser Ile Leu
385                 390                 395                 400

Leu Glu His Gly Leu Thr Gln Phe Gly Glu Ser Phe Ser Arg Gln Ile
                405                 410                 415

Ala Gly Arg Val Ala Gly Gly Arg Asn Val Pro Ala Ala Val Gln Gln
            420                 425                 430

Glu Gln Arg Ala Ser Ile Asp Gln Ser Arg Gln Met Lys Tyr Gln Ser
        435                 440                 445

Leu Asn Glu Tyr Arg Lys Arg Phe Ser Val Lys Pro Tyr Ala Ser Phe
        450                 455                 460

Glu Glu Leu Thr Gly Glu Lys Glu Met Ala Gly Glu Leu Lys Ala Leu
465                 470                 475                 480

Tyr Gln Asp Ile Asp Ala Met Glu Leu Tyr Pro Ala Leu Leu Val Glu
                485                 490                 495

Lys Pro Arg Pro Asp Ala Ile Phe Gly Glu Thr Met Val Glu Ile Gly
            500                 505                 510

Ala Pro Phe Ser Leu Lys Gly Leu Met Gly Asn Pro Ile Cys Ser Pro
        515                 520                 525
```

```
Asp Tyr Trp Lys Pro Ser His Phe Gly Gly Glu Val Gly Phe Lys Ile
        530                 535                 540

Ile Asn Thr Ala Ser Ile Gln Ser Leu Ile Cys Asn Asn Val Lys Gly
545                 550                 555                 560

Cys Pro Phe Thr Ala Phe Ser Val Gln Asp Pro Gln Leu Thr Lys Thr
                565                 570                 575

Val Thr Ile Asn Gly Ser Ser Ser His Ser Gly Leu Asp Asp Ile Asn
            580                 585                 590

Pro Thr Val Leu Leu Lys Glu Arg Ser Thr Glu Leu
        595                 600

<210> SEQ ID NO 47
<211> LENGTH: 599
<212> TYPE: PRT
<213> ORGANISM: Homo sapiens

<400> SEQUENCE: 47

Met Ser Arg Ser Leu Leu Leu Arg Phe Leu Leu Phe Leu Leu Leu Leu
 1               5                  10                  15

Pro Pro Leu Pro Val Leu Leu Ala Asp Pro Gly Ala Pro Thr Pro Val
            20                  25                  30

Asn Pro Cys Cys Tyr Tyr Pro Cys Gln His Gln Gly Ile Cys Val Arg
        35                  40                  45

Phe Gly Leu Asp Arg Tyr Gln Cys Asp Cys Thr Arg Thr Gly Tyr Ser
    50                  55                  60

Gly Pro Asn Cys Thr Ile Pro Gly Leu Trp Thr Trp Leu Arg Asn Ser
65                  70                  75                  80

Leu Arg Pro Ser Pro Ser Phe Thr His Phe Leu Leu Thr His Gly Arg
                85                  90                  95

Trp Phe Trp Glu Phe Val Asn Ala Thr Phe Ile Arg Glu Met Leu Met
            100                 105                 110

Arg Leu Val Leu Thr Val Arg Ser Asn Leu Ile Pro Ser Pro Pro Thr
        115                 120                 125

Tyr Asn Ser Ala His Asp Tyr Ile Ser Trp Glu Ser Phe Ser Asn Val
    130                 135                 140

Ser Tyr Tyr Thr Arg Ile Leu Pro Ser Val Pro Lys Asp Cys Pro Thr
145                 150                 155                 160

Pro Met Gly Thr Lys Gly Lys Lys Gln Leu Pro Asp Ala Gln Leu Leu
                165                 170                 175

Ala Arg Arg Phe Leu Leu Arg Arg Lys Phe Ile Pro Asp Pro Gln Gly
            180                 185                 190

Thr Asn Leu Met Phe Ala Phe Phe Ala Gln His Phe Thr His Gln Phe
        195                 200                 205

Phe Lys Thr Ser Gly Lys Met Gly Pro Gly Phe Thr Lys Ala Leu Gly
    210                 215                 220

His Gly Val Asp Leu Gly His Ile Tyr Gly Asp Asn Leu Glu Arg Gln
225                 230                 235                 240

Tyr Gln Leu Arg Leu Phe Lys Asp Gly Lys Leu Lys Tyr Gln Val Leu
                245                 250                 255

Asp Gly Glu Met Tyr Pro Pro Ser Val Glu Glu Ala Pro Val Leu Met
            260                 265                 270

His Tyr Pro Arg Gly Ile Pro Pro Gln Ser Gln Met Ala Val Gly Gln
        275                 280                 285

Glu Val Phe Gly Leu Leu Pro Gly Leu Met Leu Tyr Ala Thr Leu Trp
    290                 295                 300
```

```
Leu Arg Glu His Asn Arg Val Cys Asp Leu Leu Lys Ala Glu His Pro
305                 310                 315                 320

Thr Trp Gly Asp Glu Gln Leu Phe Gln Thr Thr Arg Leu Ile Leu Ile
            325                 330                 335

Gly Glu Thr Ile Lys Ile Val Ile Glu Glu Tyr Val Gln Gln Leu Ser
            340                 345                 350

Gly Tyr Phe Leu Gln Leu Lys Phe Asp Pro Glu Leu Leu Phe Gly Val
            355                 360                 365

Gln Phe Gln Tyr Arg Asn Arg Ile Ala Met Glu Phe Asn His Leu Tyr
    370                 375                 380

His Trp His Pro Leu Met Pro Asp Ser Phe Lys Val Gly Ser Gln Glu
385                 390                 395                 400

Tyr Ser Tyr Glu Gln Phe Leu Phe Asn Thr Ser Met Leu Val Asp Tyr
            405                 410                 415

Gly Val Glu Ala Leu Val Asp Ala Phe Ser Arg Gln Ile Ala Gly Arg
            420                 425                 430

Ile Gly Gly Gly Arg Asn Met Asp His His Ile Leu His Val Ala Val
            435                 440                 445

Asp Val Ile Arg Glu Ser Arg Glu Met Arg Leu Gln Pro Phe Asn Glu
450                 455                 460

Tyr Arg Lys Arg Phe Gly Met Lys Pro Tyr Thr Ser Phe Gln Glu Leu
465                 470                 475                 480

Val Gly Glu Lys Glu Met Ala Ala Glu Leu Glu Glu Leu Tyr Gly Asp
            485                 490                 495

Ile Asp Ala Leu Glu Phe Tyr Pro Gly Leu Leu Leu Glu Lys Cys His
            500                 505                 510

Pro Asn Ser Ile Phe Gly Glu Ser Met Ile Glu Ile Gly Ala Pro Phe
            515                 520                 525

Ser Leu Lys Gly Leu Leu Gly Asn Pro Ile Cys Ser Pro Glu Tyr Trp
            530                 535                 540

Lys Pro Ser Thr Phe Gly Gly Glu Val Gly Phe Asn Ile Val Lys Thr
545                 550                 555                 560

Ala Thr Leu Lys Lys Leu Val Cys Leu Asn Thr Lys Thr Cys Pro Tyr
            565                 570                 575

Val Ser Phe Arg Val Pro Asp Ala Ser Gln Asp Gly Pro Ala Val
            580                 585                 590

Glu Arg Pro Ser Thr Glu Leu
            595

<210> SEQ ID NO 48
<211> LENGTH: 600
<212> TYPE: PRT
<213> ORGANISM: Ovis aries

<400> SEQUENCE: 48

Met Ser Arg Gln Ser Ile Ser Leu Arg Phe Pro Leu Leu Leu Leu Leu
1               5                   10                  15

Leu Ser Pro Ser Pro Val Phe Ser Ala Asp Pro Gly Ala Pro Ala Pro
            20                  25                  30

Val Asn Pro Cys Cys Tyr Tyr Pro Cys Gln His Gln Gly Ile Cys Val
            35                  40                  45

Arg Phe Gly Leu Asp Arg Tyr Gln Cys Asp Cys Thr Arg Thr Gly Tyr
    50                  55                  60

Ser Gly Pro Asn Cys Thr Ile Pro Glu Ile Trp Thr Trp Leu Arg Thr
```

-continued

```
                65                  70                  75                  80
Thr Leu Arg Pro Ser Pro Ser Phe Ile His Phe Met Leu Thr His Gly
                    85                  90                  95
Arg Trp Leu Trp Asp Phe Val Asn Ala Thr Phe Ile Arg Asp Thr Leu
                100                 105                 110
Met Arg Leu Val Leu Thr Val Arg Ser Asn Leu Ile Pro Ser Pro Pro
                115                 120                 125
Thr Tyr Asn Ile Ala His Asp Tyr Ile Ser Trp Glu Ser Phe Ser Asn
                130                 135                 140
Val Ser Tyr Tyr Thr Arg Ile Leu Pro Ser Val Pro Arg Asp Cys Pro
145                 150                 155                 160
Thr Pro Met Gly Thr Lys Gly Lys Lys Gln Leu Pro Asp Ala Glu Phe
                165                 170                 175
Leu Ser Arg Arg Phe Leu Leu Arg Arg Lys Phe Ile Pro Asp Pro Gln
                180                 185                 190
Gly Thr Asn Leu Met Phe Ala Phe Phe Ala Gln His Phe Thr His Gln
                195                 200                 205
Phe Phe Lys Thr Ser Gly Lys Met Gly Pro Gly Phe Thr Lys Ala Leu
                210                 215                 220
Gly His Gly Val Asp Leu Gly His Ile Tyr Gly Asp Asn Leu Glu Arg
225                 230                 235                 240
Gln Tyr Gln Leu Arg Leu Phe Lys Asp Gly Lys Leu Lys Tyr Gln Met
                245                 250                 255
Leu Asn Gly Glu Val Tyr Pro Pro Ser Val Glu Glu Ala Pro Val Leu
                260                 265                 270
Met His Tyr Pro Arg Gly Ile Pro Pro Gln Ser Gln Met Ala Val Gly
                275                 280                 285
Gln Glu Val Phe Gly Leu Leu Pro Gly Leu Met Leu Tyr Ala Thr Ile
                290                 295                 300
Trp Leu Arg Glu His Asn Arg Val Cys Asp Leu Leu Lys Ala Glu His
305                 310                 315                 320
Pro Thr Trp Gly Asp Glu Gln Leu Phe Gln Thr Ala Arg Leu Ile Leu
                325                 330                 335
Ile Gly Glu Thr Ile Lys Ile Val Ile Glu Glu Tyr Val Gln Gln Leu
                340                 345                 350
Ser Gly Tyr Phe Leu Gln Leu Lys Phe Asp Pro Glu Leu Leu Phe Gly
                355                 360                 365
Ala Gln Phe Gln Tyr Arg Asn Arg Ile Ala Met Glu Phe Asn Gln Leu
                370                 375                 380
Tyr His Trp His Pro Leu Met Pro Asp Ser Phe Arg Val Gly Pro Gln
385                 390                 395                 400
Asp Tyr Ser Tyr Glu Gln Phe Leu Phe Asn Thr Ser Met Leu Val Asp
                405                 410                 415
Tyr Gly Val Glu Ala Leu Val Asp Ala Phe Ser Arg Gln Pro Ala Gly
                420                 425                 430
Arg Ile Gly Gly Gly Arg Asn Ile Asp His His Ile Leu His Val Ala
                435                 440                 445
Val Asp Val Ile Lys Glu Ser Arg Val Leu Arg Leu Gln Pro Phe Asn
450                 455                 460
Glu Tyr Arg Lys Arg Phe Gly Met Lys Pro Tyr Thr Ser Phe Gln Glu
465                 470                 475                 480
Leu Thr Gly Glu Lys Glu Met Ala Ala Glu Leu Glu Glu Leu Tyr Gly
                485                 490                 495
```

```
Asp Ile Asp Ala Leu Glu Phe Tyr Pro Gly Leu Leu Leu Glu Lys Cys
            500                 505                 510

His Pro Asn Ser Ile Phe Gly Glu Ser Met Ile Glu Met Gly Ala Pro
            515                 520                 525

Phe Ser Leu Lys Gly Leu Leu Gly Asn Pro Ile Cys Ser Pro Glu Tyr
            530                 535                 540

Trp Lys Ala Ser Thr Phe Gly Gly Glu Val Gly Phe Asn Leu Val Lys
545                 550                 555                 560

Thr Ala Thr Leu Lys Lys Leu Val Cys Leu Asn Thr Lys Thr Cys Pro
                565                 570                 575

Tyr Val Ser Phe His Val Pro Asp Pro Arg Gln Glu Asp Arg Pro Gly
            580                 585                 590

Val Glu Arg Pro Pro Thr Glu Leu
            595                 600

<210> SEQ ID NO 49
<211> LENGTH: 414
<212> TYPE: PRT
<213> ORGANISM: Canis familiaris

<400> SEQUENCE: 49

Met Ser Arg Glu Phe Asp Pro Glu Ala Pro Arg Asn Pro Leu Arg Leu
1               5                   10                  15

Pro Gly Glu Pro Arg Met Pro Gly Pro Ala Leu Thr Ser Arg Ser Ala
            20                  25                  30

Gly Gly Ser Arg Leu His Arg Trp Pro Leu Leu Leu Leu Leu Leu Leu
        35                  40                  45

Leu Leu Pro Pro Pro Val Leu Pro Ala Glu Ala Arg Thr Pro Ala
    50                  55                  60

Pro Val Asn Pro Cys Cys Tyr Tyr Pro Cys Gln His Gln Gly Ile Cys
65                  70                  75                  80

Val Arg Phe Gly Leu Asp Arg Tyr Gln Cys Asp Cys Thr Arg Thr Gly
                85                  90                  95

Tyr Ser Gly Pro Asn Cys Thr Ile Pro Glu Leu Trp Thr Trp Leu Arg
            100                 105                 110

Asn Ser Leu Arg Pro Ser Pro Ser Phe Leu His Phe Leu Leu Thr His
            115                 120                 125

Gly Arg Trp Phe Trp Glu Phe Ile Asn Ala Thr Phe Ile Arg Asp Met
        130                 135                 140

Leu Met Arg Leu Val Leu Thr Gly Glu Thr Ile Lys Ile Val Ile Glu
145                 150                 155                 160

Glu Tyr Val Gln Gln Leu Ser Gly Tyr Phe Leu Gln Leu Lys Phe Asp
                165                 170                 175

Pro Glu Leu Leu Phe Ser Ala Gln Phe Gln Tyr Arg Asn Arg Ile Ala
            180                 185                 190

Met Glu Phe Asn Gln Leu Tyr His Trp His Pro Leu Met Pro Asp Ser
            195                 200                 205

Phe Trp Val Gly Ser Gln Glu Tyr Ser Tyr Glu Gln Phe Leu Phe Asn
        210                 215                 220

Thr Ser Met Leu Thr His Tyr Gly Ile Glu Ala Leu Val Asp Ala Phe
225                 230                 235                 240

Ser Arg Gln Ser Ala Gly Arg Ile Gly Gly Gly Arg Asn Ile Asp His
                245                 250                 255

His Val Leu His Val Ala Val Glu Thr Ile Lys Glu Ser Arg Glu Leu
```

```
                    260                 265                 270
Arg Leu Gln Pro Phe Asn Glu Tyr Arg Lys Arg Phe Gly Met Arg Pro
            275                 280                 285

Tyr Met Ser Phe Gln Glu Leu Thr Gly Glu Lys Glu Met Ala Ala Glu
        290                 295                 300

Leu Glu Glu Leu Tyr Gly Asp Ile Asp Ala Leu Glu Phe Tyr Pro Gly
305                 310                 315                 320

Leu Leu Leu Glu Lys Cys His Pro Asn Ser Ile Phe Gly Glu Ser Met
                325                 330                 335

Ile Glu Ile Gly Ala Pro Phe Ser Leu Lys Gly Leu Leu Gly Asn Pro
            340                 345                 350

Ile Cys Ser Pro Glu Tyr Trp Lys Pro Ser Thr Phe Gly Gly Glu Met
        355                 360                 365

Gly Phe Asn Met Val Lys Thr Ala Thr Leu Lys Lys Leu Val Cys Leu
370                 375                 380

Asn Thr Lys Thr Cys Pro Tyr Val Ser Phe Arg Val Pro Asp Pro His
385                 390                 395                 400

Gln Asp Gly Gly Pro Gly Val Gln Arg Pro Ser Thr Glu Leu
                405                 410

<210> SEQ ID NO 50
<211> LENGTH: 606
<212> TYPE: PRT
<213> ORGANISM: Oryctolagus cuniculus

<400> SEQUENCE: 50

Met Ser Arg Ser Ser Pro Ser Leu Arg Leu Pro Val Leu Leu Leu Leu
1               5                   10                  15

Leu Leu Leu Leu Leu Pro Pro Pro Pro Val Leu Pro Ala Asp
            20                  25                  30

Pro Gly Ala Pro Ala Pro Val Asn Pro Cys Cys Tyr Phe Pro Cys Gln
        35                  40                  45

His Gln Gly Val Cys Val Arg Val Ala Leu Asp Arg Tyr Gln Cys Asp
    50                  55                  60

Cys Thr Arg Thr Gly Tyr Ser Gly Pro Asn Cys Thr Val Pro Asp Leu
65                  70                  75                  80

Trp Thr Trp Leu Arg Ser Ser Leu Arg Pro Ser Pro Thr Phe Val His
                85                  90                  95

Tyr Leu Leu Thr His Val Arg Trp Phe Trp Glu Phe Val Asn Ala Thr
            100                 105                 110

Phe Ile Arg Asp Thr Leu Met Arg Leu Val Leu Thr Val Arg Ser Asn
        115                 120                 125

Leu Ile Pro Ser Pro Pro Thr Tyr Asn Leu Asp Tyr Asp Tyr Ile Ser
    130                 135                 140

Trp Glu Ala Phe Ser Asn Val Ser Tyr Tyr Thr Arg Val Leu Pro Ser
145                 150                 155                 160

Val Pro Lys Asp Cys Pro Thr Pro Met Gly Thr Lys Gly Lys Lys Gln
                165                 170                 175

Leu Pro Asp Ala Gln Val Leu Ala His Arg Phe Leu Leu Arg Arg Thr
            180                 185                 190

Phe Ile Pro Asp Pro Gln Gly Thr Asn Leu Met Phe Ala Phe Phe Ala
        195                 200                 205

Gln His Phe Thr His Gln Phe Phe Lys Thr Ser Gly Lys Met Gly Pro
    210                 215                 220
```

```
Gly Phe Thr Lys Ala Leu Gly His Gly Val Asp Leu Gly His Ile Tyr
225                 230                 235                 240

Gly Asp Ser Leu Glu Arg Gln Tyr His Leu Arg Leu Phe Lys Asp Gly
            245                 250                 255

Lys Leu Lys Tyr Gln Val Leu Asp Gly Glu Val Tyr Pro Pro Ser Val
        260                 265                 270

Glu Glu Ala Pro Val Leu Met His Tyr Pro Arg Gly Val Pro Pro Arg
    275                 280                 285

Ser Gln Met Ala Val Gly Gln Glu Val Phe Gly Leu Leu Pro Gly Leu
290                 295                 300

Met Leu Tyr Ala Thr Leu Trp Leu Arg Glu His Asn Arg Val Cys Asp
305                 310                 315                 320

Leu Leu Lys Ala Glu His Pro Thr Trp Asp Asp Glu Gln Leu Phe Gln
            325                 330                 335

Thr Thr Arg Leu Ile Leu Ile Gly Glu Thr Ile Lys Ile Val Ile Glu
        340                 345                 350

Glu Tyr Val Gln Gln Leu Ser Gly Tyr Phe Leu Gln Leu Lys Phe Asp
    355                 360                 365

Pro Glu Met Leu Phe Ser Val Gln Phe Gln Tyr Arg Asn Arg Ile Ala
370                 375                 380

Met Glu Phe Asn His Leu Tyr His Trp His Pro Leu Met Pro Asp Ser
385                 390                 395                 400

Phe Gln Val Gly Ser Gln Glu Tyr Ser Tyr Glu Gln Phe Leu Phe Asn
            405                 410                 415

Thr Ser Met Leu Val Asp Tyr Gly Val Glu Ala Leu Val Asp Ala Phe
        420                 425                 430

Ser Arg Gln Ser Ala Gly Arg Ile Gly Gly Arg Asn Ile Asp His
    435                 440                 445

His Val Leu His Val Ala Val Glu Val Ile Lys Glu Ser Arg Glu Met
450                 455                 460

Arg Leu Gln Pro Phe Asn Glu Tyr Arg Lys Arg Phe Gly Leu Lys Pro
465                 470                 475                 480

Tyr Ala Ser Phe Gln Glu Leu Thr Gly Glu Thr Glu Met Ala Ala Glu
            485                 490                 495

Leu Glu Glu Leu Tyr Gly Asp Ile Asp Ala Leu Glu Phe Tyr Pro Gly
        500                 505                 510

Leu Leu Leu Glu Lys Cys Gln Pro Asn Ser Ile Phe Gly Glu Ser Met
    515                 520                 525

Ile Glu Ile Gly Ala Pro Phe Ser Leu Lys Gly Leu Leu Gly Asn Pro
530                 535                 540

Ile Cys Ser Pro Glu Tyr Trp Lys Pro Ser Thr Phe Gly Gly Glu Val
545                 550                 555                 560

Gly Ser Asn Leu Ile Lys Thr Ala Thr Leu Lys Lys Leu Val Cys Leu
            565                 570                 575

Asn Thr Lys Thr Cys Pro Tyr Val Ser Phe Arg Val Pro Arg Ser Ser
        580                 585                 590

Gly Asp Asp Gly Pro Ala Ala Glu Arg Arg Ser Thr Glu Leu
    595                 600                 605

<210> SEQ ID NO 51
<211> LENGTH: 602
<212> TYPE: PRT
<213> ORGANISM: Mus musculus

<400> SEQUENCE: 51
```

-continued

```
Met Ser Arg Arg Ser Leu Ser Leu Trp Phe Pro Leu Leu Leu Leu
1               5                   10                  15

Leu Leu Pro Pro Thr Pro Ser Val Leu Leu Ala Asp Pro Gly Val Pro
            20                  25                  30

Ser Pro Val Asn Pro Cys Cys Tyr Pro Cys Gln Asn Gln Gly Val
        35                  40                  45

Cys Val Arg Phe Gly Leu Asp Asn Tyr Gln Cys Asp Cys Thr Arg Thr
    50                  55                  60

Gly Tyr Ser Gly Pro Asn Cys Thr Ile Pro Glu Ile Trp Thr Trp Leu
65                  70                  75                  80

Arg Asn Ser Leu Arg Pro Ser Pro Ser Phe Thr His Phe Leu Leu Thr
                85                  90                  95

His Gly Tyr Trp Leu Trp Glu Phe Val Asn Ala Thr Phe Ile Arg Glu
            100                 105                 110

Val Leu Met Arg Leu Val Leu Thr Val Arg Ser Asn Leu Ile Pro Ser
            115                 120                 125

Pro Pro Thr Tyr Asn Ser Ala His Asp Tyr Ile Ser Trp Glu Ser Phe
    130                 135                 140

Ser Asn Val Ser Tyr Tyr Thr Arg Ile Leu Pro Ser Val Pro Lys Asp
145                 150                 155                 160

Cys Pro Thr Pro Met Gly Thr Lys Gly Lys Lys Gln Leu Pro Asp Val
                165                 170                 175

Gln Leu Leu Ala Gln Gln Leu Leu Leu Arg Arg Glu Phe Ile Pro Ala
            180                 185                 190

Pro Gln Gly Thr Asn Ile Leu Phe Ala Phe Phe Ala Gln His Phe Thr
    195                 200                 205

His Gln Phe Phe Lys Thr Ser Gly Lys Met Gly Pro Gly Phe Thr Lys
    210                 215                 220

Ala Leu Gly His Gly Val Asp Leu Gly His Ile Tyr Gly Asp Asn Leu
225                 230                 235                 240

Glu Arg Gln Tyr His Leu Arg Leu Phe Lys Asp Gly Lys Leu Lys Tyr
                245                 250                 255

Gln Val Leu Asp Gly Glu Val Tyr Pro Pro Ser Val Glu Gln Ala Ser
            260                 265                 270

Val Leu Met Arg Tyr Pro Pro Gly Val Pro Pro Glu Arg Gln Met Ala
            275                 280                 285

Val Gly Gln Glu Val Phe Gly Leu Leu Pro Gly Leu Met Leu Phe Ser
            290                 295                 300

Thr Ile Trp Leu Arg Glu His Asn Arg Val Cys Asp Leu Leu Lys Glu
305                 310                 315                 320

Glu His Pro Thr Trp Asp Asp Glu Gln Leu Phe Gln Thr Thr Arg Leu
                325                 330                 335

Ile Leu Ile Gly Glu Thr Ile Lys Ile Val Ile Glu Glu Tyr Val Gln
            340                 345                 350

His Leu Ser Gly Tyr Phe Leu Gln Leu Lys Phe Asp Pro Glu Leu Leu
            355                 360                 365

Phe Arg Ala Gln Phe Gln Tyr Arg Asn Arg Ile Ala Met Glu Phe Asn
    370                 375                 380

His Leu Tyr His Trp His Pro Leu Met Pro Asn Ser Phe Gln Val Gly
385                 390                 395                 400

Ser Gln Glu Tyr Ser Tyr Glu Gln Phe Leu Phe Asn Thr Ser Met Leu
            405                 410                 415
```

-continued

```
Val Asp Tyr Gly Val Glu Ala Leu Val Asp Ala Phe Ser Arg Gln Arg
            420                 425                 430

Ala Gly Arg Ile Gly Gly Gly Arg Asn Phe Asp Tyr His Val Leu His
            435                 440                 445

Val Ala Val Asp Val Ile Lys Glu Ser Arg Glu Met Arg Leu Gln Pro
            450                 455                 460

Phe Asn Glu Tyr Arg Lys Arg Phe Gly Leu Lys Pro Tyr Thr Ser Phe
465                 470                 475                 480

Gln Glu Leu Thr Gly Glu Lys Glu Met Ala Ala Glu Leu Glu Glu Leu
            485                 490                 495

Tyr Gly Asp Ile Asp Ala Leu Glu Phe Tyr Pro Gly Leu Leu Leu Glu
            500                 505                 510

Lys Cys Gln Pro Asn Ser Ile Phe Gly Glu Ser Met Ile Glu Met Gly
            515                 520                 525

Ala Pro Phe Ser Leu Lys Gly Leu Leu Gly Asn Pro Ile Cys Ser Pro
            530                 535                 540

Glu Tyr Trp Lys Pro Ser Thr Phe Gly Gly Asp Val Gly Phe Asn Leu
545                 550                 555                 560

Val Asn Thr Ala Ser Leu Lys Lys Leu Val Cys Leu Asn Thr Lys Thr
            565                 570                 575

Cys Pro Tyr Val Ser Phe Arg Val Pro Asp Tyr Pro Gly Asp Asp Gly
            580                 585                 590

Ser Val Leu Val Arg Arg Ser Thr Glu Leu
            595                 600

<210> SEQ ID NO 52
<211> LENGTH: 602
<212> TYPE: PRT
<213> ORGANISM: Rattus norvegicus

<400> SEQUENCE: 52

Met Ser Arg Arg Ser Leu Ser Leu Gln Phe Pro Leu Leu Leu Leu Leu
1               5                   10                  15

Leu Leu Leu Pro Pro Pro Pro Val Leu Leu Thr Asp Ala Gly Val Pro
            20                  25                  30

Ser Pro Val Asn Pro Cys Cys Tyr Tyr Pro Cys Gln Asn Gln Gly Val
            35                  40                  45

Cys Val Arg Phe Gly Leu Asp His Tyr Gln Cys Asp Cys Thr Arg Thr
        50                  55                  60

Gly Tyr Ser Gly Pro Asn Cys Thr Ile Pro Glu Ile Trp Thr Trp Leu
65              70                  75                  80

Arg Ser Ser Leu Arg Pro Ser Pro Ser Phe Thr His Phe Leu Leu Thr
            85                  90                  95

His Gly Tyr Trp Ile Trp Glu Phe Val Asn Ala Thr Phe Ile Arg Glu
            100                 105                 110

Val Leu Met Arg Leu Val Ile Thr Val Arg Ser Asn Leu Ile Pro Ser
            115                 120                 125

Pro Pro Thr Tyr Asn Thr Ala His Asp Tyr Ile Ser Trp Glu Ser Phe
            130                 135                 140

Ser Asn Val Ser Tyr Tyr Thr Arg Ile Leu Pro Ser Val Pro Lys Asp
145                 150                 155                 160

Cys Pro Thr Pro Met Gly Thr Lys Gly Lys Lys Gln Leu Pro Asp Ile
            165                 170                 175

His Leu Leu Ala Gln Arg Leu Leu Leu Arg Arg Glu Phe Ile Pro Gly
            180                 185                 190
```

```
Pro Gln Gly Thr Asn Val Leu Phe Ala Phe Ala Gln His Phe Thr
            195                 200                 205
His Gln Phe Phe Lys Thr Ser Gly Lys Met Gly Pro Gly Phe Thr Lys
    210                 215                 220
Ala Leu Gly His Gly Val Asp Leu Gly His Ile Tyr Gly Asp Ser Leu
225                 230                 235                 240
Glu Arg Gln Tyr His Leu Arg Leu Phe Lys Asp Gly Lys Leu Lys Tyr
                245                 250                 255
Gln Val Leu Asp Gly Glu Val Tyr Pro Pro Ser Val Glu Gln Ala Ser
            260                 265                 270
Val Leu Met Arg Tyr Pro Pro Gly Val Pro Pro Glu Lys Gln Met Ala
        275                 280                 285
Val Gly Gln Glu Val Phe Gly Leu Leu Pro Gly Leu Met Leu Phe Ser
    290                 295                 300
Thr Ile Trp Leu Arg Glu His Asn Arg Val Cys Asp Leu Leu Lys Glu
305                 310                 315                 320
Glu His Pro Thr Trp Asp Asp Glu Gln Leu Phe Gln Thr Thr Arg Leu
                325                 330                 335
Ile Leu Ile Gly Glu Thr Ile Lys Ile Ile Glu Glu Tyr Val Gln
            340                 345                 350
His Leu Ser Gly Tyr Phe Leu Gln Leu Lys Phe Asp Pro Glu Leu Leu
        355                 360                 365
Phe Arg Ala Gln Phe Gln Tyr Arg Asn Arg Ile Ala Leu Glu Phe Asn
    370                 375                 380
His Leu Tyr His Trp His Pro Leu Met Pro Asp Ser Phe Gln Val Gly
385                 390                 395                 400
Ser Gln Glu Tyr Ser Tyr Glu Gln Phe Leu Phe Asn Thr Ser Met Leu
                405                 410                 415
Val Asp Tyr Gly Val Glu Ala Leu Val Asp Ala Phe Ser Arg Gln Arg
            420                 425                 430
Ala Gly Arg Ile Gly Gly Gly Arg Asn Phe Asp Tyr His Val Leu His
        435                 440                 445
Val Ala Glu Asp Val Ile Lys Glu Ser Arg Glu Met Arg Leu Gln Ser
    450                 455                 460
Phe Asn Glu Tyr Arg Lys Arg Phe Gly Leu Lys Pro Tyr Thr Ser Phe
465                 470                 475                 480
Gln Glu Phe Thr Gly Glu Lys Glu Met Ala Ala Glu Leu Glu Glu Leu
                485                 490                 495
Tyr Gly Asp Ile Asp Ala Leu Glu Phe Tyr Pro Gly Leu Met Leu Glu
            500                 505                 510
Lys Cys Gln Pro Asn Ser Leu Phe Gly Glu Ser Met Ile Glu Met Gly
        515                 520                 525
Ala Pro Phe Ser Leu Lys Gly Leu Leu Gly Asn Pro Ile Cys Ser Pro
    530                 535                 540
Glu Tyr Trp Lys Pro Ser Thr Phe Gly Gly Asp Val Gly Phe Asn Ile
545                 550                 555                 560
Val Asn Thr Ala Ser Leu Lys Lys Leu Val Cys Leu Asn Thr Lys Thr
                565                 570                 575
Cys Pro Tyr Val Ser Phe Arg Val Pro Asp Tyr Pro Gly Asp Asp Gly
            580                 585                 590
Ser Val Phe Val Arg Pro Ser Thr Glu Leu
        595                 600
```

<210> SEQ ID NO 53
<211> LENGTH: 624
<212> TYPE: PRT
<213> ORGANISM: Oncorhynchus mykiss

<400> SEQUENCE: 53

```
Met Ser Ala Ala Tyr Ile Ile Phe Ala Leu Leu Tyr Trp Glu Asp Ala
 1               5                   10                  15

Pro Ala Glu Gly Ala Tyr Ala Val Asn Leu Thr Met Arg Glu Cys Val
                20                  25                  30

Val Trp Val Trp Ala Cys Ile Leu Leu Gln Arg Leu Pro Thr Cys Arg
            35                  40                  45

Gly Glu Glu Val Glu Asp Ala Ser Thr Val Val Asn Pro Cys Cys Tyr
 50                  55                  60

Tyr Pro Cys Gln Asn Trp Gly Val Cys Val Arg Phe Gly Ile Asp Arg
 65                  70                  75                  80

Tyr Glu Cys Asp Cys Thr Arg Thr Gly Phe Tyr Gly Gln Asn Cys Thr
                85                  90                  95

Ile Pro Glu Phe Trp Thr Arg Val His Gln Gln Leu Lys Pro Ser Pro
            100                 105                 110

Asp Val Val His Tyr Ile Leu Thr His Phe His Trp Leu Trp Asn Leu
        115                 120                 125

Ile Asn Arg Thr Phe Met Arg Asp Trp Leu Met Arg Val Val Leu Thr
130                 135                 140

Val Arg Ser Asn Leu Ile Pro Ser Pro Thr Phe Asn Ser Lys Tyr
145                 150                 155                 160

Gly Tyr Leu Ser Trp Glu Ser Tyr Ser Asn Val Ser Tyr Tyr Thr Arg
                165                 170                 175

Ile Leu Pro Pro Val Pro Glu Asp Cys Pro Thr Pro Met Gly Thr Lys
            180                 185                 190

Gly Lys Ser Val Leu Pro Asp Pro Lys Leu Val Val Glu Lys Phe Leu
        195                 200                 205

Leu Arg Arg Gln Phe Arg Arg Asp Pro Arg Gly Thr Asn Leu Met Phe
210                 215                 220

Ala Phe Phe Ala Gln His Phe Thr His Gln Phe Phe Lys Thr Arg Asn
225                 230                 235                 240

Ser Met Gly Leu Gly Phe Thr Arg Ala Leu Gly His Gly Val Asp Ala
                245                 250                 255

Gly Asn Val Tyr Gly Asp Asn Leu Val Arg Gln Leu Asn Leu Arg Leu
            260                 265                 270

Leu Lys Asp Gly Lys Met Lys Tyr Gln Val Val Lys Gly Glu Val Tyr
        275                 280                 285

Pro Pro Thr Val Ala Glu Ala Val Asn Met Arg Tyr Pro Gln Glu
290                 295                 300

Thr Pro Val Gly Gln Arg Met Ala Ile Gly Gln Glu Val Phe Gly Leu
305                 310                 315                 320

Leu Pro Gly Leu Thr Met Tyr Ala Thr Leu Trp Leu Arg Glu His Asn
                325                 330                 335

Arg Val Cys Asp Ile Leu Lys Ala Glu His Pro Thr Trp Gly Asp Glu
            340                 345                 350

Gln Leu Phe Gln Thr Ala Arg Leu Ile Val Ile Gly Glu Thr Ile Arg
        355                 360                 365

Ile Val Ile Glu Glu Tyr Val Gln His Leu Ser Gly Tyr Leu Leu Asp
370                 375                 380
```

Leu Lys Phe Asp Pro Val Leu Phe Lys Ser Thr Phe Gln Tyr Arg
385                 390                 395                 400

Asn Arg Ile Ala Val Glu Phe Lys Gln Leu Tyr His Trp His Pro Leu
            405                 410                 415

Met Pro Asp Ser Phe His Ile Asp Gly Asp Glu Val Pro Tyr Ser Gln
            420                 425                 430

Phe Ile Phe Asn Thr Ser Ile Val Thr His Tyr Gly Val Glu Lys Leu
            435                 440                 445

Val Asp Ala Phe Ser Arg Gln Cys Ala Gly Gln Ile Gly Gly Gly Arg
450                 455                 460

Asn Ile His Pro Val Val Thr Asn Val Ala Glu Gly Val Ile Glu Glu
465                 470                 475                 480

Ser Arg Thr Leu Arg Leu Gln Pro Phe Asn Glu Tyr Arg Lys Arg Phe
            485                 490                 495

Asn Leu Lys Pro Tyr Thr Ser Phe Ser Asp Phe Thr Gly Glu Glu Glu
            500                 505                 510

Met Ala Arg Glu Leu Glu Glu Leu Tyr Gly Asp Ile Asp Ala Leu Glu
            515                 520                 525

Phe Tyr Pro Ala Ile Met Leu Glu Lys Thr Arg Pro Asn Ala Ile Phe
530                 535                 540

Gly Glu Ser Met Val Glu Met Gly Ala Pro Phe Ser Leu Lys Gly Leu
545                 550                 555                 560

Leu Gly Asn Pro Ile Cys Ser Pro Glu Tyr Trp Lys Pro Ser Thr Phe
            565                 570                 575

Gly Gly Gln Thr Gly Phe Asp Ile Val Asn Ser Ala Ser Leu Glu Arg
            580                 585                 590

Leu Val Cys Leu Asn Thr Asn Trp Cys Pro Tyr Val Ala Phe Asn Val
            595                 600                 605

Pro Pro Ala Gly Gln Glu Glu Pro Pro Arg Lys Gln Ser Thr Glu Leu
610                 615                 620

<210> SEQ ID NO 54
<211> LENGTH: 598
<212> TYPE: PRT
<213> ORGANISM: Salvelinus fontinalis

<400> SEQUENCE: 54

Met Arg Gly Leu Val Val Cys Val Trp Ala Cys Ile Leu Leu Gln Arg
1               5                   10                  15

Leu Pro Thr Cys Arg Gly Glu Glu Val Lys Asp Val Ser Thr Asn Val
            20                  25                  30

Val Asn Pro Cys Cys Tyr Tyr Pro Cys Gln Asn Trp Ala Leu Cys Val
            35                  40                  45

Arg Phe Gly Ile Asp Arg Tyr Glu Cys Asp Cys Thr Arg Thr Gly Phe
50                  55                  60

Tyr Gly Gln Asn Cys Thr Ile Pro Glu Phe Trp Thr Arg Ile His Gln
65                  70                  75                  80

Gln Leu Lys Pro Ser Pro Asp Val Val His Tyr Ile Leu Thr His Phe
            85                  90                  95

His Trp Leu Trp Asn Leu Ile Asn Arg Thr Phe Met Arg Asp Trp Leu
            100                 105                 110

Met Arg Met Val Leu Thr Val Arg Ser Asn Leu Ile Pro Ser Pro Pro
            115                 120                 125

Thr Phe Asn Ser Lys Tyr Gly Tyr Leu Ser Trp Glu Ser Tyr Ser Asn

-continued

```
            130                 135                 140
Val Ser Tyr Tyr Thr Arg Ile Leu Pro Pro Val Pro Glu Asp Cys Pro
145                 150                 155                 160

Thr Pro Met Gly Thr Lys Gly Lys Ser Val Leu Pro Asp Pro Lys Leu
                165                 170                 175

Val Val Glu Lys Phe Leu Leu Arg Arg Gln Phe Arg Pro Asp Pro Lys
                180                 185                 190

Gly Thr Asn Leu Met Phe Ala Phe Ala Gln His Phe Thr His Gln
                195                 200                 205

Phe Phe Lys Thr Arg Asn Ser Met Gly Leu Gly Phe Thr Ser Ala Leu
210                 215                 220

Gly His Gly Val Asp Ala Gly Asn Val Tyr Gly Asp Asn Leu Val Arg
225                 230                 235                 240

Gln Leu Asn Leu Arg Leu Leu Lys Asp Gly Lys Met Lys Tyr Gln Val
                245                 250                 255

Val Lys Gly Glu Val Tyr Pro Pro Thr Val Ala Glu Ala Pro Val Asn
                260                 265                 270

Met Arg Tyr Pro Gln Gly Thr Pro Val Gly Gln Arg Met Ala Ile Gly
            275                 280                 285

Gln Glu Val Phe Gly Leu Leu Pro Gly Leu Thr Met Tyr Ala Thr Leu
            290                 295                 300

Trp Leu Arg Glu His Asn Arg Val Cys Asp Ile Leu Lys Ala Glu His
305                 310                 315                 320

Pro Thr Trp Gly Asp Glu Gln Leu Phe Gln Thr Ala Arg Leu Ile Val
                325                 330                 335

Ile Gly Glu Thr Ile Arg Ile Val Ile Glu Glu Tyr Val Gln His Leu
                340                 345                 350

Ser Gly Tyr Leu Leu Asp Leu Lys Phe Asp Pro Val Leu Leu Phe Lys
            355                 360                 365

Ser Thr Phe Gln Tyr Arg Asn Arg Ile Ala Val Glu Phe Asn Gln Leu
            370                 375                 380

Tyr His Trp His Pro Leu Met Pro Asp Ser Phe His Ile Asp Gly Asp
385                 390                 395                 400

Val Val Ser Tyr Ser Gln Phe Ile Phe Asn Thr Ser Ile Val Thr His
                405                 410                 415

Tyr Gly Val Glu Lys Leu Val Asp Ala Phe Ser Arg Gln Tyr Ala Gly
                420                 425                 430

Gln Ile Gly Gly Gly Arg Asn Ile His Pro Val Val Thr Lys Val Ala
            435                 440                 445

Glu Gly Val Ile Glu Glu Ser Arg Thr Leu Arg Leu Gln Pro Phe Asn
450                 455                 460

Glu Tyr Arg Lys Arg Phe Asn Leu Lys Pro Tyr Thr Ser Phe Ser Asp
465                 470                 475                 480

Phe Thr Gly Glu Glu Glu Met Ala Arg Glu Leu Glu Glu Leu Tyr Gly
                485                 490                 495

Asp Ile Asp Ala Leu Glu Phe Tyr Pro Ala Leu Met Leu Glu Lys Thr
                500                 505                 510

Arg Pro Asn Ala Ile Phe Gly Glu Ser Met Val Glu Met Gly Ala Pro
                515                 520                 525

Phe Ser Leu Lys Gly Leu Leu Gly Asn Pro Ile Cys Ser Pro Glu Tyr
            530                 535                 540

Trp Lys Pro Ser Thr Phe Gly Gly Gln Thr Gly Phe Asp Ile Val Asn
545                 550                 555                 560
```

-continued

Ser Ala Ser Leu Glu Arg Leu Val Cys Leu Asn Thr Asn Trp Cys Pro
            565                 570                 575

Tyr Val Ala Phe Asn Val Pro Pro Ala Gly Gln Glu Pro Pro Arg
            580                 585                 590

Lys Gln Ser Thr Glu Leu
        595

<210> SEQ ID NO 55
<211> LENGTH: 2587
<212> TYPE: DNA
<213> ORGANISM: Canis familiaris

<400> SEQUENCE: 55

```
gccgcccaga gctatgagcc gggggagtcg cctgcaccgg tggccgctgc tcctgctgct      60
gctgctgctg ctcccgccgc ccccggtcct gcccgcggaa gcccggaccc cggcgcctgt     120
gaacccgtgt tgttactacc catgtcagca ccaagggatc tgtgtccgct tcggccttga     180
ccgctaccag tgtgactgca cccgcacggg ctattctggc cccaactgca ccatccccga     240
gctgtggacc tggctccgga attcactgcg ccccagtccc tctttcctcc acttcctgct     300
gacgcatggg cgctggtttt gggaattcat caatgccacc ttcatccgtg acatgctcat     360
gcgtctggta ctcacagcgc gttccaacct tatccccagt cctcccacct acaacatagc     420
gcatgactac atcagctggg agtccttctc aatgtgagc tattacactc gtgttctgcc     480
ctctgtgccc caagattgcc ccacgcccat ggggaccaaa gggaagaagc agttgccaga     540
cgcccaactc ctgggccgtc gcttcctgct caggaggaag ttcatacctg accccccaagg     600
caccaacctc atgttcgcct ctttgcaca acacttcacc catcagttct tcaaaacttc     660
tggcaagatg ggtcctggct tcaccaaggc cttgggccat ggggtagatc ttggccacat     720
ttatggggac aatctggacc gtcagtatca gctgcggctc tttaaggatg ggaaactcaa     780
gtatcaggtt ctggatggag agatgtaccc gccatctgtg gaggaggcgc ctgtgttgat     840
gcactaccca cggggcattc tgccccagag tcagatggcc gtgggccaag aagtgtttgg     900
gctgcttcct gggctcatgc tctatgccac gctctggctg cgtgagcaca tcgtgtgtg     960
tgacctgctg aaggctgagc accccacttg gggtgatgag caactcttcc agacggcccg    1020
actcatcctc attggggaga ccatcaagat tgtgattgag gagtatgtgc agcagctgag    1080
tggctacttc ttgcagctga gttcgaccc ggagctgctg tttagcgccc agttccagta    1140
ccgcaaccgc atcgccatgg agttcaacca gctgtaccac tggcacccgc tcatgccaga    1200
ctccttctgg gtgggttccc aggagtacag ctatgagcag ttcctgttca cacctccat    1260
gctgacgcac tacgggatcg aggccctggt ggatgccttc tctcgccaga gcgccggccg    1320
gattggtgga ggtagaaaca tagaccacca tgtcctgcac gtggctgtgg aaaccatcaa    1380
ggaatcccgc gagttgcggc tgcagcccct caatgagtac cgcaagaggt ttggcatgag    1440
gccctacatg tccttccagg aactcacagg ggagaaggag atggcagccg agttggagga    1500
gctgtatgga gacattgatg ccttggaatt ctacccgggg cttcttctgg agaagtgcca    1560
tccaaactcc atctttggag agagtatgat agaaattggg gctccctct cccttaaggg    1620
cctcctaggg aatcccatct gttctccaga gtactggaag ccaagcacat tcggtggtga    1680
gatgggcttc aatatggtca agacagccac actgaagaag ctggtctgcc ttaacaccaa    1740
gacttgtccc tatgtttcct tccgtgtgcc tgaccccac caggatgcg ggcctggtgt    1800
ggagcggccg tccacagagc tctgagggg cagagcagca gcattctgga gggtggactt    1860
```

| | |
|---|---|
| gtcatcccag aatgctgagg ctggggttaa taatcccaaa tgttgggtct ttggtttgcc | 1920 |
| tcaagaatat caaggtcaac atttagaact ttgtgtctct cacccattat ctggaatatc | 1980 |
| atggtcttgt ttgttattct agaatgctga attcctggtt gaccatctag aatggatgga | 2040 |
| gtgatgcttc tttggcaagc cagaacactg gttcctggcc gacaacctag aatgtcagac | 2100 |
| ttctggttga cttaagacgt aggcattctc taatgtgaag ctcctgacag aatcatctag | 2160 |
| aaagatagg gattcttatt ttgcattcta gaattctggg cagccctcca gcatgttgat | 2220 |
| ttttttcact ggcagttcag aatgttgtgc tcttgattgc tgatccaaaa tagtggctgg | 2280 |
| tatgccagat cagtcttgct ctgaatgcct agaatggtaa tttgattcat ttcctgttc | 2340 |
| agtgagatac ccccaaagca ggagaatcta cagcctaacc agagtgcatt gcctgcctct | 2400 |
| gtgcctgccc caaggactta gggggcagag tgttcttcct gggatgctga ctcagaccct | 2460 |
| ggtccaagga gatagaacag gtgggcttt tccaggtcat tggttggagg ccaccagagc | 2520 |
| tctgttgcca tctttgtctt gactcatgac agctgtttct catgaaacta ataaaatttt | 2580 |
| ttttccc | 2587 |

<210> SEQ ID NO 56
<211> LENGTH: 1901
<212> TYPE: DNA
<213> ORGANISM: Canis familiaris
<400> SEQUENCE: 56

| | |
|---|---|
| cggggagctc ctggcaccgg cgccccggga gcccgcagtc tgcaccccga gcgcagcagc | 60 |
| cgcccagagc tatgagccgt gagttcgacc ctgaggcccc caggaaccct cttcgcctcc | 120 |
| cgggggagcc tcgaatgcca ggcccagccc tcacctctcg ctccgcaggg gggagtcgcc | 180 |
| tgcaccggtg gccgctgctc ctgctgctgc tgctgctgct cccgccgccc ccggtcctgc | 240 |
| ccgcggaagc ccggaccccg cgcctgtga acccgtgttg ttactaccca tgtcagcacc | 300 |
| aagggatctg tgtccgcttc ggccttgacc gctaccagtg tgactgcacc cgcacgggct | 360 |
| attctggccc caactgcacc atccccgagc tgtggacctg gctccggaat tcactgcgcc | 420 |
| ccagtccctc tttcctccac ttcctgctga cgcatgggcg ctggttttgg gaattcatca | 480 |
| atgccacctt catccgtgac atgctcatgc gtctggtact cacagggag accatcaaga | 540 |
| ttgtgattga ggagtatgtg cagcagctga gtggctactt cttgcagctg aagttcgacc | 600 |
| cggagctgct gtttagcgcc cagttccagt accgcaaccg catcgccatg gagttcaacc | 660 |
| agctgtacca ctggcacccg ctcatgccag actccttctg ggtgggttcc caggagtaca | 720 |
| gctatgagca gttcctgttc aacacctcca tgctgacgca ctacgggatc gaggccctgg | 780 |
| tggatgcctt ctctcgccag agcgccggcc ggattggtgg aggtagaaac atagaccacc | 840 |
| atgtcctgca cgtggctgtg gaaaccatca aggaatcccg cgagttgcgg ctgcagccct | 900 |
| tcaatgagta ccgcaagagg tttggcatga ggccctacat gtccttccag gaactcacag | 960 |
| gggagaagga gatggcagcc gagttggagg agctgtatgg agacattgat gccttggaat | 1020 |
| tctacccggg gcttcttctg gagaagtgcc atccaaactc catctttgga gagagtatga | 1080 |
| tagaaattgg ggctcccttc tcccttaagg gcctcctagg gaatcccatc tgttctccag | 1140 |
| agtactggaa gccaagcaca ttcggtggtg agatgggctt caatatggtc aagacagcca | 1200 |
| cactgaagaa gctggtctgc cttaacacca agacttgtcc ctatgtttcc ttccgtgtgc | 1260 |
| ctgacccca ccaggatggc gggcctggtg tgcagcggcc gtccacagag ctctgagggg | 1320 |

-continued

```
gcagagcagc agcattctgg agggtggact tgtcatccca gaatgctgag gctggggtta    1380
ataatcccaa atgttgggtc tttggtttgc ctcaagaata tcaaggtcaa catttagaac    1440
tttgtgtctc tcacccatta tctgaatat catggtcttg tttgttattc tagaatgctg    1500
aattcctggt tgaccatcta gaatggatgg agtgatgctt ctttggcaag ccagaacact    1560
ggttcctggc cgacaaccta gaatgtcaga cttctggttg acttaagacg taggcattct    1620
ctaatgtgaa gctcctgaca gaatcatcta gaaagatagg ggattcttat tttgcattct    1680
agaattctgg gcagccctcc agcatgttga ttttttcac tggcagttca gaatgttgtg    1740
ctcttgattg ctgatccaaa atagtggctg gtatgccaga tcagtcttgc tctgaatgcc    1800
tagaatggta atttgattca ttttcctgtt cagtgagata cccccaaagc aggagaatct    1860
acagcctaac cagagtgcat tgcctgcctc tgtgcctgcc c                        1901
```

<210> SEQ ID NO 57
<211> LENGTH: 2682
<212> TYPE: DNA
<213> ORGANISM: Artificial Sequence
<220> FEATURE:
<223> OTHER INFORMATION: consensus sequence

<400> SEQUENCE: 57

```
ccgagcgcag cagccgccca gagctatgag ccgtgagttc gaccctgagg cccccaggaa      60
ccctcttcgc ctcccggggg agcctcgaat gccaggccca gccctcacct ctcgctccgc     120 agggggagt cgcctgcacc ggtggccgct gctcctgctg ctgctgctgc tgctcccgcc     180 gccccggtc ctgcccgcgg aagcccggac cccggcgcct gtgaacccgt gttgttacta     240
cccatgtcag caccaaggga tctgtgtccg cttcggcctt gaccgctacc agtgtgactg     300
cacccgcacg ggctattctg gccccaactg caccatcccc gagctgtgga cctggctccg     360
gaattcactg cgccccagtc cctctttcct ccacttcctg ctgacgcatg ggcgctggtt     420
ttgggaattc atcaatgcca ccttcatccg tgacatgctc atgcgtctgg tactcacagc     480
gcgttccaac cttatcccca gtcctccacc ctacaacata gcgcatgact acatcagctg     540
ggagtccttc tccaatgtga gctattacac tcgtgttctg ccctctgtgc cccaagattg     600
ccccacgccc atgggaccaa agggaagaa gcagttgcca gacgcccaac tcctgggccg     660
tcgcttcctg ctcaggagga agttcatacc tgaccccaa ggcaccaacc tcatgttcgc     720
cttctttgca caacacttca cccatcagtt cttcaaaact ctggcaaga tgggtcctgg     780 cttcaccaag gccttgggcc atgggtaga tcttggccac atttatgggg acaatctgga     840
ccgtcagtat cagctgcggc tctttaagga tgggaaactc aagtatcagg ttctggatgg     900
agagatgtac ccgccatctg tggaggaggc gcctgtgttg atgcactacc acggggcat     960 tctgccccag agtcagatgg ccgtgggcca gagtgtttgg gctgcttcct gggctcatgc    1020
tctatgccac gctctggctg cgtgagcaca atcgtgtgtg tgacctgctg aaggctgagc    1080
accccacttg gggtgatgag caactcttcc agacggcccg actcatcctc attggggaga    1140
ccatcaagat tgtgattgag gagtatgtgc agcagctgag tggctacttc ttgcagctga    1200
agttcgaccc ggagctgctg tttagcgccc agttccagta ccgcaaccgc atcgccatgg    1260
agttcaacca gctgtaccac tggcacccgc tcatgccaga ctccttctgg gtgggttccc    1320
aggagtacag ctatgagcag ttcctgttca acacctccat gctgacgcac tacgggatcg    1380 aggcctggt ggatgccttc tctgccagag gcgccggccg gattggtgga ggtagaaaca    1440
tagaccacca tgtcctgcac gtggctgtgg aaaccatcaa ggaatcccgc gagttgcggc    1500
```

-continued

```
tgcagccctt caatgagtac cgcaagaggt ttggcatgag gccctacatg tccttccagg    1560
aactcacagg ggagaaggag atggcagccg agttggagga gctgtatgga gacattgatg    1620
ccttggaatt ctacccgggg cttcttctgg agaagtgcca tccaaactcc atctttggag    1680
agagtatgat agaaattggg gctcccttct cccttaaggg cctcctaggg aatcccatct    1740
gttctccaga gtactggaag ccaagcacat tcggtggtga gatgggcttc aatatggtca    1800
agacagccac actgaagaag ctggtctgcc ttaacaccaa gacttgtccc tatgtttcct    1860
tccgtgtgcc tgaccccac caggatggcg ggcctggtgt gcagcggccg tccacagagc    1920
tctgaggggg cagagcagca gcattctgga gggtggactt gtcatcccag aatgctgagg    1980
ctggggttaa taatcccaaa tgttgggtct tggtttgcc tcaagaatat caaggtcaac    2040
atttagaact ttgtgtctct cacccattat ctggaatatc atggtcttgt ttgttattct    2100
agaatgctga attcctggtt gaccatctag aatggatgga gtgatgcttc tttggcaagc    2160
cagaacactg gttcctggcc gacaacctag aatgtcagac ttctggttga cttaagacgt    2220
aggcattctc taatgtgaag ctcctgacag aatcatctag aaagataggg gattcttatt    2280
ttgcattcta gaattctggg cagccctcca gcatgttgat tttttttcact ggcagttcag    2340 aatgttgtgc tcttgattgc tgatccaaaa tagtggctgg tatgccagat cagtcttgct    2400
ctgaatgcct agaatggtaa tttgattcat tttcctgttc agtgagatac ccccaaagca    2460
ggagaatcta cagcctaacc agagtgcatt gcctgcctct gtgcctgccc caggacttag    2520
ggggcagagt gttcttcctg ggagctgact cagaccctgg tccaaggagt agaacaggtg    2580 ggcttttttcc aggtcattgg ttggaggcca ccagagctct gttgccatct ttgtcttgac    2640
tcatgacagc tgtttctcat gaaactaata aaattttttt cc                        2682
```

<210> SEQ ID NO 58
<211> LENGTH: 603
<212> TYPE: PRT
<213> ORGANISM: Canis familiaris

<400> SEQUENCE: 58

```
Met Ser Arg Gly Ser Arg Leu His Arg Trp Pro Leu Leu Leu Leu Leu
1               5                   10                  15

Leu Leu Leu Pro Pro Pro Val Leu Pro Ala Glu Ala Arg Thr
            20                  25                  30

Pro Ala Pro Val Asn Pro Cys Cys Tyr Tyr Pro Cys Gln His Gln Gly
        35                  40                  45

Ile Cys Val Arg Phe Gly Leu Asp Arg Tyr Gln Cys Asp Cys Thr Arg
    50                  55                  60

Thr Gly Tyr Ser Gly Pro Asn Cys Thr Ile Pro Glu Leu Trp Thr Trp
65                  70                  75                  80

Leu Arg Asn Ser Leu Arg Pro Ser Pro Ser Phe Leu His Phe Leu Leu
                85                  90                  95

Thr His Gly Arg Trp Phe Trp Glu Phe Ile Asn Ala Thr Phe Ile Arg
            100                 105                 110

Asp Met Leu Met Arg Leu Val Leu Thr Ala Arg Ser Asn Leu Ile Pro
        115                 120                 125

Ser Pro Pro Thr Tyr Asn Ile Ala His Asp Tyr Ile Ser Trp Glu Ser
    130                 135                 140

Phe Ser Asn Val Ser Tyr Tyr Thr Arg Val Leu Pro Ser Val Pro Gln
145                 150                 155                 160
```

-continued

```
Asp Cys Pro Thr Pro Met Gly Thr Lys Gly Lys Lys Gln Leu Pro Asp
            165                 170                 175

Ala Gln Leu Leu Gly Arg Arg Phe Leu Leu Arg Arg Lys Phe Ile Pro
            180                 185                 190

Asp Pro Gln Gly Thr Asn Leu Met Phe Ala Phe Phe Ala Gln His Phe
            195                 200                 205

Thr His Gln Phe Phe Lys Thr Ser Gly Lys Met Gly Pro Gly Phe Thr
            210                 215                 220

Lys Ala Leu Gly His Gly Val Asp Leu Gly His Ile Tyr Gly Asp Asn
225                 230                 235                 240

Leu Asp Arg Gln Tyr Gln Leu Arg Leu Phe Lys Asp Gly Lys Leu Lys
            245                 250                 255

Tyr Gln Val Leu Asp Gly Glu Met Tyr Pro Pro Ser Val Glu Glu Ala
            260                 265                 270

Pro Val Leu Met His Tyr Pro Arg Gly Ile Leu Pro Gln Ser Gln Met
            275                 280                 285

Ala Val Gly Gln Glu Val Phe Gly Leu Leu Pro Gly Leu Met Leu Tyr
            290                 295                 300

Ala Thr Leu Trp Leu Arg Glu His Asn Arg Val Cys Asp Leu Leu Lys
305                 310                 315                 320

Ala Glu His Pro Thr Trp Gly Asp Glu Gln Leu Phe Gln Thr Ala Arg
            325                 330                 335

Leu Ile Leu Ile Gly Glu Thr Ile Lys Ile Val Ile Glu Glu Tyr Val
            340                 345                 350

Gln Gln Leu Ser Gly Tyr Phe Leu Gln Leu Lys Phe Asp Pro Glu Leu
            355                 360                 365

Leu Phe Ser Ala Gln Phe Gln Tyr Arg Asn Arg Ile Ala Met Glu Phe
            370                 375                 380

Asn Gln Leu Tyr His Trp His Pro Leu Met Pro Asp Ser Phe Trp Val
385                 390                 395                 400

Gly Ser Gln Glu Tyr Ser Tyr Glu Gln Phe Leu Phe Asn Ile Ser Met
            405                 410                 415

Leu Thr His Tyr Gly Ile Glu Ala Leu Val Asp Ala Phe Ser Arg Gln
            420                 425                 430

Ser Ala Gly Arg Ile Gly Gly Arg Asn Ile Asp His His Val Leu
            435                 440                 445

His Val Ala Val Glu Thr Ile Lys Glu Ser Arg Glu Leu Arg Leu Gln
450                 455                 460

Pro Phe Asn Glu Tyr Arg Lys Arg Phe Gly Met Arg Pro Tyr Met Ser
465                 470                 475                 480

Phe Gln Glu Leu Thr Gly Glu Lys Glu Met Ala Ala Glu Leu Glu Glu
            485                 490                 495

Leu Tyr Gly Asp Ile Asp Ala Leu Glu Phe Tyr Pro Gly Leu Leu Leu
            500                 505                 510

Glu Lys Cys His Pro Asn Ser Ile Phe Gly Glu Ser Met Ile Glu Ile
            515                 520                 525

Gly Ala Pro Phe Ser Leu Lys Gly Leu Leu Gly Asn Pro Ile Cys Ser
            530                 535                 540

Pro Glu Tyr Trp Lys Pro Ser Thr Phe Gly Gly Glu Met Gly Phe Asn
545                 550                 555                 560

Met Val Lys Thr Ala Thr Leu Lys Lys Leu Val Cys Leu Asn Thr Lys
            565                 570                 575

Thr Cys Pro Tyr Val Ser Phe Arg Val Pro Asp Pro His Gln Asp Gly
```

```
                580                 585                 590
Gly Pro Gly Val Glu Arg Pro Ser Thr Glu Leu
        595                 600

<210> SEQ ID NO 59
<211> LENGTH: 414
<212> TYPE: PRT
<213> ORGANISM: Canis familiaris

<400> SEQUENCE: 59

Met Ser Arg Glu Phe Asp Pro Glu Ala Pro Arg Asn Pro Leu Arg Leu
 1               5                  10                  15

Pro Gly Glu Pro Arg Met Pro Gly Pro Ala Leu Thr Ser Arg Ser Ala
            20                  25                  30

Gly Gly Ser Arg Leu His Arg Trp Pro Leu Leu Leu Leu Leu Leu Leu
        35                  40                  45

Leu Leu Pro Pro Pro Val Leu Pro Ala Glu Ala Arg Thr Pro Ala
50                  55                  60

Pro Val Asn Pro Cys Cys Tyr Tyr Pro Cys Gln His Gln Gly Ile Cys
65                  70                  75                  80

Val Arg Phe Gly Leu Asp Arg Tyr Gln Cys Asp Cys Thr Arg Thr Gly
                85                  90                  95

Tyr Ser Gly Pro Asn Cys Thr Ile Pro Glu Leu Trp Thr Trp Leu Arg
            100                 105                 110

Asn Ser Leu Arg Pro Ser Pro Ser Phe Leu His Phe Leu Leu Thr His
        115                 120                 125

Gly Arg Trp Phe Trp Glu Phe Ile Asn Ala Thr Phe Ile Arg Asp Met
130                 135                 140

Leu Met Arg Leu Val Leu Thr Gly Glu Thr Ile Lys Ile Val Ile Glu
145                 150                 155                 160

Glu Tyr Val Gln Gln Leu Ser Gly Tyr Phe Leu Gln Leu Lys Phe Asp
                165                 170                 175

Pro Glu Leu Leu Phe Ser Ala Gln Phe Gln Tyr Arg Asn Arg Ile Ala
            180                 185                 190

Met Glu Phe Asn Gln Leu Tyr His Trp His Pro Leu Met Pro Asp Ser
        195                 200                 205

Phe Trp Val Gly Ser Gln Glu Tyr Ser Tyr Glu Gln Phe Leu Phe Asn
210                 215                 220

Thr Ser Met Leu Thr His Tyr Gly Ile Glu Ala Leu Val Asp Ala Phe
225                 230                 235                 240

Ser Arg Gln Ser Ala Gly Arg Ile Gly Gly Gly Arg Asn Ile Asp His
                245                 250                 255

His Val Leu His Val Ala Val Glu Thr Ile Lys Glu Ser Arg Glu Leu
            260                 265                 270

Arg Leu Gln Pro Phe Asn Glu Tyr Arg Lys Arg Phe Gly Met Arg Pro
        275                 280                 285

Tyr Met Ser Phe Gln Glu Leu Thr Gly Glu Lys Glu Met Ala Ala Glu
    290                 295                 300

Leu Glu Glu Leu Tyr Gly Asp Ile Asp Ala Leu Glu Phe Tyr Pro Gly
305                 310                 315                 320

Leu Leu Leu Glu Lys Cys His Pro Asn Ser Ile Phe Gly Glu Ser Met
                325                 330                 335

Ile Glu Ile Gly Ala Pro Phe Ser Leu Lys Gly Leu Leu Gly Asn Pro
            340                 345                 350
```

```
Ile Cys Ser Pro Glu Tyr Trp Lys Pro Ser Thr Phe Gly Gly Glu Met
            355                 360                 365

Gly Phe Asn Met Val Lys Thr Ala Thr Leu Lys Lys Leu Val Cys Leu
        370                 375                 380

Asn Thr Lys Thr Cys Pro Tyr Val Ser Phe Arg Val Pro Asp Pro His
385                 390                 395                 400

Gln Asp Gly Gly Pro Gly Val Gln Arg Pro Ser Thr Glu Leu
                405                 410

<210> SEQ ID NO 60
<211> LENGTH: 632
<212> TYPE: PRT
<213> ORGANISM: Artificial Sequence
<220> FEATURE:
<223> OTHER INFORMATION: consensus sequence

<400> SEQUENCE: 60

Met Ser Arg Glu Phe Asp Pro Glu Ala Pro Arg Asn Pro Leu Arg Leu
  1               5                  10                  15

Pro Gly Glu Pro Arg Met Pro Gly Pro Ala Leu Thr Ser Arg Ser Ala
                 20                  25                  30

Gly Gly Ser Arg Leu His Arg Trp Pro Leu Leu Leu Leu Leu Leu Leu
             35                  40                  45

Leu Leu Pro Pro Pro Val Leu Pro Ala Glu Ala Arg Thr Pro Ala
 50                  55                  60

Pro Val Asn Pro Cys Cys Tyr Tyr Pro Cys Gln His Gln Gly Ile Cys
 65                  70                  75                  80

Val Arg Phe Gly Leu Asp Arg Tyr Gln Cys Asp Cys Thr Arg Thr Gly
                 85                  90                  95

Tyr Ser Gly Pro Asn Cys Thr Ile Pro Glu Leu Trp Thr Trp Leu Arg
                100                 105                 110

Asn Ser Leu Arg Pro Ser Pro Ser Phe Leu His Phe Leu Leu Thr His
            115                 120                 125

Gly Arg Trp Phe Trp Glu Phe Ile Asn Ala Thr Phe Ile Arg Asp Met
130                 135                 140

Leu Met Arg Leu Val Leu Thr Ala Arg Ser Asn Leu Ile Pro Ser Pro
145                 150                 155                 160

Pro Thr Tyr Asn Ile Ala His Asp Tyr Ile Ser Trp Glu Ser Phe Ser
                165                 170                 175

Asn Val Ser Tyr Tyr Thr Arg Val Leu Pro Ser Val Pro Gln Asp Cys
            180                 185                 190

Pro Thr Pro Met Gly Thr Lys Gly Lys Lys Gln Leu Pro Asp Ala Gln
        195                 200                 205

Leu Leu Gly Arg Arg Phe Leu Leu Arg Arg Lys Phe Ile Pro Asp Pro
210                 215                 220

Gln Gly Thr Asn Leu Met Phe Ala Phe Ala Gln His Phe Thr His
225                 230                 235                 240

Gln Phe Phe Lys Thr Ser Gly Lys Met Gly Pro Gly Phe Thr Lys Ala
                245                 250                 255

Leu Gly His Gly Val Asp Leu Gly His Ile Tyr Gly Asp Asn Leu Asp
            260                 265                 270

Arg Gln Tyr Gln Leu Arg Leu Phe Lys Asp Gly Lys Leu Lys Tyr Gln
        275                 280                 285

Val Leu Asp Gly Glu Met Tyr Pro Pro Ser Val Glu Glu Ala Pro Val
290                 295                 300
```

Leu Met His Tyr Pro Arg Gly Ile Leu Pro Gln Ser Gln Met Ala Val
305                 310                 315                 320

Gly Gln Glu Val Phe Gly Leu Leu Pro Gly Leu Met Leu Tyr Ala Thr
            325                 330                 335

Leu Trp Leu Arg Glu His Asn Arg Val Cys Asp Leu Leu Lys Ala Glu
            340                 345                 350

His Pro Thr Trp Gly Asp Glu Gln Leu Phe Gln Thr Ala Arg Leu Ile
            355                 360                 365

Leu Ile Gly Glu Thr Ile Lys Ile Val Ile Glu Glu Tyr Val Gln Gln
370                 375                 380

Leu Ser Gly Tyr Phe Leu Gln Leu Lys Phe Asp Pro Glu Leu Leu Phe
385                 390                 395                 400

Ser Ala Gln Phe Gln Tyr Arg Asn Arg Ile Ala Met Glu Phe Asn Gln
            405                 410                 415

Leu Tyr His Trp His Pro Leu Met Pro Asp Ser Phe Trp Val Gly Ser
            420                 425                 430

Gln Glu Tyr Ser Tyr Glu Gln Phe Leu Phe Asn Thr Ser Met Leu Thr
            435                 440                 445

His Tyr Gly Ile Glu Ala Leu Val Asp Ala Phe Ser Arg Gln Ser Ala
            450                 455                 460

Gly Arg Ile Gly Gly Gly Arg Asn Ile Asp His His Val Leu His Val
465                 470                 475                 480

Ala Val Glu Thr Ile Lys Glu Ser Arg Glu Leu Arg Leu Gln Pro Phe
            485                 490                 495

Asn Glu Tyr Arg Lys Arg Phe Gly Met Arg Pro Tyr Met Ser Phe Gln
            500                 505                 510

Glu Leu Thr Gly Glu Lys Glu Met Ala Ala Glu Leu Glu Glu Leu Tyr
            515                 520                 525

Gly Asp Ile Asp Ala Leu Glu Phe Tyr Pro Gly Leu Leu Leu Glu Lys
530                 535                 540

Cys His Pro Asn Ser Ile Phe Gly Glu Ser Met Ile Glu Ile Gly Ala
545                 550                 555                 560

Pro Phe Ser Leu Lys Gly Leu Leu Gly Asn Pro Ile Cys Ser Pro Glu
            565                 570                 575

Tyr Trp Lys Pro Ser Thr Phe Gly Gly Glu Met Gly Phe Asn Met Val
            580                 585                 590

Lys Thr Ala Thr Leu Lys Lys Leu Val Cys Leu Asn Thr Lys Thr Cys
            595                 600                 605

Pro Tyr Val Ser Phe Arg Val Pro Asp Pro His Gln Asp Gly Gly Pro
            610                 615                 620

Gly Val Arg Pro Ser Thr Glu Leu
625                 630

<210> SEQ ID NO 61
<211> LENGTH: 83
<212> TYPE: DNA
<213> ORGANISM: Artificial Sequence
<220> FEATURE:
<223> OTHER INFORMATION: consensus sequence

<400> SEQUENCE: 61
gtgagtcgac cccggtgccc cgtgggaatt tcttggcctc cggggagcct tgaatgccag    60
gcccaccctc acctctctct cga                                           83

<210> SEQ ID NO 62

```
<211> LENGTH: 30
<212> TYPE: PRT
<213> ORGANISM: Canis familiaris

<400> SEQUENCE: 62

Arg Glu Phe Asp Pro Glu Ala Pro Arg Asn Pro Leu Arg Leu Pro Gly
 1               5                  10                  15

Glu Pro Arg Met Pro Gly Pro Ala Leu Thr Ser Arg Ser Ala
            20                  25                  30

<210> SEQ ID NO 63
<211> LENGTH: 31
<212> TYPE: PRT
<213> ORGANISM: Homo sapiens

<400> SEQUENCE: 63

Arg Glu Cys Asp Pro Gly Ala Arg Trp Gly Ile Phe Leu Ala Ser Trp
 1               5                  10                  15

Trp Ser Leu Glu Cys Gln Leu Ser Pro Ser Ser Leu Ser Ser Ala
            20                  25                  30

<210> SEQ ID NO 64
<211> LENGTH: 34
<212> TYPE: PRT
<213> ORGANISM: Mus musculus

<400> SEQUENCE: 64

Arg Glu Ser Asp Pro Ser Gly Ala Pro Thr Arg Pro Gly Ile Arg Trp
 1               5                  10                  15

Pro Ala Gly Gly Ala Leu Asn Ala Arg Leu Asn Ser Leu Phe Leu Leu
            20                  25                  30

Gln Glu

<210> SEQ ID NO 65
<211> LENGTH: 14
<212> TYPE: PRT
<213> ORGANISM: Artificial Sequence
<220> FEATURE:
<223> OTHER INFORMATION: consensus sequence
<220> FEATURE:
<221> NAME/KEY: VARIANT
<222> LOCATION: 11
<223> OTHER INFORMATION: Xaa = Met or Leu

<400> SEQUENCE: 65

Arg Glu Asp Pro Arg Gly Ile Arg Leu Pro Xaa Leu Ser Leu
 1               5                  10

<210> SEQ ID NO 66
<211> LENGTH: 16
<212> TYPE: PRT
<213> ORGANISM: Canis familiaris

<400> SEQUENCE: 66

Phe Ala Phe Phe Ala Gln His Phe Thr His Gln Phe Phe Lys Thr Ser
 1               5                  10                  15

<210> SEQ ID NO 67
<211> LENGTH: 16
<212> TYPE: PRT
<213> ORGANISM: Canis familiaris

<400> SEQUENCE: 67

Phe Ala Phe Phe Ala Gln His Phe Thr His Gln Phe Phe Lys Thr Asp
```

-continued

```
                1               5              10              15
```

<210> SEQ ID NO 68
<211> LENGTH: 16
<212> TYPE: PRT
<213> ORGANISM: Plexaura homomalla

<400> SEQUENCE: 68

```
Phe Met Phe Phe Ala Gln His Phe Thr His Glu Phe Phe Lys Thr Ile
 1               5                  10                  15
```

<210> SEQ ID NO 69
<211> LENGTH: 16
<212> TYPE: PRT
<213> ORGANISM: Oryza sativa

<400> SEQUENCE: 69

```
Ala Ala Ala Trp Ile Gln Phe Met Val His Asp Trp Met Asp His Met
 1               5                  10                  15
```

<210> SEQ ID NO 70
<211> LENGTH: 16
<212> TYPE: PRT
<213> ORGANISM: Arabidopsis thaliana

<400> SEQUENCE: 70

```
Ala Ala Ser Trp Ile Gln Phe Met Ile His Asp Trp Ile Asp His Leu
 1               5                  10                  15
```

<210> SEQ ID NO 71
<211> LENGTH: 16
<212> TYPE: PRT
<213> ORGANISM: Nicotiana tabacum

<400> SEQUENCE: 71

```
Ala Ala Ser Trp Ile Gln Phe Met Ile His Asp Trp Ile Asp His Leu
 1               5                  10                  15
```

<210> SEQ ID NO 72
<211> LENGTH: 16
<212> TYPE: PRT
<213> ORGANISM: Gaeumannomyces graminis

<400> SEQUENCE: 72

```
Leu Phe Tyr Leu Ala Thr Ile Ile Thr His Asp Ile Phe Gln Thr Ser
 1               5                  10                  15
```

<210> SEQ ID NO 73
<211> LENGTH: 8
<212> TYPE: PRT
<213> ORGANISM: Artificial Sequence
<220> FEATURE:
<223> OTHER INFORMATION: consensus sequence

<400> SEQUENCE: 73

```
Ala Ala Gln Thr His Asp Phe Thr
 1               5
```

<210> SEQ ID NO 74
<211> LENGTH: 14
<212> TYPE: PRT
<213> ORGANISM: Canis familiaris

<400> SEQUENCE: 74

```
Tyr Ala Thr Leu Trp Leu Arg Glu His Asn Arg Val Cys Asp
 1               5                  10
```

<210> SEQ ID NO 75
<211> LENGTH: 14
<212> TYPE: PRT
<213> ORGANISM: Canis familiaris

<400> SEQUENCE: 75

Tyr Ala Thr Ile Trp Leu Arg Glu His Asn Arg Val Cys Asp
1               5                   10

<210> SEQ ID NO 76
<211> LENGTH: 14
<212> TYPE: PRT
<213> ORGANISM: Plexaura homomalla

<400> SEQUENCE: 76

Tyr Ala Ser Ile Trp Leu Arg Glu His Asn Arg Val Cys Thr
1               5                   10

<210> SEQ ID NO 77
<211> LENGTH: 14
<212> TYPE: PRT
<213> ORGANISM: Oryza sativa

<400> SEQUENCE: 77

Leu Gln Ala Leu Phe Val Lys Glu His Asn Ala Val Cys Asp
1               5                   10

<210> SEQ ID NO 78
<211> LENGTH: 14
<212> TYPE: PRT
<213> ORGANISM: Arabidopsis thaliana

<400> SEQUENCE: 78

Leu Gln Ala Leu Phe Ile Lys Glu His Asn Ala Val Cys Asp
1               5                   10

<210> SEQ ID NO 79
<211> LENGTH: 14
<212> TYPE: PRT
<213> ORGANISM: Nicotiana tabacum

<400> SEQUENCE: 79

Leu Gln Ala Leu Phe Val Gln Glu His Asn Ser Val Cys Asp
1               5                   10

<210> SEQ ID NO 80
<211> LENGTH: 14
<212> TYPE: PRT
<213> ORGANISM: Gaeumannomyces graminis

<400> SEQUENCE: 80

Phe Leu Ile Met Phe Asn Arg Phe His Asn Tyr Val Val Thr
1               5                   10

<210> SEQ ID NO 81
<211> LENGTH: 9
<212> TYPE: PRT
<213> ORGANISM: Artificial Sequence
<220> FEATURE:
<223> OTHER INFORMATION: consensus sequence

<400> SEQUENCE: 81

Leu Phe Arg Glu His Asn Val Cys Asp
1               5

-continued

```
1               5
```

<210> SEQ ID NO 82
<211> LENGTH: 12
<212> TYPE: PRT
<213> ORGANISM: Canis familiaris

<400> SEQUENCE: 82

```
Glu Phe Asn Gln Leu Tyr His Trp His Pro Leu Met
1               5                   10
```

<210> SEQ ID NO 83
<211> LENGTH: 12
<212> TYPE: PRT
<213> ORGANISM: Canis familiaris

<400> SEQUENCE: 83

```
Glu Phe Asn Thr Leu Tyr His Trp His Pro Leu Leu
1               5                   10
```

<210> SEQ ID NO 84
<211> LENGTH: 12
<212> TYPE: PRT
<213> ORGANISM: Plexaura homomalla

<400> SEQUENCE: 84

```
Glu Phe Asn His Met Tyr His Trp His Pro Phe Ser
1               5                   10
```

<210> SEQ ID NO 85
<211> LENGTH: 12
<212> TYPE: PRT
<213> ORGANISM: Oryza sativa

<400> SEQUENCE: 85

```
Glu Phe Thr Ser Val Tyr Arg Met His Ser Leu Ile
1               5                   10
```

<210> SEQ ID NO 86
<211> LENGTH: 12
<212> TYPE: PRT
<213> ORGANISM: Arabidopsis thaliana

<400> SEQUENCE: 86

```
Asp Phe Thr Ser Val Tyr Arg Met His Ser Leu Leu
1               5                   10
```

<210> SEQ ID NO 87
<211> LENGTH: 12
<212> TYPE: PRT
<213> ORGANISM: Nicotiana tabacum

<400> SEQUENCE: 87

```
Glu Phe Thr Ser Val Tyr Arg Met His Gln Leu Leu
1               5                   10
```

<210> SEQ ID NO 88
<211> LENGTH: 12
<212> TYPE: PRT
<213> ORGANISM: Gaeumannomyces graminis

<400> SEQUENCE: 88

```
Glu Phe Asn Leu Ile Tyr Arg Trp His Cys Thr Ile
1               5                   10
```

```
<210> SEQ ID NO 89
<211> LENGTH: 8
<212> TYPE: PRT
<213> ORGANISM: Artificial Sequence
<220> FEATURE:
<223> OTHER INFORMATION: consensus sequence

<400> SEQUENCE: 89

Glu Phe Asn Tyr Arg Trp His Leu
 1               5
```

ANTIBODIES TO CYCLOOXYGENASE VARIANTS

CROSS REFERENCE TO RELATED APPLICATIONS

This application is a divisional of U.S. application Ser. No. 10/260,937 (now U.S. Pat. No. 7,179,627) filed Sep. 28, 2002, which claims priority from U.S. Provisional Application Ser. No. 60/326,133, filed Sep. 28, 2001, and from U.S. Provisional Application Ser. No. 60/373,225, filed Apr. 15, 2002, and from U.S. Provisional Application Ser. No. 60/373,661, filed Apr. 16, 2002, and from U.S. Provisional Application Ser. No. 60/411,575, filed Sep. 16, 2002, which are incorporated herein by reference.

STATEMENT AS TO FEDERALLY SPONSORED RESEARCH

This invention was made with government support under grant AR46688 awarded by the National Institutes of Health (NIH). The U.S. Government has certain rights in this invention.

TECHNICAL FIELD

This invention relates to novel nucleic acids encoding novel-mammalian cyclooxygenase (Cox) polypeptides and methods of use therefore. The invention further relates to compounds that modulate Cox activity and methods of identifying such compounds.

BACKGROUND

In eukaryotic cells, polyunsaturated fatty acids are oxygenated by three general systems: 1) cyclooxygenases (COXs) and related fatty acid oxygenases, including pathogen-inducible oxygenases (PIOXs) identified in plants, animals and bacteria; 2) lipoxygenases; and 3) cytochrome P-450. Presently there are 2 COX isozymes known, COX-1 and COX-2. The predicted amino acid sequences of COX-1 cloned in chicken and mammals possesses approximately 60% amino acid sequence identity with COX-2.

The cyclooxygenation of arachidonic acid, catalyzed by two forms of cyclooxygenase produces prostaglandins which, in turn, regulate neurotransmission and immune and inflammatory responses by activating receptors coupled to cAMP formation. (Goetzl et al., FASEB J., 9:1051, 1995). For example, inflammation is both initiated and maintained, at least in part, by the overproduction of prostaglandins in injured cells. The central role that prostaglandins play in inflammation is underscored by the fact that those aspirin-like non-steroidal anti-inflammatory drugs (NSAIDS) that are most effective in the therapy of many pathological inflammatory states all act by inhibiting prostaglandin synthesis. NSAIDs are analgesic/antiinflammatory/antipyretic medications that act as inhibitors of the cyclooxygenase active site of COX isozymes. Important mechanistic differences in the actions of individual NSAIDs with the COX active site exist. Of the NSAIDs in medical use, only aspirin is a covalent modifier of COX-1 and COX-2.

There is increasing emphasis on the development of compounds that modulate cyclooxygenase activity and methods for identifying such compounds. Therefore, there is a need for improved methods to study the effectiveness of existing anti-inflammatory drugs and to evaluate the effectiveness of potential anti-inflammatory agents, at the molecular level, as well as for reagents for use in such methods.

SUMMARY

The present invention is based, at least in part, on the discovery of novel nucleic acid molecules and polypeptides encoded by such nucleic acid molecules, referred to herein as cyclooxygenase type 1 (COX-1) variant proteins. A COX-1 variant nucleic acid molecules include those derived from the COX-1 genomic sequence and possessing intron 1. Similarly, a COX-1 variant amino acid sequence is encoded by a COX-1 variant nucleic acid sequence containing intron 1. COX-3 (i.e., pCox-1), PCOX-1a (i.e., pCox-1Δ657) or PCOX-1b are examples of COX-1 variants encompassed by the invention. Further COX-1 variants include hCOX-3(cc) (human COX-3 derived from cerebral cortex), hCOX-3(af) (human COX-3 derived from lung cells), hCOX-3 (del10) (human COX-3 derived from lung cells with exon 10 deleted) and hCOX-3 (cs) (human COX-3 consensus sequence). Such variants are useful for identifying compounds or agents that modulate the activity of a COX-1 variant. Accordingly, in one aspect, this invention provides isolated nucleic acid molecules encoding COX-1 variant proteins or biologically active portions thereof, as well as nucleic acid fragments suitable as primers or hybridization probes for the detection of COX-1 variant-encoding nucleic acids.

In one embodiment, a COX-1 variant nucleic acid molecule of the invention comprises intron 1, or fragment thereof, of cyclooxygenase type 1. In one aspect, the nucleic acid molecule is an mRNA transcript. In another aspect, the nucleic acid molecule is cDNA. In another aspect, the nucleic acid molecule encodes a polypeptide comprising at least one domain that catalyzes the cyclization and/or oxygenation of a fatty acid radical, at least one membrane-binding domain, and at least one heme binding domain. In yet another aspect the nucleic acid molecule encodes a cyclooxygenase polypeptide, or naturally occurring allelic variant thereof, which comprises intron 1, or fragment thereof, of cyclooxygenase 1.

In another embodiment, the invention provides an isolated COX-1 variant polypeptide comprising an amino acid sequence encoded by intron 1, or fragment thereof, of cyclooxygenase 1, wherein the polypeptide catalyzes the oxygenation and/or cyclization of a fatty acid. In one aspect, the isolated polypeptide further comprises at least one membrane-binding domain and at least one heme binding domain.

In another embodiment, a COX-1 variant nucleic acid molecule of the invention is at least 60%, 65%, 70%, 75%, 80%, 85%, 90%, 95%, 98% or more homologous to a nucleotide sequence (e.g., to the entire length of the nucleotide sequence) including SEQ ID NO:1, SEQ ID NO:3 (i.e., COX-3) or a complement thereof. In another embodiment, a COX-1 variant nucleic acid molecule is 60%, 65%, 70%, 75%, 80%, 85%, 90%, 95%, 98% homologous to a nucleotide sequence including SEQ ID NO:4, SEQ ID NO:6 (i.e., PCOX-1a), or a complement thereof. In another embodiment, a COX-1 variant nucleic acid molecule is 60%, 65%, 70%, 75%, 80%, 85%, 90%, 95%, 98% homologous to a nucleotide sequence including SEQ ID NO:7, SEQ ID NO:9 (i.e., PCOX-1b), or a complement thereof. In another embodiment, a COX-1 variant nucleic acid molecule is 60%, 65%, 70%, 75%, 80%, 85%, 90%, 95%, 98% homologous to a nucleotide sequence including SEQ ID NO:10 (i.e., hCOX-3(cc)), or a complement thereof. In another embodiment, a COX-1 variant nucleic acid molecule is 60%, 65%, 70%, 75%, 80%, 85%, 90%, 95%, 98% homologous to a nucleotide sequence-including SEQ ID NO:11 (i.e., hCOX-3(af), or a complement thereof. In another embodiment, a COX-1 variant nucleic acid molecule is 60%, 65%, 70%, 75%, 80%, 85%, 90%, 95%, 98% homologous to a nucleotide sequence including SEQ ID NO:12 (i.e., hCOX-3(del10)), or a complement thereof. In yet another embodiment, a COX-1 variant nucleic acid molecule is 60%, 65%, 70%, 75%, 80%, 85%, 90%, 95%, 98% homologous to a nucleotide sequence including SEQ ID NO:13 (i.e., hCOX-3(cs)), or a complement thereof.

In one embodiment, the isolated nucleic acid molecule includes the nucleotide sequence shown SEQ ID NO:1 or 3, or a complement thereof. In another preferred embodiment, the nucleic acid molecule has the nucleotide sequence shown in SEQ ID NO:1 or 3.

In another embodiment, the isolated nucleic acid molecule includes the nucleotide sequence shown SEQ ID NO:4 or 6, or a complement thereof. In another preferred embodiment, the nucleic acid molecule has the nucleotide sequence shown in SEQ ID NO:4 or 6.

In yet another embodiment, the isolated nucleic acid molecule includes the nucleotide sequence shown SEQ ID NO:10, or a complement thereof. In another embodiment, the nucleic acid molecule has the nucleotide sequence shown in SEQ ID NO:10.

In yet another embodiment, the isolated nucleic acid molecule includes the nucleotide sequence shown SEQ ID NO:11, or a complement thereof. In another embodiment, the nucleic acid molecule has the nucleotide sequence shown in SEQ ID NO:11.

In yet another embodiment, the isolated nucleic acid molecule includes the nucleotide sequence shown SEQ ID NO:12, or a complement thereof. In another embodiment, the nucleic acid molecule has the nucleotide sequence shown in SEQ ID NO:12.

In yet another embodiment, the isolated nucleic acid molecule includes the nucleotide sequence shown SEQ ID NO:13, or a complement thereof. In another embodiment, the nucleic acid molecule has the nucleotide sequence shown in SEQ ID NO:13.

In another embodiment, a COX-1 variant nucleic acid molecule includes a nucleotide sequence encoding a polypeptide having an amino acid sequence homologous to the amino acid sequence of SEQ ID NO:2 (i.e., COX-3), SEQ ID NO:5 (i.e., PCOX-1a), SEQ ID NO:14 (hCOX-3(cs1), SEQ ID NO:15 (i.e., hCOX-3(cs2) and SEQ ID NO:16 (i.e., hCOX-3(cs3). In a one embodiment, a COX-1 variant nucleic acid molecule includes a nucleotide sequence encoding a polypeptide having an amino acid sequence at least 50%, 55%, 60%, 65%, 70%, 75%, 80%, 85%, 90%, 95%, 98% or more homologous to an amino acid sequence including SEQ ID NO:2, SEQ ID NO:5, SEQ ID NO:14, SEQ ID NO:15 or SEQ ID NO:16 (e.g., the entire amino acid sequence of SEQ ID NO:2, 5, 14, 15 or 16).

In one embodiment, an isolated nucleic acid molecule encoding the amino acid sequence of a COX-1 variant is derived from a mammalian source, for example, ovine, porcine, lupine or canine. In another embodiment, a COX-1 variant is derived from chicken. In yet another embodiment, a COX-1 variant is derived from human.

Another embodiment of the invention features nucleic acid molecules, preferably COX-1 variant nucleic acid molecules, which specifically detect COX-1 variant nucleic acid molecules encoding a COX-1 variant polypeptide relative to nucleic acid molecules encoding non-COX-1 variant polypeptides. For example, in one embodiment, such a nucleic acid molecule is at least 50, 100, 150, 200, 250, 300, 350, 400, 450, 500, 550, 600, 650, 700, 750, or 800 nucleotides in length and hybridizes under stringent conditions to a nucleic acid molecule comprising the nucleotide sequence shown in SEQ ID NO:1, SEQ ID NO:4, SEQ ID NO:10, SEQ ID NO:11, SEQ ID NO:12 or SEQ ID NO:13, or a complement thereof.

In other preferred embodiments, the nucleic acid molecule encodes a naturally occurring allelic variant of a polypeptide which includes the amino acid sequence of SEQ ID NO:2, SEQ ID NO:5, SEQ ID NO:14, SEQ ID NO:15 or SEQ ID NO:16, wherein the nucleic acid molecule hybridizes to a nucleic acid molecule which includes SEQ ID NO:1, SEQ ID NO:4, SEQ ID NO:10, SEQ ID NO:11, SEQ ID NO:12 or SEQ ID NO:13 under stringent conditions.

Another embodiment of the invention provides an isolated nucleic acid molecule that is antisense to a COX-1 variant nucleic acid molecule, e.g., the coding strand of a COX-1 variant nucleic acid molecule.

Another aspect of the invention provides a vector comprising a COX-1 variant nucleic acid molecule. In certain embodiments, the vector is a recombinant expression vector. In another embodiment, the invention provides a host cell containing a vector of the invention. The invention also provides a method for producing a protein or polypeptide, preferably a COX-1 variant protein or polypeptide, by culturing in a suitable medium, a host cell, e.g., a mammalian host cell or insect cell, of the invention containing a recombinant expression vector, such that the protein is produced.

Another aspect of this invention features isolated or recombinant COX-1 variant proteins and polypeptides. In one embodiment, the isolated protein, preferably a COX-1 variant protein (e.g., COX-3, PCOX-1a, hCOX-3(cc), hCOX-3(af), hCOX-3 (del10) and hCOX-3(cs)), includes at least one domain that catalyzes the cyclization and/or oxygenation of an fatty acid radical, at least one membrane-binding domain, and at least one heme binding domain. In another embodiment, the isolated protein, preferably a COX-1 variant protein, includes at least one domain that catalyzes the cyclization and/or oxygenation of an fatty acid radical, at least one membrane-binding domain, at least one heme binding domain, and has an amino acid sequence which is at least 50%, 55%, 60%, 65%, 70%, 75%, 80%, 85%, 90%, 95%, 98% or more homologous to an amino acid sequence including SEQ ID NO:2, SEQ ID NO:5, SEQ ID NO:14, SEQ ID NO:15 or SEQ ID NO:16. In yet another embodiment, the isolated protein, preferably a COX-1 variant protein, includes at least one domain that catalyzes the cyclization and/or oxygenation of an fatty acid radical, at least one membrane-binding domain, at least one heme binding domain, and is expressed and/or functions in cells of the central nervous system. In an even further embodiment, the isolated protein, preferably a COX-1 variant protein, includes at least one domain that catalyzes the cyclization and/or oxygenation of an fatty acid radical, at least one membrane-binding domain, at least one heme binding domain and plays a role in signaling pathways associated with cellular growth, e.g., signaling pathways associated with cell cycle regulation and central nervous system function. In another embodiment, the isolated protein, preferably a COX-1 variant protein, includes at least one domain that catalyzes the cyclization and/or oxygenation of an fatty acid radical, at least one membrane-binding domain, at least one heme binding domain, and is encoded by a nucleic acid molecule having a nucleotide sequence which hybridizes under stringent hybridization conditions to a nucleic acid molecule comprising the nucleotide sequence of SEQ ID NO:1, SEQ ID NO:4, SEQ ID NO:10, SEQ ID NO:11, SEQ ID NO:12 or SEQ ID NO:13.

In another embodiment, the isolated protein has an amino acid sequence homologous to the amino acid sequence of SEQ ID NO:2, SEQ ID NO:5, SEQ ID NO:14, SEQ ID NO:15 or SEQ ID NO:16. In one embodiment, the protein has an amino acid sequence at least about 50%, 55%, 60%, 65%, 70%, 75%, 80%, 85%, 90%, 95%, 98% or more homologous to an amino acid sequence including SEQ ID NO:2, SEQ ID NO:5, SEQ ID NO:14, SEQ ID NO:15 or SEQ ID NO:16, (e.g., the entire amino acid sequence of SEQ ID NO:2, 5, 14, 15 or 16). In another embodiment, the invention features fragments of the proteins having the amino acid sequence of SEQ ID NO:2, SEQ ID NO:5, SEQ ID NO:14, SEQ ID NO:15 or SEQ ID NO:16, wherein the fragment comprises at least 15 amino acids (e.g., contiguous amino acids) of the amino acid sequence of SEQ ID NO:2, SEQ ID NO:5, SEQ ID NO:14, SEQ ID NO:15 or SEQ ID NO:16. In another embodiment, the protein has the amino acid sequence of SEQ ID NO:2, SEQ ID NO:5, SEQ ID NO:14, SEQ ID NO:15 or SEQ ID NO:16.

Another embodiment of the invention features an isolated protein, preferably a COX-1 variant protein, which is encoded by a nucleic acid molecule having a nucleotide sequence at least about 60%, 65%, 70%, 75%, 80%, 85%, 90%, 95%, 98% or more homologous to a nucleotide sequence (e.g., to the entire length of the nucleotide sequence) including SEQ ID NO:1, SEQ ID NO:3, SEQ ID NO:4, SEQ ID NO:6, SEQ ID NO:10, SEQ ID NO:11, SEQ ID NO:12 or SEQ ID NO:13, or a complement thereof. This invention further features an isolated protein, preferably a COX-1 variant protein, which is encoded by a nucleic acid molecule having a nucleotide sequence which hybridizes under stringent hybridization conditions to a nucleic acid molecule comprising the nucleotide sequence of SEQ ID NO:1, SEQ ID NO:3, SEQ ID NO:4, SEQ ID NO:6, SEQ ID NO:10, SEQ ID NO:11, SEQ ID NO:12 or SEQ ID NO:13, or a complement thereof.

The proteins of the present invention or biologically active portions thereof, can be operatively linked to a non-COX-1 variant polypeptide (e.g., heterologous amino acid sequences) to form fusion proteins. The invention further features antibodies, such as monoclonal or polyclonal antibodies, that specifically bind proteins of the invention, preferably COX-1 variant proteins (e.g., COX-3, PCOX-1a, PCOX1b, hCOX-3(cc), hCOX-3(af), hCOX-3 (del10) or hCOX-3(cs)). In addition, the COX-1 variant proteins or biologically active portions thereof can be incorporated into pharmaceutical compositions, which optionally include pharmaceutically acceptable carriers.

In another embodiment, the present invention provides a method for detecting the presence of a Cox-1 variant nucleic acid molecule, protein or polypeptide in a biological sample by contacting the biological sample with an agent capable of detecting a COX-1 variant nucleic acid molecule, protein or polypeptide such that the presence of a COX-1 variant nucleic acid molecule, protein or polypeptide is detected in the biological sample.

In another embodiment, the present invention provides a method for detecting the presence of COX-1 variant activity in a biological sample by contacting the biological sample with an agent capable of detecting an indicator of COX-1 variant activity such that the presence of COX-1 variant activity is detected in the biological sample.

In another aspect the invention provides a method for identifying a compound that modulates the activity of a COX-1 variant protein or nucleic acid by providing an indicator composition comprising a COX-1 variant protein having COX-1 variant activity, contacting the indicator composition with a test compound, and determining the effect of the test compound on COX-1 variant activity in the indicator composition to identify a compound that modulates the activity of a COX-1 variant protein.

In another aspect, the invention provides a method for modulating COX-1 variant activity comprising contacting a cell capable of expressing COX-1 variant with an agent that modulates COX-1 variant activity such that COX-1 variant activity in the cell is modulated. In one embodiment, the agent inhibits COX-1 variant activity. In another embodiment, the agent stimulates COX-1 variant activity. In one embodiment, the agent is an antibody that specifically binds to a COX-1 variant protein. In another embodiment, the agent modulates expression of a COX-1 variant by modulating transcription of a COX-1 variant gene or translation of a COX-1 variant mRNA. In yet another embodiment, the agent is a nucleic acid molecule having a nucleotide sequence that is antisense to the coding strand of a COX-1 variant mRNA or a COX-1 variant gene.

In one embodiment, the methods of the present invention are used to treat a subject having a disorder characterized by aberrant COX-1 variant protein or nucleic acid expression or activity by administering an agent that is a COX-1 variant modulator to the subject. In one embodiment, the COX-1 variant modulator is a COX-1 variant protein. In another embodiment the COX-1 variant modulator is a COX-1 variant nucleic acid molecule. In yet another embodiment, the COX-1 variant modulator is a peptide, peptidomimetic, or other small molecule. In a preferred embodiment, the disorder characterized by aberrant COX-1 variant protein or nucleic acid expression is a cellular growth related disorder, e.g., a neoplastic disorder, or a disorder of the central nervous system, e.g., Alzheimer's Disease.

The present invention also provides a diagnostic assay for identifying the presence or absence of a genetic alteration characterized by at least one of (i) aberrant modification or mutation of a gene encoding a COX-1 variant protein; (ii) mis-regulation of the gene; and (iii) aberrant post-translational modification of a COX-1 variant protein, wherein a wild-type form of the gene encodes a protein with a COX-1 variant activity. A diagnostic assay can include, for example, an array-based system for detecting the presence or absence of a COX-1 variant or the presence or absence of a genetic alteration in a COX-1 variant.

In another embodiment, the invention provides a method for ameliorating a neurodegenerative condition in a subject by administering a specific inhibitor of a COX-1 variant encoded by a nucleic acid as set forth in the present invention, in a pharmaceutically acceptable carrier.

In another embodiment, the invention provides a method for selectively inhibiting COX-3, PCOX-1a, PCOX1b, hCOX-3(cc), hCOX-3(af), hCOX-3 (del10) or hCOX-3(cs) activity in a subject by administering a compound that selectively inhibits activity of the COX-3, PCOX-1a, PCOX1b, hCOX-3(cc), hCOX-3(af), hCOX-3 (del10) or hCOX-3(cs) gene product to a subject in need of such treatment.

In another embodiment, the invention provides a method for selectively inhibiting COX-3, PCOX-1a, PCOX1b, hCOX-3(cc), hCOX-3(af), hCOX-3 (del10) or hCOX-3(cs) activity in a subject by administering a non-steroidal compound that selectively inhibits activity of the COX-3, PCOX-1a, PCOX1b, hCOX-3(cc), hCOX-3(af), hCOX-3 (del10) or hCOX-3(cs) gene product in a subject in need of such treatment, wherein the activity of the non-steroidal compound does not result in significant toxic side effects in the subject.

In yet another embodiment, the invention provides a method for selectively inhibiting COX-1 variant activity in a subject by administering a non-steroidal compound that selectively inhibits activity of a COX-1 variant gene product in a subject in need of such treatment, wherein the ability of the non-steroidal compound to selectively inhibit the activity of the COX-1 variant gene product is determined by contacting a genetically engineered cell that expresses, for example, COX-3, PCOX-1a, PCOX1b, hCOX-3(cc), hCOX-3(af), hCOX-3 (del10) or hCOX-3(cs), and not COX-1 or COX-2, with the compound and exposing the cell to a pre-determined amount of arachidonic acid; contacting a genetically engineered cell that expresses COX-1 or COX-2, and not a COX-1 variant, with the compound and exposing the cell to a pre-determined amount of arachidonic acid; measuring the conversion of arachidonic acid to its prostaglandin metabolite; and comparing the amount of the converted arachidonic acid converted by each cell exposed to the compound to the amount of the arachidonic acid converted by control cells that were not exposed to the compound, so that the compounds that inhibit a COX-1 variant activity and not COX-1 or COX-2 activity are identified.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1A depicts an alignment of known COX-2 sequences. "Guinea" represents guinea pig, "Rainbow" is rainbow trout, and "Brook" is brook trout. Asterisks (*) are placed above cysteine residues that are known to be involved in disulfide bonding and gaps in the sequence are represented by a dash (-). All numbering in these alignments uses the ovine sequence as a reference. Domains are indicated.

FIG. 1B depicts an alignment of known COX-1 amino acid sequences for human (SEQ ID NO:22), ovine (SEQ ID NO:23), canine (SEQ ID NO:24), bovine (SEQ ID NO:25), equine (SEQ ID NO:26), rabbit (SEQ ID NO:27), guinea (SEQ ID NO:28), murine (SEQ ID NO:29), rat (SEQ ID NO:30), mink (SEQ ID NO:30), chicken (SEQ ID NO:31), rainbow trout (SEQ ID NO:32), and brook trout (SEQ ID NO:33). Asterisks, dashes and alignment are the same as those indicated for FIG. 1A. Domains are indicated.

FIG. 1C depicts an alignment of the consensus amino acid sequences of COX-1 (SEQ ID NO:34) and COX-2 (SEQ ID NO:35) with the sequences of cyclooxygenases from *Gersemia fruticosa* (SEQ ID NO:36) and *Plexaura homomalla* (SEQ ID NO:37), which are two species of coral. A period represents a residue for which no clear consensus (50% or greater) could be seen.

FIG. 2 depicts the primary sequence alignment of the consensus cyclooxygenase sequences with three plant PIOXs isolated from rice (SEQ ID NO:38), *A. Thaliana* (SEQ ID NO:39), and tobacco (SEQ ID NO:40). The domains shown are for cyclooxygenase. Periods represent residues for which there is no consensus (less than 50% of known sequences have the same residue here). The signal peptide and EGF-like, binding, and dimerization domains are not present in the PIOX sequences. Additionally, the distal histidine is not present in the PIOX sequences. The "REHN" sequence is part of the peroxidase catalytic domain of cyclooxygenases, and represents a stretch of 9 amino acids that is absolutely conserved in all known cyclooxygenases. This sequence is degenerated in the PIOXs. The active site tyrosine and proximal histidine heme ligand are conserved in all of the PIOX sequences.

FIG. 5, panel B, depicts Northern blot analysis of the distribution of COX-1 in chicken tissues. Arrows indicate additional COX-1 transcripts in brain tissue. v=seminal vesicle; p=pancreas; t=testicle; h=heart; ly=bursal lymph. The blots were hybridized as described for FIG. 5, panel a).

FIG. 5, panel C, depicts a Northern blot analysis of PCOX-1 (i.e., COX-3) and PCOX-1Δ657 (i.e., PCOX1a) RNA.

FIG. 6B depicts the predicted amino acid sequence of canine COX-1, PCOX-1 (i.e., COX-3) and PCOX-1Δ657 (i.e., PCOX1a) as compared with a consensus sequence.

FIG. 7 depicts an analysis of the structure of intron-1 of a COX-1 variant in human (SEQ ID NO:41) and mouse (SEQ ID NO:42) as compared with canine (SEQ ID NO:43). The human and mouse sequences contain an intron-1 that is similar in size to that in canine which, when retained, would provide an in-frame insertion into the signal peptide encoding the protein.

FIG. 9A depicts the nucleotide coding sequence of COX-3.
FIG. 9B depicts the amino acid sequence of a COX-3 polypeptide.
FIG. 9C depicts the cDNA sequence of COX-3 transcript.
FIG. 9D depicts the nucleotide coding sequence of PCOX-1a.

FIG. 9E depicts the amino acid sequence of PCOX-1a polypeptide.

FIG. 9F depicts the cDNA sequence of PCOX-1b transcript.

FIG. 10, panel B, depicts PCR amplification of PCOX-1 in canine cerebral cortex. Lane 1, ethidium bromide-stained gel of amplified products corresponding to PCOX-1a containing intron 1 (upper band) and PCOX-1b (lower band) lacking intron 1; lane 2, Southern blot of the amplified products probed with antisense oligonucleotide (CCI) to intron 1; and lane 3, Southern blot using COX-3 cDNA as probe.

FIG. 10, panel C, depicts human Multiple Tissue Northern blots (MTNR) probed with a $^{32}$P-labeled human antisense oligonucleotide to intron 1 (HCI). The ~5.2 kb mRNA was detected in blots 1-3 (adult tissues), and 4 (fetal tissues). Abbreviations: Am, amygdala; B, brain; C, cerebellum: Cc, cerebral cortex; Fl, frontal lobe; H, hippocampus; Ht, heart; K, kidney; L, lung; Li, liver; M, skeletal muscle; Md, medulla; N, caudate nucleus; Op, occipital pole; P, placenta; Pn, pancreas; Pu, putamen; Sc, spinal cord; T, thalamus; Tl, temporal lobe; X, corpus callosum.

FIG. 15, panel A, depicts a Western blot of human aorta lysate probed with COX-1 and COX-3 antibodies. The blot (lanes 3-8, 20 µg total aorta protein each lane) probed with primary, secondary, or blocked antibodies as indicated. A solid horizontal arrow indicates the 65 kDa protein, an open arrow indicates the 53 kDa proteins, and an upward diagonal solid arrow indicates the 50 kDa protein. A single asterisk (*) denotes unglycosylated canine COX-3, and a double asterisk (**) denotes unglycosylated canine PCOX-1a.

FIG. 15, panel B, depicts a densitometric analysis of 65, 53, and 50 kDa proteins. Percent relative densitometric units (% rdu) were calculated by comparison to the signal from unblocked primary antibodies. The 50 kDa protein is not detected (n/d) by unblocked or blocked COX-3 PAb.

FIG. 16 depicts a comparison of hCOX-3(cc), hCOX-3(af) and hCOX-3(del10) cDNA and provides a hCOX-3(cs) consensus sequence (SEQ ID NO:13) which is a consensus sequence of hCOX-3(af), hCOX-3(cc) and hCOX-3(del10).

FIG. 17 depicts the cDNA sequence of hCOX-3(cc) transcript (SEQ ID NO:10).

FIG. 18 depicts the cDNA sequence of hCOX-3(af) transcript (SEQ ID NO:11).

FIG. 19 depicts the cDNA sequence of hCOX-3(del10) transcript (SEQ ID NO:12).

FIG. 20A-F depicts consensus amino acid sequences (SEQ ID NO:14, SEQ ID NO:15 and SEQ ID NO:16) for different reading frames of hCOX-3(cs) (SEQ ID NO:13).

Like reference symbols in the various drawings indicate like elements.

DETAILED DESCRIPTION

Figure 3B:
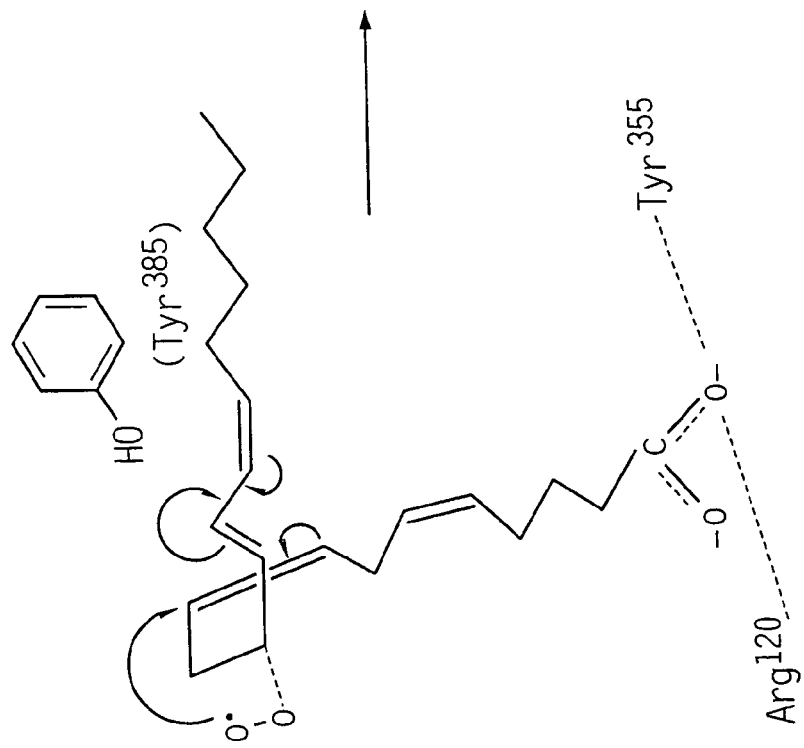
FIG. 3 depicts activation of arachidonic acid by COX enzymes showing the essential role of Tyr385—an amino acid residue conserved in COXs and PIOXs. Step 1: Arachidonate is coordinated in the COX active site in an extended L shape, its carboxyl group being coordinated by ARG120 and TYR355. The Pro-S hydrogen from carbon 13 is abstracted by Tyr385 to form an arachidonyl radical. Step 2: Oxygen presumed to have diffused in to the COX active site through the mouth of the channel attacks the arachidonyl radical forming an endoperoxyl and cyclopentane ring. Step 3: The endoperoxyl radical is attacked by a second molecule of oxygen at carbon 15. Step 4: Tyr385 donates its hydrogen to form PGG2 and to reform the radical at Tyr385.
Figure 3A:
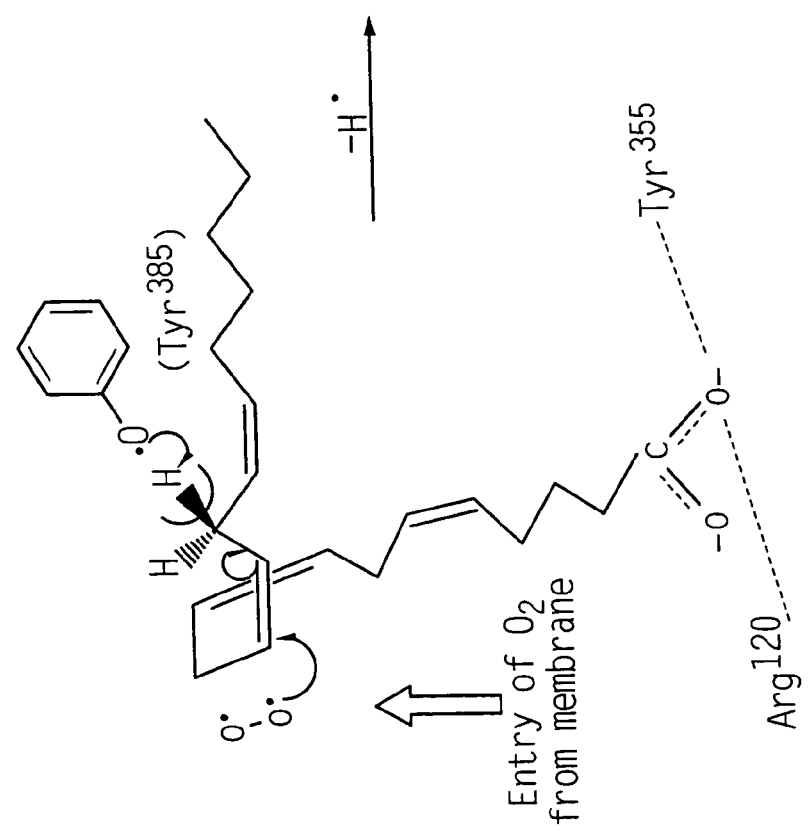
Figure 3D:
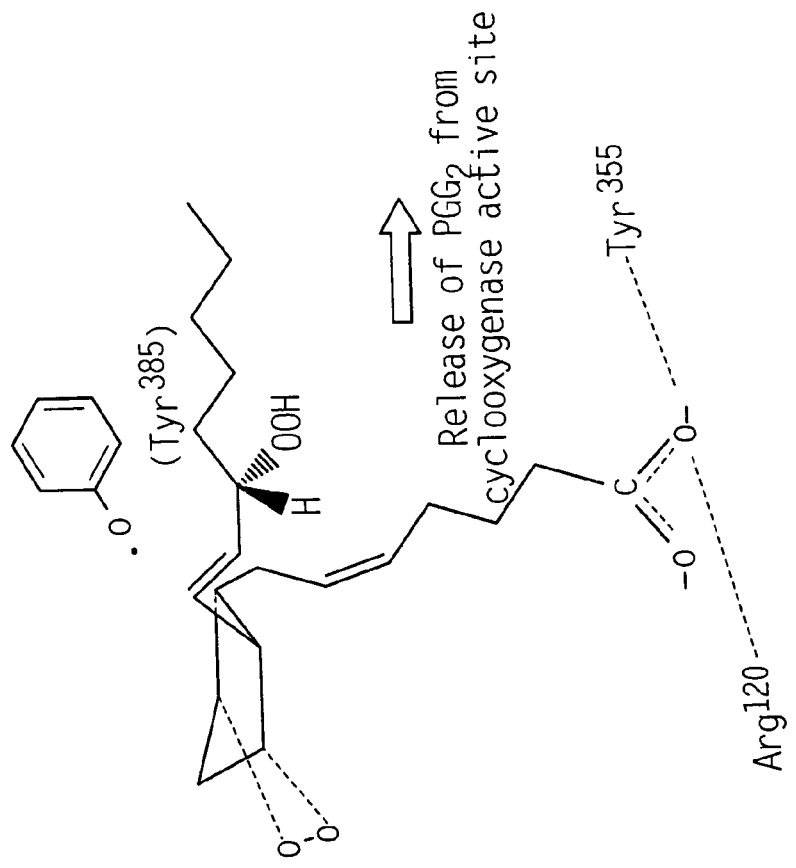
Figure 3C:
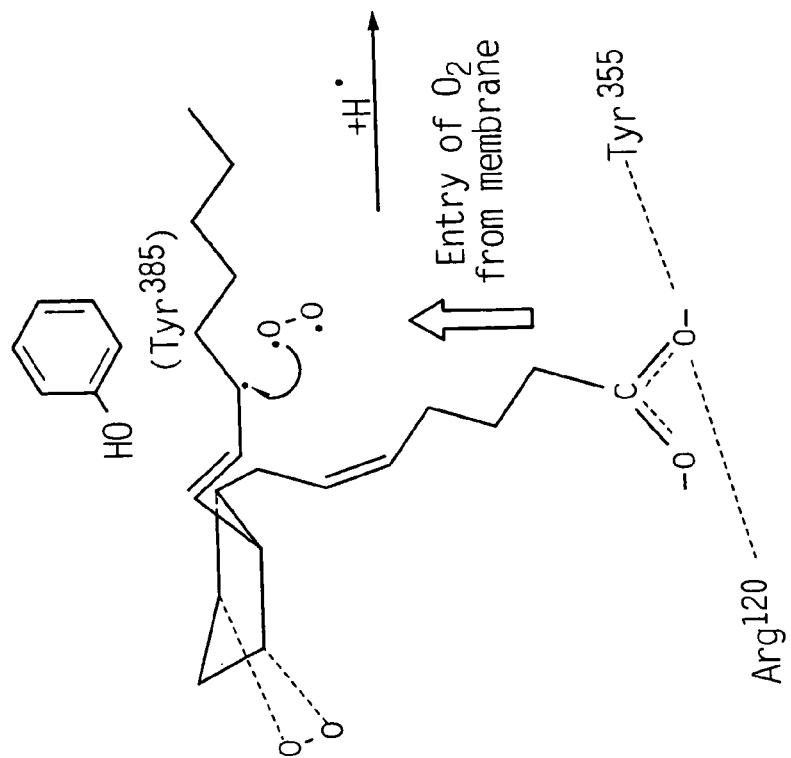
Figure 4:
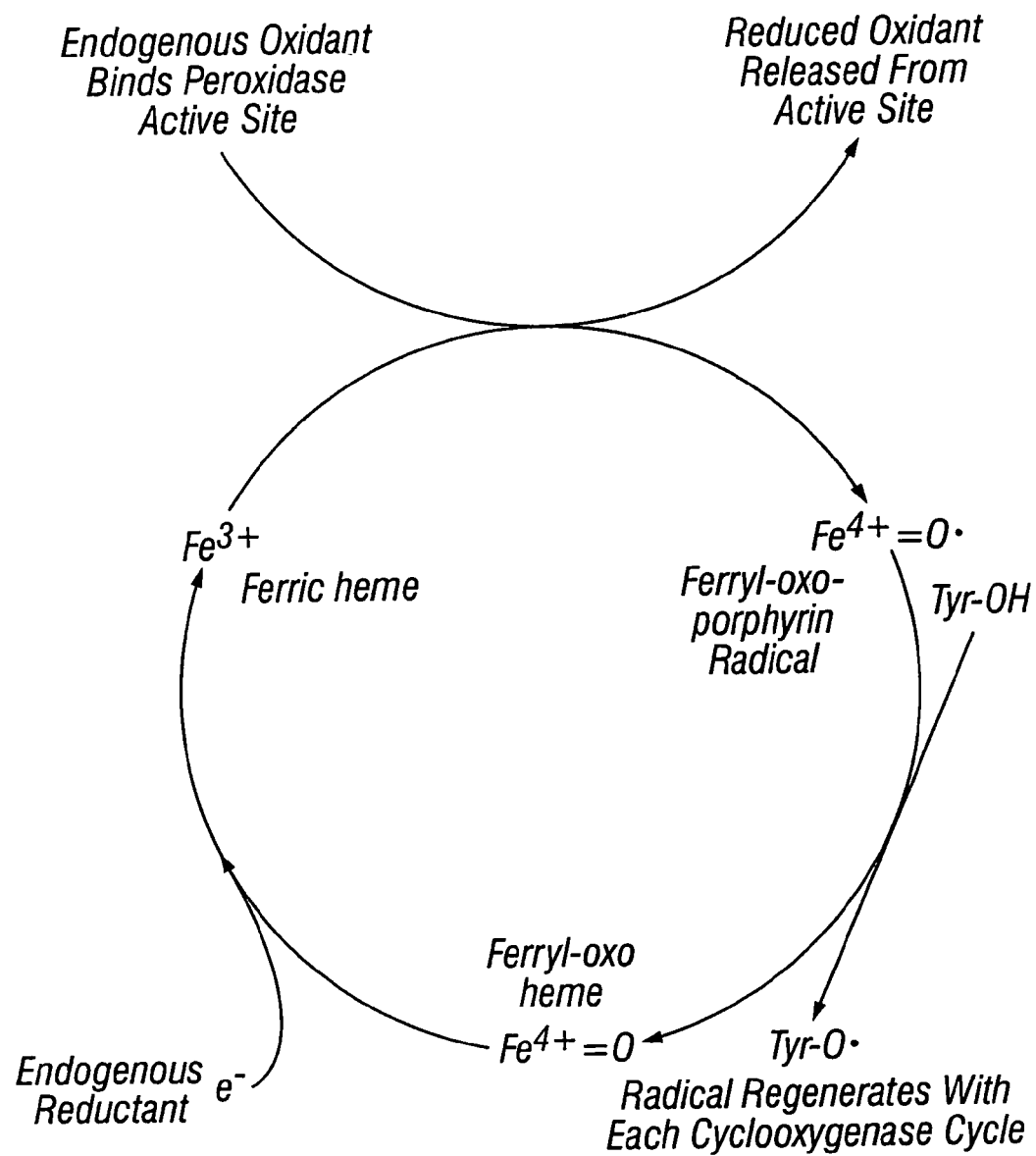
FIG. 4 depicts a diagram of the catalytic cycle responsible for activation of $Tyr^{385}$—an amino acid residue conserved in COXs and PIOXs. An endogenous oxidant binds the peroxidase active site and oxidizes ferric heme to ferryl-oxo-porphyrin radical which in turn abstracts hydrogen from $Tyr^{385}$ to form a tyrosyl radical. Only one oxidation event at the peroxidase is needed to activate the enzyme, since the $Tyr^{385}$ radical is regenerated with each cyclooxygenase cycle.

The present invention is based, at least in part, on the discovery of novel molecules, referred to herein as "cyclooxygenase type 1 variants," "COX-1 variants" or "COX-1 variant nucleic acid and polypeptide molecules," which play a role in or function in signaling pathways associated with cell processes in brain and other tissues. Exemplary COX-1 variants of the invention include COX-3, PCOX-1a, PCOX-1b, hCOX-3(cc), hCOX-3(af), hCOX-3 (del10) and hCOX-3(cs). In one embodiment, the COX-1 variant molecules modulate the activity of one or more proteins involved in cellular growth or differentiation. In another embodiment, the COX-1 variant molecules of the present invention are capable of modulating the function of the central nervous system.

Cyclooxygenase isozymes are the cellular targets of nonsteroidal antiinflammatory drugs (NSAIDs), which include pharmaceutically-important therapeutic agents such as aspirin, ibuprofen, and naproxen. The present invention provides novel COX-1 variant enzymes. Fatty acid oxygenase activity is central to the production of prostaglandins, thromboxanes, hydroxy- and hydroperoxy-fatty acids by cyclooxygenases and is also shared by a related group of enzymes, which in plants are called pathogen inducible fatty acid oxygenases (PIOXs). The present data indicate that PIOX-like enzymes are found widely in nature. PIOXs make hydroperoxy-fatty acids and their derivatives. Thus, the present COX-1 variants, like PIOXs, contain the critical amino acid residues needed to synthesize important oxygenated fatty acid-derived messengers in the brain and in other tissue.

As previously noted, cyclooxygenases play a role in prostaglandin synthesis. Inhibition or over stimulation of the activity of cyclooxygenases involved in signaling pathways associated with cellular growth can lead to perturbed cellular growth, which can in turn lead to cellular growth related disorders. As used herein, a "cellular growth related disorder" includes a disorder, disease, or condition characterized by a deregulation, e.g., an upregulation or a downregulation, of cellular growth. Cellular growth deregulation may be due to a deregulation of cellular proliferation, cell cycle progression, cellular differentiation and/or cellular hypertrophy. Examples of cellular growth related disorders include disorders such as cancer, e.g., melanoma, prostate cancer, cervical cancer, breast cancer, colon cancer, or sarcoma. Cellular growth related disorders further include disorders related to unregulated or dysregulated apoptosis (i.e., programmed cell death). Apoptosis is a cellular suicide process in which damaged or harmful cells are eliminated from multicellular organisms. Cells undergoing apoptosis have distinct morphological changes including cell shrinkage, membrane blebbing, chromatin condensation, apoptotic body formation and fragmentation. This cell suicide program is evolutionarily conserved across animal and plant species. Apoptosis plays an important role in the development and homeostasis of metazoans and is also critical in insect embryonic development and metamorphosis. Furthermore, apoptosis acts as a host defense mechanism. For example, virally infected cells are eliminated by apoptosis to limit the propagation of viruses. Apoptosis mechanisms are involved in plant reactions to biotic and abiotic insults. Dysregulation of apoptosis has been associated with a variety of human diseases including cancer, neurodegenerative disorders and autoimmune diseases. Accordingly, identification of novel mechanisms to manipulate apoptosis provides new means to study and manipulate this process.

The present invention is based, at least in part, on the discovery of novel molecules, referred to herein as COX-1 variant protein and nucleic acid molecules, which comprise a family of molecules having certain conserved structural and functional features. The term "family" when referring to the protein and nucleic acid molecules of the invention is intended to mean two or more proteins or nucleic acid molecules having a common structural domain or motif and having sufficient amino acid or nucleotide sequence homology as defined herein. Such family members can be naturally or non-naturally occurring and can be from either the same or different species. For example, a family can contain a first protein of human origin, as well as other, distinct proteins of human origin or alternatively, can contain homologues of non-human origin. Members of a family may also have common functional characteristics. One embodiment of the invention features exemplary COX-1 variants including COX-3, PCOX-1a, PCOX-1b, hCOX-3(cc), hCOX-3(af), hCOX-3 (del10) and hCOX-3(cs). The nucleic acid and protein molecules of the invention are described in further detail in the following subsections.

In one embodiment, a COX-1 variant nucleic acid molecule of the invention comprises intron 1, or fragment thereof, of cyclooxygenase type 1. In one aspect, the nucleic acid molecule is an mRNA transcript. In another aspect, the nucleic acid molecule is cDNA. In another aspect, the nucleic acid molecule encodes a polypeptide comprising at least one domain that catalyzes the cyclization and/or oxygenation of a fatty acid radical, at least one membrane-binding domain, and at least one heme binding domain. In yet another aspect the nucleic acid molecule encodes a cyclooxygenase polypeptide, or naturally occurring allelic variant thereof, which comprises intron 1, or fragment thereof, of cyclooxygenase 1.

The present invention provides nucleic acid molecules and polypeptides of COX-1 variants that possess a cyclooxygenase intron-1. Retention of intron-1 in these mRNA transcripts and cDNAs disrupts the signal peptide of the protein and, therefore, is predicted to change the subcellular localization of the proteins encoded by these mRNA transcripts and any cDNA derived therefrom. Changing the subcellular localization of these proteins from the lumen of the endoplasmic reticulum, where COX-1 is normally found, to the cytosol or other location will change posttranslational modifications, redox states, and protein-protein interactions of the proteins encoded by our cDNAs. These changes are predicted to have significant effect on the enzymatic activities of the proteins that will make them novel drug targets separate from COX-1.

Northern blot and RT-PCR data provided herein suggest that analogous sequences exist in humans. These data show that human tissues contain mRNAs encoded from the COX-1 gene that possess intron-1 sequences. Although cyclooxygenase intron-1 has been previously sequenced, the inventions disclosed herein provide the first evidence that intron-1 sequences are contained in mature cyclooxygenase transcripts. Alignment of these sequences shows that in each species intron one is short (90-102 nt), the length of its sequence is a multiple of three, and the sequence is evolutionarily conserved. Because the sequence is a multiple of three, intron-1 constitutes an in-frame insertion when the sequence is retained in a COX-1 mRNA. The evolutionary conservation of the sequence predicts a conserved sequence encoded by the 5' end of the intron that is present in all 3 species and may be important in subcellular targeting of the protein.

An exemplary COX-1 variant includes COX-3. Northern blot analysis of (polyA) RNA from human tissues using an anti-sense oligonucleotide probe to intron 1 shows that a ~5.2 kb mRNA and, in some cases smaller mRNAs, are specifically detected by this probe. Expression of this human ~5.2 kb, intron-1-hybridizing RNA was highest in brain cortex, the same tissue which possesses a high amount of intron-1 containing COX-1 mRNA in dog. The ~5.2 kb RNA, from which COX-3 is expressed, was also found to be present in other parts of the brain and in other tissues such as heart and muscle. Reverse-transcriptase-coupled polymerase chain reaction (RT-PCR) using a primer pair consisting of a sense primer specific for intron-1 and an antisense primer to the region of the stop codon of the COX-1 open reading frame was performed using human brain RNA as template. This experiment produced a 1.8 kb fragment, which is the correct size for amplification of human COX-1 cDNA containing intron-1. Moreover, hybridization of this blot with murine-COX-1 cDNA hybridized strongly at high stringency to the amplified fragment, demonstrating that this fragment contains human COX-1 cDNA.

In one embodiment, the isolated COX-1 variant proteins or polypeptides are identified based on the presence of at least one domain that catalyzes the cyclization and/or oxygenation of an fatty acid radical, at least one membrane-binding domain, and at least one heme binding domain.

Isolated proteins of the present invention have an amino acid sequence homologous to the amino acid sequence of COX-3, PCOX-1a, hCOX-3(cc), hCOX-3(af), hCOX-3 (del10) and hCOX-3(cs) or are encoded by a nucleotide sequence homologous to SEQ ID NO:1, SEQ ID NO:3, SEQ ID NO:4, SEQ ID NO:6, SEQ ID NO:10, SEQ ID NO:11, SEQ ID NO:12 or SEQ ID NO:13. As used herein, the term "homologous" refers to a first amino acid or nucleotide sequence which contains a sufficient or minimum number of identical or equivalent (e.g., an amino acid residue which has a similar side chain) amino acid residues or nucleotides to a second amino acid or nucleotide sequence such that the first and second amino acid or nucleotide sequences share common structural domains or motifs and/or a common functional activity. For example, amino acid or nucleotide sequences which share common structural domains have at least 30%, 40%, or 50% homology, preferably 60% homology, more preferably 70%-80%, and even more preferably 90-95% homology across the amino acid sequences of the domains and contain at least one and preferably two structural domains or motifs, are defined herein as sufficiently homologous. Furthermore, amino acid or nucleotide sequences which share at least 30%, 40%, or 50%, preferably 60%, more preferably 70-80%, or 90-95% homology and share a common functional activity are defined herein as sufficiently homologous.

As used interchangeably herein a "COX-3 activity", "biological activity of COX-3" or "functional activity of COX-3", refers to an activity exerted by a COX-3 protein, polypeptide or nucleic acid molecule on a COX-3 responsive cell or a COX-3 protein substrate, as determined in vivo, or in vitro, according to standard techniques. The biological activity of COX-3 is described herein. Similarly, "PCOX-1a activity", "biological activity of PCOX-1a" or "functional activity of PCOX-1a", refers to an activity exerted by a PCOX-1a protein, polypeptide or nucleic acid molecule on a PCOX-1a responsive cell or a PCOX-1a protein substrate, as determined in vivo, or in vitro, according to standard techniques. The biological activity of PCOX-1a is described herein. The previously described terms are applicable to all exemplary COX-1 variants described herein, including PCOX-1b, hCOX-3(cc), hCOX-3(af), hCOX-3 (del10) and hCOX-3(cs).

Figure 16A:
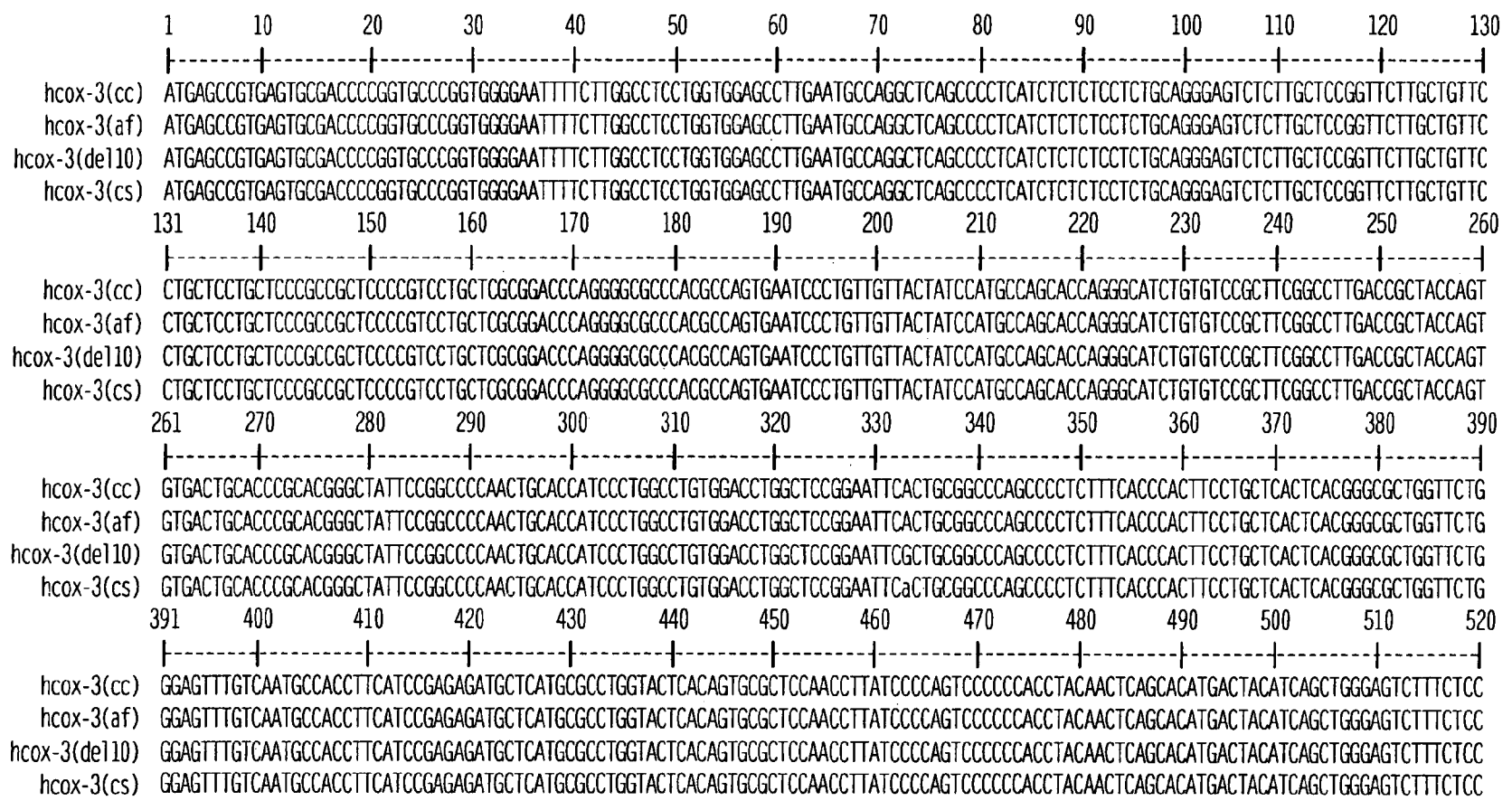
Figure 16B:
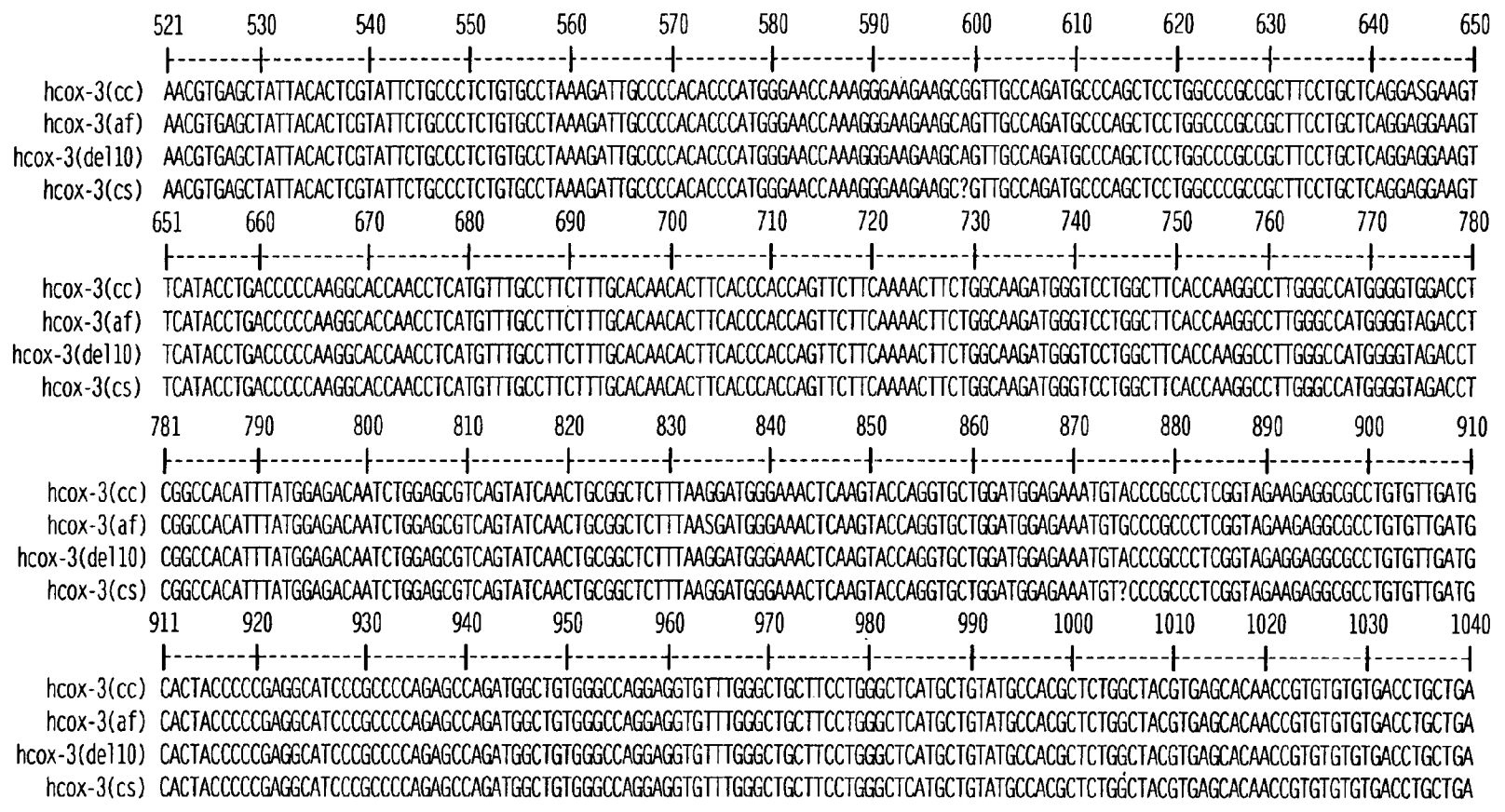

The nucleotide sequence of the isolated COX-3 cDNA and the predicted amino acid sequence of the COX-3 polypeptide are shown in FIGS. 9A (SEQ ID NO:1) and 9B (SEQ ID NO:2), respectively. The nucleotide sequence of the isolated PCOX-1a cDNA and the predicted amino acid sequence of the PCOX-1a polypeptide are shown in FIGS. 9D (SEQ ID NO:4) and 9E (SEQ ID NO:5), respectively. The consensus nucleotide sequence of hCOX-3(cc), hCOX-3(af) and hCOX-3(del10) cDNA is shown in FIG. 16 (SEQ ID NO:13). The nucleotide sequence of the isolated hCOX-3(cc) cDNA is shown in FIG. 17 (SEQ ID NO:10). The nucleotide sequence of the isolated hCOX-3(af) cDNA is shown in FIG. 18 (SEQ ID NO:11). The nucleotide sequence of the isolated hCOX-3(del10) cDNA is shown in FIG. 19 (SEQ ID NO:12). The amino acid sequences derived from the consensus sequence is shown in FIG. 20A-F (SEQ ID NO:14, SEQ ID NO:15 and SEQ ID NO:16).

One embodiment of the invention pertains to isolated nucleic acid molecules that encode proteins or biologically active portions thereof, as well as nucleic acid fragments sufficient for use as hybridization probes to identify COX-1 variants (i.e., COX-3, PCOX-1a, hCOX-3(cc), hCOX-3(af), hCOX-3 (del10) and hCOX-3(cs)-encoding nucleic acids (e.g., mRNA) and fragments for use as PCR primers for the amplification or mutation of nucleic acid molecules. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

An "isolated" nucleic acid molecule is one which is separated from other nucleic acid molecules which are present in the natural source of the nucleic acid. For example, with regards to genomic DNA, the term "isolated" includes nucleic acid molecules which are separated from the chromosome with which the genomic DNA is naturally associated. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived. Moreover, an "isolated" nucleic acid molecule, such as a COX-1 variant cDNA molecule, can be substantially free of other cellular material, or culture medium when produced by recombinant techniques, or substantially free of chemical precursors or other chemicals when chemically synthesized.

A nucleic acid molecule of the present invention, e.g., a nucleic acid molecule having the nucleotide sequence of SEQ ID NO:1, SEQ ID NO:3, SEQ ID NO:4, SEQ ID NO:6, SEQ ID, SEQ ID NO:10, SEQ ID NO:11, SEQ ID NO:12 or SEQ ID NO:13, or a portion thereof, can be isolated using standard molecular biology techniques and the sequence information provided herein. For example, using all or portion of the nucleic acid sequence of SEQ ID NO:1, or the nucleotide sequence of SEQ ID NO:3, as a hybridization probe, nucleic acid molecules can be isolated using standard hybridization and cloning techniques (e.g., as described in Sambrook, J., Fritsh, E. F., and Maniatis, T. Molecular Cloning: A Laboratory Manual. 2nd, ed., Cold Spring Harbor Laboratory, Cold Spring Harbor Laboratory Press, Cold Spring Harbor, N.Y., 1989).

Moreover, a nucleic acid molecule encompassing all or a portion of SEQ ID NO:1, SEQ ID NO:3, SEQ ID NO:4, SEQ ID NO:6, SEQ ID NO:10, SEQ ID NO:11, SEQ ID NO:12 or SEQ ID NO:13 can be isolated by the polymerase chain reaction (PCR) using synthetic oligonucleotide primers designed based upon the sequence of SEQ ID NO:1, SEQ ID NO:3, SEQ ID NO:4, SEQ ID NO:6, SEQ ID NO:10, SEQ ID NO:11, SEQ ID NO:12 or SEQ ID NO:13, respectively.

A nucleic acid of the invention can be amplified using cDNA, mRNA or alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to COX-1 variant nucleotide sequences can be prepared by standard synthetic techniques, e.g., using an automated DNA synthesizer.

In various embodiments, an isolated nucleic acid molecule of the invention comprises the nucleotide sequence shown in SEQ ID NO:1, SEQ ID NO:4, SEQ ID NO:10, SEQ ID NO:11, SEQ ID NO:12 or SEQ ID NO:13 corresponding to the coding region of COX-3, PCOX-1a, PCOX-1b, hCOX-3 (cc), hCOX-3(af), hCOX-3 (del10) and hCOX-3(cs), respectively.

In another preferred embodiment, an isolated nucleic acid molecule of the invention comprises a nucleic acid molecule which is a complement of the nucleotide sequence shown in SEQ ID NO:1, SEQ ID NO:4, SEQ ID NO:10, SEQ ID NO:11, SEQ ID NO:12 or SEQ ID NO:13, or a portion of any of these nucleotide sequences. A nucleic acid molecule which is complementary to the nucleotide sequence shown in SEQ ID NO:1, SEQ ID NO:4, SEQ ID NO:10, SEQ ID NO:11, SEQ ID NO:12 or SEQ ID NO:13, is one which is sufficiently complementary to the nucleotide sequence shown in SEQ ID NO:1, SEQ ID NO:4, SEQ ID NO:10, SEQ ID NO:11, SEQ ID NO:12 or SEQ ID NO:13, respectively, such that it can hybridize to the nucleotide sequence shown in SEQ ID NO:1, SEQ ID NO:4, SEQ ID NO:10, SEQ ID NO:11, SEQ ID NO:12 or SEQ ID NO:13, respectively, thereby forming a stable duplex.

In still another preferred embodiment, an isolated nucleic acid molecule of the present invention comprises a nucleotide sequence which is at least about 50%, 54%, 55%, 60%, 62%, 65%, 70%, 75%, 78%, 80%, 85%, 86%, 90%, 95%, 97%, 98% or more homologous to the nucleotide sequence (e.g., to the entire length of the nucleotide sequence) shown in SEQ ID NO:1, SEQ ID NO:4, SEQ ID NO:10, SEQ ID NO:11, SEQ ID NO:12 or SEQ ID NO:13, or a portion of any of these nucleotide sequences.

Moreover, the nucleic acid molecule of the invention can comprise only a portion of the nucleic acid sequence of SEQ ID NO:1, SEQ ID NO:4, SEQ ID NO:10, SEQ ID NO:11, SEQ ID NO:12 or SEQ ID NO:13, for example a fragment which can be used as a probe or primer or a fragment encoding a biologically active portion of a protein. The nucleotide sequence determined from the cloning of the COX-1 variant transcript allows for the generation of probes and primers designed for use in identifying and/or cloning other COX-1 variant family members, as well as homologues from other species. The probe/primer typically comprises substantially purified oligonucleotide. The oligonucleotide typically comprises a region of nucleotide sequence that hybridizes under stringent conditions to at least about 12 or 15, preferably about 20 or 25, more preferably about 30, 35, 40, 45, 50, 55, 60, 65, or 75 consecutive nucleotides of a sense sequence of SEQ ID NO:1, SEQ ID NO:4, SEQ ID NO:10, SEQ ID NO:11, SEQ ID NO:12 or SEQ ID NO:13, of an anti-sense sequence of SEQ ID NO:1, SEQ ID NO:4, SEQ ID NO:10, SEQ ID NO:11, SEQ ID NO:12 or SEQ ID NO:13, or of a naturally occurring allelic variant or mutant of SEQ ID NO:1, SEQ ID NO:4, SEQ ID NO:10, SEQ ID NO:11, SEQ ID NO:12 or SEQ ID NO:13. In an exemplary embodiment, a nucleic acid molecule of the present invention comprises a nucleotide sequence which is at least 350, 400, 450, 500, 550, 600, 650, 700, 750, or 800 nucleotides in length and hybridizes under stringent hybridization conditions to a nucleic acid molecule of SEQ ID NO:1, SEQ ID NO:4, SEQ ID NO:10, SEQ ID NO:11, SEQ ID NO:12 or SEQ ID NO:13

As defined herein, nucleic acids that do not hybridize to each other under stringent conditions are still substantially homologous to one another if they encode polypeptides that are substantially identical to each other. This occurs, for example, when a nucleic acid is created synthetically or recombinantly using a high codon degeneracy as permitted by the redundancy of the genetic code.

Probes based on COX-1 variant nucleotide sequences can be used to detect transcripts or genomic sequences encoding the same or homologous proteins. In preferred embodiments, the probe further comprises a label group attached thereto, e.g., the label group can be a radioisotope, a fluorescent compound, an enzyme, or an enzyme co-factor. Such probes can be used as a part of a diagnostic test kit for identifying cells or tissues which misexpress a COX-1 variant protein, such as by measuring a level of a COX-1 variant-encoding nucleic acid in a sample of cells from a subject e.g., detecting COX-1 variant mRNA levels.

A nucleic acid fragment encoding a "biologically active portion of a COX-1 variant protein" can be prepared by isolating a portion of the nucleotide sequence of SEQ ID NO:1, SEQ ID NO:4, SEQ ID NO:10, SEQ ID NO:11, SEQ ID NO:12 or SEQ ID NO:13, which encodes a polypeptide having a biological activity (the biological activities of the proteins are described herein), expressing the encoded portion of the protein (e.g., by recombinant expression in vitro) and assessing the activity of the encoded portion of the protein.

The invention further encompasses nucleic acid molecules that differ from the nucleotide sequence shown in SEQ ID NO:1, SEQ ID NO:4, SEQ ID NO:10, SEQ ID NO:11, SEQ ID NO:12 or SEQ ID NO:13, due to the degeneracy of the genetic code and, thus, encode the same proteins as those encoded by the nucleotide sequence shown in SEQ ID NO:1, SEQ ID NO:4, SEQ ID NO:10, SEQ ID NO:11, SEQ ID NO:12 or SEQ ID NO:13. In another embodiment, an isolated nucleic acid molecule of the invention has a nucleotide sequence encoding a protein having an amino acid sequence shown in SEQ ID NO:2, SEQ ID NO:5, SEQ ID NO:14, SEQ ID NO:15 or SEQ ID NO:16.

In addition to the COX-1 variant nucleotide sequences shown in SEQ ID NO:1, SEQ ID NO:4, SEQ ID NO:10, SEQ ID NO:11, SEQ ID NO:12 or SEQ ID NO:13, it will be appreciated by those skilled in the art that DNA sequence polymorphisms that lead to changes in the amino acid sequences of the proteins may exist within a population (e.g., the human population). Such genetic polymorphism may exist among individuals within a population due to natural allelic variation. As used herein, the terms "gene" and "recombinant gene" refer to nucleic acid molecules which include an open reading frame encoding a COX-1 protein, preferably a mammalian protein, and can further include non-coding regulatory sequences, and introns. Since natural allelic variations can arise in the COX-1 gene, variant mRNA transcripts encoding COX-1 variant polypeptides can include such allelic variations. Any and all such nucleotide variations and resulting amino acid polymorphisms in COX-1 variant genes that are the result of natural allelic variation and that do not alter the functional activity of a COX-1 variant protein are intended to be within the scope of the invention.

Moreover, nucleic acid molecules encoding other COX-1 family members and, thus, which have a nucleotide sequence which differs from the sequences of SEQ ID NO:1, SEQ ID NO:3, SEQ ID NO:4, SEQ ID NO:6, SEQ ID NO:10, SEQ ID NO:11, SEQ ID NO:12 or SEQ ID NO:13, are intended to be within the scope of the invention. For example, another COX-1 variant cDNA can be identified based on the nucleotide sequence of the disclosed human, canine or chicken sequences. Moreover, nucleic acid molecules encoding proteins of the invention from different species, and thus which have a nucleotide sequence which differs from the disclosed sequences of SEQ ID NO:1, SEQ ID NO:3, SEQ ID NO:4, SEQ ID NO:6, SEQ ID NO:10, SEQ ID NO:11, SEQ ID NO:12 or SEQ ID NO:13 are intended to be within the scope of the invention. For example, a mouse COX-1 variant cDNA can be identified based on the nucleotide sequence of a human, canine or ovine.

Nucleic acid molecules corresponding to natural allelic variants and homologues of the cDNAs of the invention can be isolated based on their homology to the COX-1 variant nucleic acids disclosed herein using the cDNAs disclosed herein, or a portion thereof, as a hybridization probe according to standard hybridization techniques under stringent hybridization conditions.

Accordingly, in another embodiment, an isolated nucleic acid molecule of the invention is at least 15, 20, 25, 30 or more nucleotides in length and hybridizes under stringent conditions to the nucleic acid molecule comprising the nucleotide sequence of SEQ ID NO:1, SEQ ID NO:3, SEQ ID NO:4, SEQ ID NO:6, SEQ ID NO:10, SEQ ID NO:11, SEQ ID NO:12 or SEQ ID NO:13. In other embodiment, the nucleic acid is at least 30, 50, 100, 150, 200, 250, 300, 350, 400, 450, 500, 550, or 600 nucleotides in length. As used herein, the term "hybridizes under stringent conditions" is intended to describe conditions for hybridization and washing under which nucleotide sequences at least 30%, 40%, 50%, or 60% homologous to each other typically remain hybridized to each other. Preferably, the conditions are such that sequences at least about 70%, more preferably at least about 80%, even more preferably at least about 85% or 90% homologous to each other typically remain hybridized to each other. Such stringent conditions are known to those skilled in the art and can be found in Current Protocols in Molecular Biology, John Wiley & Sons, N.Y. (1989), 6.3.1-6.3.6. A preferred, non-limiting example of stringent hybridization conditions are hybridization in 6× sodium chloride/sodium citrate (SSC) at about 45° C., followed by one or more washes in 0.2×SSC, 0.1% SDS at 50-65° C. Preferably, an isolated nucleic acid molecule of the invention that hybridizes under stringent conditions to the sequence of SEQ ID NO:1, SEQ ID NO:3, SEQ ID NO:4, SEQ ID NO:6, SEQ ID NO:10, SEQ ID NO:11, SEQ ID NO:12 or SEQ ID NO:13 corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein).

In addition to naturally-occurring allelic variants of the sequences that may exist in the population, the skilled artisan will further appreciate that changes can be introduced by mutation into the nucleotide sequences of SEQ ID NO:1, SEQ ID NO:3, SEQ ID NO:4, SEQ ID NO:6, SEQ ID NO:10, SEQ ID NO:11, SEQ ID NO:12 or SEQ ID NO:13, thereby leading to changes in the amino acid sequence of the encoded proteins, without altering the functional ability of the proteins. For example, nucleotide substitutions leading to amino acid substitutions at "non-essential" amino acid residues can be made in the sequence of SEQ ID NO:1, SEQ ID NO:3, SEQ ID NO:4, SEQ ID NO:6, SEQ ID NO:10, SEQ ID NO:11, SEQ ID NO:12 or SEQ ID NO:13. A "non-essential" amino acid residue is a residue that can be altered from the wild-type sequence of (e.g., the sequence of SEQ ID NO:2, SEQ ID NO:5, SEQ ID NO:14, SEQ ID NO:15 or SEQ ID NO:16) without altering the biological activity, whereas an "essential" amino acid residue is required for biological activity. For example, amino acid residues that are conserved among the COX-3, PCOX-1a, PCOX-1b, hCOX-3 (cc), hCOX-3(af), hCOX-3 (del10) and hCOX-3(cs) proteins of the present invention, are predicted to be particularly unamenable to alteration. Furthermore, additional amino acid residues that are conserved between the proteins of the present invention and other family members are not likely to be amenable to alteration.

Accordingly, another aspect of the invention pertains to nucleic acid molecules encoding proteins of the invention that contain changes in amino acid residues that are not essential for activity. Such proteins differ in amino acid sequence from SEQ ID NO:2, SEQ ID NO:5, SEQ ID NO:14, SEQ ID NO:15 or SEQ ID NO:16, yet retain biological activity. In one embodiment, the isolated nucleic acid molecule comprises a nucleotide sequence encoding a protein, wherein the protein comprises an amino acid sequence at least about 41%, 42%, 45%, 50%, 55%, 59%, 60%, 65%, 70%, 75%, 80%, 81%, 85%, 90%, 95%, 98% or more homologous to the amino acid sequence of SEQ ID NO:2, SEQ ID NO:5, SEQ ID NO: 14, SEQ ID NO:15 or SEQ ID NO:16, (e.g., the entire amino acid sequence of SEQ ID NO:2; SEQ ID NO:5, SEQ ID NO:14, SEQ ID NO15 or SEQ ID NO:16).

An isolated nucleic acid molecule encoding a protein of the invention which is homologous to the protein of SEQ ID NO:2, SEQ ID NO:5, SEQ ID NO:14, SEQ ID NO:15 or SEQ ID NO:16 can be created by introducing one or more nucleotide substitutions, additions or deletions into the nucleotide sequence of SEQ ID NO:1, SEQ ID NO:3, SEQ ID NO:4, SEQ ID NO:6, SEQ ID NO:10, SEQ ID NO:11, SEQ ID NO:12 or SEQ ID NO:13, respectively, such that one or more amino acid substitutions, additions or deletions are introduced into the encoded protein. Mutations can be introduced into SEQ ID NO:1, SEQ ID NO:3, SEQ ID NO:4, SEQ ID NO:6, SEQ ID NO:10, SEQ ID NO:11, SEQ ID NO:12 or SEQ ID NO:13, by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in a protein of the invention is preferably replaced with another amino acid residue from the same side chain family. Alternatively, in another embodiment, mutations can be introduced randomly along all or part of a COX-1 variant coding sequence, such as by saturation mutagenesis, and the resultant mutants can be screened for COX-1 variant biological activity to identify mutants that retain activity. Following mutagenesis SEQ ID NO:1, SEQ ID NO:3, SEQ ID NO:4, SEQ ID NO:6, SEQ ID NO:10, SEQ ID NO:11, SEQ ID NO:12 or SEQ ID NO:13, the encoded protein can be expressed recombinantly and the activity of the protein can be determined.

In addition to the nucleic acid molecules encoding COX-3, PCOX-1a, hCOX-3(cc), hCOX-3(af), hCOX-3 (del10) and hCOX-3(cs) proteins described above, another aspect of the invention pertains to isolated nucleic acid molecules which are antisense thereto. An "antisense" nucleic acid comprises a nucleotide sequence which is complementary to a "sense" nucleic acid encoding a protein, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire COX-1 variant coding strand, or only to a portion thereof. In one embodiment, an antisense nucleic acid molecule is antisense to a "coding region" of the coding strand of a nucleotide sequence encoding a COX-1 variant. The term "coding region" refers to the region of the nucleotide sequence comprising codons which are translated into amino acid residues. In another embodiment, the antisense nucleic acid molecule is antisense to a "noncoding region" of the coding strand of a nucleotide sequence encoding a protein of the invention. The term "noncoding region" refers to 5' and 3' sequences which flank the coding region that are not translated into amino acids (i.e., also referred to as 5' and 3' untranslated regions).

Given the coding strand sequences encoding COX-3, PCOX-1a, PCOX-1b, hCOX-3(cc), hCOX-3(af), hCOX-3 (del10) and hCOX-3(cs) disclosed herein, antisense nucleic acids of the invention can be designed according to the rules of Watson and Crick base pairing. The antisense nucleic acid molecule can be complementary to the entire coding region of mRNA, but more preferably is an oligonucleotide which is antisense to only a portion of the coding or noncoding region of mRNA. For example, the antisense oligonucleotide can be complementary to the region surrounding the translation start site of mRNA. An antisense oligonucleotide can be, for example, about 5, 10, 15, 20, 25, 30, 35, 40, 45 or 50 nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomet-hyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding a protein to thereby inhibit expression of the protein, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. An example of a route of administration of antisense nucleic acid molecules of the invention include direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

In still another embodiment, an antisense nucleic acid of the invention is a ribozyme. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haselhoff and Gerlach (1988) Nature 334:585-591)) can be used to catalytically cleave COX-1 variant mRNA transcripts to thereby inhibit translation of mRNA. A ribozyme having specificity for an encoding nucleic acid can be designed based upon the nucleotide sequence of a COX-1 variant cDNA disclosed herein (i.e., SEQ ID NO:1, SEQ ID NO:3, SEQ ID NO:4, SEQ ID NO:6, SEQ ID NO:10, SEQ ID NO:11, SEQ ID NO:12 or SEQ ID NO:13). For example, a derivative of a Tetrahymena L-19 IVS RNA can be constructed in which the nucleotide sequence of the active site is complementary to the nucleotide sequence to be cleaved in a encoding mRNA. See, e.g., Cech et al. U.S. Pat. No. 4,987,071; and Cech et al. U.S. Pat. No. 5,116,742. Alternatively, mRNA can be used to select a catalytic RNA having a specific ribonuclease activity from a pool of RNA molecules. See, e.g., Bartel, D. and Szostak, J. W. (1993) Science 261:1411-1418.

Alternatively, COX-1 variant gene expression can be inhibited by targeting nucleotide sequences complementary to the regulatory region of the (e.g., the promoter and/or enhancers) to form triple helical structures that prevent transcription of the gene in target cells. See generally, Helene, C. (1991) Anticancer Drug Des. 6(6):569-84; Helene, C. et al. (1992) Ann. N.Y. Acad. Sci. 660:27-36; and Maher, L. J. (1992) Bioassays 14(12):807-15.

In yet another embodiment, the nucleic acid molecules of the present invention can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acids (see Hyrup B. et al. (1996) Bioorganic & Medicinal Chemistry 4 (1): 5-23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup B. et al. (1996) supra; Perry-O'Keefe et al. Proc. Natl. Acad. Sci. 93: 14670-675.

PNAs of nucleic acid molecules disclosed herein can be used in therapeutic and diagnostic applications. For example, PNAs can be used as antisense or antigene agents for sequence-specific modulation of gene expression by, for example, inducing transcription or translation arrest or inhibiting replication. PNAs of the present nucleic acid molecules can also be used in the analysis of single base pair mutations in a gene, (e.g., by PNA-directed PCR clamping); as 'artificial restriction enzymes' when used in combination with other enzymes, (e.g., S1 nucleases (Hyrup B. (1996) supra)); or as probes or primers for DNA sequencing or hybridization (Hyrup B. et al. (1996) supra; Perry-O'Keefe supra).

In another embodiment, PNAs of a COX-1 variant can be modified, (e.g., to enhance their stability or cellular uptake), by attaching lipophilic or other helper groups to PNA, by the formation of PNA-DNA chimeras, or by the use of liposomes or other techniques of drug delivery known in the art. For example, PNA-DNA chimeras of COX-1 variant nucleic acid molecules can be generated which may combine the advantageous properties of PNA and DNA. Such chimeras allow DNA recognition enzymes, (e.g., RNAse H and DNA polymerases), to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup B. (1996) supra). The synthesis of PNA-DNA chimeras can be performed as described in Hyrup B. (1996) supra and Finn P. J. et al. (1996) Nucleic Acids Res. 24 (17): 3357-63. For example, a DNA chain can be synthesized on a solid support using standard phosphoramidite coupling chemistry and modified nucleoside analogs, e.g., 5'-(4-methoxytrityl) amino-5'-deoxy-thymidine phosphoramidite, can be used as a between the PNA and the 5' end of DNA (Mag, M. et al. (1989) Nucleic Acid Res. 17: 5973-88). PNA monomers are then coupled in a stepwise manner to produce a chimeric molecule with a 5' PNA segment and a 3' DNA segment (Finn P. J. et al. (1996) supra). Alternatively, chimeric molecules can be synthesized with a 5' DNA segment and a 3' PNA segment (Peterser, K. H. et al. (1975) Bioorganic Med. Chem. Lett. 5: 1119-11124).

In other embodiments, the oligonucleotide may include other appended groups such as peptides (e.g., for targeting host cell receptors in vivo), or agents facilitating transport across the cell membrane (see, e.g., Letsinger et al. (1989) Proc. Natl. Acad. Sci. US. 86:6553-6556; Lemaitre et al. (1987) Proc. Natl. Acad. Sci. USA 84:648-652; PCT Publication No. WO88/09810) or the blood-brain barrier (see, e.g., PCT Publication No. WO89/10134). In addition, oligonucleotides can be modified with hybridization-triggered cleavage agents (See, e.g., Krol et al. (1988) Bio-Techniques 6:958-976) or intercalating agents. (See, e.g., Zon (1988) Pharm. Res. 5:539-549). To this end, the oligonucleotide may be conjugated to another molecule, (e.g., a peptide, hybridization triggered cross-linking agent, transport agent, or hybridization-triggered cleavage agent).

Another aspect of the invention pertains to isolated COX-1 variant proteins, and biologically active portions thereof, as well as polypeptide fragments suitable for use as immunogens to raise anti-COX-1 variant antibodies. In one embodiment, native pCox-1 and COX-3, PCOX-1a, PCOX-1b, hCOX-3(cc), hCOX-3(af), hCOX-3 (del10) and hCOX-3(cs) proteins can be isolated from cells or tissue sources by an appropriate purification scheme using standard protein purification techniques. In another embodiment, COX-3, PCOX-1a, PCOX-1b, hCOX-3(cc), hCOX-3(af), hCOX-3 (del10) and hCOX-3(cs) proteins are produced by recombinant DNA techniques. Alternative to recombinant expression, a COX-3, PCOX-1a, PCOX-1b, hCOX-3(cc), hCOX-3(af), hCOX-3 (del10) and hCOX-3(cs) protein or polypeptide can be synthesized chemically using standard peptide synthesis techniques.

An "isolated" or "purified" protein or biologically active portion thereof is substantially free of cellular material or other contaminating proteins from the cell or tissue source from which the COX-1 variant protein is derived, or substantially free from chemical precursors or other chemicals when chemically synthesized. The language "substantially free of cellular material" includes preparations of a COX-1 variant protein in which the protein is separated from cellular components of the cells from which it is isolated or recombinantly produced. In one embodiment, the language "substantially free of cellular material" includes preparations of a COX-1 variant protein having less than about 30% (by dry weight) of non-protein (also referred to herein as a "contaminating protein"), more preferably less than about 20% of non-protein, still more preferably less than about 10% of non-protein, and most preferably less than about 5% non-protein. When the COX-1 variant protein or biologically active portion thereof is recombinantly produced, it is also preferably substantially free of culture medium, i.e., culture medium represents less than about 20%, more preferably less than about 10%, and most preferably less than about 5% of the volume of the protein preparation.

The language "substantially free of chemical precursors or other chemicals" includes preparations of a protein of the invention in which the protein is separated from chemical precursors or other chemicals that are involved in the synthesis of the protein. In one embodiment, the language "substantially free of chemical precursors or other chemicals" includes preparations of a COX-1 variant protein such as a COX-3, PCOX-1a, PCOX-1b, hCOX-3(cc), hCOX-3(af), hCOX-3 (del10) or hCOX-3(cs) protein having less than about 30% (by dry weight) of chemical precursors or non-chemicals, more preferably less than about 20% chemical precursors or non-chemicals, still more preferably less than about 10% chemical precursors or non-chemicals, and most preferably less than about 5% chemical precursors or non-chemicals.

Biologically active portions of a COX-1 variant protein include peptides comprising amino acid sequences sufficiently homologous to or derived from the amino acid sequence of the COX-1 variant protein, e.g., the amino acid sequence shown in COX-1 variant, which include less amino acids than the full length proteins, and exhibit at least one activity of a protein. Typically, biologically active portions comprise a domain or motif with at least one activity of the COX-1 variant protein. A biologically active portion of a protein can be a polypeptide which is, for example, at least 10, 25, 50, 100 or more amino acids in length.

In a preferred embodiment, the COX-1 variant protein has an amino acid sequence shown in SEQ ID NO:2, SEQ ID NO:5, SEQ ID NO:14, SEQ ID NO15 or SEQ ID NO:16. In other embodiments, the COX-1 variant protein is substantially homologous to SEQ ID NO:2, SEQ ID NO:5, SEQ ID NO:14, SEQ ID NO15 or SEQ ID NO:16, and retains the functional activity of the protein of SEQ ID NO:2, SEQ ID NO:5, SEQ ID NO:14, SEQ ID NO15 or SEQ ID NO:16, yet differs in amino acid sequence due to natural allelic variation or mutagenesis, as described in detail in subsection I above. Accordingly, in another embodiment, the COX-1 variant protein is a protein which comprises an amino acid sequence at least about 50%, 55%, 59%, 60%, 65%, 70%, 75%, 80%, 85%, 90%, 95%, 98% or more homologous to the amino acid sequence of SEQ ID NO:2 or SEQ ID NO:5 (e.g., the entire amino acid sequence of SEQ ID NO:2, SEQ ID NO:5, SEQ ID NO:14, SEQ ID NO15 or SEQ ID NO:16).

To determine the percent identity of two amino acid sequences or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, or 90% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the GAP program in the GCG software package, using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package, using a NWSgapdna.CMP matrix and a gap weight of 40, 50, 60, 70, or 80 and a length weight of 1, 2, 3, 4, 5, or 6.

The nucleic acid and protein sequences of the present invention can further be used as a "query sequence" to perform a search against public databases to, for example, identify other family members or related sequences. Such searches can be performed using the NBLAST and XBLAST programs (version 2.0) of Altschul, et al. (1990) J. Mol. Biol. 215:403-10. BLAST nucleotide searches can be performed with the NBLAST program, score=100, wordlength=12 to obtain nucleotide sequences homologous to nucleic acid molecules of the invention. BLAST protein searches can be performed with the XBLAST program, score=50, wordlength=3 to obtain amino acid sequences homologous to protein molecules of the invention. To obtain gapped alignments for comparison purposes, Gapped BLAST can be utilized as described in Altschul et al., (1997) Nucleic Acids Res. 25(17): 3389-3402. When utilizing BLAST and Gapped BLAST programs, the default parameters of the respective programs (e.g., XBLAST and NBLAST) can be used.

The invention also provides COX-1 variant chimeric or fusion proteins. As used herein, a "chimeric protein" or "fusion protein" comprises a COX-1 variant polypeptide operatively linked to a non-COX-1 variant polypeptide. An "COX-1 variant polypeptide" refers to a polypeptide having an amino acid sequence corresponding to a COX-1 variant, including COX-3, PCOX-1a, PCOX-1b, hCOX-3(cc), hCOX-3(af), hCOX-3 (del10) or hCOX-3(cs), whereas a "non-COX-1 variant polypeptide" refers to a polypeptide having an amino acid sequence corresponding to a protein which is not substantially homologous to a protein of the invention, e.g., a protein which is different from a COX-3, PCOX-1a, PCOX-1b, hCOX-3 (cc), hCOX-3(af), hCOX-3 (del10) or hCOX-3(cs) protein and which is derived from the same or a different organism. Within a COX-1 variant fusion protein the COX-1 variant polypeptide can correspond to all or a portion of a protein. In a preferred embodiment, a COX-1 variant fusion protein comprises at least one biologically active portion of a COX-1 variant protein. In another preferred embodiment, a COX-1 variant fusion protein comprises at least two biologically active portions of a COX-1 variant protein. Within the fusion protein, the term "operatively linked" is intended to indicate that the COX-1 variant polypeptide and the non-polypeptide are fused in-frame to each other. The non-polypeptide can be fused to the N-terminus or C-terminus of the COX-1 variant polypeptide.

For example, in one embodiment, the fusion protein is a GST-fusion protein in which the sequences are fused to the C-terminus of the GST sequences. Such fusion proteins can facilitate the purification of recombinant COX-1 variants.

In another embodiment, the fusion protein is a COX-1 variant protein containing a heterologous signal sequence at its N-terminus. In certain host cells (e.g., mammalian host cells), expression and/or secretion of a COX-1 variant can be increased through use of a heterologous signal sequence.

The fusion proteins of the invention can be incorporated into pharmaceutical compositions and administered to a subject in vivo. The fusion proteins can be used to affect the bioavailability of a COX-1 variant substrate. Use of COX-1 variant fusion proteins may be useful therapeutically for the treatment of cellular growth related disorders or disorders associated with neurodegenerative diseases. Moreover, the COX-1 variant-fusion proteins of the invention can be used as immunogens to produce anti-COX-1 variant antibodies in a subject, to purify ligands and in screening assays to identify molecules which inhibit the interaction of the enzyme with a substrate.

Preferably, a chimeric or fusion protein of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, Current Protocols in Molecular Biology, eds. Ausubel et al. John Wiley & Sons: 1992). Moreover, many expression vectors are commercially available that already encode a fusion moiety (e.g., a GST polypeptide). An encoding nucleic acid can be cloned into such an expression vector such that the fusion moiety is linked in-frame to the protein.

The present invention also pertains to variants of the COX-1 variant proteins which function as either COX-1 variant agonists (mimetics) or as COX-1 variant antagonists. Variants of the COX-1 variant proteins can be generated by mutagenesis, e.g., discrete point mutation or truncation of a COX-1 variant protein. An agonist of the proteins can retain substantially the same, or a subset, of the biological activities of the naturally occurring form of a protein. An antagonist of a protein of the invention can inhibit one or more of the activities of the naturally occurring form of a protein of the invention by, for example, competitively modulating a cardiovascular system activity of a protein. Thus, specific biological effects can be elicited by treatment with a variant of limited function. In one embodiment, treatment of a subject with a variant having a subset of the biological activities of the naturally occurring form of the protein has fewer side effects in a subject relative to treatment with the naturally occurring form of the protein.

A polypeptide "mutein" refers to a polypeptide whose sequence contains substitutions, insertions or deletions of one or more amino acids compared to the amino acid sequence of the native or wild type protein. A mutein has at least 50% sequence homology to the wild type protein, preferred is 60% sequence homology, more preferred is 70% sequence homology. Most preferred are muteins having 80%, 90% or 95% sequence homology to the wild type protein, in which sequence homology is measured by any common sequence analysis algorithm, such as Gap or Bestfit.

A "derivative" refers to polypeptides or fragments thereof that are substantially homologous in primary structural sequence but which include, e.g., in vivo or in vitro chemical and biochemical modifications or which incorporate unusual amino acids. Such modifications include but are not limited to, for example, acetylation, carboxylation, phosphorylation, glycosylation, ubiquitination, labeling, e.g., with radionuclides, and various enzymatic modifications, or conservative substitutions, as will be readily appreciated by those well skilled in the art. A variety of methods for labeling polypeptides and of substituents or labels useful for such purposes are well known in the art, and include radioactive isotopes such as $^{125}$I, $^{32}$P, $^{35}$S, and $^3$H, ligands which bind to labeled antiligands (e.g., antibodies), fluorophores, chemiluminescent agents, enzymes, and antiligands which can serve as specific binding pair members for a labeled ligand. The choice of label depends on the sensitivity required, ease of conjugation with the primer, stability requirements, and available instrumentation. Methods for labeling polypeptides are well known in the art. See Ausubel et al., 1992.

In one embodiment, a modified COX-1 variant protein which function as either a COX-1 variant agonists (mimetics) or as COX-1 variant antagonists can be identified by screening combinatorial libraries of mutants, e.g., truncation mutants, of a COX-1 variant protein (e.g., COX-3, PCOX-1a, PCOX-1b, hCOX-3(cc), hCOX-3(af), hCOX-3 (del10) or hCOX-3(cs)) agonist or antagonist activity. In one embodiment, a variegated library of modified COX-1 variants is generated by combinatorial mutagenesis at the nucleic acid level and is encoded by a variegated gene library. A variegated library of modified COX-1 variants can be produced by, for example, enzymatically ligating a mixture of synthetic oligonucleotides into gene sequences such that a degenerate set of potential COX-1 variant sequences is expressible as individual polypeptides, or alternatively, as a set of larger fusion proteins (e.g., for phage display) containing the set of COX-1 variant sequences therein. There are a variety of methods which can be used to produce libraries of potential modified COX-1 variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential sequences. Methods for synthesizing degenerate oligonucleotides are known in the art (see, e.g., Narang, S. A. (1983) Tetrahedron 39:3; Itakura et al. (1984) Annu. Rev. Biochem. 53:323; Itakura et al. (1984) Science 198:1056; Ike et al. (1983) Nucleic Acid Res. 11:477.

In addition, libraries of fragments of a COX-1 variants protein coding sequence can be used to generate a variegated population of COX-1 variants fragments for screening and subsequent selection of modified COX-1 variant protein. In one embodiment, a library of coding sequence fragments can be generated by treating a double stranded PCR fragment of a COX-1 variant coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal and internal fragments of various sizes of the protein.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of COX-1 variant proteins. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a new technique which enhances the frequency of functional mutants in the libraries, can be used in combination with the screening assays to identify modified COX-1 variants (Arkin and Yourvan (1992) Proc. Natl. Acad. Sci. USA 89:7811-7815; Deigrave et al. (1993) Protein Engineering 6(3):327-331).

An isolated COX-1 variant protein, or a portion or fragment thereof, can be used as an immunogen to generate antibodies that bind a COX-1 variant disclosed herein using standard techniques for polyclonal and monoclonal antibody preparation. A full-length protein can be used or, alternatively, the invention provides antigenic peptide fragments of, for example, COX-3, PCOX-1a, PCOX-1b, hCOX-3(cc), hCOX-3(af), hCOX-3 (del10) or hCOX-3(cs) for use as immunogens. The antigenic peptide of a COX-1 variant comprises at least 8 amino acid residues of the amino acid sequence shown in SEQ ID NO:2, SEQ ID NO:5, SEQ ID NO:8, SEQ ID NO:14, SEQ ID NO15 or SEQ ID NO:16, and encompasses an epitope of such that an antibody raised against the peptide forms a specific immune complex with. Preferably, the antigenic peptide comprises at least 10 amino acid residues, more preferably at least 15 amino acid residues, even more preferably at least 20 amino acid residues, and most preferably at least 30 amino acid residues.

Preferred epitopes encompassed by the antigenic peptide are regions of a COX-1 variant that are located on the surface of the protein, e.g., hydrophilic regions.

A COX-1 variant immunogen typically is used to prepare antibodies by immunizing a suitable subject, (e.g., rabbit, goat, mouse or other mammal) with the immunogen. An appropriate immunogenic preparation can contain, for example, recombinantly expressed protein or a chemically synthesized COX-1 variant polypeptide. The preparation can further include an adjuvant, such as Freund's complete or incomplete adjuvant, or similar immunostimulatory agent. Immunization of a suitable subject with an immunogenic COX-1 variant preparation induces a polyclonal anti-antibody response.

Accordingly, another aspect of the invention pertains to anti-antibodies. The term "antibody" as used herein refers to immunoglobulin molecules and immunologically active portions of immunoglobulin molecules, i.e., molecules that contain an antigen binding site which specifically binds (immunoreacts with) an antigen, such as a COX-1 variant. Examples of immunologically active portions of immunoglobulin molecules include F(ab) and F(ab')2 fragments which can be generated by treating the antibody with an enzyme such as pepsin. The invention provides polyclonal and monoclonal antibodies that bind a COX-1 variant. The term "monoclonal antibody" or "monoclonal antibody composition", as used herein, refers to a population of antibody molecules that contain only one species of an antigen binding site capable of immunoreacting with a particular epitope of a COX-1 variant. A monoclonal antibody composition thus typically displays a single binding affinity for a particular COX-1 variant protein with which it immunoreacts.

Polyclonal anti-antibodies can be prepared as described above by immunizing a suitable subject with a COX-1 variant immunogen. The anti-antibody titer in the immunized subject can be monitored over time by standard techniques, such as with an enzyme linked immunosorbent assay (ELISA) using immobilized COX-1 variant. If desired, the antibody molecules directed against a COX-1 variant can be isolated from the mammal (e.g., from the blood) and further purified by well-known techniques, such as protein A chromatography to obtain the IgG fraction. At an appropriate time after immunization, e.g., when the anti-antibody titers are highest, antibody-producing cells can be obtained from the subject and used to prepare monoclonal antibodies by standard techniques, such as the hybridoma technique originally described by Kohler and Milstein (1975) Nature 256:495-497) (see also, Brown et al. (1981) J. Immunol. 127:539-46; Brown et al. (1980) J. Biol. Chem. 255:4980-83; Yeh et al. (1976) Proc. Natl. Acad. Sci. USA 76:2927-31; and Yeh et al. (1982) Int. J. Cancer 29:269-75), the more recent human B cell hybridoma technique (Kozbor et al. (1983) Immunol Today 4:72), the EBV-hybridoma technique (Cole et al. (1985), Monoclonal Antibodies and Cancer Therapy, Alan R. Liss, Inc., pp. 77-96) or trioma techniques. The technology for producing monoclonal antibody hybridomas is well known (see generally R. H. Kenneth, in Monoclonal Antibodies: A New Dimension In Biological Analyses, Plenum Publishing Corp., New York, N.Y. (1980); E. A. Lerner (1981) Yale J. Biol. Med., 54:387-402; M. L. Gefter et al. (1977) Somatic Cell Genet. 3:231-36). Briefly, an immortal cell line (typically a myeloma) is fused to lymphocytes (typically splenocytes) from a mammal immunized with a immunogen as described above, and the culture supernatants of the resulting hybridoma cells are screened to identify a hybridoma producing a monoclonal antibody that binds.

Any of the many well known protocols used for fusing lymphocytes and immortalized cell lines can be applied for the purpose of generating an anti-monoclonal antibody (see, e.g., G. Galfre et al. (1977) Nature 266:55052; Gefter et al. Somatic Cell Genet., cited supra; Lerner, Yale J. Biol. Med., cited supra; Kenneth, Monoclonal Antibodies, cited supra). Moreover, the ordinarily skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, e.g., the P3-NS1/1-Ag4-1, P3-x63-Ag8.653 or Sp2/O-Ag14 myeloma lines. These myeloma lines are available from ATCC. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind, e.g., using a standard ELISA assay.

Alternative to preparing monoclonal antibody-secreting hybridomas, a monoclonal anti-antibody can be identified and isolated by screening a recombinant combinatorial immunoglobulin library (e.g., an antibody phage display library) with a COX-1 variant to thereby isolate immunoglobulin library members that bind a COX-1 variant. Kits for generating and screening phage display libraries are commercially available (e.g., the Pharmacia Recombinant Phage Antibody System, Catalog No. 27-9400-01; and the Stratagene SurfZAP™ Phage Display Kit, Catalog No. 240612). Additionally, examples of methods and reagents particularly amenable for use in generating and screening antibody display library can be found in, for example, Ladner et al. U.S. Pat. No. 5,223,409; Kang et al. PCT International Publication No. WO 92/18619; Dower et al. PCT International Publication No. WO 91/17271; Winter et al. PCT International Publication WO 92/20791; Markland et al. PCT International Publication No. WO 92/15679; Breitling et al. PCT International Publication WO 93/01288; McCafferty et al. PCT International Publication No. WO 92/01047; Garrard et al. PCT International Publication No. WO 92/09690; Ladner et al. PCT International Publication No. WO 90/02809; Fuchs et al. (1991) Bio/Technology 9:1370-1372; Hay et al. (1992) Hum. Antibod. Hybridomas 3:81-85; Huse et al. (1989) Science 246:1275-1281; Griffiths et al. (1993) EMBO J. 12:725-734; Hawkins et al. (1992) J. Mol. Biol. 226:889-896; Clarkson et al. (1991) Nature 352:624-628; Gram et al. (1992) Proc. Natl. Acad. Sci. USA 89:3576-3580; Garrad et al. (1991) Bio/Technology 9:1373-1377; Hoogenboom et al. (1991) Nuc. Acid Res. 19:4133-4137; Barbas et al. (1991) Proc. Natl. Acad. Sci. USA 88:7978-7982; and McCafferty et al. Nature (1990) 348:552-554.

Additionally, recombinant anti-COX-1 variant antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in Robinson et al. International Application No. PCT/US86/02269; Akira, et al. European Patent Application 184,187; Taniguchi, M., European Patent Application 171,496; Morrison et al. European Patent Application 173,494; Neuberger et al. PCT International Publication No. WO 86/01533; Cabilly et al. U.S. Pat. No. 4,816,567; Cabilly et al. European Patent Application 125,023; Better et al. (1988) Science 240:1041-1043; Liu et al. (1987) Proc. Natl. Acad. Sci. USA 84:3439-3443; Liu et al. (1987) J. Immunol. 139:3521-3526; Sun et al. (1987) Proc. Natl. Acad. Sci. USA 84:214-218; Nishimura et al. (1987) Canc. Res. 47:999-1005; Wood et al. (1985) Nature 314:446-449; and Shaw et al. (1988) J. Natl. Cancer Inst. 80:1553-1559); Morrison, S. L. (1985) Science 229:1202-1207; Oi et al. (1986) BioTechniques 4:214; Winter U.S. Pat. No. 5,225,539; Jones et al. (1986) Nature 321:552-525; Verhoeyan et al. (1988) Science 239:1534; and Beidler et al. (1988) J. Immunol. 141:4053-4060.

An anti-COX-1 variant antibody (e.g., monoclonal antibody) can be used to isolate additional COX-1 variants, particularly those proteins retaining intron 1 of the COX-1 gene, by standard techniques, such as affinity chromatography or immunoprecipitation. An anti-COX-1 variant antibody can facilitate the purification of natural COX-1 variant from cells and of recombinantly produced COX-1 variant expressed in host cells. Moreover, an anti-antibody can be used to detect a COX-1 variant protein (e.g., in a cellular lysate or cell supernatant) in order to evaluate the abundance and pattern of expression of the COX-1 variant protein. Anti-COX-1 variant antibodies can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

Another aspect of the invention pertains to vectors, preferably expression vectors, containing a nucleic acid encoding a COX-1 variant protein (or a portion thereof). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to includes promoters, enhancers and other expression control elements (e.g., polyadenylation signals). Such regulatory sequences are described, for example, in Goeddel; Gene Expression Technology: Methods in Enzymology 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like. The expression vectors of the invention can be introduced into host cells to thereby produce proteins or peptides, including fusion proteins or peptides, encoded by nucleic acids as described herein (e.g., COX-1 variant proteins, modified forms of COX-1 variant proteins, fusion proteins, and the like).

The recombinant expression vectors of the invention can be designed for expression of COX-1 variant proteins in prokaryotic or eukaryotic cells. For example, COX-1 variant proteins can be expressed in bacterial cells such as E. coli, insect cells (using baculovirus expression vectors) yeast cells or mammalian cells. Suitable host cells are discussed further in Goeddel, Gene Expression Technology: Methods in Enzymology 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in E. coli with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) Gene 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Purified fusion proteins can be utilized in COX-1 variant activity assays, (e.g., direct assays or competitive assays described in detail below), or to generate antibodies specific for COX-1 variant proteins, for example.

Examples of suitable inducible non-fusion E. coli expression vectors include pTrc (Amann et al., (1988) Gene 69:301-315) and pET 11d (Studier et al., Gene Expression Technology: Methods in Enzymology 185, Academic Press, San Diego, Calif. (1990) 60-89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21(DE3) or HMS174(DE3) from a resident prophage harboring a T7 gn1 gene under the transcriptional control of the lacUV 5 promoter.

One strategy to maximize recombinant protein expression in E. coli is to express the protein in a host bacteria with an impaired capacity to proteolytically cleave the recombinant protein (Gottesman, S., Gene Expression Technology: Methods in Enzymology 185, Academic Press, San Diego, Calif. (1990) 119-128). Another strategy is to alter the nucleic acid sequence of the nucleic acid to be inserted into an expression vector so that the individual codons for each amino acid are those preferentially utilized in E. coli (Wada et al., (1992) Nucleic Acids Res. 20:2111-2118). Such alteration of nucleic acid sequences of the invention can be carried out by standard DNA synthesis techniques.

In another embodiment, the COX-1 variant expression vector is a yeast expression vector. Examples of vectors for expression in yeast S. cerevisiae include pYepSec1 (Baldari, et al., (1987) Embo J. 6:229-234), pMFa (Kurjan and Herskowitz, (1982) Cell 30:933-943), pJRY88 (Schultz et al., (1987) Gene 54:113-123), pYES2 (Invitrogen Corporation, San Diego, Calif.), and picZ (InVitrogen Corp, San Diego, Calif.).

Alternatively, COX-1 variant proteins can be expressed in insect cells using baculovirus expression vectors. Baculovirus vectors available for expression of proteins in cultured insect cells (e.g., Sf 9 cells) include the pAc series (Smith et al. (1983) Mol. Cell. Biol. 3:2156-2165) and the pVL series (Lucklow and Summers (1989) Virology 170:31-39).

In yet another embodiment, a nucleic acid of the invention is expressed in mammalian cells using a mammalian expression vector. Examples of mammalian expression vectors include pCDM8 (Seed, B. (1987) Nature 329:840) and pMT2PC (Kaufman et al. (1987) EMBO J. 6:187-195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook, J., Fritsh, E. F., and Maniatis, T. Molecular Cloning: A Laboratory Manual. 2nd, ed., Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) Genes Dev. 1:268-277), lymphoid-specific promoters (Calame and Eaton (1988) Adv. Immunol. 43:235-275), in particular promoters of T cell receptors (Winoto and Baltimore (1989) EMBO J. 8:729-733) and immunoglobulins (Banerji et al. (1983) Cell 33:729-740; Queen and Baltimore (1983) Cell 33:741-748), neuron-specific promoters (e.g., the neurofilament promoter; Byrne and Ruddle (1989) Proc. Natl. Acad. Sci. USA 86:5473-5477), pancreas-specific promoters (Edlund et al. (1985) Science 230:912-916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss (1990) Science 249:374-379) and the a-fetoprotein promoter (Campes and Tilghman (1989) Genes Dev. 3:537-546).

The invention further provides a recombinant expression vector comprising a DNA molecule of the invention cloned into the expression vector in an antisense orientation. That is, the DNA molecule is operatively linked to a regulatory sequence in a manner which allows for expression (by transcription of the DNA molecule) of an RNA molecule which is antisense to COX-1 variant mRNA. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub, H. et al., "Antisense RNA as a molecular tool for genetic analysis," Reviews—Trends in Genetics, Vol. 1(1) 1986.

Another aspect of the invention pertains to host cells into which a recombinant expression vector of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a COX-1 variant protein can be expressed in bacterial cells such as E. coli, insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (Molecular Cloning: A Laboratory Manual. 2nd, ed., Cold Spring Harbor Laboratory, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker can be introduced into a host cell on the same vector as that encoding a pCox-1 or pCox-1Δ657 protein or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) a COX-1 variant protein. Accordingly, the invention further provides methods for producing a COX-1 variant protein using the host cells of the invention. In one embodiment, the method comprises culturing the host cell of invention (into which a recombinant expression vector encoding COX-1 variant protein has been introduced) in a suitable medium such that a COX-1 variant protein is produced. In another embodiment, the method further comprises isolating a COX-1 variant protein from the medium or the host cell.

The host cells of the invention can also be used to produce non-human transgenic animals. For example, in one embodiment, a host cell of the invention is a fertilized oocyte or an embryonic stem cell into which coding sequences have been introduced. Such host cells can then be used to create non-human transgenic animals in which exogenous COX-1 variant sequences have been introduced into their genome or homologous recombinant animals in which endogenous COX-1 variant sequences have been altered. Such animals are useful for studying the function and/or activity of a COX-1 variant such as COX-3, PCOX-1a, PCOX-1b, hCOX-3(cc), hCOX-3(af), hCOX-3 (del10) and hCOX-3(cs) and for identifying and/or evaluating modulators of their activity. A transgenic animal of the invention would include those animals that have been modified to express only a COX-1 variant protein (as opposed to co-expression of COX-1 and COX-1 variants). As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, and the like. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, a "homologous recombinant animal" is a non-human animal, preferably a mammal, more preferably a mouse, in which an endogenous COX-1 variant gene has been altered by homologous recombination between the endogenous gene and an exogenous DNA molecule introduced into a cell of the animal, e.g., an embryonic cell of the animal, prior to development of the animal.

The nucleic acid molecules, proteins, protein homologues, and antibodies described herein can be used in one or more of the following methods: 1) screening assays; 2) predictive medicine (e.g., diagnostic assays, prognostic assays, monitoring clinical trials, and pharmacogenetics); and 3) methods of treatment (e.g., therapeutic and prophylactic). The isolated nucleic acid molecules of the invention can be used, for example, to express COX-1 variant proteins (e.g., via a recombinant expression vector in a host cell), to detect COX-1 variant mRNA (e.g., in a biological sample), to modulate the activity of prostaglandins, and to identify compounds that modify the activity of a COX-1 variant. For example, the COX-1 variant proteins can be used to treat disorders characterized by insufficient or excessive production of a substrate or production of COX-1 variant inhibitors. In addition, the proteins of the invention can be used to screen for naturally occurring cyclooxygenase substrates, to screen for drugs or compounds which modulate the activity of a COX-1 variant, as well as to treat disorders characterized by insufficient or excessive production of a COX-1 variant protein. Moreover, the anti-COX-1 variant antibodies of the invention can be used to detect and isolate COX-1 variant proteins, regulate the bioavailability of COX-1 variant proteins, and modulate COX-1 variant activity.

The invention provides a method (also referred to herein as a "screening assay") for identifying modulators, i.e., candidate or test compounds or agents (e.g., peptides, peptidomimetics, small molecules or other drugs) which bind to COX-1 variant proteins (e.g., COX-3, PCOX-1a, PCOX-1b, hCOX-3 (cc), hCOX-3(af), hCOX-3 (del10) or hCOX-3(cs)), have a stimulatory or inhibitory effect on, for example, COX-1 variant expression or COX-1 variant activity, or have a stimulatory or inhibitory effect on, for example, the expression or activity of a COX-1 variant substrate. It is understood that the processes and methods for identifying (i.e., screening) compounds for COX-1 variant modulating activity include manufacturing any compound so identified. Accordingly, the invention contemplates a method for making a compound that modulates the activity of a COX-1 variant by providing a cell transfected with a DNA encoding a COX-1 variant, wherein the cell expresses the variant; contacting said cell, in an intact or disrupted state, with a test compound; and determining whether the activity of the COX-1 variant is decreased or increased in the presence of the test compound, wherein a decrease or increase in said Cox-3 activity is an indication that the test compound modulates the activity of Cox-3 and manufacturing the compound so identified.

In one embodiment, the invention provides assays for screening candidate or test compounds which are substrates of COX-1 variant protein or polypeptide or biologically active portion thereof. In another embodiment, the invention provides assays for screening candidate or test compounds which bind to or modulate the activity of a COX-1 variant protein or polypeptide or biologically active portion thereof, e.g., modulate the ability of COX-1 variant to interact with its cognate ligand. The test compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other four approaches are applicable to peptide, non-peptide oligomer or small molecule libraries of compounds (Lam, K. S. (1997) Anticancer Drug Des. 12:145). Combinatorial libraries are described in detail below.

In another embodiment, an assay is a cell-based assay comprising contacting a cell expressing a COX-1 variant target molecule (e.g., arachidonic acid) with a test compound and determining the ability of the test compound to modulate (e.g. stimulate or inhibit) the activity of the COX-1 variant target molecule. Determining the ability of the test compound to modulate the activity of a COX-1 variant on a target molecule can be accomplished, for example, by determining the ability of the COX-1 variant protein to bind to or interact with the compound target molecule, or by determining the ability of the COX-1 variant protein to modify the test molecule.

Determining the ability of the COX-1 variant protein to bind to or interact with a target molecule can be accomplished by determining direct binding. Determining the ability of the COX-1 variant protein to bind to or interact with a COX-1 variant target molecule can be accomplished, for example, by coupling the COX-1 variant protein with a radioisotope or enzymatic label such that binding of the COX-1 variant protein to a COX-1 variant target molecule can be determined by detecting the labeled COX-1 variant protein in a complex. For example, COX-1 variant molecules, e.g., COX-1 variant proteins, can be labeled with $^{125}I$, $^{35}S$, $^{14}C$, or $^{3}H$, either directly or indirectly, and the radioisotope detected by direct counting of radioemmission or by scintillation counting. Alternatively, COX-1 variant molecules can be enzymatically labeled with, for example, horseradish peroxidase, alkaline phosphatase, or luciferase, and the enzymatic label detected by determination of conversion of an appropriate substrate to product.

It is also within the scope of this invention to determine the ability of a compound to modulate the interaction between COX-1 variant and its target molecule, without the labeling of any of the interactants. For example, a microphysiometer can be used to detect the interaction of COX-1 variant with its target molecule without the labeling of a COX-1 variant or the target molecule. McConnell, H. M. et al. (1992) Science 257:1906-1912. As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between compound and receptor.

In a preferred embodiment, determining the ability of the COX-1 variant protein to bind to or interact with a COX-1 variant target molecule can be accomplished by determining the activity of the target molecule. For example, the activity of the target molecule can be determined by detecting induction of a cellular second messenger of the target (e.g., intracellular $Ca^{2+}$, diacylglycerol, IP3, etc.), detecting catalytic/enzymatic activity of the target an appropriate substrate, detecting the induction of a reporter gene (comprising a target-responsive regulatory element operatively linked to a nucleic acid encoding a detectable marker, e.g., chloramphenicol acetyl transferase), or detecting a target-regulated cellular response.

One example of a simple in vitro system for the screening of compounds that modulate the activity of a COX-1 variant protein includes assays performed on living cells or on microsomal extracts prepared from the cultured cells. The COX-1 variant-synthesizing cell lines disclosed herein are useful for evaluating the activity of a compound on the activity of a COX-1 variant in comparison to the activity of the same compound on, for example, COX-1 or COX-2.

Thus, the present invention also provides a method to evaluate the relative inhibitory activity of a compound to selectively inhibit a COX-1 variant versus COX-1 or COX-2 activity, and thus to specifically inhibit the COX-1 variant activities associated with, for example, inflamed mammalian tissues, preferably human tissues, or in other physiological or pathological conditions in a mammalian host, preferably a human host. Such an assay can comprise contacting a COX-1 variant-expressing cell line or a microsomal extract thereof with a preselected amount of the compound in a suitable culture medium or buffer, adding a substrate (e.g., arachidonic acid) to the mixture, and measuring the level of synthesis of a COX-1 variant-mediated arachidonic acid metabolite, or the synthesis of any other metabolite unique to the cyclooxygenase pathway, by the cell line, or microsomal extract, as compared to a control cell line or portion of microsomal extract in the absence of said compound. The compound can be evaluated for its ability to selectively inhibit COX-1 variants or COX-1 or COX-2 by performing a second assay, in parallel, employing the above-described steps, with a COX-1 and/or COX-2 expressing cell line.

In yet another embodiment, an assay of the present invention is a cell-free assay in which a COX-1 variant protein or biologically active portion thereof is contacted with a test compound and the ability of the test compound to bind to the COX-1 variant protein or biologically active portion thereof is determined. Binding of the test compound to the COX-1 variant protein can be determined either directly or indirectly as described above. In a preferred embodiment, the assay includes contacting the COX-1 variant protein or biologically active portion thereof with a known compound which binds COX-1 variant to form an assay mixture, contacting the assay mixture with a test compound, and determining the ability of the test compound to interact with a COX-1 variant protein, wherein determining the ability of the test compound to interact with a COX-1 variant protein comprises determining the ability of the test compound to preferentially bind to or biologically active portion thereof as compared to the known compound.

For example, the present studies have identified COX-1 variants that are inhibited by compounds that have little or no inhibitory activity against COX-1 or COX-2, including analgesic/antipyretic compounds such as acetaminophen, phenacetin, antipyrine and dipyrone (see Table 1, and FIG. 13). The screening methods described herein provide the means by which derivatives of such compounds can be identified for their selective inhibition of COX-1 variant activity. Such compounds are useful for treating a COX-1 variant-associated disorder in a subject. For example, acetaminophen is often categorized as a nonsteroidal antiinflammatory drug (NSAID) despite the fact that in clinical practice and in animal models it possesses little anti-inflammatory activity. Like NSAIDs, however, acetaminophen inhibits pain and fever. It has been shown that acetaminophen generally inhibits COX activity in dog brain homogenates more than in homogenates from spleen (Flower and Vane, (1972) Nature 240:410-411). However, as previous and current studies indicate, neither COX-1 nor COX-2 is inhibited by acetaminophen at physiological concentrations of the drug in whole cells or homogenates (Botting (2000) Clin. Infect. Dis. 31:8202-8210.) suggesting that neither isozyme is a good candidate for the site of action of acetaminophen. The present study indicates that COX-1 variants are clearly enriched in dog brain and the human 5.2 kb transcript is highest in brain cortex. Further, epidemiologic evidence indicates that NSAID use is associated with a lower incidence or risk of Alzheimer's Disease (AD). An inverse relationship is seen between NSAID use (particularly aspirin), and AD incidence in case-controlled studies of patients who have osteoarthritis, rheumatoid arthritis, or who use NSAIDs for other purposes. A similar inverse correlation was seen in a co-twin control study of 50 elderly twins with AD onset separated by 3 years or more. Both decreased risk of AD among NSAID users as well as an decreased risk of AD with increased duration of NSAID use was found in the prospective Baltimore Longitudinal Study of Aging and a decrease in cognitive decline was associated with NSAID use in the 1-year Rotterdam Study.

In another embodiment, the assay is a cell-free assay in which a COX-1 variant protein or biologically active portion thereof is contacted with a test compound and the ability of the test compound to modulate (e.g., stimulate or inhibit) the activity of the COX-1 variant protein or biologically active portion thereof is determined. Determining the ability of the test compound to modulate the activity of a COX-1 variant protein can be accomplished, for example, by determining the ability of the COX-1 variant protein to bind to a COX-1 variant target molecule by one of the methods described above for determining direct binding. Determining the ability of the COX-1 variant protein to bind to a COX-1 variant target molecule can also be accomplished using a technology such as real-time Biomolecular Interaction Analysis (BIA). Sjolander, S. and Urbaniczky, C. (1991) Anal. Chem. 63:2338-2345 and Szabo et al. (1995) Curr. Opin. Struct. Biol. 5:699-705. As used herein, "BIA" is a technology for studying biospecific interactions in real time, without labeling any of the interactants (e.g., BIAcore). Changes in the optical phenomenon of surface plasmon resonance (SPR) can be used as an indication of real-time reactions between biological molecules.

In yet another embodiment, the cell-free assay involves contacting a COX-1 variant protein or biologically active portion thereof with a known compound which binds the COX-1 variant protein to form an assay mixture, contacting the assay mixture with a test compound, and determining the ability of the test compound to interact with the COX-1 variant protein, wherein determining the ability of the test compound to interact with the COX-1 variant protein comprises determining the ability of the protein to preferentially bind to or modulate the activity of a target molecule.

In more than one embodiment of the above assay methods of the present invention, it may be desirable to immobilize either COX-1 variant or its target molecule to facilitate separation of complexed from uncomplexed forms of one or both of the proteins, as well as to accommodate automation of the assay. Binding of a test compound to a COX-1 variant protein, or interaction of a COX-1 variant protein with a target molecule in the presence and absence of a candidate compound, can be accomplished in any vessel suitable for containing the reactants. Examples of such vessels include microtitre plates, test tubes, and micro-centrifuge tubes. In one embodiment, a fusion protein can be provided which adds a domain that allows one or both of the proteins to be bound to a matrix. For example, glutathione-S-transferase/COX-1 variant fusion proteins or glutathione-S-transferase/target fusion proteins can be adsorbed onto glutathione sepharose beads (Sigma Chemical, St. Louis, Mo.) or glutathione derivatized microtitre plates, which are then combined with the test compound or the test compound and either the non-adsorbed target protein or COX-1 variant protein, and the mixture incubated under conditions conducive to complex formation (e.g., at physiological conditions for salt and pH). Following incubation, the beads or microtitre plate wells are washed to remove any unbound components, the matrix immobilized in the case of beads, complex determined either directly or indirectly, for example, as described above. Alternatively, the complexes can be dissociated from the matrix, and the level of COX-1 variant binding or activity determined using standard techniques.

In another embodiment, modulators of COX-1 variant expression are identified in a method wherein a cell is contacted with a candidate compound and the expression of COX-1 variant mRNA or protein in the cell is determined. The level of expression of COX-1 variant mRNA or protein in the presence of the candidate compound is compared to the level of expression of COX-1 variant mRNA or protein in the absence of the candidate compound. The candidate compound can then be identified as a modulator of COX-1 variant expression based on this comparison. For example, when expression of COX-1 variant mRNA or protein is greater (statistically significantly greater) in the presence of the candidate compound than in its absence, the candidate compound is identified as a stimulator of COX-1 variant mRNA or protein expression. Alternatively, when expression of COX-1 variant mRNA or protein is less (statistically significantly less) in the presence of the candidate compound than in its absence, the candidate compound is identified as an inhibitor of COX-1 variant mRNA or protein expression. The level of COX-1 variant mRNA or protein expression in the cells can be determined by methods described herein for detecting COX-1 variant mRNA or protein.

In another embodiment, the nucleic acid and polypeptide sequences disclosed herein provide a method for making structure-based predictions about the behavior of a COX-1 variant enzyme in the presence or absence of a test compound. Such in silico methods are based on mathematical algorithms that manipulate various types of structural information based in part on the primary amino acid structure of a polypeptide. Additional information generated from homologous or partially homologous proteins can be integrated into the method in order to augment the amino acid structure information. Thus, the polypeptide sequence information disclosed herein for novel COX-1 variant proteins can be used, in conjunction with structural information available from COX-1 and COX-2 studies, to predict which compounds, or family of compounds, will specifically interact with a COX-1 variant protein. The entire process can be accomplished in silico by algorithms known to those skilled in the art.

For example, substantial information regarding COX structural motifs and their effect on functional activity is available. COX-1 and COX-2 dimers are held together via molecular interactions involving the dimerization domains of each monomer. Heterodimerization of COX-1 and COX-2 subunits does not occur. The dimerization domain is encoded by approximately 50 amino acids near the amino terminus of the proteolytically processed protein. Three disulfide bonds hold this domain together in a structure reminiscent of epidermal growth factor (EGF). A fourth disulfide bond links the dimerization domain with the globular catalytic domain. The presence of disulfide bonds, which require an oxidizing environment to form, is consistent with the concept that COX-1 and COX-2 are located inside the lumen of the nuclear envelope, ER, or golgi, which have redox states that are significantly less reduced than cytosol.

COX isozymes associate with the intralumenal surface of microsomal membranes in an unusual fashion. Rather than employing transmembrane spanning sequences or covalently-bound lipids for attachment, COX isozymes contain a tandem series of four amphipathic helices which creates a hydrophobic surface that penetrates into the lumenal-side of the hydrophobic core of the lipid bilayer. These helices are encoded by approximately 50 amino acids found immediately carboxyterminal to the bulk of the dimerization domain. The helices allow COX dimers to attach to the inside surface of the lumen of the ER/nuclear envelope, with the majority of the protein protruding into the lumenal space of these compartments. The membrane binding domain also forms the mouth of a narrow, hydrophobic channel that is the cyclooxygenase active site.

Carboxy-terminal to the membrane binding domain in COX primary structures is the catalytic domain, which comprises 80% (approximately 480 amino acids) of the protein and contains two distinct enzymatic active sites. The first is a peroxidase (POX) active site. The entire catalytic domain of COX isozymes is globular with 2 distinct intertwining lobes. The interface of these lobes creates a shallow cleft on the upper surface of the enzyme (i.e. the surface furthest from the membrane) where the peroxidase active site is located and where heme is bound. Coordination of the heme is via an iron-histidine bond involving His 388 in sheep COX-1. Other important interactions between the protoporphyrin also occur and specific amino acids which may function in coordinating PGG2 have been identified. The geometry of heme binding leaves a large portion of one side of the heme exposed in the open cleft of the peroxidase active site for interaction with PGG2 and other lipid peroxides.

The second distinct enzymatic active site in the catalytic domain is a cyclooxygenase (COX) active site. The cyclooxygenase active site is a long, narrow, dead-end channel of largely hydrophobic character whose entrance is framed by the four amphipathic helices of the membrane binding domain. The channel extends approximately 25 angstroms into the globular catalytic domain and is on average about 8 angstroms wide. However, significant narrowing of the channel is observed where arginine 120, one of only two ionic residues found in the COX active site, protrudes into the channel and forms a hydrogen bonded network with glutamate 524 (the other ionic residue in the channel) and tyrosine 355. Arginine 120 is essential for substrate binding in COX-1 but appears to be significantly less important in COX-2. Arginine 120 is also clearly important in the binding of carboxylate-containing NSAIDs in the COX-1 active site but as with AA binding, it is significantly less important in coordinating these NSAIDs in COX-2.

The upper portion of the channel, or catalytic pocket, contains tyrosine 385 that forms a tyrosyl radical, abstracts hydrogen from the pro-S side of carbon 13 of AA, and creates an activated fatty acid radical that undergoes the cyclization and/or oxygenation reaction (see FIG. 3). Also in the hydrophobic pocket is Ser 530, which is transacetylated by aspirin. The hydroxyl of serine 530 itself is not essential for catalysis. However, its acetylation prevents abstraction of hydrogen from AA in COX-1 by sterically preventing AA from binding productively in the active site. In contrast, abstraction of hydrogen does occur in acetylated COX-2, but cyclization of the fatty acid radical and formation of the endoperoxide does not occur, yielding 15-R-hydroxyeicosotetraenoic acid (15R-HETE) rather than COX-2.

A structural difference between the active sites of COX-1 and COX-2 is a substitution of isoleucine 523 in COX-1 for a valine in COX-2. This single difference opens a hydrophobic outpocketing in COX-2 that can be accessed by some COX-2 selective drugs. There are other changes in residues that are near but do not line the COX active site, so-called second shell residues, that result in subtle changes and a slightly enlarged COX-2 active site relative to COX-1.

As previously noted, NSAIDs are analgesic/antiinflammatory/antipyretic medications that act as inhibitors of the cyclooxygenase active site of COX isozymes. Important mechanistic differences in the actions of individual NSAIDs with the COX active site exist. Of the NSAIDs in medical use, only aspirin is a covalent modifier of COX-1 and COX-2. The crystallographic studies of Garavito and colleagues demonstrated why this drug so efficiently acetylates serine 530 of COX-1 (Loll, 1995, cite). Like other NSAIDs, aspirin diffuses into the COX active site of enzyme through the mouth of the channel and traverses up the channel to the constriction point formed by Arg 120, Tyr 355, and Glu 524. At this point in the channel, the carboxyl of aspirin forms a weak ionic bond with the side-chain of Arg 120. This positions aspirin only 5 angstroms below Ser 530 and in the correct orientation for transacetylation. Because the catalytic pocket of the channel is somewhat larger in COX-2 than in COX-1, orientation of aspirin for attack on Ser 530 is not as good in COX-2 and transacetylation efficiency is reduced. This accounts for the 10-100-fold lowered sensitivity to aspirin of COX-2 in comparison to COX-1.

Other NSAIDs in addition to aspirin inhibit COX-1 and COX-2 by competing with AA for binding in the COX active site. However, NSAIDs significantly differ from each other in whether they bind the COX active site in a time-dependent or independent fashion. For example, NSAIDs differ dramatically with regard to how quickly they productively bind in the COX active site and how quickly they come out of the COX channel. Some NSAIDs, such as ibuprofen, have very rapid on and off rates. They inhibit COX activity essentially instantaneously after addition of the NSAID and they readily wash out of the COX active site when the NSAID is removed from the environment of the enzyme. In contrast, many NSAIDs such as indomethacin and diclofenac are time-dependent. They require typically seconds to minutes to bind the COX active site. Once bound, however, these drugs typically have low off-rates that may require many hours for the NSAID to wash out of the active site. Time-dependent NSAIDs compete very poorly with AA in instantaneous assays of COX activity. Co-crystallization studies have been performed for flurbiprofen and COX-1 and COX-2 as well as indomethacin and COX-1 which define the precise binding interactions of carboxyl-containing NSAIDs in the COX binding site.

NS398 is a particularly important COX-2 inhibitor which is commercially available and, therefore, is widely used in pharmacology studies. Celecoxib, rofecoxib, and NS398 have been co-crystallized with COX-2. Celecoxib and rofecoxib are diaryl compounds containing a sulfonamide and methylsulfone, respectively, rather than a carboxyl group. Hence, the identification of COX isozymes has allowed the eventual synthesis and testing of NSAIDs, in the form of celecoxib, rofecoxib, that have resulted in important therapeutic agents.

By combining the structural information available for COX-1 and COX-2 with the novel sequence information for COX-1 variants disclosed herein and the compound inhibition studies disclosed herein, one skilled in the art can predict the three-dimensional structure of a COX-1 variant and subsequently select potential inhibitors of a COX-1 variant. Accordingly, the invention encompasses a method for identifying a potential inhibitor for a COX-1 variant by providing a three-dimensional structure of the COX-1 variant as defined by atomic coordinates and employing the three-dimensional structure to design or select a potential inhibitor. The method further involves synthesizing the potential inhibitor and contacting the potential inhibitor with the COX-1 variant in the presence or absence of a substrate of COX-1 variant to determine the ability of the potential inhibitor to inhibit enzyme Z.

The invention further provides a method for identifying a potential inhibitor of a COX-1 variant by providing the three-dimensional coordinates of an inhibitor when it is bound to COX-1 variant and comparing the three-dimensional coordinates of the inhibitor when it is bound to the COX-1 variant to the three-dimensional coordinates of compounds in a database of compound structures and selecting from the database at least one compound that is structurally similar to the inhibitor when it is bound to the COX-1 variant.

The invention further provides a method for identifying a potential inhibitor of a COX-1 variant by providing the three-dimensional coordinates and identities of the atoms of inhibitor I when it is bound to the COX-1 variant; selecting a subset of atoms of the inhibitor that govern its interaction with the COX-1 variant; comparing the three-dimensional coordinates of the selected subset of atoms of the inhibitor with the three-dimensional coordinates of compounds in a database of compound structures; and selecting from the database at least one compound comprising three-dimensional coordinates that are identical to the three-dimensional coordinates of the selected subset of atoms of inhibitor, wherein the selected compound is a potential inhibitor of a COX-1 variant.

In another embodiment, the novel polypeptides of the invention can be expressed and crystallized in the presence of absence of a test compound. Once crystallized, the three-dimensional structure of a COX-1 variant polypeptide may be determined in a number of ways. Many of the most precise methods employ X-ray crystallography (for a general review, see, Van Holde, Physical Biochemistry, Prentice-Hall, N.J. pp. 221-239, (1971), which is incorporated herein by reference). This technique relies on the ability of crystalline lattices to diffract X-rays or other forms of radiation. Diffraction experiments suitable for determining the three-dimensional structure of macromolecules typically require high-quality crystals. Various methods for preparing crystalline proteins and polypeptides are known in the art (see, for example, McPherson, et al. "Preparation and Analysis of Protein Crystals", A. McPherson, Robert E. Krieger Publishing Company, Malabar, Fla. (1989); Weber, Advances in Protein Chemistry 41:1-36 (1991); U.S. Pat. No. 4,672,108; and U.S. Pat. No. 4,833,233; all of which are incorporated herein by reference for all purposes).

This invention further pertains to novel agents or compounds identified by the above-described screening assays. Accordingly, it is within the scope of this invention to further use an compound identified as described herein in an appropriate animal model. For example, an compound identified as described herein (e.g., a COX-1 variant modulating compound, an antisense COX-1 variant nucleic acid molecule, a COX-1 variant-specific antibody, or a COX-1 variant-binding partner) can be used in an animal model to determine the efficacy, toxicity, or side effects of treatment with such an compound. Alternatively, an compound identified as described herein can be used in an animal model to determine the mechanism of action of such an compound. Furthermore, this invention pertains to uses of novel compounds identified by the above-described screening assays for treatments as described herein.

The invention further contemplates the use of high-throughput screening techniques to identify candidate compounds that modulate the activity of COX-1 variants of the invention. Conventionally, new chemical entities with useful properties are generated by identifying a chemical compound (called a "lead compound") with some desirable property or activity, creating variants of the lead compound, and evaluating the property and activity of those variant compounds. However, the current trend is to shorten the time scale for all aspects of drug discovery. Because of the ability to test large numbers quickly and efficiently, high throughput screening (HTS) methods are replacing conventional lead compound identification methods.

In one preferred embodiment, high throughput screening methods involve providing a library containing a large number of potential therapeutic compounds (candidate compounds). Such "combinatorial chemical libraries" are then screened in one or more assays, as described herein, to identify those library members (particular chemical species or subclasses) that display a desired characteristic activity. The compounds thus identified can serve as conventional "lead compounds" or can themselves be used as potential or actual therapeutics.

Combinatorial chemical libraries are a preferred means to assist in the generation of new chemical compound leads. A combinatorial chemical library is a collection of diverse chemical compounds generated by either chemical synthesis or biological synthesis by combining a number of chemical "building blocks" such as reagents. For example, a linear combinatorial chemical library such as a polypeptide library is formed by combining a set of chemical building blocks called amino acids in every possible way for a given compound length (i.e., the number of amino acids in a polypeptide compound). Millions of chemical compounds can be synthesized through such combinatorial mixing of chemical building blocks. For example, one commentator has observed that the systematic, combinatorial mixing of 100 interchangeable chemical building blocks results in the theoretical synthesis of 100 million tetrameric compounds or 10 billion pentameric compounds (Gallop et al. (1994) 37(9): 1233-1250).

Preparation and screening of combinatorial chemical libraries are well known to those of skill in the art. Such combinatorial chemical libraries include, but are not limited to, peptide libraries (see, e.g., U.S. Pat. No. 5,010,175, Furka (1991) Int. J. Pept. Prot. Res., 37: 487-493, Houghton et al. (1991) Nature, 354: 84-88). Peptide synthesis is by no means the only approach envisioned and intended for use with the present invention. Other chemistries for generating chemical diversity libraries can also be used. Such chemistries include, but are not limited to: peptoids (PCT Publication No WO 91/19735, 26 Dec. 1991), encoded peptides (PCT Publication WO 93/20242, 14 Oct. 1993), random bio-oligomers (PCT Publication WO 92/00091, 9 Jan. 1992), benzodiazepines (U.S. Pat. No. 5,288,514), diversomers such as hydantoins, benzodiazepines and dipeptides (Hobbs et al., (1993) Proc. Nat. Acad. Sci. USA 90: 6909-6913), vinylogous polypeptides (Hagihara et al. (1992) J. Amer. Chem. Soc. 114: 6568), nonpeptidal peptidomimetics with a Beta-D-Glucose scaffolding (Hirschmann et al., (1992) J. Amer. Chem. Soc. 114: 9217-9218), analogous organic syntheses of small compound libraries (Chen et al. (1994) J. Amer. Chem. Soc. 116: 2661), oligocarbamates (Cho, et al., (1993) Science 261:1303), and/or peptidyl phosphonates (Campbell et al., (1994) J. Org. Chem. 59: 658). See, generally, Gordon et al., (1994) J. Med. Chem. 37:1385, nucleic acid libraries, peptide nucleic acid libraries (see, e.g., U.S. Pat. No. 5,539,083) antibody libraries (see, e.g., Vaughn et al. (1996) Nature Biotechnology, 14(3): 309-314), and PCT/US96/10287), carbohydrate libraries (see, e.g., Liang et al. (1996) Science, 274: 1520-1522, and U.S. Pat. No. 5,593,853), and small organic molecule libraries (see, e.g., benzodiazepines, Baum (1993) C&EN, January 18, page 33, isoprenoids U.S. Pat. No. 5,569,588, thiazolidinones and metathiazanones U.S. Pat. No. 5,549,974, pyrrolidines U.S. Pat. Nos. 5,525,735 and 5,519,134, morpholino compounds U.S. Pat. No. 5,506,337, benzodiazepines U.S. Pat. No. 5,288,514, and the like).

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). A number of well known robotic systems have also been developed for solution phase chemistries. These systems include automated workstations like the automated synthesis apparatus developed by Takeda Chemical Industries, LTD. (Osaka, Japan) and many robotic systems utilizing robotic arms (Zymate II®, Zymark Corporation, Hopkinton, Mass.; Orca, Hewlett-Packard, Palo Alto, Calif.) which mimic the manual synthetic operations performed by a chemist. Any of the above devices are suitable for use with the present invention. The nature and implementation of modifications to these devices (if any) so that they can operate as discussed herein will be apparent to persons skilled in the relevant art. In addition, numerous combinatorial libraries are themselves commercially available (see, e.g., ComGenex, Princeton, N.J., Asinex, Moscow, Ru, Tripos, Inc., St. Louis, Mo., ChemStar, Ltd, Moscow, RU, 3D Pharmaceuticals, Exton, Pa., Martek Biosciences, Columbia, Md., etc.).

Portions or fragments of the novel cDNA sequences identified herein can be used in numerous ways as polynucleotide reagents. For example, these sequences can be used to: (i) map their respective genes on a chromosome; and, thus, locate gene regions associated with genetic disease; (ii) identify an individual from a minute biological sample (tissue typing); and (iii) aid in forensic identification of a biological sample.

Monitoring the influence of agents (e.g., drugs or compounds) on the expression or activity of a COX-1 variant protein can be applied not only in basic drug screening, but also in clinical trials. For example, the effectiveness of an agent determined by a screening assay as described herein to increase COX-1 variant gene expression, protein levels, or upregulate COX-1 variant activity, can be monitored in clinical trials of subjects exhibiting decreased COX-1 variant transcript expression, protein levels, or downregulated COX-1 variant activity. Alternatively, the effectiveness of an agent determined by a screening assay to decrease COX-1 variant gene expression, protein levels, or downregulate COX-1 variant activity, can be monitored in clinical trials of subjects exhibiting increased COX-1 variant gene expression, protein levels, or upregulated COX-1 variant activity. In such clinical trials, the expression or activity of a gene, and preferably, other genes that have been implicated in a disorder can be used as a "read out" or markers of the phenotype of a particular cell.

In a preferred embodiment, the present invention provides a method for monitoring the effectiveness of treatment of a subject with an agent (e.g., an agonist, antagonist, peptidomimetic, protein, peptide, nucleic acid, small molecule, or other drug candidate identified by the screening assays described herein) comprising the steps of (i) obtaining a pre-administration sample from a subject prior to administration of the agent; (ii) detecting the level of expression of a COX-1 variant protein, mRNA in the pre-administration sample; (iii) obtaining one or more post-administration samples from the subject; (iv) detecting the level of expression or activity of the protein or mRNA in the post-administration samples; (v) comparing the level of expression or activity of the protein or mRNA in the pre-administration sample with the protein or mRNA in the post administration sample or samples; and (vi) altering the administration of the agent to the subject accordingly. For example, increased administration of the agent may be desirable to increase the expression or activity of a COX-1 variant to higher levels than detected, i.e., to increase the effectiveness of the agent. Alternatively, decreased administration of the agent may be desirable to decrease expression or activity of COX-1 variant to lower levels than detected, i.e. to decrease the effectiveness of the agent. According to such an embodiment, COX-1 variant expression or activity may be used as an indicator of the effectiveness of an agent, even in the absence of an observable phenotypic response.

The present invention provides for both prophylactic and therapeutic methods of treating a subject at risk of (or susceptible to) a disorder or having a disorder associated with aberrant COX-1 variant expression or activity. With regards to both prophylactic and therapeutic methods of treatment, such treatments may be specifically tailored or modified, based on knowledge obtained from the field of pharmacogenomics. "Pharmacogenomics", as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype", or "drug response genotype".) Thus, another aspect of the invention provides methods for tailoring an individual's prophylactic or therapeutic treatment with either the COX-1 variant molecules of the present invention or modulators according to that individual's drug response genotype. Pharmacogenomics allows a clinician or physician to target prophylactic or therapeutic treatments to patients who will most benefit from the treatment and to avoid treatment of patients who will experience toxic drug-related side effects.

Accordingly, the present invention also provides diagnostic assays for identifying the presence or absence of a genetic alteration characterized by at least one of (i) aberrant modification or mutation of a gene encoding a COX-1 variant protein; (ii) mis-regulation of the gene; and (iii) aberrant post-translational modification of a COX-1 variant protein, wherein a wild-type form of the gene encodes a protein with a COX-1 variant activity. The invention further provides diagnostic assays for determining the relative expression levels of a COX-1 variant transcript or polypeptide in relation to a COX-1 or COX-2 transcript or polypeptide. A diagnostic assay can include, for example, an array-based system for detecting the presence or absence of a COX-1 variant or the presence or absence of a genetic alteration in a COX-1 variant. An array-based system can include a) bead arrays, bead based arrays, bioarrays, bioelectronic arrays, cDNA arrays, cell arrays, DNA arrays, encoded bead arrays, gel pad arrays, gene arrays, gene expression arrays, genome arrays, genomic arrays, high density oligonucleotide arrays, high density protein arrays, hybridization arrays, in situ arrays, low density arrays, microelectronic arrays, multiplex DNA hybridization arrays, nanoarrays, nylon macroarrays, oligo arrays, oligonucleotide arrays, oligosaccharide arrays, peptide arrays, planar arrays, protein arrays, solution arrays, spotted arrays, tissue arrays, exon arrays, filter arrays, macroarrays, small molecule microarrays, suspension arrays, theme arrays, tiling arrays or transcript arrays that incorporate.

For example, an array comprising a nucleic acid, protein or polypeptide of the invention or molecule that interacts with a nucleic acid, protein or polypeptide of the invention can be used in detection assays, diagnostic assays and in assays for monitoring the effects of a compound during clinical trials. Accordingly, such an array can include a nucleic acid, protein or polypeptide of the invention or molecule that interacts with a nucleic acid, protein or polypeptide disclosed herein, including COX-3, PCOX-1a, PCOX1b, hCOX-3(cc), hCOX-3(af), hCOX-3 (del10) or hCOX-3(cs).

In one aspect, the invention provides a method for preventing, in a subject, a disease or condition associated with an aberrant COX-1 variant expression or activity, by administering to the subject a COX-1 variant or a compound which modulates COX-1 variant expression or at least one COX-1 variant activity. Subjects at risk for a disease which is caused or contributed to by aberrant COX-1 variant expression or activity can be identified by, for example, any or a combination of diagnostic or prognostic assays as described herein. Administration of a prophylactic agent can occur prior to the manifestation of symptoms characteristic of the COX-1 variant aberrancy, such that a disease or disorder is prevented or, alternatively, delayed in its progression. Depending on the type of COX-1 variant aberrancy, for example, a COX-1 variant, agonist or antagonist agent can be used for treating the subject. The appropriate agent can be determined based on screening assays described herein.

Accordingly, the invention provides a method of selecting a therapy for a patient by providing a subject expression profile of a sample from said patient; providing a plurality of reference profiles, each associated with a therapy, wherein the subject expression profile and each reference profile has a plurality of values, each value representing the expression level of a COX-1 variant transcript or polypeptide; and selecting the reference profile most similar to the subject expression profile, to thereby select a therapy for said patient.

The invention further provides an array comprising a substrate having a plurality of addresses, wherein each address has disposed thereon a capture probe that can specifically bind a COX-1 variant nucleic acid. The nucleic acids can be selected from the group consisting of COX-1 variant SEQ ID NO:1, SEQ ID NO:4, SEQ ID NO:10, SEQ ID NO:11, SEQ ID NO:12 or SEQ ID NO:13. The substrate can possess a range of addresses, each corresponding to a unique COX-1 variant sequence. The range of addresses can include 5-10,000, depending on the density of the array.

The invention further provides a method of choosing a therapy for a patient, by providing a plurality of reference expression profiles, each associated with a therapy; providing a nucleic acid obtained from a patient; contacting the nucleic acid with the array comprising a substrate having a plurality of addresses, wherein each address has disposed thereon a capture probe that can specifically bind a COX-1 variant nucleic acid; detecting binding of the nucleic acid to each address of the plurality of addresses to thereby provide a subject expression profile; and selecting the reference profile most similar to the subject expression profile, to thereby choose a therapy for said patient.

The invention further provides a method for evaluating whether or not a pharmaceutical composition will be effective for interacting with a COX-1 variant. The method can utilize an array having a substrate including a plurality of addresses, wherein each address has disposed thereon a capture probe that can specifically bind a COX-1 variant nucleic acid; and a computer-readable medium having a plurality of digitally-encoded expression profiles wherein each profile of the plurality has a plurality of values, each value representing the expression of a COX-1 variant nucleic acid detected by the array.

The invention further encompasses a method of selecting a therapy for a subject by obtaining a subject sample from a caregiver; obtaining a nucleic acid from the subject sample; identifying a subject expression profile from the nucleic acid; selecting from a plurality of reference profiles a matching reference profile most similar to the subject expression profile, wherein the reference profiles and the subject expression profile have a plurality of values, each value representing the expression level of a COX-1 variant, wherein each reference profile of the plurality of reference profiles is associated with a therapy; and transmitting a descriptor of the therapy associated with the matching reference profile to the caregiver, thereby selecting a therapy for said subject.

The invention further provides a kit for evaluating a pharmaceutical composition, the kit comprising an array as described above and a computer-readable medium having a plurality of expression profiles, wherein each profile of the plurality has a plurality of values, each value representing the expression of a COX-1 variant nucleic acid detected by the array.

Another aspect of the invention pertains to methods of modulating COX-1 variant expression or activity for therapeutic purposes. Accordingly, in an exemplary embodiment, the modulatory method of the invention involves contacting a cell with a COX-1 variant or agent that modulates one or more of the activities of COX-1 variant protein activity associated with the cell. A compound or agent that modulates COX-1 variant protein activity can be an agent as described herein, such as a nucleic acid or a protein, a naturally-occurring target molecule of a COX-1 variant protein, a COX-1 variant antibody, a COX-1 variant agonist or antagonist, a peptidomimetic of a COX-1 variant agonist or antagonist, or other small molecule. In one embodiment, the agent stimulates one or more COX-1 variant activities. Examples of such stimulatory agents include active COX-1 variant protein and a nucleic acid molecule encoding COX-1 variant that has been introduced into the cell. In another embodiment, the agent inhibits one or more COX-1 variant activities. Examples of such inhibitory compounds or agents include antisense COX-1 variant nucleic acid molecules, anti-COX-1 variant antibodies, and COX-1 variant inhibitors. These modulatory methods can be performed in vitro (e.g., by culturing the cell with the agent) or, alternatively, in vivo (e.g., by administering the agent to a subject) or even in silico, as described elsewhere. As such, the present invention provides methods of treating an individual afflicted with a disease or disorder characterized by aberrant expression or activity of COX-1 variant protein or nucleic acid molecule.

The COX-1 variant nucleic acid molecules, COX-1 variant proteins, compounds identified as modulating a COX-1 variant activity and anti-COX-1 variant antibodies (also referred to herein as "active compounds") of the invention can be incorporated into pharmaceutical compositions suitable for administration. Such compositions typically comprise the nucleic acid molecule, protein, compound or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

For example, epidemiologic and clinical data suggest that the use non-steroidal anti-inflammatory drugs (NSAIDs) delays the onset of AD and reduces the progression of pathologic symptoms in Alzheimer's disease. McGeer and McGeer, Brain Res. Rev. 21, 195 (1995). Aspirin, like most NSAIDs, prevent inflammation and pain by inhibiting both COX-1 and COX-2 enzymes. Resveratrol, a phenolic antioxidant and COX inhibitor found in grapes, inhibits prostaglandin production, and has anti-cancer and anti-inflammatory properties. Jang et al., Science 275, 218 (1997). Alzheimer's Disease (AD) is the most common neurodegenerative disorder of aging, and is characterized by progressive dementia and personality dysfunction. The abnormal accumulation of amyloid plaques in the vicinity of degenerating neurons and reactive astrocytes is a pathological characteristic of AD. The present invention further relates to compositions and methods for the treatment of various neurological diseases and neurodegenerative disorders. For example, a composition that modulates a COX-1 variant of the invention can be used to treat neurodegenerative diseases associated with an overabundance of Amyloid Precursor Protein (APP). Cytosolic phospholipase A2, which releases arachidonic acid from cellular phospholipids, is elevated in AD brain and after transient global ischemia. The cyclooxygenation of arachidonic acid, catalyzed by two forms of cyclooxygenase (COX), COX-1 and COX-2, produces prostaglandins which, in turn, regulate neurotransmission, immune and inflammatory responses by activating receptors coupled to cAMP formation. cAMP elevations caused by activation of neurotransmitter receptors increased APP mRNA and holoprotein production in astrocytes.

Accordingly, active compounds identified by a screening assay disclosed herein can be in included in a pharmaceutical composition in order to ameliorate a COX-1 variant associated disorder such as, for example, a neurodegenerative condition or disease. The condition can be treated in a subject by administering a specific inhibitor of COX-1 variant activity as disclosed in the invention, in a pharmaceutically acceptable carrier. It is further object of the invention to provide a method for preventing or treating Alzheimer's Disease in a subject by administering an effective amount of a specific inhibitor of COX-1 variant activity as disclosed in the present invention.

The invention further provides a method for treating immune or inflammatory conditions associated with a neurodegenerative condition in a subject by administering a specific inhibitor of a COX-1 variant as provided in the this disclosure. The invention encompasses a method of modulating expression, production, or formation of amyloid precursor protein (APP) in a subject by administering an effective amount of an antagonist of a COX-1 variant of the invention. The antagonist can be, for example, a non-steroidal anti-inflammatory agent that is a specific inhibitor of COX-1 variant activity, in a pharmaceutically acceptable carrier. Thus, the present invention provides methods and compositions that can modulate or regulate the production or formation of APP in patients, including the expression of APP gene products and the transcription or translation of the APP gene in central nervous system. For example, the production of APP by mammalian cells, in particular, by cells in the brain, can be increased or reduced. In attaining this objective, it is also an objective of the invention to inhibit excessive amyloid formation, prevent neurite dystrophy and alleviate pathological symptoms, such as neurodegeneration or cognitive deficits that may arise from the negative effects of inappropriately expressed, produced, or formed amounts of APP.

Accordingly, the present invention is useful in the treatment or alleviation of disease, especially those disorders related to neurological diseases or neurodegenerative disorders, such as Alzheimer's disease, Parkinson's disease, Lou Gehrig's disease, or multiple sclerosis, to name a few, not to mention central or peripheral nervous system damage, dysfunction, or complications involving same stemming from edema, injury, or trauma. Such damage, dysfunction, or complications may be characterized by an apparent neurological, neurodegenerative, physiological, psychological, or behavioral aberrations, the symptoms of which can be reduced by the administration of an effective amount of the active compounds or substances of the present invention.

According to one embodiment, the administration of effective amounts of a composition that modulates the activity of a COX-1 variant of the invention can be used to suppress, inhibit, or neutralize the action of increased cAMP activity, which activity if unchecked leads to the overproduction of APP. A variety of non-steroidal anti-inflammatory agents (NSAIDs) are found to be suitable for reversing the stimulatory effects of cAMP, its derivatives, a ligand, an agonist, or an antagonist of a receptor that is coupled to the cellular levels of cAMP, or a compound that enhances the nuclear actions of cAMP. Examples of suitable NSAIDs include, but are not limited to, Advil®, Aspirin, Aleve®, Anaprox®, Diclofenac, Docosahexaenoic acid, Dolobid®, Etodolac, Feldene®, Flurbiprofen, Ibuprofen, Indomethacin, Ketorolac tromethamine, Lodine®, Meclofenamate, 6-MNA, Motrin®, Nalfon®, Naprosyn®, Nuprin®, Orudis®, Phenylbutazone, Piroxicam, Phenylbutazone, Ponstel®, Relafen®, Salicylic acid, Sulindac sulfide, Tolectin®, Toradol®, Voltaren®; also 5-lipoxygenase inhibitors, phosphodiesterase inhibitors, or cyclooxygenase inhibitors (e.g., cyclosalicylazosulfapyridine, azulfasalazine, DFU (5,5-dimethyl-3-(3-fluorophenyl)-4-(4-methylsulfonyl)phenyl-2(5H)-furanone), or DFP (5,5-dimethyl-3-isopropyloxy-4-(4'-methylsulfonylphenyl)-2 (5H)-furanone).

As used herein, the term "central nervous system" refers to all structures within the dura mater. Such structures include, but are not limited to, the brain and spinal cord.

As used herein, the terms "subject suffering from Alzheimer's disease," "subject suffering from a disease with an inflammatory component," and "subject suffering from central nervous system injury," refer to subjects that are identified as having or likely having the particular disease, injury, or condition, respectively. As used herein the terms "subject susceptible to Alzheimer's disease" and "subject susceptible to a disease with an inflammatory component," refer to subjects identified as having a risk of contracting or developing the particular disease, injury, or condition, respectively. As used herein, the term "disease with an inflammatory component" refers to diseases and conditions that are associated with an inflammatory element. The inflammatory element can comprise a symptom, side-effect, or causative event associated with the disease or condition. Diseases with an inflammatory component include, but are not limited to, stroke, ischemic damage to the nervous system, neural trauma (e.g., percussive brain damage, spinal cord injury, and traumatic damage to the nervous system), multiple sclerosis and other immune-mediated neuropathies (e.g., Guillain-Barre syndrome and its variants, acute motor axonal neuropathy, acute inflammatory demyelinating polyneuropathy, and Fisher Syndrome), HIV/AIDs dementia complex, and bacterial and viral meningitis. Such diseases further include degenerative diseases, such as Alzheimer's Disease (AD), Parkinson's Disease (PD), Amyotrophic lateral sclerosis (ALS), Huntington's Disease (HD), Pick's disease, progressive supranuclear palsy, striatonigral degeneration, cortico-basal degeneration, olivopontocerebellar atrophy, Leigh's disease, infantile necrotizing encephalomyelopathy, Hunter's disease, mucopolysaccharidosis, various leukodystrophies (such as Krabbe's disease, Pelizaeus-Merzbacher disease and the like), amaurotic (familial) idiocy, Kuf's disease, Spielmayer-Vogt disease, Tay Sachs disease, Batten disease, Jansky-Bielschowsky disease, Reye's disease, cerebral ataxia, chronic alcoholism, beriberi, Hallervorden-Spatz; syndrome, cerebellar degeneration, and the like.

As used herein, the term "neurological defect" refers to a defect involving or relating to the nervous system. Some neurological defects are caused by defective tissues or cells of the nervous system, while other defects are caused by defective tissues or cells that affect the nervous system. As used herein, the term "neurologically defective mammal" refers to a mammal having one or more neurological defects. When a neurological defect is "ameliorated," the condition of the host is improved. For example, amelioration can occur when defective tissue is returned partially or entirely to a normal state. However, amelioration can also occur when tissue remains subnormal, but is otherwise altered to benefit the host. As used herein, the term "lesion" refers to a wound or injury, or to a pathologic change in a tissue.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bactenostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, PRIMOGEL, or corn starch; a lubricant such as magnesium stearate or STEROTES; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) Proc. Natl. Acad. Sci. USA 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The invention also encompasses pharmaceutical compositions comprising a compound identified by a method of the invention contained in a container and labeled with instructions for use as a COX-1 variant specific inhibitor. The pharmaceutical composition can be included in a kit with instructions for use of the composition in the treatment of a COX-1 variant associated disorder. The kit can further comprise instructions for using dosage. Accordingly, the invention contemplates an article of manufacture comprising packaging material and, contained within the packaging material, a compound that modulates the activity of a COX-1 variant, such as, for example, Cox-3, wherein the packaging material comprises a label or package insert indicating that said compound modulates the activity of a COX-1 variant and can be used for treating (pain/inflammation) in a subject. The invention further contemplates an article of manufacture comprising packaging material and, contained within the packaging material, a compound that preferentially modulates the activity of a COX-1 variant in comparison to Cox-1 and Cox-2, wherein the packaging material comprises a label or package insert indicating that said compound modulates the activity of a COX-1 variant and can be used for treating (pain/inflammation) in a subject.

EXAMPLES

Recent studies have demonstrated that COX-1 possesses at least three distinct domains responsible for dimerization, membrane binding, and catalysis. A fourth domain, the N-terminal signal peptide, which is clearly evident in the primary structure of COX-1, was not observed because this sequence typically is co-translationally cleaved from the nascent polypeptide by microsomal signal peptidase. The amino terminal signal peptide directs synthesis of the COX isozymes into the lumen of the endoplasmic reticulum/nuclear envelope. Although cleaved from the nascent polypeptide, the amino terminal hydrophobic signal peptide shows a size difference between COX-1 and COX-2 that, prior to the present invention, had unknown biological significance. The signal peptide for COX-1 is generally 22-29 amino acids in length with a large hydrophobic core comprised of 4 or more leucines or isoleucines. This sequence is encoded by exons 1 and 2 of the COX-1 gene. Exon 2 of COX-1 terminates precisely at the cleavage site for the signal peptide. In contrast to COX-1, COX-2's signal peptide is 17 amino acids long in all species and it is encoded entirely by exon 1 of the COX-2 gene, which terminates precisely at the cleavage site for the signal peptide. Therefore, the hydrophobic signal peptide is precisely encoded by exons 1 and 2 in COX-1 and exon 1, alone, in the COX-2 gene. Intron 1 of the COX-1 gene is missing in the COX-2 gene. This represents a major difference in structure between the COX-1 and COX-2 genes.

In vitro translation experiments have demonstrated that COX-1 is rapidly translocated into the lumen of canine pancreatic microsomes, whereas COX-2 is inefficiently translocated (Xie, et al. (1991) Proc. Natl. Acad. Sci. USA 88:2692-2696). To date this is the only known biochemical property of the COX-1 and COX-2 isozymes to be affected by this difference in the length of the signal peptide. However, the discovery described herein shows that regulation of this important signal sequence by intron retention in COX-1 occurs in brain and other tissues to create unique variants (i.e., COX-1 variants) of COX isozymes.

Accordingly, novel mRNAs encoding COX-variant proteins (e.g., COX-3, PCOX-1a, hCOX-3(cc), hCOX-3(af), hCOX-3 (del10) and hCOX-3(cs)) are expressed in mammalian tissue and are provided herein. For example, canine and human cerebral cortex express COX-1 variant mRNA. In addition, human COX-3 mRNA (~5.2 kb transcript) has been identified from heart tissue. Intron 1 is conserved in length and in sequence in mammalian COX-1 genes. This intron contains an open reading frame that introduces an insertion of 30-34 amino acids, depending on the mammalian species, into the hydrophobic signal peptide that directs COX-1 into the lumen of the endoplasmic reticulum and nuclear envelope. Also provided in the present invention are COX-variant proteins expressed efficiently in insect cells as membrane-bound proteins. COX-3 and PCOX-1a are examples of COX-1 variants described herein. While the expression and activities of COX-3 and PCOX-1a are specifically described, it is noted that such expression is applicable to any of the COX-1 variants provided in the disclosure. Accordingly, expression of PCOX1b, hCOX-3(cc), hCOX-3(af), hCOX-3 (del10) or hCOX-3(cs) can be easily accomplished by the techniques described herein and by the knowledge of one skilled in the art of molecular biology.

Exemplary COX-3, but not PCOX-1a, possesses cyclooxygenase activity and this activity is dependent on the enzyme being glycosylated. Methods of screening for compounds that selectively inhibit COX-1 variants are also provided. For example, COX-1 variant activity can be inhibited by analgesic/antipyretic drugs such as acetaminophen, phenacetin, antipyrine, dipyrone and NSAIDs. Therefore, methods for identifying compounds useful for treating, for example, central nervous system disorders (e.g., decrease pain and/or fever) are provided.

By way of example only but not by way of limitation, the invention provides specific compounds that target a COX-1 variant for inhibition. Methods of manufacturing derivatives of such compounds are well known to those skilled in the art of biochemistry. Thus, the invention encompasses derivatives of the disclosed compounds that are identified as possessing COX-1 variant inhibitory activity. Examples of COX inhibitors include Celecoxib (Celebrex®) and rofecoxib (Vioxx®) which were developed as COX-2 selective inhibitors. Other NSAIDs including meloxicam (Mobic®), nimesulide, and etodolac (Lodine®), were also identified COX-2 preferential inhibitors. The invention provides a mechanism for identifying variants of the above-described compounds that preferentially inhibit a COX-1 variant over that of COX-1 and or COX-2.

Figure 5C:
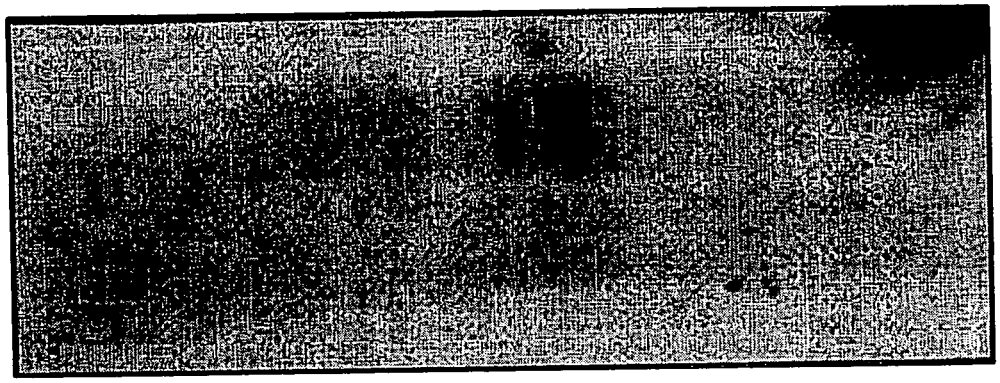
FIG. 5, panel A, depicts Northern blot analysis of the distribution of COX-1 in dog tissues. Arrows indicate additional COX-1 transcripts in brain tissue. S=stomach; d=duodenum; i=ileum; j=jejunum; c=colon; l=liver; s=spleen; b=brain; lu=lung; o=ovary; k=kidney; m=MDKC cells (ind). The blots were hybridized with $^{32}$P-labeled canine COX-1 DNA (specific activity $8.8 \times 10^8$ cpm/µg, $6 \times 10^6$ cpm/ml). Post hybridization washes were carried out for 3 h with 3-4 changes in 2×SSC/0.5% SDS at about 65° C.
Figure 5A:
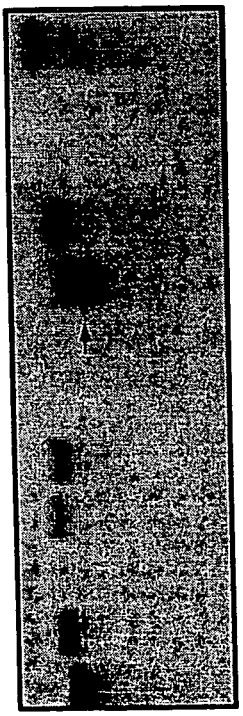
Figure 5B:
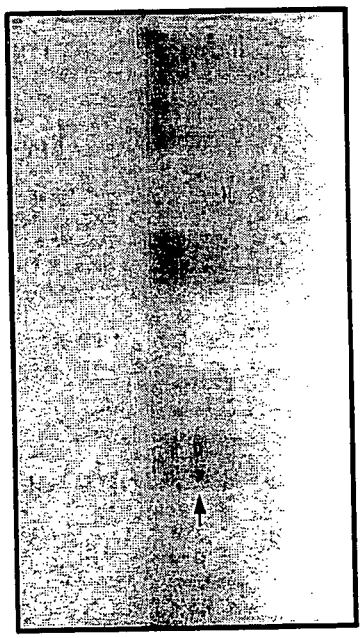
Figures 1, 6A:
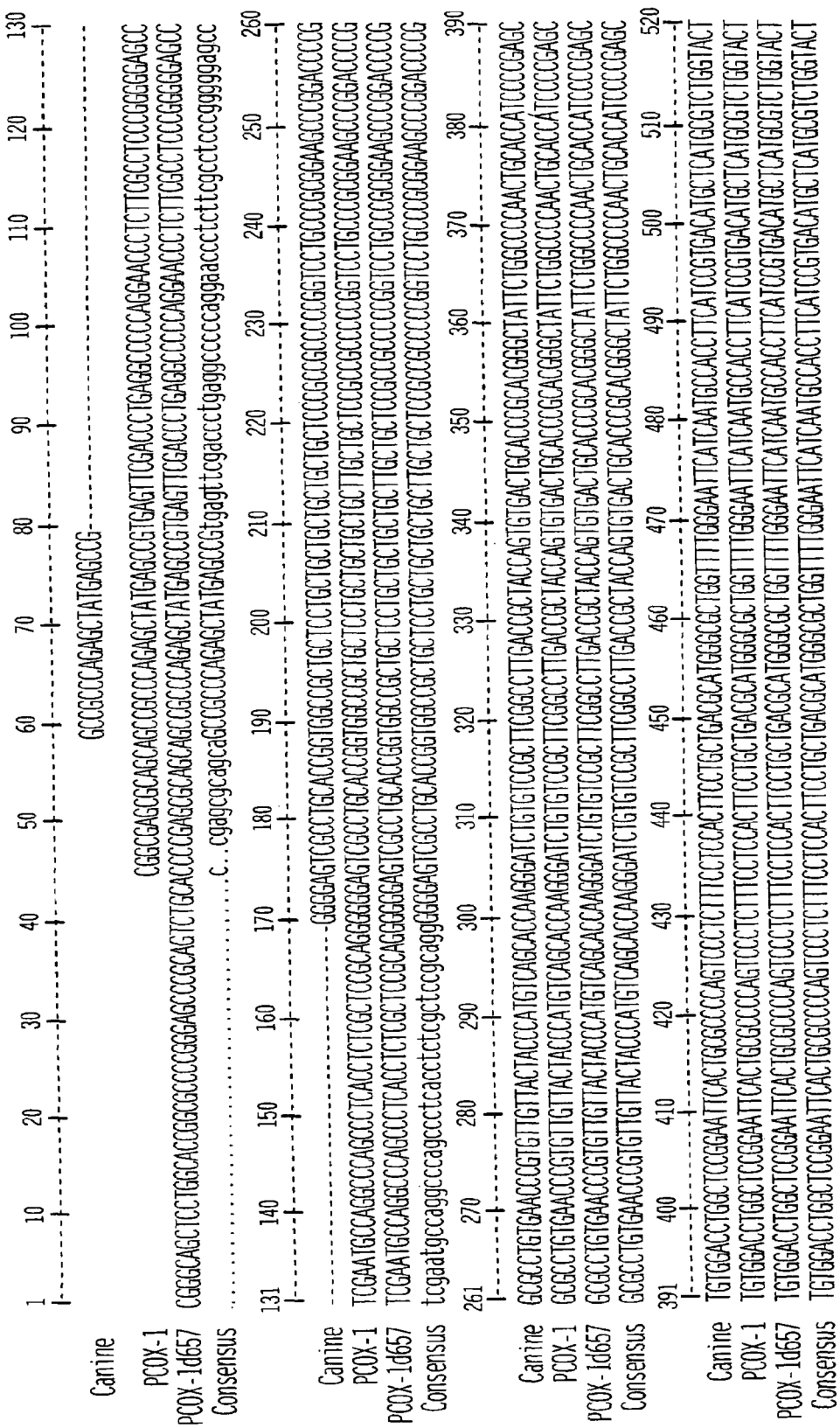
FIG. 6A depicts a nucleic acid sequence alignment of canine COX-1, PCOX-1 (i.e., COX-3) and PCOX-1Δ657 (i.e., PCOX1a) and a consensus sequence.
Figures 4, 6A:
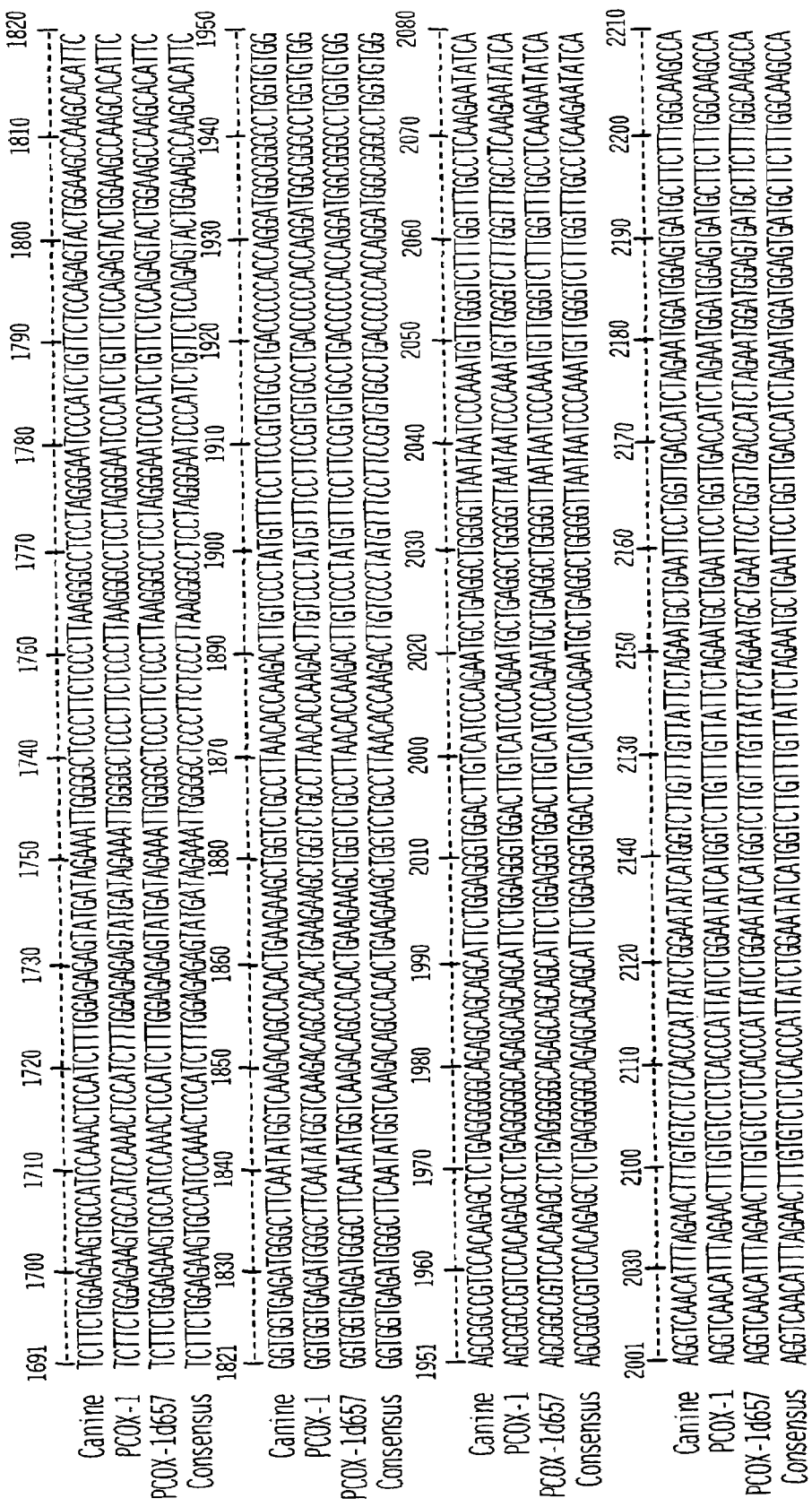

Analysis by Northern blot of COX mRNAs isolated from a variety of canine tissues demonstrated that all RNA samples, with the exception of those from brain (cortex), contained primarily a single 2.6 kb mRNA that hybridized to a canine COX-1 cDNA probe. The canine probe was ~1.0 kbp in size and was made to the coding region of the COX-1 mRNA. This probe used in these experiments was generated by reverse transcription-coupled polymerase chain reaction (RT-PCR) using degenerate oligonucleotides made to conserved sequences in COX isozymes. The identity of the probe was confirmed by DNA sequencing. In contrast to what was observed in other tissues, this probe detected a novel COX-1 mRNA in total RNA isolated from brain tissue (FIG. 5, panel A). This novel RNA was approximately 1.9 kb in size in contrast to the 2.6 kb mRNA that encodes COX-1 in dogs. A similarly sized message was detected in chicken brain mRNA (FIG. 5, panel b).

Further Northern blot experimentation showed that the 1.9 kb mRNA was enriched in the poly A fraction of RNA and, therefore, was not likely a breakdown product of unprocessed RNA transcripts (FIG. 5 panel c). Moreover, (RT-PCR) experiments demonstrated that this novel 1.9 kb COX-1-related mRNA was not the product of an alternative polyadenylation process which would change the length of the 3' untranslated region of the COX-1 RNA but otherwise leave the coding region unchanged. This was confirmed by Southern blot analysis of a PCR generated fragment using probes specific for the 3' untranslated region of the message. In these experiments the same 3' untranslated region was found to be present in both the 2.0 and 2.8 kb COX-1 RNAs. Therefore, the 1.9 kb RNA appeared to reflect changes in the coding region of a COX-1 mRNA or in a highly related mRNA.

To identify changes in the coding region present in the 1.9 kb RNA, cDNA libraries were created in both lambda ZIPLOX® and lambda ZAP® cloning vectors purchased from Gibco BRL and Stratagene, respectively. Methods of cDNA synthesis, vector ligation, and phage propagation are known to those skilled in the art. Approximately 45,000 recombinants from the ZIPLOX® library and ~149,000 recombinants from the lambdaZAP® libraries were probed with the canine 1.0 kb COX-1 cDNA fragment, radiolabeled with $\alpha^{32}$PCTP and hybridized at a concentration of $2\times10^6$ cpm/ml.

Eleven clones were isolated that strongly hybridized to the canine COX-1 clone and were subjected to DNA sequencing by automated DNA sequencing. All of these clones contained some DNA sequence that was essentially identical with canine COX-1 cDNA. However, three clones contained an insertion of 90 nucleotides of extra sequence near or at the 5' end of their respective cDNAs. The analysis of this inserted sequence found that it was located at the position where intron-1 of the canine COX-1 gene would be predicted to be located based on the position of this intron in mouse and human COX-1 genes. Moreover, it was determined that the retained 90-nucleotide sequence in these canine cDNAs showed striking sequence similarity to intron-1 in human and mouse COX-1 genes and contained 5' and 3' consensus splice sites indicative of a retained intron. The present study shows that these novel transcripts reflect an in-frame retention in the mRNA of intron-1 which would be predicted to cause significant changes in the biochemical properties of the COX-related protein encoded by these cDNAs.

Of the three intron-1 containing clone identified, one was found to contain, in addition to the 90-nucleotide insertion, an approximately 657 bp in-frame deletion. This in-frame deletion corresponded approximately to the removal of exons 5-8 of the COX-1 message. Additionally, one codon appears to be deleted from the 5' end of exon 4 and another codon appears to be added from the 3' end of exon 8. This deletion is predicted to remove parts of the catalytic domain that might decrease peroxidase activity and might alter, but not destroy the fatty acid oxygenation activity of the enzyme encoded by this enzyme.

COX-1 variants (e.g. COX-3, PCOX-1a, hCOX-3(cc), hCOX-3(af), hCOX-3 (del10) and hCOX-3(cs)) contain an in-frame insertion of intron-1. Insertion of this sequence in these RNAs occurs 2 amino acid residues downstream from the initiating methionine of the protein and results in the addition of about 30 amino acids into the signal peptide. This addition may change the subcellular location of this enzyme in the cell. In particular, it is predicted to target this protein to specific organelles, such as the endoplasmic reticulum, nuclear envelope, lipid bodies or of the membrane structures in the cytoplasm where the enzyme would bind to cytosolic surfaces of cell membranes by virtue of its retained membrane binding domain. The location of these enzymes to the cytosolic surface of cellular membranes or lipid bodies would be predicted to alter folding of the protein since it would lack glycosylation provided by microsomal enzyme. Also the enzyme would contain approximately 60 amino acids at to its amino terminus that would not normally be in this protein. This addition, itself, would alter folding and likely prevent dimerization. The present data indicate that a COX-1 variant protein, although containing all or significant portions of the COX-1 sequence, would have different enzymatic properties then those of the COX-1 proteins.

One example of a COX-1 variant includes PCOX-1a which exhibits a significant (219 amino acid) deletion in addition to having an insertion of intron −1 at its amino terminus. This enzyme possesses structural motifs for binding heme, having peroxidase activity, and oxygenating fatty acids similar to PIOXs. This means that, unlike COX-1 and COX-2, PCOX-1a will not likely produce products such as prostaglandins that contain cyclopentane rings, since formation of such products require interaction of the fatty acid with hydrophobic residues deleted in PCOX-1a. Instead, it is likely that PCOX-1a forms monooxygenated hydroperoxy- or hydroxy-derivatives of fatty acids similar to PIOXs.

Figure 8:
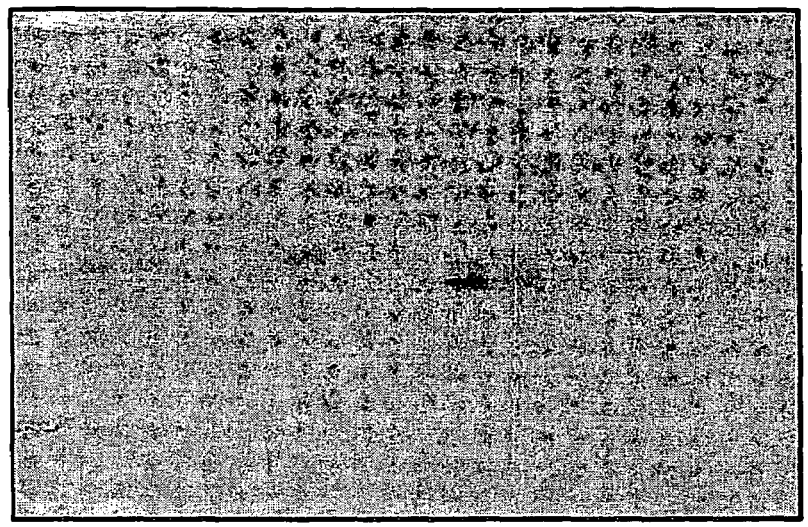
FIG. 8 depicts a Northern blot analysis of canine total RNA (25 ug) probed with $^{32}$P-end labeled oligo (50 mer) designed from within the first intron of COX-1 in canine. The blot was washed at a final stringency of Tm-4 (Tm=calculated melting temperature). S=stomach; D=duodenum; I=ileum; J=jejunum; C=colon; L=liver; Sp=spleen; Bm=brain (cerebral cortex)-mRNA (2.5 ug); Bt=brain (cerebral cortex)-total RNA; Lu=lung; O=ovary; K=kidney; Cl=CCl 34 cells. The 5.2 kb mRNA that was detected in panels A, B and C and is designated by an arrow in FIG. 8.

The structure of the COX-1 gene is known in human and mouse. Analysis of the structure of intron-1 in these species show that both organisms contain an intron-1 that is similar in size to that in dogs which, when retained, would provide an in-frame insertion into the signal peptide encoding the protein (FIG. 7). Four amino acids (ArgGluXAspPro) at the amino terminus of this intron are conserved in all three species. RNA's were analyzed by Northern blot using oligonucleotide antisense probes specific to intron 1. Canine tissues were analyzed with a oligonucleotide (50 bp in length) found in intron 1. It detected specific RNA species containing this intron in a variety of tissues, including extensively in brain (FIG. 8). RNA isolated from a variety of human tissues were analyzed by Northern Blot using an anti-sense oligo (50 nucleotides in length) to intron-1. Washing conditions for this blot included two 30-minute washes at a temperature −20 degrees below the calculated melting temperature (Tm) of the probe. This was followed by one 10 minute wash at 4° C. degrees below the calculated melting temperature. This high degree of stringency predicts an authentic rather than non-specific interaction of the probe with any interacting RNA. A 5.2 kb RNA was detected by the intron-1 specific oligonucleotide probe in human tissues of the forebrain, particularly the cortex, as well as in heart, muscle, liver, placenta, kidney and pancreas. The amygdala, hippocampus, whole brain, and lung and other tissues showed low expression of this RNA. In addition to the 5.2 kilobase transcript, several smaller RNAs of ~2-2.8 kb were detected by the probe in the cortex and other regions of the brain.

To further assure that intron-1 containing COX-1 transcripts exist in humans, reverse transcription coupled PCR was performed using RNA from human cells and tissues. Amplification of a predicted ~1.8 kb fragment was achieved using a forward primer located in intron 1 of the human gene and a reverse primer located immediately 3' to the predicted stop codon of the message. This amplicon hybridized in a Southern blot procedure with canine COX-1 cDNA. In the Southern blot procedure the blot was washed at several times at 65° C. in 2×SSC.

Antisense oligonucleotides to the first intron of human and canine cyclooxygenase (COX)-1 genes were synthesized and end-labeled using $(\gamma$-$^{32}$P$)$-dATP. A canine cerebral cortex cDNA library was screened using a ~1.0 kb canine COX-1 fragment by reverse transcription-coupled PCR (RT-PCR). The library was also screened with a $^{32}$P-labeled canine COX-1 intron 1 antisense oligonucleotide. Two full-length clones were isolated, completely sequenced, and designated COX-3 and PCOX-1a. Both were derived from the canine COX-1 gene but retain intron 1. PCOX-1a also has a 657 bp in-frame deletion spanning exons 5-8.

Canine cerebral cortex cDNA was synthesized, and primers were designed for PCR amplification. The sense primer (5'-CGGATCCGCCGCCCAGAGCTATGAG-3' (SEQ ID NO:7)) corresponded to nucleotides 15-32 of canine COX-3 sequence (submitted to GenBank under accession no. AF535138), with the 3' end of the primer being 2 nucleotides downstream of the initiating methionine. The antisense primer (5'-CGCCATCCTGGTGGGGGTCAGGCAC ACGGA-3' (SEQ ID NO:8)) corresponded to nucleotides 1865-1894, located 32 nucleotides upstream of the stop codon.

Northern blot analysis of human tissues with an intron-1 probe detected an ~5.2 kb mRNA. Marathon-ready™ human cerebral cortex cDNA (Clontech) was amplified by PCR (Clontech-Advantage® 2 PCR enzyme system) using 5' and 3' primers, and a ~4.2 kb amplified fragment was recovered and found to contain the entire coding region of human COX-1 with intron 1 retained.

Both COX-3 and PCOX-1a were cloned into the baculovirus expression vector pBlueBac 4.5/V5-His (Invitrogen). Sf9 cells (~1×10$^6$) were infected with viral stocks at a multiplicity of infection (MOI) of 3 for expression of COX-3, PCOX-1a, mouse COX-1 and mouse COX-2.

Total protein (20 μg) from human aorta was analyzed by Western blotting, using COX-1 monoclonal antibody (MAb) (Cayman Chemical, Ann Arbor, Mich.) and COX-3 antipeptide polyclonal antibodies (PAb). Primary antibodies were either preincubated with a mixture of human and mouse COX-1 intron 1 peptide (described below) for 1 hr, 4° C., or left unblocked. Blots were processed with appropriate rabbit-anti-mouse secondary antibody (1:2000) or goat-anti-rabbit secondary antibody (1:10,000) from Sigma. Densitometry of the autoradiographic image was performed using the AlphaImager™ 2000 Documentation and Analysis System (Alpha Innotech Corporation).

Tunicamycin was added to a final concentration of 10 μg/ml to insect cells 1 hr after infection with baculovirus constructs. The cells were cultured and harvested after 48 hr. COX activity of intact cells was determined by radioimmunoassay (RIA) (Salmon, 1978). COX activity in intact Tu-treated cells was compared with activity in untreated cells infected with the appropriate virus (MOI=3).

Sf9 cells were infected with a high titer viral stock at a MOI of 3 and cultured for 48 hr. Infected cells expressing COX-3 were aliquoted into tubes (~1.5×10$^6$ cells) and centrifuged (1000×g, 5 min). The supernatant was discarded and the cell pellet resuspended in 100 μl serum-free media containing the drug to be tested and preincubated at room temperature for 30 minutes. Arachidonic acid (100 μl, final concentration 5 or 30 μM) was then added, mixed and incubated (37° C., 10 min). Samples were then centrifuged and 100 μl of the supernatant was assayed for COX activity by RIA for PGE$_2$. Assays were performed multiple times in triplicate. Inhibition curves were constructed and IC$_{50}$ values were determined using Prism® 3.0 (GraphPad, San Diego).

Peptides corresponding to the first 13 amino acids of human and mouse COX-3 primary sequence, as predicted by genomic clone sequences, were synthesized and coupled to keyhole limpet hemocyanin. A mixture of the human (MSR-ECDPGARWGC (SEQ ID NO:20)) and mouse (MSREFD-PEAPRNC (SEQ ID NO:21)) peptides were injected into New Zealand white rabbits. The resulting polyclonal antibodies were then affinity purified using the above peptides immobilized on a Sulfolink™ coupling gel (Pierce) according to the manufacturer's instructions.

Figure 10A:
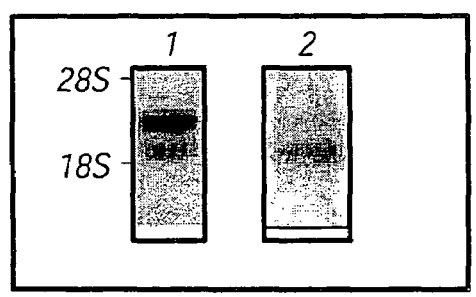
FIG. 10, panel A, depicts a Northern blot analysis and RT-PCR of canine cerebral cortex poly(A) RNA (lane 1, 5.0 µg; lane 2, 2.5 µg) probed with 1) $^{32}$P-labeled canine COX-1 cDNA fragment, 2) $^{32}$P-labeled canine antisense oligonucleotide to intron 1 (CCI).
Figure 10B:
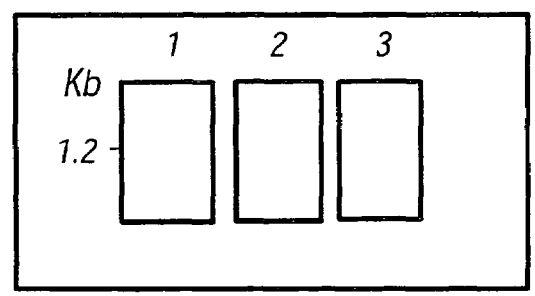
Figure 10C:
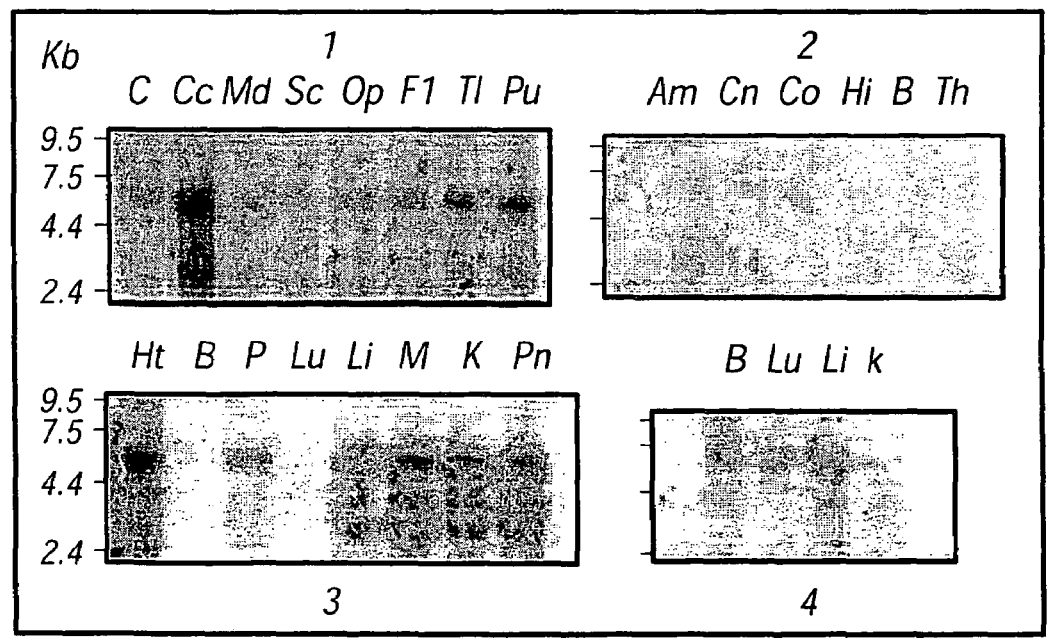

Northern blot analysis detected a ~5.2 kb mRNA containing intron 1 (FIG. 10, panel B). The antisense primer (HCLE: 5'-CGGATCCTGGA ATAGGCCACCGGATGGAAGGA-3' (SEQ ID NO:9)) was designed from the 3' end of the published sequence and the sense primer (HCF: 5'-CGGATCCT-GCGTCCC GCACCCCAGCA-3' (SEQ ID NO:17) from a site 5 nucleotides upstream from the initiation codon of the human COX-1 gene (Gen-Bank, accession number L 08404). The primers were designed with a BamHI recognition sequence at their 5' ends to facilitate cloning.

Marathon-ready™ human cerebral cortex cDNA (Clontech) was amplified by PCR (Clontech-Advantage® 2 PCR enzyme system) using the above primers. The resulting .about.4.2 kb amplified fragment was recovered from a low melting agarose gel and reamplified using nested primers (sense, HCEI: 5'-CGGATCCGCGCCATGAGCC GTGA-3' (SEQ ID NO: 18); antisense, HCS: 5'-CGGATCCTCA-GAGCTCTGTGGATGGTCGCT-3' (SEQ ID NO: 19). The resulting fragment (~2.0 kb) containing the entire coding region of human COX-1 (with intron 1 retained) was then cloned in the plasmid Bluescript® and sequenced.

Two distinct mRNA species (~2.6 and ~1.9 kb) were detected on a Northern blot with a canine COX-1 coding region cDNA probe utilizing RNA isolated from canine cerebral cortex (FIG. 10, panel A, lane 1). To further investigate these transcripts, a canine cerebral cortex cDNA library was constructed and the non-amplified library was screened as described above. Eleven clones were isolated and subsequently characterized by automated DNA sequencing. All of the eleven clones were found to contain canine COX-1 cDNA sequence. However, three clones harbored an insertion of 90 nucleotides at, or near, the 5' end of their respective cDNAs, which showed 75% sequence identity to intron 1 of either human or mouse COX-1 genes. This extra sequence also contained 5' and 3' consensus splice sites indicative of a retained intron. In addition to the retention of intron 1, one of the three clones had a 657 bp in-frame deletion corresponding to exons 5-8 of the COX-1 message.

Figure 11:
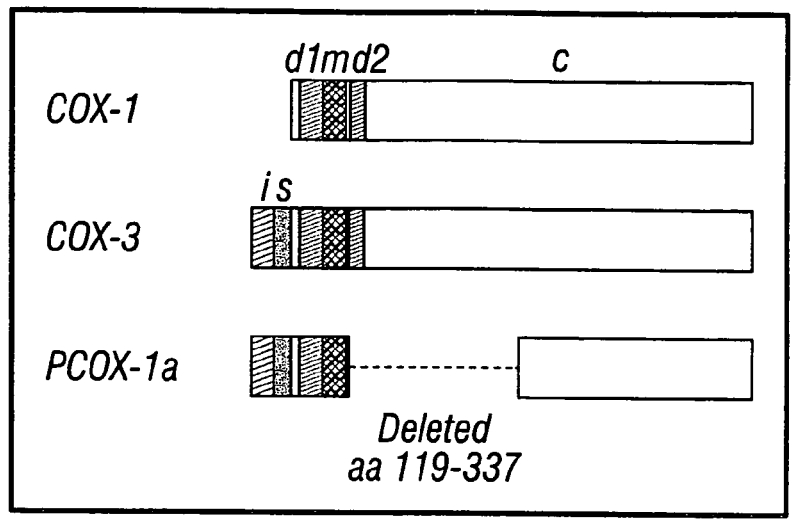
FIG. 11 depicts a schematic representation of the domains of COX-3 and PCOX-1 in comparison to COX-1. Abbreviations: s, signal peptide; d1, dimerization domain/EGF-like domain 1; d2, dimerization domain 2; m, membrane binding domain; c, catalytic domain; i, 90 bp sequence encoded by intron 1.

To determine whether the two previously detected COX mRNA transcripts (i.e. ~2.6 and ~1.9 kb) harbored intron 1, the Northern blot experiment was repeated utilizing a radio-labeled antisense canine COX-1 intron 1-specific oligonucleotide probe (CCI) (FIG. 10, panel A, lane 2). Importantly, the ~1.9 kb mRNA transcript and the ~2.6 kb transcript were detected suggesting that novel COX-1 mRNA splice variants were indeed expressed in canine cerebral cortex. Therefore the novel COX cDNA clone, which harbored a non-spliced intron 1 and corresponded to the ~2.6 kb mRNA transcript has been designated as COX-3. Additionally, the novel COX cDNA clone which harbored intron 1, lacked exons 5-8, and corresponded to the ~1.9 kb mRNA transcript, has been designated partial COX-1a or PCOX-1a (FIG. 11).

Reverse transcription-coupled PCR of canine cerebral cortex RNA as well as analysis of Northern blots, indicated that COX-3 mRNA is present in this brain region at about 5% of the level of COX-1 mRNA (FIG. 10, panel A). Interestingly, these analyses also demonstrated that the ~1.9 kb mRNA corresponding to PCOX-1a was actually a mixture of two mRNAs that differed in size by ~90 nucleotides (FIG. 10, panel B). One of these mRNAs was PCOX-1a and the other (PCOX-1b) was identical to PCOX-1a except that PCOX-1b lacked intron 1. PCOX-1a and PCOX-1b are expressed in equal amounts in brain cortex (FIG. 10, panel B).

To determine whether novel COX-1 related mRNA transcripts were also expressed in human tissues, human Northern blot experiments were performed utilizing a human-intron-1 specific (HCI) probe. Importantly, these results demonstrated the existence of a novel ~5.2 and ~2.8 kb mRNA transcripts (FIG. 10, panel C). Faint hybridization signals were also seen around 1.9 kb. Hybridization of HCl to the ~5.2 kb form was tissue-specific, with highest levels present in the cerebral cortex followed by the heart. These observations differ from the characterized expression patterns of COX-1 mRNA.

COX enzymes are intralumenal residents of the endoplasmic reticulum and depend on N-linked glycosylation for proper folding and activity. Retention of intron 1 could prevent COX-3 and PCOX-1 expression by preventing export of these mRNAs from the nucleus or by targeting these proteins to another subcellular compartment, preventing glycosylation. Therefore, insect cells (Sf9) were infected with recombinant baculovirus expressing COX-3, PCOX-1, and COX-1 and cell homogenates were assayed for protein expression by Western blotting. Antibodies specific for the conserved amino acid sequence (MSREXDPXA) predicted to be encoded by intron 1 in mammals were used to probe for COX-3 and PCOX-1a and b. This analysis demonstrated that both COX-3 and PCOX-1 are efficiently expressed in insect cells. No detectable products resulting from removal of intron 1 by splicing were detected immunologically or by RT-PCR analysis of RNA extracted from infected Sf9 cells. Moreover, the signal peptide, which in COX-3 and PCOX-1a or b contains an additional intron 1 encoded sequence, was not removed by signal peptidase as it is in COX-1 and COX-2.

Figure 12:
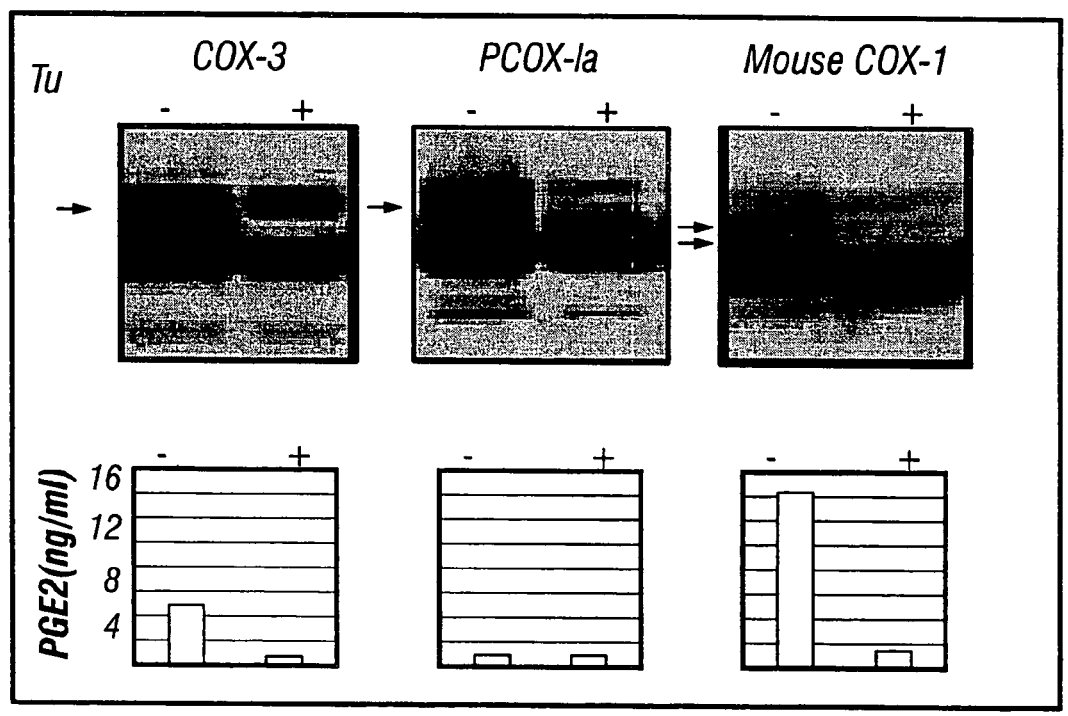
FIG. 12 depicts Western blots showing the expression of COX-3, PCOX-1a and COX-1 in insect cells treated with (+) and without (−) tunicamycin (top panels). Arrows indicate glycosylated forms of COX-1 which are not present in cells treated with tunicamycin. Polyclonal antibodies to human and mouse COX-1 intron 1 sequence were used to probe the COX-3 and PCOX-1a blots while a monoclonal antibody to ovine COX-1 (Cayman) was used to probe the mouse COX-1 blot. COX activity in insect cells expressing COX-3, PCOX-1a, and COX-1. Cells were treated with (+) and without (−) tunicamycin (bottom panels).
Figure 13A:
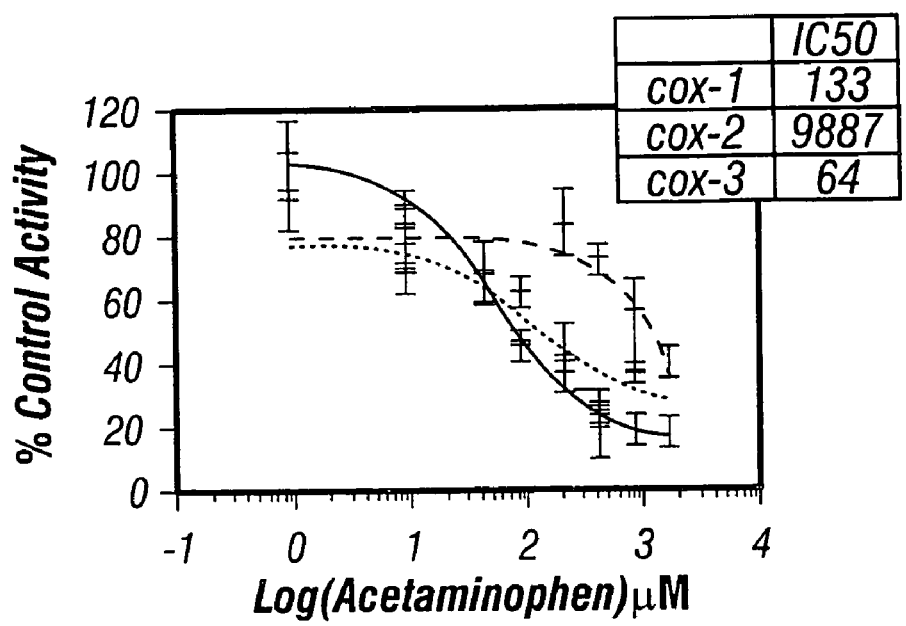
FIG. 13 depicts line graphs of drug inhibition studies showing the effects of acetaminophen (panel A and panel B), phenacetin (panel C), and dipyrone (panel D) on COX-1 (♦), COX-2 (●) and COX-3 (■) activity in insect cells. COX activity was measured by the formation of PGE$_2$ after exposure to exogenous 5 µM (A) or 30 µM (B, C, D) arachidonic acid for 10 minutes. Data are expressed as mean±SEM (n=6–9).
Figure 13B:
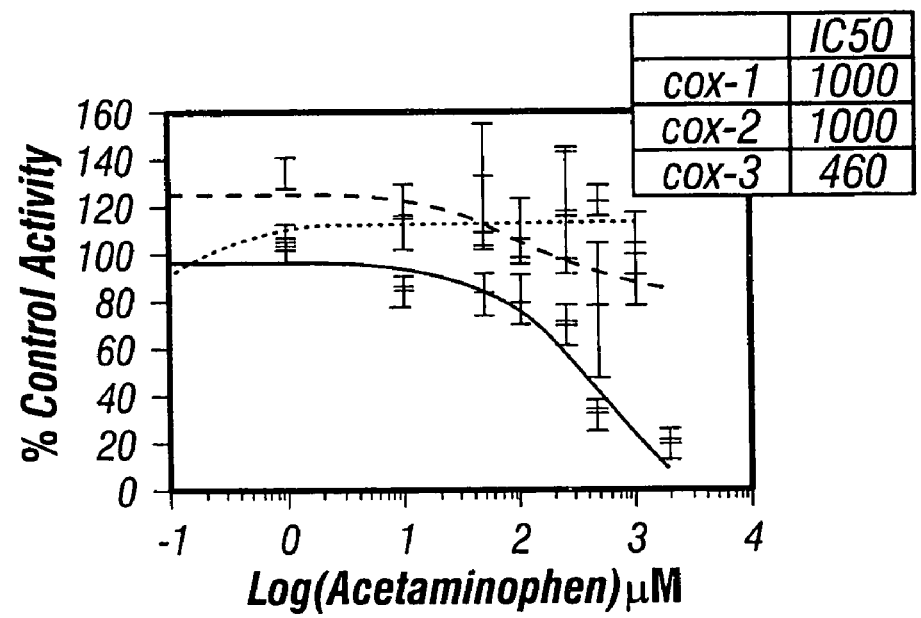
Figure 13C:
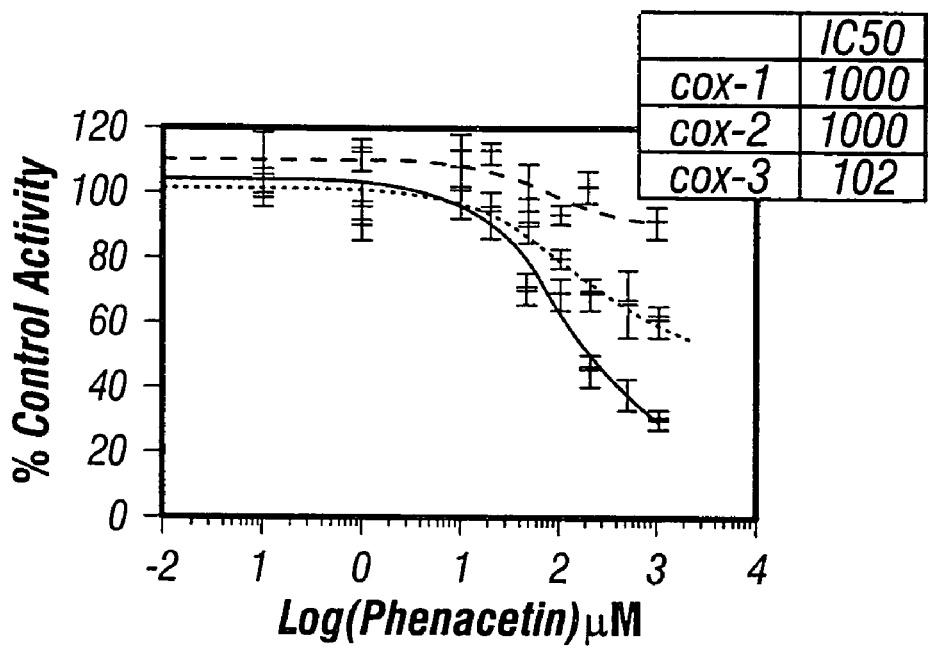
Figure 13D:
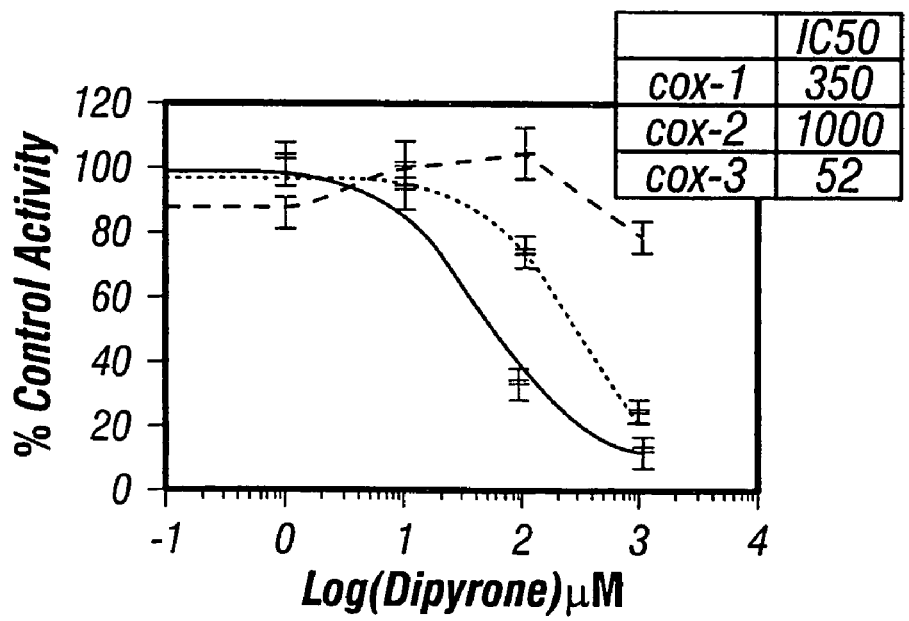

Posttranslational N-linked glycosylation of COX-3 and PCOX-1 was compared to that of COX-1 using tunicamycin to inhibit core glycosylation. Immunoblot analysis demonstrated a decrease in or disappearance of glycosylated forms of COX-3, PCOX-1, and COX-1 (FIG. 12 Top; left, middle and right panels, respectively). Expression systems were then assayed for cyclooxygenase activity by measuring the production of $PGE_2$ in whole insect cells. COX-3 activity was found to be ~20% of that of COX-1 and PCOX-1 completely lacked detectable COX activity (FIG. 12 bottom panels). COX activity in cells treated with tunicamycin was found to be significantly decreased or abolished by this drug, indicating that N-linked glycosylation is necessary for COX activity of COX-3.

Figure 15A:
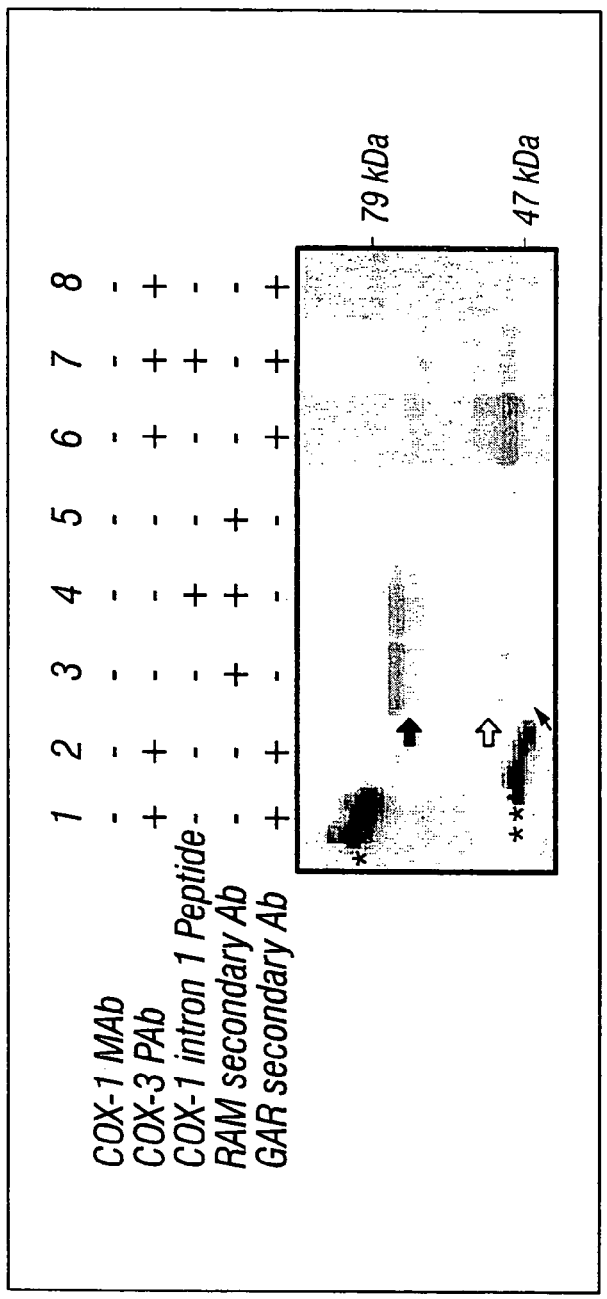
Figure 15B:
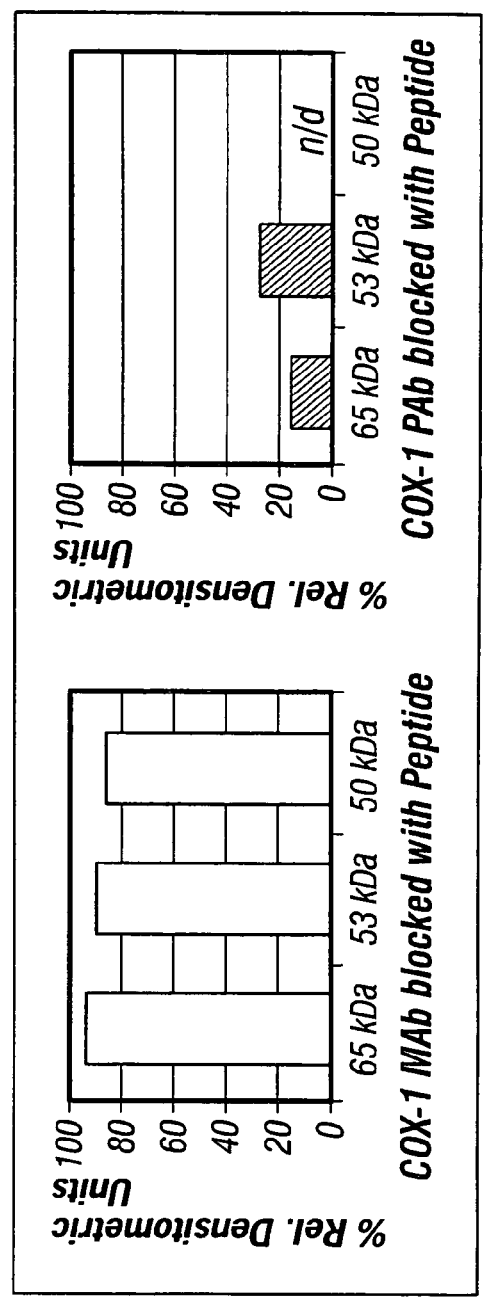

RNA studies in human tissues indicated highest levels of COX-3 message to be in the cerebral cortex and heart. Western blot analysis of human aorta (FIG. 15) using either COX-1 monoclonal antibody or COX-3 antipeptide polyclonal antibody detected the presence of distinct 65 and 53 kDa COX-1 related proteins. Additionally, the COX-1 but not COX-3 antibody, detected a 69 kDa protein, corresponding to glycosylated COX-1, as well as a 50 kDa protein, which may represent a proteolytic fragment of COX-1 or PCOX-1b. Detection of both of the 65 and 53 kDa proteins was selectively reduced by preincubation of the anti-peptide sera with its cognate peptide, whereas detection of the same proteins by the COX-1 monoclonal antibody was unaffected by this treatment.

Analgesic/antipyretic drugs and NSAIDs were tested for their ability to inhibit COX activity of COX-3 as compared to their ability to inhibit COX-1 and COX-2. Analyses were done in the presence of exogenously added arachidonic acid at 30 and 5 μM concentrations. At the higher concentration of substrate, only COX-3 was inhibited by acetaminophen (FIG. 13, panel A). Moreover, COX-3 was found to be significantly more sensitive to acetaminophen than either COX-1 or COX-2 at the lower substrate concentration (FIG. 13, panel B). Acetaminophen inhibited COX-3 at an $IC_{50}$ value of 64 μM when done in the presence of 5 μM arachidonic acid, whereas $IC_{50}$ values for COX-1 and COX-2 were 2.1- and 92.4-fold higher, respectively.

Acetaminophen is considered to be the active metabolite of phenacetin, a once popular analgesic/antipyretic drug that is no longer extensively used due to the occurrence of methemoglobinemia, renal toxicity, and suspected renal and bladder carcinogenesis. Phenacetin is rapidly O-de-ethylated in the body to form acetaminophen and is further metabolized to other minor but toxic compounds. Thus only small levels of phenacetin circulate in the blood. Interestingly, however, phenacetin was much more potent at inhibiting COX-3 than was acetaminophen (FIG. 13, panel C). Under substrate conditions of 30 μM, phenacetin inhibited COX-3 at an $IC_{50}$ value of 102 μM as opposed to 460 μM for acetaminophen tested under similar conditions. As with acetaminophen, phenacetin preferentially inhibited COX-3.

Another analgesic/antipyretic drug, dipyrone, was also significantly more potent at inhibiting COX-3 than either COX-1 or COX-2 (FIG. 13, panel D). Dipyrone inhibited COX-3 with an $IC_{50}$ value of 52 μM and COX-1 at a 6.6-fold higher concentration. No detectable inhibition of COX-2 by dipyrone was observed below 1 mM. Dipyrone is a pro-drug that spontaneously breaks down in aqueous solutions to a variety of structurally related pyrazolone compounds that differ in their potency as analgesic/antipyretic agents. Antipyrine and dimethylaminopyrene are similar to two breakdown products of dipyrone, and possess markedly reduced therapeutic potency and similarly show markedly reduced inhibition of COX-3 as compared to dipyrone (Table 1). However, these compounds, like other analgesic/antipyretic agents, preferentially inhibit COX-3.

COX-3 was also found to differ in its sensitivity to inhibition by a selection of NSAIDs. Diclofenac was the most potent inhibitor of COX-3 tested and diclofenac, aspirin and ibuprofen preferentially inhibited COX-3 over COX-1 and COX-2. The $IC_{50}$ values of these drugs are tabulated (Table 1). Importantly, the overall results indicate that COX-3 possesses a COX activity which differs pharmacologically from both COX-1 and COX-2.

Both COX-3 and PCOX-1a are formed by intron retention. We have previously shown that COX-2 in chicken is regulated by intron 1 retention, similar to that seen with COX-3. Unspliced mRNAs are largely retained in the nucleus. In the case of chicken COX-2, retention of intron 1 prevents translation and nuclear export of the mRNA. However, both COX-3 and PCOX-1a mRNAs in insect cells retain the intron and are exported from the nucleus and are translated (FIG. 12). The polypeptides produced from COX-3 and PCOX-1a include sequence encoded by the intron 1 and are functionally different from fully-spliced COX-1. Therefore retention of intron 1 provides a mechanism by which a novel COX enzyme, COX-3, can be produced in cells and tissues. Consistent with the concept that retention of intron 1 is important in creating COX-3 and/or regulating COX-1 is the finding that the DNA sequence of intron 1 from dog, human, and mouse COX-1 genes displays a high degree of conservation. This is most evident in the 5' and central regions of the intron. Overall intron 1 shows 41% sequence identity between all three species with the sequence 5'-GCCTcNGGNGGAGCCTYGA-AYGCYAG-3' (SEQ ID NO:44) in the central region of the intron being highly conserved. In fact intron 1, is more conserved in these species than is exon 1, suggesting that intron 1 plays an important and similar role in mammals. Highly conserved elements of intron 1 may also play a role in regulation of its retention. Further buttressing the concept that intron 1 plays an important role in regulating COX-3 expression is the fact that the gene structure of COX-1 and COX-2 differ only in their placement of intron 1. COX-1 has 10 introns while COX-2 has 9. The additional intron in the COX-1 gene is intron 1, which is retained in COX-3.

COX-3 shares all the catalytic features and important structural features of COX-1 and COX-2. However, the insertion of intron 1, two amino acids downstream from the initiating methionine would result in the addition of 30 amino acids to the signal peptide. Despite having a signal peptide and intron-1-encoded sequence retained, COX-3 co-migrates with COX-1 in SDS-PAGE gels. It also appears to enter the endoplasmic reticulum where it is glycosylated and its glycosylation is required for activity. In insect cells COX-3 shows approximately 20% of the activity of COX-1, which in turn exhibits about 20% of the activity of COX-2. COX-1, COX-2, COX-3, and PCOX-1a all show equivalent expression in our baculovirus system, and so a lowered ability of insect cells to express active COX-1 relative to COX-2 may be due to the inability of insect cells to posttranslationally process COX-1 correctly. Subcellular localization studies done by differential centrifugation demonstrate that neither COX-3 nor PCOX-1a is cytosolic. Membrane binding of both proteins is predicted from the fact that both retain a membrane binding domain and both appear to enter the lumen of the endoplasmic reticulum. Retention of intron 1 could alter folding and may affect dimerization and the active site. These effects could be through structural changes or altered protein targeting. COX-1 site-directed mutagenesis of either $Cys^{313}$ or $Cys^{540}$, both of which are more than 25 Å from the heme iron, was observed to reduce the activity of the enzyme by 80-90%. Therefore, although COX-3 contains all of the COX-1 sequence, the retained intron sequence could significantly alter its enzymatic properties. The present inhibition studies of COX-3 indicate this to be the case.

The present studies shows that the COX-1 variant COX-3 is sensitive to drugs that are analgesic/antipyretic, but which have low anti-inflammatory activity. Pain and fever have many etiologies that employ complex cellular and biochemical pathways. The finding that COX-3 is sensitive to analgesic/antipyretic drugs suggests that the COX-1 gene plays an integral role in pain and/or fever. Depending on the physiological context, pain pathways involve products from either the COX-1 or COX-2 genes. COX-2 selective drugs, for example, are clinically useful in inhibiting inflammatory pain in humans and are more potent than COX-1-selective NSAIDs at inhibiting pain induced by pro-inflammatory agents (e.g. carrageenan) in some paw inflammation assays in rodents. COX-1 selective drugs, in contrast, are superior to COX-2-selective agents at inhibiting visceronociception caused by a variety of chemical pain stimulators. Moreover, Ballou et al. (*Proc. Natl. Acad. Sci. USA* 97:10272, 2000) found that visceronociception was greatly decreased in COX-1 but not COX-2 knockout mice. Both COX-1 and COX-2, on the other hand, have been implicated in nociception models that measure analgesia outside the gut, such as in formalin and urate crystal tests. A role for COX-1 in pain is further supported by the fact that COX-1-selective NSAIDs (e.g. aspirin, ketorolac, ketoprofen, ibuprofen, and suprofen—are clinically important analgesic agents in humans and animals). Despite their relative exclusion from the brain, these drugs may reach sufficient concentration to effect COX-3 in the brain. Furthermore, the analgesic effects of these drugs often occur at significantly lower doses than those needed to inhibit inflammation. Clinical and experimental association of COX-1 and pain may be functionally explained by the finding that COX-1 is a marker for subpopulations of putative nociceptor neurons in the dorsal root ganglion.

With regard to pyresis, COX-2 but not COX-1 knockout mice demonstrate reduction in LPS- and interleukin-1-induced fevers, and some new COX-1 selective inhibitors, such as SC-560, have proven ineffective at inhibiting LPS-induced fever in animal models. Clinically, rofecoxib, a COX-2 selective inhibitor, inhibits naturally occurring fever and also inhibits the maintenance of fever in animal models. Yet aspirin, a COX-1 preferential inhibitor is one of the most effective antipyretic NSAIDs, and inhibits fever at doses ranging from 5-15 mg/kg, far below the 60-80 mg/kg used to treat inflammatory disease. Furthermore, nimesulide, a COX-2 preferential inhibitor, was found to be antipyretic in dogs only at plasma concentrations that would also inhibit COX-1. Thus a role for COX-1 in fever may exist.

The mechanism of action of acetaminophen has been unknown and postulated to be through inhibition of a brain COX that has never been identified. Northern blot analysis and cDNA cloning show that COX-3 is expressed in canine brain. COX-3 also appears from Northern blot studies (FIG. 10) to be expressed in specific regions of the human brain, in particular cerebral cortex. Moreover, our studies using ectopically expressed COX-3 in insect cells demonstrate that COX-3 is significantly more sensitive to acetaminophen than COX-1 and COX-2. Under physiological conditions, where steady-state acetaminophen concentrations reach approximately 100 μM, and where free arachidonic acid levels are 1-5 μM, only COX-3 is predicted to be appreciably inhibited. These findings suggest that inhibition of COX-3 in brain and the spinal cord could be the long sought-after target for acetaminophen.

The proposed mechanism of action for acetaminophen inhibition of COX-3 also appears to extend to pyrazolone drugs such as dipyrone and related compounds aminopyrine and antipyrine. Dipyrone is a potent analgesic/antipyretic drug which, like acetaminophen, lacks antiinflammatory activity. Dypyrone however is structurally unrelated to acetaminophen. Consistent with COX-3 being the target for analgesic and antipyretic drugs is the finding that these structurally dissimilar agents preferentially inhibit COX-3 and that their therapeutic potencies follow their ability to inhibit COX-3. The $IC_{50}$ values are as follows: dipyrone (52 μM), 4-dimethylaminoantipyrine (688 μM), and antipyrine (862 μM). Only dipyrone is therapeutically effective as an analgesic/antipyretic drug. Its active breakdown product, 4-methylaminoantipyrine reaches concentrations of 104 μM and 86 μM in plasma and the central nervous system, respectively. Thus, COX-3 inhibition occurs at known physiological concentrations of pyralazone drugs as well as acetaminophen. Additionally, inhibition of COX-3 does not require addition of glutathione, epinephrine, or other exogenously added "cofactors" which have been required in other systems.

Analgesic/antipyretic drugs inhibit COX-3 activity at higher concentrations than standard NSAIDs. From a therapeutic standpoint this may be rationalized by the fact that these drugs penetrate the blood brain barrier well, thus accumulating in the CNS at high enough concentrations to inhibit COX-3. Analgesic/antipyretic drugs, like acetaminophen, have long been postulated to have a central mechanism of action. Carboxylate-containing NSAIDs, on the other hand, cross the blood-brain barrier poorly and have a well-defined ability to reduce pain peripherally by reducing prostaglandin synthesis that sensitizes nociceptors. Several central analgesic mechanisms of action for NSAIDs have also been proposed wherein inhibition of prostaglandin synthesis in brain or spinal cord, potentially via COX-3, could contribute to the analgesic action of NSAIDs. Thus, action of NSAIDs in the body is likely to be central (COX-3) as well as peripheral (COX-1, COX-2 and COX-3). COX-1 variants in the CNS may be an essential target of both analgesic/antipyretics and standard NSAIDs.

A comparison of COX-3 inhibition by analgesic/antipyretics and NSAIDs in these studies (FIG. 13 and Table 1) suggest that both types of drugs may be capable of modulating a COX-variant activity (e.g., COX-3). Table 1 shows IC50 values of selected analgesic/antipyretic drugs and NSAIDs. Also shown are relevant inhibition ratios of COX-1/COX-3 and COX-2/COX-3 indicating preferential inhibition towards COX-3. All assays were carried out at 30 mM arachidonic acid. Asterisks in the table indicate the following notations: *, 4-dimethylaminoantipyrine; , no detectable inhibition at 1 mM; *, ratios not applicable.

TABLE 1

| DRUG | $IC_{50}$, μM | | |
|---|---|---|---|
| | COX-1 | COX-2 | COX-3 |
| Acetaminophen | >1000 | >1000 | 460 |
| Aminopyrine* | >1000 | >1000 | 688 |
| Antipyrine | >1000 | >1000 | 863 |
| Aspirin | 10 | >1000 | 3.1 |
| Diclofenac | 0.035 | 0.041 | 0.008 |
| Dipyrone | 350 | >1000 | 52 |
| Ibuprofen | 2.4 | 5.7 | 0.24 |
| Indomethacin | 0.010 | 0.66 | 0.016 |
| Phenacetin | >1000 | >1000 | 102 |
| Caffeine | >1000 | >1000 | >1000 |
| Thalidomide | >1000 | >1000 | >1000 |

Comparison of COX-1, COX-2 and COX-3 demonstrated that COX-3 is most like COX-1 in its sensitivity to NSAIDs but is significantly more sensitive to many drugs, such as diclofenac and ibuprofen, and less sensitive to others like sodium salicylate than is either COX-1 or COX-2. The higher sensitivity of COX-3 to NSAID inhibition may allow it to be preferentially inhibited in the CNS by low levels of NSAIDs that cross the blood-brain barrier. Furthermore, the differential sensitivity of COX-3 to analgesic/antipyretic drugs and NSAIDs suggests that highly selective inhibitors can be made for COX-3.

Human COX-3 is mainly expressed as a ~5.2 kb mRNA and has a tissue-specific pattern of expression (FIG. 10, panel C). This ~5.2 kb mRNA is an alternatively polyadenylated human COX-1 message previously reported and partly characterized in its 3' region (5). It appears, therefore, that the retention of intron 1 may influence the site at which the mRNA is polyadenylated. This finding suggests that the 3' untranslated regions of the mRNA may play a functional role in expression of COX-3 and perhaps PCOX-1a. The functional significance and the mechanism by which intron retention and alternative polyadenylation are coordinated need to be elucidated. It is also interesting to note that the ~5.2 kb mRNA has been shown to be regulatable (36) and hence may be regulated in response to physiological stimuli and signal transduction. Indeed, the levels of COX-3 mRNA in human and canine cerebral cortex are relatively low. This may be due to cell type-specific expression such as has been shown for COX-1 immunoreactive protein in a subpopulation of putative nociceptor neurons (23). However, COX-3 in human will require further experimentation since some of the published sequences differ by one nucleotide in intron 1 and hence are out of frame. These may constitute genuine polymorphisms or sequencing errors. Alternatively, intron 1 may be out of frame in humans, requiring other mechanisms such as ribosomal frame shifting to produce a functional COX-3 protein.

The present studies have identified novel COX-1 variants, including COX-3 protein of about 65 kDa in human aorta and a PCOX-1a protein of about 53 kDa. These proteins are detected by both COX-3 antipeptide polyclonal antibody and a COX-1 monoclonal antibody and appear to be present at about 25% of the level of COX-1. The 65 kDa protein is smaller than would be predicted if the protein is glycosylated to the same extent as COX-1, suggesting hypoglycosylation or other differences exist between the 65 kDa protein and COX-1. The 53 kDa proteins are present as a doublet, and are of a higher molecular weight than that predicted by the PCOX-1a protein primary sequence. This suggests that, like canine PCOX-1a expressed in insect cells, the human protein may be glycosylated, and that different glycosylation states may exist giving rise to the doublet observed. A 50 kDa protein is also detected only by the COX-1 monoclonal antibody, and is a candidate for being PCOX-1b. It appears to be present at about 15% of the level of COX-1.

Figure 14:
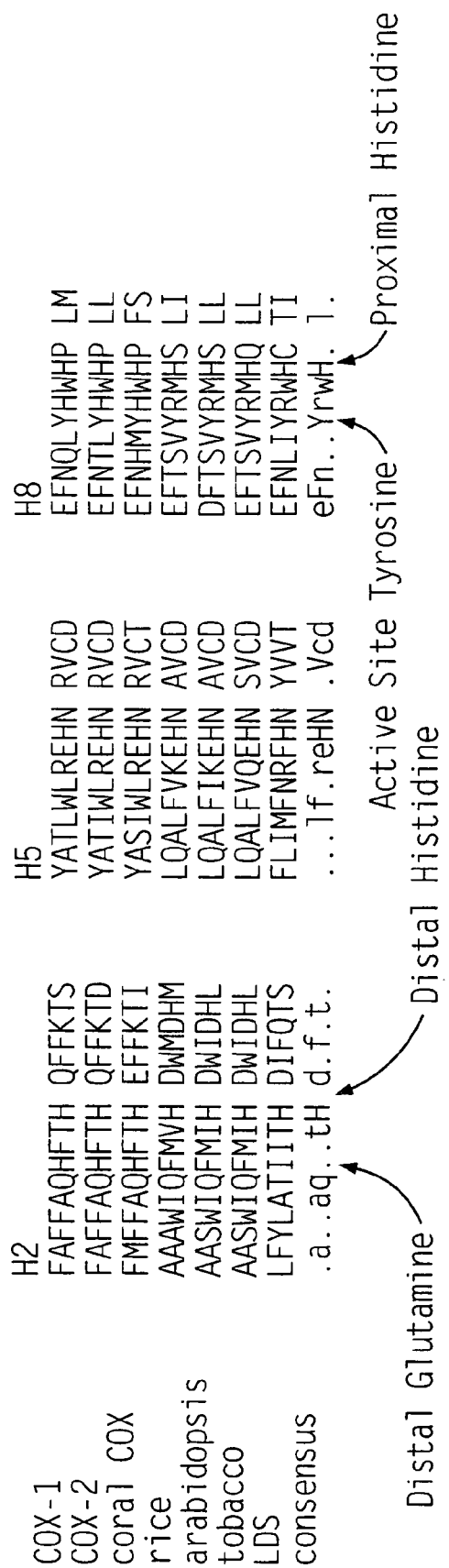
FIG. 14 depicts an alignment of the consensus sequences of COX-1, COX-2 and coral COX corresponding to structural helices H2, H5, and H8 with plant PIOXs and LDS. The PIOXs are from *Oryza sativa* (rice), *Arabidopsis thaliana* (arabidopsis) and *Nicotiana tabacum* (tobacco). Also aligned is linoleate diol synthase from *Gaeumannomyces graminis* (LDS). The consensus is shown using small letters for >50% homology and capital letters for 100% homology. Periods indicate that <50% homology was seen.

PCOX-1a is identical to COX-3 except for a deletion of 219 amino acids in the catalytic domain of the protein, corresponding to exons 5-8. It lacks detectable cyclooxygenase activity, as shown by its inability to make prostaglandins from arachidonic acid. The deleted portion contains structural helices HE, H1, H2, H3, H5, and part of H6 defined for COX-1 and COX-2. Of these helices, H2 and H5 form part of the core peroxidase catalytic site. Because of the lack of H2 and H5, PCOX-1 most likely lacks detectable peroxidase-activity. In this way it is similar to plant PIOX enzymes and *Gaeumannomyces graminis* linoleate diol synthase (LDS), which also lack peroxidase activity. They do, however, have fatty acid oxygenase activity that is similar in mechanism to the oxygenase activity of cyclooxygenase, and contain sequences similar to those found in COX-1 and -2. FIG. 14 shows an alignment of H2, H5, and H8 (helix containing $Tyr^{385}$ and the proximal histidine) from the consensus sequences of COX-1 and -2 with PIOXs and LDS.

Although the peroxidase activity of cyclooxygenase is needed to create the protein radical used in the cyclooxygenase reaction, continued peroxidase activity is not essential for continued cyclooxygenase activity. After the enzyme has been primed by one peroxidase reaction, it can continue to catalyze oxygenation of the substrate, because the tyrosine radical is regenerated after each oxygenation reaction. This priming mechanism for cyclooxygenase also seems to work with PIOXs and LDS. The active site tyrosine and proximal histidine of cyclooxygenase are conserved in PIOXs and LDS. It is believed that these enzymes have a reaction mechanism similar to COX, based on their similarity with cyclooxygenases. It is likely, then, that they do retain a low level of peroxidase activity that, although undetectable, is sufficient to prime them for oxygenase activity.

Because only one turnover of the peroxidase active site is required for cyclooxygenase activity in COX-1 and -2, there may be enough residual peroxidase activity in PCOX-1 proteins to prime them. However, we have shown that PCOX-1a does not have cyclooxygenase activity. It is possible, based on comparison with PIOXs that PCOX-1 proteins do retain lipid oxygenase activity, similar to the lipid oxygenase activity of PIOXs. Further studies are required to determine what the substrate of PCOX-1 proteins would be.

Because PCOX-1a and PCOX-1b are missing such a large portion of its catalytic domain, it is possible that it needs to be bound to another protein for it to be catalytically active. We have previously found that cyclooxygenases bind to nucleobindin (Ballif, 1996). Nucleobindin is a candidate for binding to PCOX-1 proteins as well. Additionally, a form of COX-1 has been described that co-localizes with prostacyclin synthase in filamentous structures of cultured endothelial cells. This filamentous form of COX-1 has no cyclooxygenase activity, and is a candidate for being a PCOX-1 protein.

Human COX-3 is mainly expressed as a ~5.2 kb mRNA and has a tissue-specific pattern of expression (FIG. 10, panel C). This ~5.2 kb mRNA is an alternatively polyadenylated human COX-1 message and partly characterized its 3' region. The data provided herein indicates that retention of intron 1 influences the site at which the mRNA is polyadenylated. The functional significance and the mechanism by which intron retention and alternative polyadenylation are coordinated need to be elucidated. It is also interesting to note that the ~5.2 kb mRNA has been shown to be inducible and may be regulated in response to physiological stimuli and signal transduction. Indeed, the levels of COX-3 mRNA in human and canine cerebral cortex are relatively low and may be due to cell type-specific expression requiring specific signals. However, COX-3 in human will require further experimentation since some of the published sequences differ by one nucleotide in intron 1 and hence are out of frame. These may constitute genuine polymorphisms or sequencing errors. Alternatively, intron 1 may be out of frame in humans, requiring other mechanisms such as ribosomal frame shifting to produce a functional COX-3 protein. The finding that retention of intron 1 is coordinately tied to alternative polyadenylation suggests that the 3' untranslated regions of the mRNA may play a functional role in expression.

A number of embodiments of the invention have been described. Nevertheless, it will be understood that various modifications may be made without departing from the spirit and scope of the invention.

What is claimed is:

1. An isolated antibody which selectively binds to an epitope comprised within SEQ ID NO:20.

2. An isolated antibody which selectively binds to an epitope comprised within at least 10 contiguous amino acids of SEQ ID NO:20.

3. An isolated antibody which selectively binds to an epitope comprised within the first 13 amino acids of SEQ ID NO:14.

4. An isolated antibody which selectively binds to an epitope comprised within the first 15, 20 or 30 amino acids of SEQ ID NO:14.

5. The antibody of claim 4, wherein said epitope is comprised within the first 15 amino acids of SEQ ID NO:14.

6. The antibody of claim 4, wherein said epitope is comprised within the first 20 amino acids of SEQ ID NO:14.

7. An isolated antibody raised against SEQ ID NO:20.

8. An isolated antibody raised against 10 or more contiguous amino acids of SEQ ID NO:20.

9. An isolated antibody raised against the first 13 amino acids of SEQ ID NO:14.

10. An isolated antibody raised against the first 15, 20 or 30 amino acids of SEQ ID NO:14.

* * * * *